(12) United States Patent
Heyes et al.

(10) Patent No.: US 8,865,675 B2
(45) Date of Patent: *Oct. 21, 2014

(54) COMPOSITIONS AND METHODS FOR SILENCING APOLIPOPROTEIN B

(75) Inventors: James Heyes, Vancouver (CA); Mark Wood, Port Moody (CA); Alan Martin, Vancouver (CA); Amy C. H. Lee, Burnaby (CA); Adam Judge, Vancouver (CA); Marjorie Robbins, Vancouver (CA); Ian MacLachlan, Mission (CA)

(73) Assignee: Protiva Biotherapeutics, Inc., Burnaby, British Columbia (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/697,000

(22) PCT Filed: May 12, 2011

(86) PCT No.: PCT/GB2011/000721
§ 371 (c)(1),
(2), (4) Date: Jan. 18, 2013

(87) PCT Pub. No.: WO2011/141703
PCT Pub. Date: Nov. 17, 2011

(65) Prior Publication Data
US 2013/0123339 A1    May 16, 2013

Related U.S. Application Data

(60) Provisional application No. 61/334,111, filed on May 12, 2010, provisional application No. 61/351,276, filed on Jun. 3, 2010.

(51) Int. Cl.
| | | |
|---|---|---|
| *C12N 15/11* | (2006.01) | |
| *C12Q 1/68* | (2006.01) | |
| *A61K 31/713* | (2006.01) | |
| *C12N 15/88* | (2006.01) | |
| *C12N 15/113* | (2010.01) | |

(52) U.S. Cl.
CPC ........... *A61K 31/713* (2013.01); *C12N 2320/32* (2013.01); *C12N 15/88* (2013.01); *C12N 15/113* (2013.01); *C12N 15/111* (2013.01); *C12N 2310/14* (2013.01)
USPC ......................................... 514/44 A; 435/6.1

(58) Field of Classification Search
None
See application file for complete search history.

(56) References Cited

U.S. PATENT DOCUMENTS

2012/0027796 A1*  2/2012  Manoharan et al. ....... 424/204.1

FOREIGN PATENT DOCUMENTS

| WO | WO 2006/036916 A2 | 4/2006 |
|---|---|---|
| WO | WO 2006/053430 A1 | 5/2006 |
| WO | WO 2007051303 A1 * | 5/2007 |
| WO | WO 2009/127060 A1 | 10/2009 |
| WO | WO 2009/132131 A1 | 10/2009 |
| WO | WO 2010/042877 A1 | 4/2010 |
| WO | WO 2010/054401 A1 | 5/2010 |
| WO | WO 2010054401 A1 * | 5/2010 |
| WO | WO 2011/000106 A1 | 1/2011 |
| WO | WO 2011/000108 A1 | 1/2011 |

OTHER PUBLICATIONS

Heyes et al., "Cationic lipid saturation influences intracellular delivery of encapsulated nucleic acids", *Journal of Controlled Release* 107, 276-287 (2005).
Patent Cooperation Treaty, International Searching Authority, Search Report and Written Opinion for PCT/GB2011/000721, 11 pages, Sep. 20, 2011.
Semple et al., "Rational design of cationic lipids for siRNA delivery", *Nature Biotechnology*, vol. 28 (2), 172-176 (2010).

* cited by examiner

*Primary Examiner* — Tracy Vivlemore
*Assistant Examiner* — Kate Poliakova-Georgantas
(74) *Attorney, Agent, or Firm* — Viksnins Harris & Padys PLLP

(57) ABSTRACT

The present invention provides compositions and methods for the delivery of interfering RNAs such as siRNAs that silence APOB expression in cells such as liver cells. In particular, the nucleic acid-lipid particles provide efficient encapsulation of nucleic acids and efficient delivery of the encapsulated nucleic acid to cells such as liver cells in vivo. The compositions of the present invention are highly potent, thereby allowing effective knock-down of APOB at relatively low doses. In addition, the compositions and methods of the present invention are less toxic and provide a greater therapeutic index compared to compositions and methods previously known in the art.

46 Claims, 6 Drawing Sheets

COMPOSITIONS AND METHODS FOR SILENCING APOLIPOPROTEIN B

CROSS-REFERENCES TO RELATED APPLICATIONS

The present application claims priority to U.S. Provisional Application No. 61/351,276, filed Jun. 3, 2010, and U.S. Provisional Application No. 61/334,111, filed May 12, 2010, the disclosures of which are hereby incorporated by reference in their entirety for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file—109-2.TXT, created on Dec. 5, 2012, 8,192 bytes, machine format IBM-PC, MS-Windows operating system, is hereby incorporated by reference in its entirety for all purposes.

BACKGROUND OF THE INVENTION

Apolipoprotein B (also known as ApoB, apolipoprotein B-100; ApoB-100, apolipoprotein B-48; ApoB-48 and Ag(x) antigen), is a large glycoprotein that serves an indispensable role in the assembly and secretion of lipids and in the transport and receptor-mediated uptake and delivery of distinct classes of lipoproteins. Apolipoprotein 13 was cloned (Law et al., *PNAS USA* 82:8340-8344 (1985)) and mapped to chromosome 2p23-2p24 in 1986 (Deeb et al., *PNAS USA* 83, 419-422 (1986)). ApoB has a variety of functions, from the absorption and processing of dietary lipids to the regulation of circulating lipoprotein levels (Davidson and Shelness, *Annu. Rev. Nutr.*, 20:169-193 (2000)). Two forms of ApoB have been characterized: ApoB-100 and ApoB-48. ApoB-100 is the major protein component of LDL, contains the domain required for interaction of this lipoprotein species with the LDL receptor, and participates in the transport and delivery of endogenous plasma cholesterol (Davidson and Shelness, 2000, supra). ApoB-48 circulates in association with chylomicrons and chylomicron remnants which are cleared by the LDL-receptor-related protein (Davidson and Shelness, 2000, supra). ApoB-48 plays a role in the delivery of dietary lipid from the small intestine to the liver.

Susceptibility to atherosclerosis is highly correlated with the ambient concentration of apolipoprotein B-containing lipoproteins (Davidson and Shelness, 2000, supra). Elevated plasma levels of the ApoB-100-containing lipoprotein Lp(a) are associated with increased risk for atherosclerosis and its manifestations, which may include hypercholesterolemia (Seed et al., *N. Engl. J. Med.* 322:1494-1499 (1990), myocardial infarction (Sandkamp et al., *Clin. Chem.* 36:20-23 (1990), and thrombosis (Nowak-Gottl et al., *Pediatrics*, 99:E11 (1997)).

Apolipoprotein B knockout mice (bearing disruptions of both ApoB-100 and ApoB-48) have been generated which are protected from developing hypercholesterolemia when fed a high-fat diet (Farese et al., *PNAS USA.* 92:1774-1778 (1995) and Kim and Young, *J. Lipid Res.*, 39:703-723 (1998)). The incidence of atherosclerosis has been investigated in mice expressing exclusively ApoB-100 or ApoB-48 and susceptibility to atherosclerosis was found to be dependent on total cholesterol levels.

In view of such findings, significant efforts have been made to modulate serum cholesterol levels by modulating ApoB expression using therapeutic nucleic acids, e.g., antisense oligonucleotides, ribozymes, etc. (see, e.g., U.S. Pat. No. 7,407,943, which is directed to modulation of ApoB using antisense oligonucleotides). More recent efforts have focused on the use of interfering RNA molecules, such as siRNA and miRNA, to modulate ApoB (see, Zimmermann et al., *Nature*, 441: 111-114 (2006), U.S. Patent Publication Nos. 20060134189 and 20060105976, and PCT Publication No. WO 04/091515). Interfering RNA molecules can down-regulate intracellular levels of specific proteins, such as ApoB, through a process termed RNA interference (RNAi). Following introduction of interfering RNA into the cell cytoplasm, these double-stranded RNA constructs can bind to a protein termed RISC. The sense strand of the interfering RNA is displaced from the RISC complex, providing a template within RISC that can recognize and bind mRNA with a complementary sequence to that of the bound interfering RNA. Having bound the complementary mRNA, the RISC complex cleaves the mRNA and releases the cleaved strands. RNAi can provide down-regulation of specific proteins, such as ApoB, by targeting specific destruction of the corresponding mRNA that encodes for protein synthesis.

Despite the high therapeutic potential of RNAi, two problems currently faced by interfering RNA constructs are, first, their susceptibility to nuclease digestion in plasma and, second, their limited ability to gain access to the intracellular compartment where they can bind RISC when administered systemically as free interfering RNA molecules. These double-stranded constructs can be stabilized by the incorporation of chemically modified nucleotide linkers within the molecule, e.g., phosphothioate groups. However, such chemically modified linkers provide only limited protection from nuclease digestion and may decrease the activity of the construct.

In an attempt to improve efficacy, investigators have employed various lipid-based carrier systems to deliver chemically modified or unmodified therapeutic nucleic acids, including anionic (conventional) liposomes, pH sensitive liposomes, immunoliposomes, fusogenic liposomes, and cationic lipid/nucleic acid aggregates. In particular, one lipid-based carrier system, i.e., the stable nucleic-acid lipid particle (SNALP) system, has been found to be particularly effective for delivering interfering RNA (see, U.S. Patent Publication No. 20050064595 and U.S. Patent Publication No. 20060008910 (collectively referred to as "MacLachlan et al.")). MacLachlan et al, have demonstrated that interfering RNA, such as siRNA, can be effectively systemically administered using nucleic acid-lipid particles containing a cationic lipid, and that these nucleic acid-lipid particles provide improved down-regulation of target proteins in mammals including non-human primates (see, Zimmermann et al., *Nature*, 441: 111-114 (2006)).

Even in spite of this progress, there remains a need in the art for improved SNALPs that are useful for delivering therapeutic nucleic acids, such as siRNA and miRNA, to the liver of a mammal (e.g., a human), and that result in increased silencing of target genes of interest in the liver, such as ApoB. Preferably, these compositions would encapsulate nucleic acids with high-efficiency, have high drug:lipid ratios, protect the encapsulated nucleic acid from degradation and clearance in serum, be suitable for systemic delivery, and provide intracellular delivery of the encapsulated nucleic acid. In addition, these nucleic acid-lipid particles should be well-tolerated and provide an adequate therapeutic index, such that patient treatment at an effective dose of the nucleic acid is not associated with significant toxicity and/or risk to the patient. The present invention provides such compositions, methods of making the compositions, and methods of using the compositions to introduce nucleic acids, such as siRNA and miRNA, into the liver, including for the treatment of diseases, such as hypercholesterolemia (e.g., atherosclerosis, angina pectoris or high blood pressure).

BRIEF SUMMARY OF THE INVENTION

The present invention is based, in part, on the discovery that the use of certain cationic (amino) lipids in nucleic acid-lipid particles provides advantages when the particles are used for the in vivo delivery of therapeutic nucleic acids, such as siRNA, into the liver of a mammal. In particular, it has been unexpectedly found that the nucleic acid-lipid particles of the present invention comprising at least one cationic lipid of Formulas I-III and at least one interfering RNA as described herein demonstrate increased potency (i.e., increased silencing activity) and/or increased tolerability (e.g., a more favorable toxicity profile) when targeting a gene of interest in the liver such as APOB, APOC3, PCSK9, DGAT1, and/or DGAT2 when compared to other nucleic acid-lipid particle compositions previously described. In preferred embodiments, the present invention provides nucleic acid-lipid particles (e.g., SNALP) comprising APOB siRNA ⅗ and at least one cationic lipid of Formulas I-II (e.g., Compound 1, 4, 5, 8, 9, 10, 11, 12, 13, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 51, 56, 63, 64, 65, or combinations thereof) and methods of use thereof, which nucleic acid-lipid particles unexpectedly possess increased potency and/or increased tolerability when silencing APOB expression in vivo compared to other nucleic acid-lipid particle compositions previously described.

In particular embodiments, the present invention provides cationic lipids that enable the formulation of compositions for the in vitro and in vivo delivery of interfering RNA, such as siRNA, to the liver that result in increased silencing of the target gene of interest, such as APOB. It is shown herein that these improved lipid particle compositions are particularly effective in down-regulating (e.g., silencing) the protein levels and/or mRNA levels of target genes in the liver, such as APOB. Furthermore, it is shown herein that the activity of these improved lipid particle compositions is dependent on the presence of the cationic lipids of Formulas I-III of the invention.

In one aspect, the present invention provides a nucleic acid-lipid particle (e.g., SNALP) comprising:

(a) an interfering RNA that silences Apolipoprotein B (APOB) expression and/or the expression of another liver target gene such as APOC3, PCSK9, DGAT1, and/or DGAT2;

(b) a cationic lipid of Formula I having the following structure:

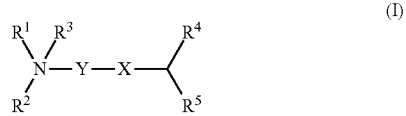

(I)

or salts thereof, wherein:

R$^1$ and R$^2$ are either the same or different and are independently hydrogen (H) or an optionally substituted C$_1$-C$_6$ alkyl, C$_2$-C$_6$ alkenyl, or C$_2$-C$_6$ alkynyl, or R$^1$ and R$^2$ may join to form an optionally substituted heterocyclic ring;

R$^3$ is either absent or is hydrogen (H) or a C$_1$-C$_6$ alkyl to provide a quaternary amine;

R$^4$ and R$^5$ are either the same or different and are independently an optionally substituted C$_{10}$-C$_{24}$ alkyl, C$_{10}$-C$_{24}$ alkenyl, C$_{10}$-C$_{24}$ alkynyl, or C$_{10}$-C$_{24}$ acyl;

X is O, S, N(R$^6$), C(O), C(O)O, OC(O), C(O)N(R$^6$), N(R$^6$)C(O), OC(O)N(R$^6$), N(R$^6$)C(O)O, C(O)S, C(S)O, S(O), S(O)(O), C(S), or an optionally substituted heterocyclic ring, wherein R$^6$ is hydrogen (H) or an optionally substituted C$_1$-C$_{10}$ alkyl, C$_2$-C$_{10}$ alkenyl, or C$_2$-C$_{10}$ alkynyl; and Y is either absent or is an optionally substituted C$_1$-C$_6$ alkyl, C$_2$-C$_6$ alkenyl, or C$_2$-C$_6$ alkynyl; and (c) a non-cationic lipid.

In another aspect, the present invention provides a nucleic acid-lipid particle (e.g., SNALP) comprising:

(a) an interfering RNA that silences Apolipoprotein B (APOB) expression and/or the expression of another liver target gene such as APOC3, PCSK9, DGAT1, and/or DGAT2;

(b) a cationic lipid of Formula II having the following structure:

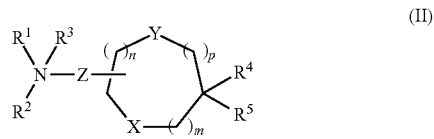

(II)

or salts thereof, wherein:

R$^1$ and R$^2$ are either the same or different and are independently an optionally substituted C$_1$-C$_6$ alkyl, C$_2$-C$_6$ alkenyl, or C$_2$-C$_6$ alkynyl, or R$^1$ and R$^2$ may join to form an optionally substituted heterocyclic ring;

R$^3$ is either absent or, if present, is hydrogen (H) or a C$_1$-C$_6$ alkyl to provide a quaternary amine;

R$^4$ and R$^5$ are either the same or different and are independently an optionally substituted C$_{10}$-C$_{24}$ alkyl, C$_{10}$-C$_{24}$ alkenyl, C$_{10}$-C$_{24}$ alkynyl, or C$_{10}$-C$_{24}$ acyl, wherein at least one of R$^4$ and R$^5$ comprises at least one optionally substituted cyclic alkyl group;

m, n, and p are either the same or different and are independently either 0, 1, or 2, with the proviso that m, n, and p are not simultaneously 0;

X and Y are either the same or different and are independently O, S, N(R$^6$), C(O), C(O)O, OC(O), C(O)N(R$^6$), N(R$^6$)C(O), OC(O)N(R$^6$), N(R$^6$)C(O)O, C(O)S, C(S)O, S(O), S(O)(O), or C(S), wherein R$^6$ is hydrogen (H) or an optionally substituted C$_1$-C$_{10}$ alkyl, C$_2$-C$_{10}$ alkenyl, or C$_2$-C$_{10}$ alkynyl; and Z is either absent or, if present, is an optionally substituted C$_1$-C$_6$ alkyl, C$_2$-C$_6$ alkenyl, or C$_2$-C$_6$ alkynyl; and (c) a non-cationic lipid.

In yet another aspect, the present invention provides a nucleic acid-lipid particle (e.g., SNALP) comprising:

(a) an interfering RNA that silences Apolipoprotein B (APOB) expression and/or the expression of another liver target gene such as APOC3, PCSK9, DGAT1, and/or DGAT2;

(b) a cationic lipid of Formula III having the following structure:

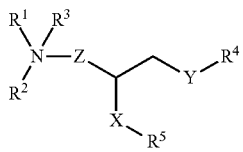

or salts thereof, wherein:
R¹ and R² are either the same or different and are independently hydrogen (H) or an optionally substituted $C_1$-$C_6$ alkyl, $C_2$-$C_6$ alkenyl, or $C_2$-$C_6$ alkynyl, or R¹ and R² may join to form an optionally substituted heterocyclic ring;
R³ is either absent or, if present, is hydrogen (H) or a $C_1$-$C_6$ alkyl to provide a quaternary amine;
R⁴ and R⁵ are either the same or different and are independently an optionally substituted $C_{10}$-$C_{24}$ alkyl, $C_{10}$-$C_{24}$ alkenyl, $C_{10}$-$C_{24}$ alkynyl, or $C_{10}$-$C_{24}$ acyl, wherein at least one of R⁴ and R⁵ comprises at least one optionally substituted cyclic alkyl group;
X and Y are either the same or different and are independently O, S, N(R⁶), C(O), C(O)O, OC(O), C(O)N(R⁶), N(R⁶)C(O), OC(O)N(R⁶), N(R⁶)C(O)O, C(O)S, C(S) O, S(O), S(O)(O), C(S), or an optionally substituted heterocyclic ring, wherein R⁶ is hydrogen (H) or an optionally substituted $C_1$-$C_{10}$ alkyl, $C_2$-$C_{10}$ alkenyl, or $C_2$-$C_{10}$ alkynyl; and
Z is either absent or, if present, is an optionally substituted $C_1$-$C_6$ alkyl, $C_2$-$C_6$ alkenyl, or $C_2$-$C_6$ alkynyl; and
(c) a non-cationic lipid.

In some embodiments, the lipid particles of the invention preferably comprise one or more interfering RNA that silence APOB and/or other liver target genes such as APOC3, PCSK9, DGAT1, DGAT2, or combinations thereof, one or more cationic lipids of Formulas I-III as disclosed herein, one or more non-cationic lipids, and one or more conjugated lipids that inhibit aggregation of particles.

In certain embodiments, the non-cationic lipid component of the lipid particle may comprise a phospholipid, cholesterol (or cholesterol derivative), or a mixture thereof. In one particular embodiment, the phospholipid comprises dipalmitoylphosphatidylcholine (DPPC), distearoylphosphatidylcholine (DSPC), or a mixture thereof. In some embodiments, the conjugated lipid component of the lipid particle comprises a polyethyleneglycol (PEG)-lipid conjugate. In certain instances, the PEG-lipid conjugate comprises a PEG-diacylglycerol (PEG-DAG) conjugate, a PEG-dialkyloxypropyl (PEG-DAA) conjugate, or a mixture thereof. In other embodiments, the lipid conjugate comprises a polyoxazoline (POZ)-lipid conjugate such as a POZ-DAA conjugate.

In some embodiments, the interfering RNA is fully encapsulated within the lipid portion of the lipid particle such that the interfering RNA in the lipid particle is resistant in aqueous solution to enzymatic degradation, e.g., by a nuclease or protease. Non-limiting examples of interfering RNA include any double-stranded RNA capable of mediating RNAi, such as, e.g., an siRNA, Dicer-substrate dsRNA, shRNA, aiRNA, pre-miRNA, or mixtures thereof. In other embodiments, the lipid particles described herein are substantially non-toxic to mammals such as humans.

In other embodiments, the nucleic acid-lipid particle comprises an interfering RNA (e.g., siRNA) that targets APOB, wherein the interfering RNA comprises an antisense strand comprising the sequence 5'-UAUUCAGUGUGAUGA-CACU-3' (SEQ ID NO:13). In still other embodiments, the nucleic acid-lipid particle further comprises a sense strand comprising the sequence 5'-AGUGUCAUCA-CACUGAAUA-3' (SEQ ID NO:14). In certain embodiments, the interfering RNA comprises a 3' overhang in one or both strands of the interfering RNA molecule. In certain embodiments, the interfering RNA comprises an antisense strand comprising a 5'-UG-3' overhang and/or a sense strand comprising a 5'-CC-3' overhang.

In yet other embodiments, the nucleic acid-lipid particle comprises an interfering RNA (e.g., siRNA) that targets APOB, wherein the interfering RNA comprises at least one modified nucleotide. In certain embodiments, one or more of the nucleotides in the double-stranded region of the interfering RNA comprise modified nucleotides. In certain other embodiments, one or more of the nucleotides in the 3' overhang in one or both strands of the interfering RNA comprise modified nucleotides. In particular embodiments, the modified nucleotides comprise 2'-O-methyl (2'OMe) nucleotides.

In further embodiments, the nucleic acid-lipid particle comprises an interfering RNA (e.g., siRNA) that targets APOB, wherein the interfering RNA comprises an antisense strand comprising the sequence 5'-UA<u>U</u>UCAGUG<u>U</u>GA <u>U</u>GACAC<u>U</u>-3' (SEQ ID NO:15), wherein the bolded and underlined nucleotides are 2'OMe nucleotides. In other embodiments, the particle further comprises a sense strand comprising the sequence 5'-AG<u>U</u>G<u>U</u>CA<u>U</u>CACAC<u>U</u>GAA <u>U</u>A-3' (SEQ ID NO:16), wherein the bolded and underlined nucleotides are 2'OMe nucleotides. In certain embodiments, the interfering RNA comprises a 3' overhang in one or both strands of the interfering RNA molecule. In some embodiments, the interfering RNA comprises an antisense strand comprising a 5'-<u>UG</u>-3' overhang and/or a sense strand comprising a 5'-CC-3' overhang, wherein the bolded and underlined nucleotides are 2'OMe nucleotides. In other embodiments, the nucleic acid-lipid particle comprises an interfering RNA consisting of the following sequences:

```
5'-AG<u>UGU</u>CA<u>U</u>CACAC<u>U</u>G<u>AAU</u>ACC-3'    (SEQ ID NO: 4)
and 3'-<u>GUU</u>CACAG<u>U</u>AG<u>U</u>G<u>U</u>GAC<u>UU</u>AU-5'   (SEQ ID NO: 11)
``` wherein the bolded and underlined nucleotides are 2'OMe nucleotides.

The present invention also provides pharmaceutical compositions comprising a nucleic acid-lipid particle described herein (e.g., SNALP) and a pharmaceutically acceptable carrier.

In another aspect, the present invention provides methods for introducing one or more interfering RNA molecules (e.g., siRNAs that silence APOB expression and/or the expression of other liver target genes such as APOC3, PCSK9, DGAT1, and/or DGAT2) into a cell (e.g., a liver cell), the method comprising contacting the cell with a nucleic acid-lipid particle described herein (e.g., SNALP). In one embodiment, the cell is in a mammal and the mammal is a human.

In yet another aspect, the present invention provides methods for the in vivo delivery of one or more interfering RNA molecules (e.g., siRNAs) to liver cells, the method comprising administering to a mammal a nucleic acid-lipid particle described herein (e.g., SNALP). Advantageously, the nucleic acid-lipid particles of the invention are particularly effective at silencing target gene expression in the liver and, thus, are well suited for targeting genes such as APOB, APOC3, PCSK9, DGAT1, DGAT2, and combinations thereof. In certain embodiments, the nucleic acid-lipid particles (e.g., SNALP) are administered by one of the following routes of administration: oral, intranasal, intravenous, intraperitoneal, intramuscular, intra-articular, intralesional, intratracheal, subcutaneous, and intradermal. In particular embodiments, the nucleic acid-lipid particles (e.g., SNALP) are administered systemically, e.g., via enteral or parenteral routes of administration. In preferred embodiments, the mammal is a human.

In certain embodiments, the present invention provides methods for treating a liver disease or disorder by administering an interfering RNA (e.g., one or more siRNAs targeting APOB, APOC3, PCSK9, DGAT1, and/or DGAT2 expression) in nucleic acid-lipid particles (e.g., SNALP) as described herein, alone or in combination with a lipid-lowering agent. Examples of lipid diseases and disorders include, but are not limited to, dyslipidemia (e.g., hyperlipidemias such as elevated triglyceride levels (hypertriglyceridemia) and/or elevated cholesterol levels (hypercholesterolemia)), atherosclerosis, coronary heart disease, coronary artery disease, atherosclerotic cardiovascular disease (CVD), fatty liver disease (hepatic steatosis), abnormal lipid metabolism, abnormal cholesterol metabolism, diabetes (including Type 2 diabetes), obesity, cardiovascular disease, and other disorders relating to abnormal metabolism. Non-limiting examples of lipid-lowering agents include statins, fibrates, ezetimibe, thiazolidinediones, niacin, beta-blockers, nitroglycerin, calcium antagonists, and fish oil.

In one particular embodiment, the present invention provides a method for lowering or reducing cholesterol levels in a mammal (e.g., human) in need thereof (e.g., a mammal with elevated blood cholesterol levels), the method comprising administering to the mammal a therapeutically effective amount of a nucleic acid-lipid particle (e.g., a SNALP formulation) described herein comprising one or more interfering RNAs (e.g., siRNAs) that target one or more genes associated with metabolic diseases and disorders (e.g., APOB, APOC3, PCSK9, DGAT1, and/or DGAT2). In another particular embodiment, the present invention provides a method for lowering or reducing triglyceride levels in a mammal (e.g., human) in need thereof (e.g., a mammal with elevated blood triglyceride levels), the method comprising administering to the mammal a therapeutically effective amount of a nucleic acid-lipid particle (e.g., a SNALP formulation) described herein comprising one or more interfering RNAs (e.g., siRNAs) that target one or more genes associated with metabolic diseases and disorders (e.g., APOB, APOC3, PCSK9, DGAT1, and/or DGAT2). These methods can be carried out in vitro using standard tissue culture techniques or in vivo by administering the interfering RNA (e.g., siRNA) using any means known in the art. In preferred embodiments, the interfering RNA (e.g., siRNA) is delivered to a liver cell (e.g., hepatocyte) in a mammal such as a human.

Additional embodiments related to treating a liver disease or disorder using a lipid particle are described in, e.g., PCT Patent Publication No. WO 2010/083615 and U.S. Patent Publication No. 20060134189, the disclosures of which are herein incorporated by reference in their entirety for all purposes.

In a further aspect, the present invention provides methods for treating a disease or disorder associated with overexpression of APOB in a mammal (e.g., human) in need thereof, the method comprising administering to the mammal a therapeutically effective amount of a nucleic acid-lipid particle (e.g., SNALP) comprising one (or more) interfering RNA that silences APOB expression. Diseases and disorders associated with overexpression of APOB include, but are not limited to, atherosclerosis, angina pectoris, high blood pressure, diabetes, and hypothyroidism. In preferred embodiments, the mammal (e.g., human) has a disease or disorder involving hypercholesterolemia and serum cholesterol levels are lowered when expression of APOB is silenced by the interfering RNA delivered using the nucleic acid-lipid particles of the present invention.

The nucleic acid-lipid particles of the invention (e.g., SNALP) comprising one or more cationic lipids of Formulas I-III or salts thereof are particularly advantageous and suitable for use in the administration of interfering RNA to a subject (e.g., a mammal such as a human) because they are stable in circulation, of a size required for pharmacodynamic behavior resulting in access to extravascular sites, and are capable of reaching target cell populations.

Other objects, features, and advantages of the present invention will be apparent to one of skill in the art from the following detailed description and figures.

DETAILED DESCRIPTION OF THE INVENTION

Introduction

Figure 1:
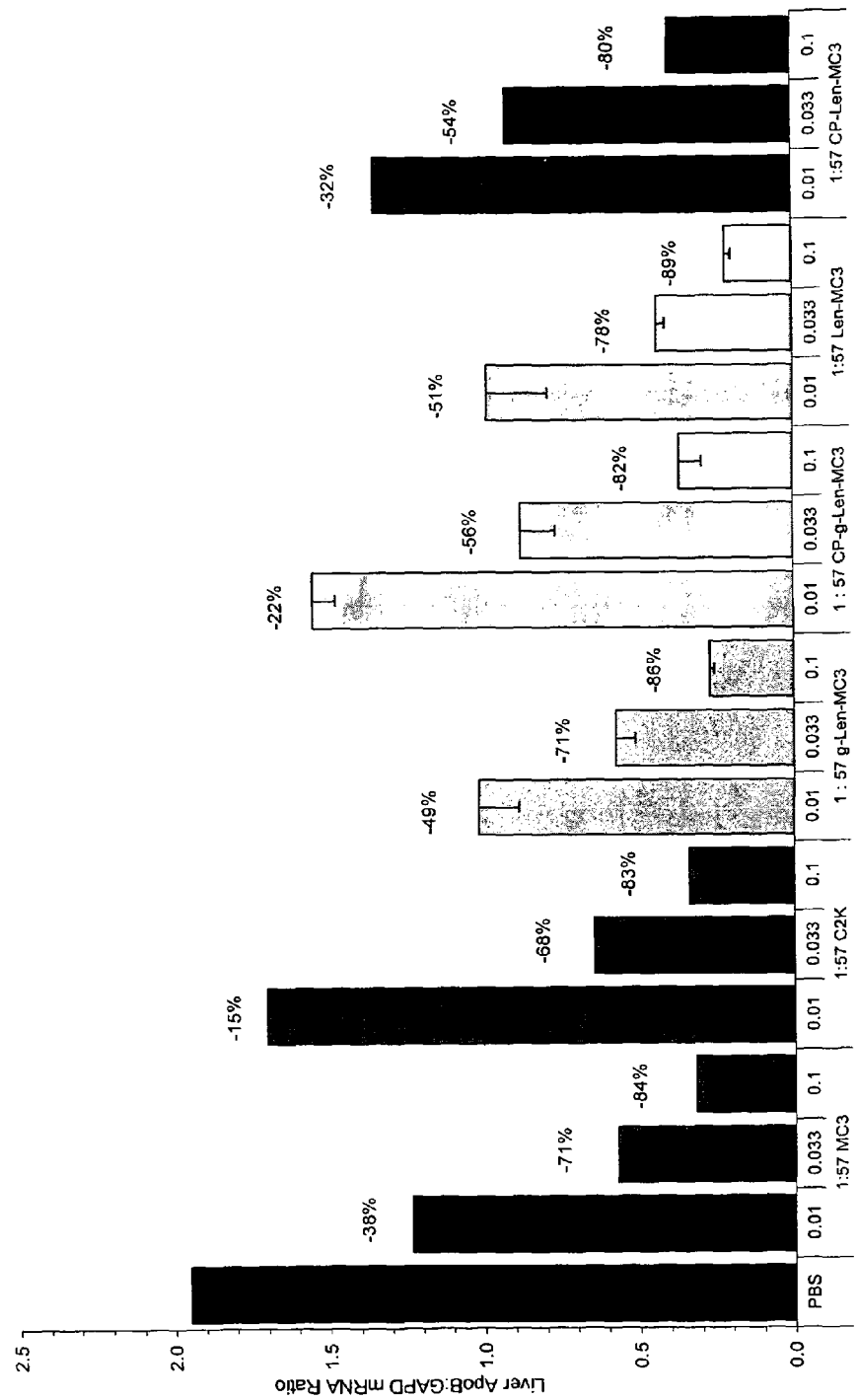
FIG. 1 shows a comparison of the liver ApoB mRNA knockdown activity of exemplary SNALP formulations containing cationic lipids of Formula I.

The present invention is based, in part, on the discovery that the use of certain cationic (amino) lipids in nucleic acid-lipid particles provide advantages when the particles are used for the in vivo delivery of therapeutic nucleic acids, such as interfering RNA (e.g., siRNA), into the liver of a mammal. In particular, it has been unexpectedly found that the nucleic acid-lipid particles of the present invention (i.e., SNALP formulations) containing at least one cationic lipid of Formulas I-III and at least one interfering RNA (e.g., siRNA) as described herein demonstrate increased potency (i.e., increased silencing activity) and/or increased tolerability (e.g., a more favorable toxicity profile) when targeting a gene of interest in the liver, such as APOB, when compared to other nucleic acid-lipid particle compositions previously described.

In particular embodiments, the present invention provides cationic lipids that enable the formulation of compositions for the in vitro and in vivo delivery of interfering RNA, such as siRNA, to the liver that result in increased silencing of the target gene of interest in the liver. It is shown herein that these improved lipid particle compositions are particularly effective in down-regulating (e.g., silencing) the protein levels and/or mRNA levels of target genes in the liver, such as APOB. Furthermore, it is shown herein that the activity of these improved lipid particle compositions is dependent on the presence of the cationic lipids of the invention.

The lipid particles and compositions of the present invention may be used for a variety of purposes, including the delivery of encapsulated interfering RNA, such as siRNA, to liver cells (e.g., hepatocytes), both in vitro and in vivo. Accordingly, the present invention further provides methods of treating metabolic diseases or disorders in a subject in need thereof by contacting the subject with a lipid particle that encapsulates or is associated with a suitable therapeutic agent, wherein the lipid particle comprises one or more of the novel cationic lipids described herein.

In particular, the lipid particles and compositions of the present invention are useful for silencing APOB expression to treat diseases or disorders associated with expression or overexpression of APOB. Such diseases include, e.g., atherosclerosis, angina pectoris, high blood pressure, diabetes, hypothyroidism, and hypercholesterolemia. In view of their enhanced potency, the nucleic acid-lipid particles of the present invention comprising an siRNA sequence that targets APOB can effectively be used to lower serum cholesterol levels.

As described herein, the lipid particles of the present invention have been found to provide more potent silencing when used to deliver interfering RNA molecules, such as siRNA, to the liver, when compared to lipid particle compositions previously described. As such, in addition to being useful for silencing APOB, the lipid particles of the present invention are also use for targeting other genes of interest in the liver. Such genes of interest include, but are not limited to, APOC3, PCSK9, DGAT1, DGAT2, and combinations thereof.

Various exemplary embodiments of the cationic lipids of the present invention, lipid particles and compositions comprising the same, and their use to deliver therapeutic nucleic acids, such as interfering RNA (e.g., siRNA), to modulate gene and protein expression and to treat metabolic diseases and disorders, are described in further detail below.

DEFINITIONS

As used herein, the following terms have the meanings ascribed to them unless specified otherwise.

The term "Apolipoprotein B" or "ApoB" refers to the main apolipoprotein of chylomicrons and low density lipoproteins (LDL). Mutations in APOB are associated with hypercholesterolemia. ApoB occurs in the plasma in 2 main forms: apoB48 and apoB100, which are synthesized in the intestine and liver, respectively, due to an organ-specific stop codon. ApoB48 contains 2,152 residues compared to 4,535 residues in apoB100. Cloning and characterization of APOB is described by, e.g., Glickman et al., *PNAS USA* 83:5296-5300 (1986); Chen et al., *J. Biol. Chem.* 261: 2918-12921 (1986); and Hospattankar et al., *J. Biol. Chem.* 261:9102-9104 (1986). APOB sequences are set forth in, e.g., Genbank Accession Nos. NM_000384 and BC051278. siRNA sequences that target APOB are set forth herein as well as in U.S. Patent Publication Nos. 20060134189 and 20060105976, PCT Publication No. WO 04/091515, Soutschek et al., *Nature* 432:173-178 (2004), and Zimmermann et al., *Nature*, 441: 111-114 (2006).

The term "interfering RNA" or "RNAi" or "interfering RNA sequence" as used herein includes single-stranded RNA (e.g., mature miRNA, ssRNAi oligonucleotides, ssDNAi oligonucleotides), double-stranded RNA (i.e., duplex RNA such as siRNA, Dicer-substrate dsRNA, shRNA, aiRNA, or pre-miRNA), a DNA-RNA hybrid (see, e.g., PCT Publication No. WO 2004/078941), or a DNA-DNA hybrid (see, e.g., PCT Publication No. WO 2004/104199) that is capable of reducing or inhibiting the expression of a target gene or sequence (e.g., by mediating the degradation or inhibiting the translation of mRNAs which are complementary to the interfering RNA sequence) when the interfering RNA is in the same cell as the target gene or sequence. Interfering RNA thus refers to the single-stranded RNA that is complementary to a target mRNA sequence or to the double-stranded RNA formed by two complementary strands or by a single, self-complementary strand. Interfering RNA may have substantial or complete identity to the target gene or sequence, or may comprise a region of mismatch (i.e., a mismatch motif). The sequence of the interfering RNA can correspond to the full-length target gene, or a subsequence thereof. Preferably, the interfering RNA molecules are chemically synthesized. The disclosures of each of the above patent documents are herein incorporated by reference in their entirety for all purposes.

Interfering RNA includes "small-interfering RNA" or "siRNA," e.g., interfering RNA of about 15-60, 15-50, or 15-40 (duplex) nucleotides in length, more typically about 15-30, 15-25, or 19-25 (duplex) nucleotides in length, and is preferably about 20-24, 21-22, or 21-23 (duplex) nucleotides in length (e.g., each complementary sequence of the double-stranded siRNA is 15-60, 15-50, 15-40, 15-30, 15-25, or 19-25 nucleotides in length, preferably about 20-24, 21-22, or 21-23 nucleotides in length, and the double-stranded siRNA is about 15-60, 15-50, 15-40, 15-30, 15-25, or 19-25 base pairs in length, preferably about 18-22, 19-20, or 19-21 base pairs in length). siRNA duplexes may comprise 3' overhangs of about 1 to about 4 nucleotides or about 2 to about 3 nucleotides and 5' phosphate termini. Examples of siRNA include, without limitation, a double-stranded polynucleotide molecule assembled from two separate stranded molecules, wherein one strand is the sense strand and the other is the complementary antisense strand; a double-stranded polynucleotide molecule assembled from a single stranded molecule, where the sense and antisense regions are linked by a nucleic acid-based or non-nucleic acid-based linker; a double-stranded polynucleotide molecule with a hairpin secondary structure having self-complementary sense and antisense regions; and a circular single-stranded polynucleotide molecule with two or more loop structures and a stem having self-complementary sense and antisense regions, where the circular polynucleotide can be processed in vivo or in vitro to generate an active double-stranded siRNA molecule. As used herein, the term "siRNA" includes RNA-RNA duplexes as well as DNA-RNA hybrids (see, e.g., PCT Publication No. WO 2004/078941).

Preferably, siRNA are chemically synthesized. siRNA can also be generated by cleavage of longer dsRNA (e.g., dsRNA greater than about 25 nucleotides in length) with the *E. coli* RNase III or Dicer. These enzymes process the dsRNA into biologically active siRNA (see, e.g., Yang et al., *Proc. Natl. Acad. Sci. USA*, 99:9942-9947 (2002); Calegari et al., *Proc. Natl. Acad. Sci. USA*, 99:14236 (2002); Byrom et al., *Ambion TechNotes*, 10(1):4-6 (2003); Kawasaki et al., *Nucleic Acids Res.*, 31:981-987 (2003); Knight et al., *Science*, 293:2269-2271 (2001); and Robertson et al., *J. Biol. Chem.*, 243:82 (1968)). Preferably, dsRNA are at least 50 nucleotides to about 100, 200, 300, 400, or 500 nucleotides in length. A dsRNA may be as long as 1000, 1500, 2000, 5000 nucleotides in length, or longer. The dsRNA can encode for an entire gene transcript or a partial gene transcript. In certain instances, siRNA may be encoded by a plasmid (e.g., transcribed as sequences that automatically fold into duplexes with hairpin loops).

As used herein, the term "mismatch motif" or "mismatch region" refers to a portion of an interfering RNA (e.g., siRNA) sequence that does not have 100% complementarity to its target sequence. An interfering RNA may have at least one, two, three, four, five, six, or more mismatch regions. The mismatch regions may be contiguous or may be separated by 1, 2, 3, 4, 5, 6, 7, 8, 9, 10, 11, 12, or more nucleotides. The mismatch motifs or regions may comprise a single nucleotide or may comprise two, three, four, five, or more nucleotides.

The phrase "inhibiting expression of a target gene" refers to the ability of a nucleic acid such as an interfering RNA (e.g., siRNA) to silence, reduce, or inhibit the expression of a target gene (e.g., APOB, APOC3, PCSK9, DGAT1, and/or DGAT2). To examine the extent of gene silencing, a test sample (e.g., a sample of cells in culture expressing the target gene) or a test mammal (e.g., a mammal such as a human or an animal model such as a rodent (e.g., mouse) or a non-human primate (e.g., monkey) model) is contacted with a nucleic acid such as an interfering RNA (e.g., siRNA) that silences, reduces, or inhibits expression of the target gene. Expression of the target gene in the test sample or test animal is compared to expression of the target gene in a control sample (e.g., a sample of cells in culture expressing the target gene) or a control mammal (e.g., a mammal such as a human or an animal model such as a rodent (e.g., mouse) or non-human primate (e.g., monkey) model) that is not contacted with or administered the nucleic acid (e.g., interfering RNA). The expression of the target gene in a control sample or a control mammal may be assigned a value of 100%. In particular embodiments, silencing, inhibition, or reduction of expression of a target gene is achieved when the level of target gene expression in the test sample or the test mammal relative to the level of target gene expression in the control sample or the control mammal is about 95%, 90%, 85%, 80%, 75%, 70%, 65%, 60%, 55%, 50%, 45%, 40%, 35%, 30%, 25%, 20%, 15%, 10%, 5%, or 0%. In other words, the nucleic acids (e.g., interfering RNAs) are capable of silencing, reducing, or inhibiting the expression of a target gene (e.g., APOB, APOC3, PCSK9, DGAT1, and/or DGAT2) by at least about 5%, 10%, 15%, 20%, 25%, 30%, 35%, 40%, 45%, 50%, 55%, 60%, 65%, 70%, 75%, 80%, 85%, 90%, 95%, or 100% in a test sample or a test mammal relative to the level of target gene expression in a control sample or a control mammal not contacted with or administered the nucleic acid (e.g., interfering RNA). Suitable assays for determining the level of target gene expression include, without limitation, examination of protein or mRNA levels using techniques known to those of skill in the art, such as, e.g., dot blots, Northern blots, in situ hybridization, ELISA, immunoprecipitation, enzyme function, as well as phenotypic assays known to those of skill in the art.

An "effective amount" or "therapeutically effective amount" of a therapeutic nucleic acid (e.g., interfering RNA such as an siRNA) is an amount sufficient to produce the desired effect, e.g., an inhibition of expression of a target sequence in comparison to the normal expression level detected in the absence of the nucleic acid (e.g., interfering RNA). Inhibition of expression of a target gene or target sequence is achieved when the value obtained with a nucleic acid such as an interfering RNA (e.g., siRNA) relative to the control is about 95%, 90%, 85%, 80%, 75%, 70%, 65%, 60%, 55%, 50%, 45%, 40%, 35%, 30%, 25%, 20%, 15%, 10%, 5%, or 0%. Suitable assays for measuring expression of a target gene or target sequence include, e.g., examination of protein or RNA levels using techniques known to those of skill in the art such as dot blots, northern blots, in situ hybridization, ELISA, immunoprecipitation, enzyme function, as well as phenotypic assays known to those of skill in the art.

By "decrease," "decreasing," "reduce," or "reducing" of an immune response by a nucleic acid such as an interfering RNA (e.g., siRNA) is intended to mean a detectable decrease of an immune response to a given nucleic acid (e.g., a modified interfering RNA). In some instances, the amount of decrease of an immune response by a nucleic acid such as a modified interfering RNA may be determined relative to the level of an immune response in the presence of an unmodified interfering RNA. As a non-limiting example, a detectable decrease can be about 5%, 10%, 15%, 20%, 25%, 30%, 35%, 40%, 45%, 50%, 55%, 60%, 65%, 70%, 75%, 80%, 85%, 90%, 95%, 100%, or more lower than the immune response detected in the presence of the unmodified interfering RNA. A decrease in the immune response to a nucleic acid (e.g., interfering RNA) is typically measured by a decrease in cytokine production (e.g., IFN-γ, IFNα, TNFα, IL-6, IL-8, or IL-12) by a responder cell in vitro or a decrease in cytokine production in the sera of a mammalian subject after administration of the nucleic acid (e.g., interfering RNA).

As used herein, the term "responder cell" refers to a cell, preferably a mammalian cell, that produces a detectable immune response when contacted with an immunostimulatory nucleic acid such as an unmodified interfering RNA (e.g., unmodified siRNA). Exemplary responder cells include, without limitation, dendritic cells, macrophages, peripheral blood mononuclear cells (PBMCs), splenocytes, and the like. Detectable immune responses include, e.g., production of cytokines or growth factors such as TNF-α, IFN-α, IFN-β, IFN-γ, IL-1, IL-2, IL-3, IL-4, IL-5, IL-6, IL-8, IL-10, IL-12, IL-13, TGF, and combinations thereof. Detectable immune responses also include, e.g., induction of interferon-induced protein with tetratricopeptide repeats 1 (IFIT1) mRNA.

The term "nucleic acid" as used herein refers to a polymer containing at least two deoxyribonucleotides or ribonucleotides in either single- or double-stranded form and includes DNA, RNA, and hybrids thereof. DNA may be in the form of, e.g., antisense molecules, plasmid DNA, DNA-DNA duplexes, pre-condensed DNA, PCR products, vectors (P1, PAC, BAC, YAC, artificial chromosomes), expression cassettes, chimeric sequences, chromosomal DNA, or derivatives and combinations of these groups. RNA may be in the form of small interfering RNA (siRNA), Dicer-substrate dsRNA, small hairpin RNA (shRNA), asymmetrical interfering RNA (aiRNA), microRNA (miRNA), mRNA, tRNA, rRNA, tRNA, viral RNA (vRNA), and combinations thereof. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides, and peptide-nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.*, 19:5081 (1991); Ohtsuka et al., *J. Biol. Chem.*, 260:2605-2608 (1985); Rossolini et al., *Mol. Cell. Probes*, 8:91-98 (1994)). "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides.

The term "gene" refers to a nucleic acid (e.g., DNA or RNA) sequence that comprises partial length or entire length coding sequences necessary for the production of a polypeptide or precursor polypeptide (e.g., ApoB).

"Gene product," as used herein, refers to a product of a gene such as an RNA transcript or a polypeptide.

The term "lipid" refers to a group of organic compounds that include, but are not limited to, esters of fatty acids and are characterized by being insoluble in water, but soluble in many organic solvents. They are usually divided into at least three classes: (1) "simple lipids," which include fats and oils as well as waxes; (2) "compound lipids," which include phospholipids and glycolipids; and (3) "derived lipids" such as steroids.

The term "lipid particle" includes a lipid formulation that can be used to deliver an active agent or therapeutic agent, such as a nucleic acid (e.g., interfering RNA) to a target site of interest (e.g., cell, tissue, organ, and the like). In preferred embodiments, the lipid particle of the invention is a nucleic acid-lipid particle, which is typically formed from a cationic lipid, a non-cationic lipid, and optionally a conjugated lipid that prevents aggregation of the particle. In other preferred embodiments, the active agent or therapeutic agent, such as a nucleic acid (e.g., interfering RNA), may be encapsulated in the lipid portion of the particle, thereby protecting it from enzymatic degradation.

As used herein, the term "SNALP" refers to a stable nucleic acid-lipid particle. A SNALP represents a particle made from lipids (e.g., a cationic lipid, a non-cationic lipid, and optionally a conjugated lipid that prevents aggregation of the particle), wherein the nucleic acid (e.g., an interfering RNA) is fully encapsulated within the lipid. In certain instances, SNALP are extremely useful for systemic applications, as they can exhibit extended circulation lifetimes following intravenous (i.v.) injection, they can accumulate at distal sites (e.g., sites physically separated from the administration site), and they can mediate silencing of target gene expression at these distal sites. The nucleic acid may be complexed with a condensing agent and encapsulated within a SNALP as set forth in PCT Publication No. WO 00/03683, the disclosure of which is herein incorporated by reference in its entirety for all purposes.

The lipid particles of the invention (e.g., SNALP) typically have a mean diameter of from about 30 nm to about 150 nm, from about 40 nm to about 150 nm, from about 50 mm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm, and are substantially non-toxic. In addition, nucleic acids, when present in the lipid particles of the present invention, are resistant in aqueous solution to degradation with a nuclease. Nucleic acid-lipid particles and their method of preparation are disclosed in, e.g., U.S. Patent Publication Nos. 20040142025 and 20070042031, the disclosures of which are herein incorporated by reference in their entirety for all purposes.

As used herein, "lipid encapsulated" can refer to a lipid particle that provides an active agent or therapeutic agent, such as a nucleic acid (e.g., an interfering RNA such as an siRNA that targets APOB), with full encapsulation, partial encapsulation, or both. In a preferred embodiment, the nucleic acid (e.g., interfering RNA) is fully encapsulated in the lipid particle (e.g., to form a SNALP or other nucleic acid-lipid particle).

The term "lipid conjugate" refers to a conjugated lipid that inhibits aggregation of lipid particles. Such lipid conjugates include, but are not limited to, PEG-lipid conjugates such as, e.g., PEG coupled to dialkyloxypropyls (e.g., PEG-DAA conjugates), PEG coupled to diacylglycerols (e.g., PEG-DAG conjugates), PEG coupled to cholesterol, PEG coupled to phosphatidylethanolamines, and PEG conjugated to ceramides (see, e.g., U.S. Pat. No. 5,885,613), cationic PEG lipids, polyoxazoline (POZ)-lipid conjugates (e.g., POZ-DAA conjugates; see, e.g., U.S. application Ser. No. 13/006,277, filed Jan. 13, 2011), polyamide oligomers (e.g., ATTA-lipid conjugates), and mixtures thereof. Additional examples of POZ-lipid conjugates are described in PCT Publication No. WO 2010/006282. PEG or POZ can be conjugated directly to the lipid or may be linked to the lipid via a linker moiety. Any linker moiety suitable for coupling the PEG or the POZ to a lipid can be used including, e.g., non-ester containing linker moieties and ester-containing linker moieties. In certain preferred embodiments, non-ester containing linker moieties, such as amides or carbamates, are used. The disclosures of each of the above patent documents are herein incorporated by reference in their entirety for all purposes.

The term "amphipathic lipid" refers, in part, to any suitable material wherein the hydrophobic portion of the lipid material orients into a hydrophobic phase, while the hydrophilic portion orients toward the aqueous phase. Hydrophilic characteristics derive from the presence of polar or charged groups such as carbohydrates, phosphate, carboxylic, sulfato, amino, sulfhydryl, nitro, hydroxyl, and other like groups. Hydrophobicity can be conferred by the inclusion of apolar groups that include, but are not limited to, long-chain saturated and unsaturated aliphatic hydrocarbon groups and such groups substituted by one or more aromatic, cycloaliphatic, or heterocyclic group(s). Examples of amphipathic compounds include, but are not limited to, phospholipids, aminolipids, and sphingolipids.

Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, and dilinoleoylphosphatidylcholine. Other compounds lacking in phosphorus, such as sphingolipid, glycosphingolipid families, diacylglycerols, and β-acyloxyacids, are also within the group designated as amphipathic lipids. Additionally, the amphipathic lipids described above can be mixed with other lipids including triglycerides and sterols.

The term "neutral lipid" refers to any of a number of lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides, and diacylglycerols.

The term "non-cationic lipid" refers to any amphipathic lipid as well as any other neutral lipid or anionic lipid.

The term "anionic lipid" refers to any lipid that is negatively charged at physiological pH. These lipids include, but are not limited to, phosphatidylglycerols, cardiolipins, diacyiphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

The term "hydrophobic lipid" refers to compounds having apolar groups that include, but are not limited to, long-chain saturated and unsaturated aliphatic hydrocarbon groups and such groups optionally substituted by one or more aromatic, cycloaliphatic, or heterocyclic group(s). Suitable examples include, but are not limited to, diacylglycerol, dialkylglycerol, N—N-dialkyamino, 1,2-diacyloxy-3-aminopropane, and 1,2-dialkyl-3-aminopropane.

The term "fusogenic" refers to the ability of a lipid particle, such as a SNALP, to fuse with the membranes of a cell. The membranes can be either the plasma membrane or membranes surrounding organelles, e.g., endosome, nucleus, etc.

As used herein, the term "aqueous solution" refers to a composition comprising in whole, or in part, water.

As used herein, the term "organic lipid solution" refers to a composition comprising in whole, or in part, an organic solvent having a lipid.

"Distal site," as used herein, refers to a physically separated site, which is not limited to an adjacent capillary bed, but includes sites broadly distributed throughout an organism.

"Serum-stable" in relation to nucleic acid-lipid particles such as SNALP means that the particle is not significantly degraded after exposure to a serum or nuclease assay that would significantly degrade free DNA or RNA. Suitable assays include, for example, a standard serum assay, a DNAse assay, or an RNAse assay.

"Systemic delivery," as used herein, refers to delivery of lipid particles that leads to a broad biodistribution of an active agent such as an interfering RNA (e.g., siRNA) within an organism. Some techniques of administration can lead to the systemic delivery of certain agents, but not others. Systemic delivery means that a useful, preferably therapeutic, amount of an agent is exposed to most parts of the body. To obtain broad biodistribution generally requires a blood lifetime such that the agent is not rapidly degraded or cleared (such as by first pass organs (liver, lung, etc.) or by rapid, nonspecific cell binding) before reaching a disease site distal to the site of administration. Systemic delivery of lipid particles can be by any means known in the art including, for example, intravenous, subcutaneous, and intraperitoneal. In a preferred embodiment, systemic delivery of lipid particles is by intravenous delivery.

"Local delivery," as used herein, refers to delivery of an active agent such as an interfering RNA (e.g., siRNA) directly to a target site within an organism. For example, an agent can be locally delivered by direct injection into a disease site or other target site such as a site of inflammation or a target organ such as the liver, heart, pancreas, kidney, and the like.

The term "mammal" refers to any mammalian species such as a human, mouse, rat, dog, cat, hamster, guinea pig, rabbit, livestock, and the like.

DESCRIPTION OF THE EMBODIMENTS

The present invention provides novel, serum-stable lipid particles comprising one or more therapeutic nucleic acids, methods of making the lipid particles, and methods of delivering and/or administering the lipid particles (e.g., for the treatment of a disease or disorder).

In certain embodiments, the therapeutic nucleic acid comprises an interfering RNA molecule such as, e.g., an siRNA, Dicer-substrate dsRNA, shRNA, aiRNA, miRNA, or mixtures thereof. In preferred embodiments, the interfering RNA targets a gene of interest in the liver. Examples of target genes of interest that are in the liver include, but are not limited to, APOB, APOC3, PCSK9, DGAT1, DGAT2, and combinations thereof.

In one aspect, the present invention provides a nucleic acid-lipid particle (e.g., SNALP) comprising:

(a) an interfering RNA that silences Apolipoprotein B (APOB) expression and/or the expression of another liver target gene such as APOC3, PCSK9, DGAT1, and/or DGAT2;

(b) a cationic lipid of Formula I having the following structure:

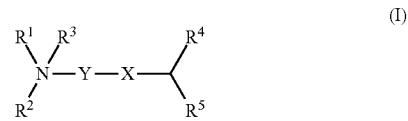

(I)

or salts thereof, wherein:

$R^1$ and $R^2$ are either the same or different and are independently hydrogen (H) or an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring;

$R^3$ is either absent or is hydrogen (H) or a $C_1$-$C_6$ alkyl to provide a quaternary amine;

$R^4$ and $R^5$ are either the same or different and are independently an optionally substituted $C_{10}$-$C_{24}$ alkyl, $C_{10}$-$C_{24}$ alkenyl, $C_{10}$-$C_{24}$ alkynyl, or $C_{10}$-$C_{24}$ acyl;

X is O, S, N($R^6$), C(O), C(O)O, OC(O), C(O)N($R^6$), N($R^6$)C(O), OC(O)N($R^6$), N($R^6$)C(O)O, C(O)S, C(S)O, S(O), S(O)(O), C(S), or an optionally substituted heterocyclic ring, wherein $R^6$ is hydrogen (H) or an optionally substituted $C_1$-$C_{10}$ alkyl, $C_2$-$C_{10}$ alkenyl, or $C_2$-$C_{10}$ alkynyl; and Y is either absent or is an optionally substituted $C_1$-$C_6$ alkyl, $C_2$-$C_6$ alkenyl, or $C_2$-$C_6$ alkynyl; and (c) a non-cationic lipid.

In one embodiment, $R^1$ and $R^2$ are independently selected from the group consisting of a methyl group and an ethyl group, i.e., $R^1$ and $R^2$ are both methyl groups, $R^1$ and $R^2$ are both ethyl groups, or $R^1$ and $R^2$ are a combination of one methyl group and one ethyl group. In another embodiment, $R^1$ and $R^2$ are joined to form an optionally substituted heterocyclic ring having from 2 to 5 carbon atoms (e.g., 2, 3, 4, or 5 carbon atoms, or from 2-5, 2-4, 2-3, 3-5, 3-4, or 4-5 carbon atoms) and from 1 to 3 heteroatoms (e.g., 1, 2, or 3 heteroatoms, or from 1-3, 1-2, or 2-3 heteroatoms) selected from the group consisting of nitrogen (N), oxygen (O), sulfur (S), and combinations thereof. In certain instances, $R^1$ and $R^2$ are joined to form an optionally substituted diazole (e.g., an optionally substituted imidazole) or an optionally substituted triazole.

In yet another embodiment, X is O, C(O)O, C(O)N($R^6$), N($R^6$)C(O)O, or C(O)S. In certain instances, $R^6$ is hydrogen (H), an optionally substituted methyl group, an optionally substituted ethyl group, or an optionally substituted $C_3$-$C_{10}$ alkyl, alkenyl, or alkynyl group (e.g., an optionally substituted $C_3$, $C_4$, $C_5$, $C_6$, $C_7$, $C_8$, $C_9$, or $C_{10}$ alkyl, alkenyl, or alkynyl group). In a further embodiment, X is an optionally substituted heterocyclic ring having from 2 to 5 carbon atoms (e.g., 2, 3, 4, or 5 carbon atoms, or from 2-5, 2-4, 2-3, 3-5, 3-4, or 4-5 carbon atoms) and from 1 to 3 heteroatoms (e.g., 1, 2, or 3 heteroatoms, or from 1-3, 1-2, or 2-3 heteroatoms) selected from the group consisting of nitrogen (N), oxygen (O), sulfur (S), and combinations thereof. In certain instances, X is an optionally substituted diazole (e.g., an optionally substituted imidazole) or an optionally substituted triazole. In other embodiments, Y is $(CH_2)_n$ and n is 0, 1, 2, 3, 4, 5, or 6. In particular embodiments, n is 1, 2, 3, or 4 (e.g., n is 1-4, 1-3, 1-2, 2-4, 2-3, or 3-4).

In one embodiment, at least one of $R^4$ and $R^5$ (e.g., both $R^4$ and $R^5$), which can be independently optionally substituted, comprises at least one site of unsaturation. In particular embodiments, $R^4$ and $R^5$ are independently selected from the group consisting of a dodecenyl moiety, a tetradecenyl (e.g., myristoleyl) moiety, a hexadecenyl (e.g., palmitoleyl) moiety, an octadecenyl (e.g., oleyl) moiety, and an icosenyl moiety. In preferred embodiments, one of $R^4$ or $R^5$ is an oleyl moiety or $R^4$ and $R^5$ are both oleyl moieties. In some embodiments, one of $R^4$ or $R^5$ comprises one site of unsaturation and the other side-chain comprises at least two or three sites of unsaturation as described herein.

In another embodiment, at least one of $R^4$ and $R^5$ (e.g., both $R^4$ and $R^5$), which can be independently optionally substituted, comprises at least two sites of unsaturation. In particular embodiments, $R^4$ and $R^5$ are independently selected from the group consisting of a dodecadienyl moiety, a tetradecadienyl moiety, a hexadecadienyl moiety, an octadecadienyl moiety, and an icosadienyl moiety. In certain instances, the octadecadienyl moiety is a linoleyl moiety. In preferred embodiments, one of $R^4$ or $R^5$ is a linoleyl moiety or $R^4$ and $R^5$ are both linoleyl moieties. In some embodiments, one of $R^4$ or $R^5$ comprises two sites of unsaturation and the other side-chain comprises at least three sites of unsaturation as described herein. In other embodiments, $R^1$ and $R^2$ are not both methyl groups when X is C(O)O, Y is $(CH_2)_2$ or $(CH_2)_3$, and $R^4$ and $R^5$ are both linoleyl moieties.

In yet another embodiment, at least one of $R^4$ and $R^5$ (e.g., both $R^4$ and $R^5$), which can be independently optionally substituted, comprises at least three sites of unsaturation. In particular embodiments, $R^4$ and $R^5$ are independently selected from the group consisting of a dodecatrienyl moiety, a tetradecatrienyl moiety, a hexadecatrienyl moiety, an octadecatrienyl moiety, and an icosatrienyl moiety. In certain instances, the octadecatrienyl moiety is a linolenyl moiety or a γ-linolenyl moiety. In preferred embodiments, one of $R^4$ or $R^5$ is a linolenyl or γ-linolenyl moiety, or $R^4$ and $R^5$ are both linolenyl or γ-linolenyl moieties. In some embodiments, one of $R^4$ or $R^5$ comprises three sites of unsaturation and the other side-chain comprises at least four sites of unsaturation as described herein.

In a further embodiment, at least one of $R^4$ and $R^5$ (e.g., both $R^4$ and $R^5$) comprises a substituted $C_{12}$-$C_{24}$ alkyl. In particular embodiments, the substituted $C_{12}$-$C_{24}$ alkyl comprises a $C_{12}$-$C_{24}$ alkyl having at least 1-6 $C_1$-$C_6$ alkyl substituents. In certain instances, one of $R^4$ or $R^5$ is a phytanyl moiety or $R^4$ and $R^5$ are both phytanyl moieties. In some embodiments, one of $R^4$ or $R^5$ comprises a substituted $C_{12}$-$C_{24}$ alkyl and the other side-chain comprises at least one, two, or three sites of unsaturation as described herein.

In still yet another embodiment, at least one of $R^4$ and $R^5$ comprises at least one, two, three, or more optionally substituted cyclic alkyl groups. In particular embodiments, both $R^4$ and $R^5$ independently comprise at least one, two, three, or more optionally substituted cyclic alkyl groups. In some instances, both $R^4$ and $R^5$ comprise the same number of (e.g., 1, 2, 3, 4, 5, 6, or more) optionally substituted cyclic alkyl groups. In other instances, $R^4$ and $R^5$ comprise a different number of optionally substituted cyclic alkyl groups. In one embodiment, each of the optionally substituted cyclic alkyl groups in $R^4$ and/or $R^5$ comprises an independently selected optionally substituted saturated cyclic alkyl group or an optionally substituted unsaturated cyclic alkyl group. In certain instances, at least one, two, three, or more of the optionally substituted cyclic alkyl groups present in one or both of $R^4$ and $R^5$ independently comprises an optionally substituted $C_{3-8}$ cycloalkyl group such as, e.g., a cyclopropyl group, an optionally substituted $C_{3-8}$ cycloalkenyl group, and combinations thereof. In some embodiments, one of $R^4$ or $R^5$ comprises at least one, two, three, or more optionally substituted cyclic alkyl groups and the other side-chain comprises an optionally substituted $C_{10}$-$C_{24}$ alkyl, $C_{10}$-$C_{24}$ alkenyl, $C_{10}$-$C_{24}$ alkynyl, or $C_{10}$-$C_{24}$ acyl group (e.g., a side-chain comprising at least one, two, or three sites of unsaturation). In some instances, $R^4$ and $R^5$ both comprise the same type or types of optionally substituted cyclic alkyl groups. In other instances, $R^4$ and $R^5$ comprise different types of optionally substituted cyclic alkyl groups.

In particular embodiments, $R^4$ and $R^5$ are both $C_{12}$-$C_{20}$ alkyl groups (e.g., $C_{18}$ alkyl groups) having at least one, two, three, or more optionally substituted cyclic alkyl groups. In preferred embodiments, $R^4$ and $R^5$ are both $C_{12}$-$C_{20}$ (e.g., $C_{18}$) alkyl groups having the same number of (e.g., at least one, two, three, or more) optionally substituted cyclic alkyl groups. In certain embodiments, the at least one, two, three, or more optionally substituted cyclic alkyl groups present in both $R^4$ and $R^5$ independently comprises an optionally substituted saturated cyclic alkyl group (e.g., a $C_{3-8}$ cycloalkyl group such as a cyclopropyl group) or an optionally substituted unsaturated cyclic alkyl group (e.g., a $C_{3-8}$ cycloalkenyl group).

In some embodiments, at least one, two, three, or more optionally substituted cyclic alkyl groups are present on each of $R^4$ and/or $R^5$ in combination with at least one, two, three, or more sites of unsaturation and/or branched alkyl and/or acyl groups. For example, $R^4$ may comprise one, two, or three $C_{3-8}$ cycloalkyl groups such as cyclopropyl groups and one, two, or three sites of unsaturation, while $R^5$ may comprise the same or different number and type of substituents.

In some embodiments, each of the at least one, two, or three sites of unsaturation present in one or both $R^4$ and $R^5$ correspond to a cis double bond, a trans double bond, or combinations thereof at specific positions in one or both $R^4$ and $R^5$. In certain instances, one or both $R^4$ and $R^5$ are $C_{18}$ alkyl groups containing any combination of double bonds in the cis and/or trans configuration at one or more positions in the side-chain (e.g., cis and/or trans double bonds at position 9, at positions 6 and 9, at positions 3, 6, and 9, at positions 6, 9, and 12, or at positions 7 and 9 of a $C_{18}$ alkyl group). One skilled in the art will understand that the at least one, two, or three sites of unsaturation present in one or both $R^4$ and $R^5$ can also be characterized by either the "E" chemical notation and/or the "Z" chemical notation.

In particular embodiments, the cationic lipid of Formula I is selected from the group consisting of Compound 1, 4, 5, 8, 9, 10, 11, 12, 13, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 63, 64, 65, or combinations thereof as described herein.

In another aspect, the present invention provides a nucleic acid-lipid particle (e.g., SNALP) comprising:

(a) an interfering RNA that silences Apolipoprotein B (APOB) expression and/or the expression of another liver target gene such as APOC3, PCSK9, DGAT1, and/or DGAT2;

(b) a cationic lipid of Formula II having the following structure:

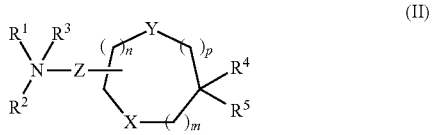

(II)

or salts thereof, wherein:
$R^1$ and $R^2$ are either the same or different and are independently an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring;

$R^3$ is either absent or, if present, is hydrogen (H) or a $C_1$-$C_6$ alkyl to provide a quaternary amine;

$R^4$ and $R^5$ are either the same or different and are independently an optionally substituted $C_{10}$-$C_{24}$ alkyl, $C_{10}$-$C_{24}$ alkenyl, $C_{10}$-$C_{24}$ alkynyl, or $C_{10}$-$C_{24}$ acyl, wherein at least one of $R^4$ and $R^5$ comprises at least one optionally substituted cyclic alkyl group;

m, n, and p are either the same or different and are independently either 0, 1, or 2, with the proviso that m, n, and p are not simultaneously 0;

X and Y are either the same or different and are independently O, S, N($R^6$), C(O), C(O)O, OC(O), C(O)N($R^6$), N($R^6$)C(O), OC(O)N($R^6$), N($R^6$)C(O)O, C(O)S, C(S) O, S(O), S(O)(O), or C(S), wherein $R^6$ is hydrogen (H) or an optionally substituted $C_1$-$C_{10}$ alkyl, $C_2$-$C_{10}$ alkenyl, or $C_2$-$C_{10}$ alkynyl; and Z is either absent or, if present, is an optionally substituted $C_1$-$C_6$ alkyl, $C_2$-$C_6$ alkenyl, or $C_2$-$C_6$ alkynyl; and (c) a non-cationic lipid.

In one embodiment, $R^1$ and $R^2$ are independently selected from the group consisting of a methyl group and an ethyl group, i.e., $R^1$ and $R^2$ are both methyl groups, $R^1$ and $R^2$ are both ethyl groups, or $R^1$ and $R^2$ are a combination of one methyl group and one ethyl group. In another embodiment, $R^1$ and $R^2$ are joined to form an optionally substituted heterocyclic ring having from 2 to 5 carbon atoms (e.g., 2, 3, 4, or 5 carbon atoms, or from 2-5, 2-4, 2-3, 3-5, 3-4, or 4-5 carbon atoms) and from 1 to 3 heteroatoms (e.g., 1, 2, or 3 heteroatoms, or from 1-3, 1-2, or 2-3 heteroatoms) selected from the group consisting of nitrogen (N), oxygen (O), sulfur (S), and combinations thereof. In certain instances, $R^1$ and $R^2$ are joined to form an optionally substituted diazole (e.g., an optionally substituted imidazole) or an optionally substituted triazole.

In yet another embodiment, X and Y are either the same or different and are independently O, C(O)O, C(O)N($R^6$), N($R^6$) C(O)O, or C(O)S. In certain instances, $R^6$ is hydrogen (H), an optionally substituted methyl group, an optionally substituted ethyl group, or an optionally substituted $C_3$-$C_{10}$ alkyl, alkenyl, or alkynyl group (e.g., an optionally substituted $C_3$, $C_4$, $C_5$, $C_6$, $C_7$, $C_8$, $C_9$, or $C_{10}$ alkyl, alkenyl, or alkynyl group). In preferred embodiments, X and Y are both O. In other embodiments, Z is $(CH_2)_q$ and q is 0, 1, 2, 3, 4, 5, or 6. In particular embodiments, q is 1, 2, 3, or 4 (e.g., q is 1-4, 1-3, 1-2, 2-4, 2-3, or 3-4).

In certain embodiments, at least one of $R^4$ and $R^5$ comprises at least one, two, three, or more optionally substituted cyclic alkyl groups. In particular embodiments, both $R^4$ and $R^5$ independently comprise at least one, two, three, or more optionally substituted cyclic alkyl groups. In some instances, both $R^4$ and $R^5$ comprise the same number of (e.g., 1, 2, 3, 4, 5, 6, or more) optionally substituted cyclic alkyl groups. In other instances, $R^4$ and $R^5$ comprise a different number of optionally substituted cyclic alkyl groups. In one embodiment, each of the optionally substituted cyclic alkyl groups in $R^4$ and/or $R^5$ comprises an independently selected optionally substituted saturated cyclic alkyl group or an optionally substituted unsaturated cyclic alkyl group. In certain instances, at least one, two, three, or more of the optionally substituted cyclic alkyl groups present in one or both of $R^4$ and $R^5$ independently comprises an optionally substituted $C_{3-8}$ cycloalkyl group such as, e.g., a cyclopropyl group, an optionally substituted $C_{3-8}$ cycloalkenyl group, and combinations thereof. In some embodiments, one of $R^4$ or $R^5$ comprises at least one, two, three, or more optionally substituted cyclic alkyl groups and the other side-chain comprises an optionally substituted $C_{10}$-$C_{24}$ alkyl, $C_{10}$-$C_{24}$ alkenyl, $C_{10}$-$C_{24}$ alkynyl, or $C_{10}$-$C_{24}$ acyl group (e.g., a side-chain comprising at least one, two, or three sites of unsaturation). In some instances, $R^4$ and $R^5$ both comprise the same type or types of optionally substituted cyclic alkyl groups. In other instances, $R^4$ and $R^5$ comprise different types of optionally substituted cyclic alkyl groups.

In particular embodiments, $R^4$ and $R^5$ are both $C_{12}$-$C_{20}$ alkyl groups (e.g., $C_{18}$ alkyl groups) having at least one, two, three, or more optionally substituted cyclic alkyl groups. In preferred embodiments, $R^4$ and $R^5$ are both $C_{12}$-$C_{20}$ (e.g., $C_{18}$) alkyl groups having the same number of (e.g., at least one, two, three, or more) optionally substituted cyclic alkyl groups. In certain embodiments, the at least one, two, three, or more optionally substituted cyclic alkyl groups present in both $R^4$ and $R^5$ independently comprises an optionally substituted saturated cyclic alkyl group (e.g., a $C_{3-8}$ cycloalkyl group such as a cyclopropyl group) or an optionally substituted unsaturated cyclic alkyl group (e.g., a $C_{3-8}$ cycloalkenyl group).

In some embodiments, at least one, two, three, or more optionally substituted cyclic alkyl groups are present on each of $R^4$ and/or $R^5$ in combination with at least one, two, three, or more sites of unsaturation and/or branched alkyl and/or acyl groups. For example, $R^4$ may comprise one, two, or three $C_{3-8}$ cycloalkyl groups such as cyclopropyl groups and one, two, or three sites of unsaturation, while $R^5$ may comprise the same or different number and type of substituents.

In particular embodiments, the cationic lipid of Formula II is selected from the group consisting of Compound 46, 51, 56, or combinations thereof as described herein.

In yet another aspect, the present invention provides a nucleic acid-lipid particle (e.g., SNALP) comprising:

(a) an interfering RNA that silences Apolipoprotein B (APOB) expression and/or the expression of another liver target gene such as APOC3, PCSK9, DGAT1, and/or DGAT2;

(b) a cationic lipid of Formula III having the following structure:

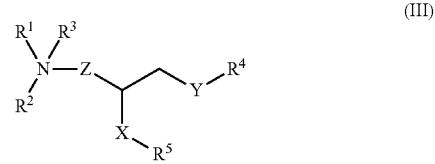

(III)

or salts thereof, wherein:
- $R^1$ and $R^2$ are either the same or different and are independently hydrogen (H) or an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring;
- $R^3$ is either absent or, if present, is hydrogen (H) or a $C_1$-$C_6$ alkyl to provide a quaternary amine;
- $R^4$ and $R^5$ are either the same or different and are independently an optionally substituted $C_{10}$-$C_{24}$ alkyl, $C_{10}$-$C_{24}$ alkenyl, $C_{10}$-$C_{24}$ alkynyl, or $C_{10}$-$C_{24}$ acyl, wherein at least one of $R^4$ and $R^5$ comprises at least one optionally substituted cyclic alkyl group;
- X and Y are either the same or different and are independently O, S, N($R^6$), C(O), C(O)O, OC(O), C(O)N($R^6$), N($R^6$)C(O), OC(O)N($R^6$), N($R^6$)C(O)O, C(O)S, C(S) O, S(O), S(O)(O), C(S), or an optionally substituted heterocyclic ring, wherein $R^6$ is hydrogen (H) or an optionally substituted $C_1$-$C_{10}$ alkyl, $C_2$-$C_{10}$ alkenyl, or $C_2$-$C_{10}$ alkynyl; and
- Z is either absent or, if present, is an optionally substituted $C_1$-$C_6$ alkyl, $C_2$-$C_6$ alkenyl, or $C_2$-$C_6$ alkynyl; and
- (c) a non-cationic lipid.

In one embodiment, $R^1$ and $R^2$ are independently selected from the group consisting of a methyl group and an ethyl group, i.e., $R^1$ and $R^2$ are both methyl groups, $R^1$ and $R^2$ are both ethyl groups, or $R^1$ and $R^2$ are a combination of one methyl group and one ethyl group. In another embodiment, $R^1$ and $R^2$ are joined to form an optionally substituted heterocyclic ring having from 2 to 5 carbon atoms (e.g., 2, 3, 4, or 5 carbon atoms, or from 2-5, 2-4, 2-3, 3-5, 3-4, or 4-5 carbon atoms) and from 1 to 3 heteroatoms (e.g., 1, 2, or 3 heteroatoms, or from 1-3, 1-2, or 2-3 heteroatoms) selected from the group consisting of nitrogen (N), oxygen (O), sulfur (S), and combinations thereof. In certain instances, $R^1$ and $R^2$ are joined to form an optionally substituted diazole (e.g., an optionally substituted imidazole) or an optionally substituted triazole.

In yet another embodiment, X and Y are either the same or different and are independently O, C(O)O, C(O)N($R^6$), N($R^6$) C(O)O, or C(O)S. In certain instances, $R^6$ is hydrogen (H), an optionally substituted methyl group, an optionally substituted ethyl group, or an optionally substituted $C_3$-$C_{10}$ alkyl, alkenyl, or alkynyl group (e.g., an optionally substituted $C_3$, $C_4$, $C_5$, $C_6$, $C_7$, $C_8$, $C_9$, or $C_{10}$ alkyl, alkenyl, or alkynyl group). In a further embodiment, X and Y are independently an optionally substituted heterocyclic ring having from 2 to 5 carbon atoms (e.g., 2, 3, 4, or 5 carbon atoms, or from 2-5, 2-4, 2-3,3-5, 3-4, or 4-5 carbon atoms) and from 1 to 3 heteroatoms (e.g., 1, 2, or 3 heteroatoms, or from 1-3, 1-2, or 2-3 heteroatoms) selected from the group consisting of nitrogen (N), oxygen (O), sulfur (S), and combinations thereof. In certain instances, X and Y are independently an optionally substituted diazole (e.g., an optionally substituted imidazole) or an optionally substituted triazole. In preferred embodiments, X and Y are both O. In other embodiments, Z is $(CH_2)_n$ and n is 0, 1, 2, 3, 4, 5, or 6. In particular embodiments, n is 1, 2, 3, or 4 (e.g., n is 1-4, 1-3, 1-2, 2-4, 2-3, or 3-4).

In certain embodiments, at least one of $R^4$ and $R^5$ comprises at least one, two, three, or more optionally substituted cyclic alkyl groups. In particular embodiments, both $R^4$ and $R^5$ independently comprise at least one, two, three, or more optionally substituted cyclic alkyl groups. In some instances, both $R^4$ and $R^5$ comprise the same number of (e.g., 1, 2, 3, 4, 5, 6, or more) optionally substituted cyclic alkyl groups. In other instances, $R^4$ and $R^5$ comprise a different number of optionally substituted cyclic alkyl groups. In one embodiment, each of the optionally substituted cyclic alkyl groups in $R^4$ and/or $R^5$ comprises an independently selected optionally substituted saturated cyclic alkyl group or an optionally substituted unsaturated cyclic alkyl group. In certain instances, at least one, two, three, or more of the optionally substituted cyclic alkyl groups present in one or both of $R^4$ and $R^5$ independently comprises an optionally substituted $C_{3-8}$ cycloalkyl group such as, e.g., a cyclopropyl group, an optionally substituted $C_{3-8}$ cycloalkenyl group, and combinations thereof. In some embodiments, one of $R^4$ or $R^5$ comprises at least one, two, three, or more optionally substituted cyclic alkyl groups and the other side-chain comprises an optionally substituted $C_{10}$-$C_{24}$ alkyl, $C_{10}$-$C_{24}$ alkenyl, $C_{10}$-$C_{24}$ alkynyl, or $C_{10}$-$C_{24}$ acyl group (e.g., a side-chain comprising at least one, two, or three sites of unsaturation). In some instances, $R^4$ and $R^5$ both comprise the same type or types of optionally substituted cyclic alkyl groups. In other instances, $R^4$ and $R^5$ comprise different types of optionally substituted cyclic alkyl groups.

In particular embodiments, $R^4$ and $R^5$ are both $C_{12}$-$C_{20}$ alkyl groups (e.g., $C_{18}$ alkyl groups) having at least one, two, three, or more optionally substituted cyclic alkyl groups. In preferred embodiments, $R^4$ and $R^5$ are both $C_{12}$-$C_{20}$ (e.g., $C_{18}$) alkyl groups having the same number of (e.g., at least one, two, three, or more) optionally substituted cyclic alkyl groups. In certain embodiments, the at least one, two, three, or more optionally substituted cyclic alkyl groups present in both $R^4$ and $R^5$ independently comprises an optionally substituted saturated cyclic alkyl group (e.g., a $C_{3-8}$ cycloalkyl group such as a cyclopropyl group) or an optionally substituted unsaturated cyclic alkyl group (e.g., a $C_{3-8}$ cycloalkenyl group).

In some embodiments, at least one, two, three, or more optionally substituted cyclic alkyl groups are present on each of $R^4$ and/or $R^5$ in combination with at least one, two, three, or more sites of unsaturation and/or branched alkyl and/or acyl groups. For example, $R^4$ may comprise one, two, or three $C_{3-8}$ cycloalkyl groups such as cyclopropyl groups and one, two, or three sites of unsaturation, while $R^5$ may comprise the same or different number and type of substituents.

In particular embodiments, the cationic lipid of Formula III is selected from the group consisting of Compound 57, 58, 59, 60, 62, or combinations thereof as described herein.

In particular embodiments, the interfering RNA (e.g., siRNA) that targets APOB and/or other target genes such as APOC3, PCSK9, DGAT1, and/or DGAT2 comprises a sense strand and a complementary antisense strand, and the interfering RNA comprises a double-stranded region of about 15 to about 60 nucleotides in length (e.g., about 15-60, 15-30, 15-25, 19-30, 19-25, 20-60, 20-55, 20-50, 20-45, 20-40, 20-35, 20-30, 20-25, 21-30, 21-29, 22-30, 22-29, 22-28, 23-30, 23-28, 24-30, 24-28, 25-60, 25-55, 25-50, 25-45, 25-40, 25-35, or 25-30 nucleotides in length, or about 15, 16, 17, 18, 19, 20, 21, 22, 23, 24, 25, 26, 27, 28, 29, 30, 31, 32, 33, 34, or 35 nucleotides in length). In one embodiment, the interfering RNA is chemically synthesized. The interfering RNA molecules of the invention are capable of silencing the expression of a target sequence such as APOB in vitro and/or in vivo.

In certain embodiments, the interfering RNA (e.g., siRNA) of the present invention may comprise at least one, two, three, four, five, six, seven, eight, nine, ten, or more modified nucleotides such as 2'OMe nucleotides, e.g., in the sense and/or antisense strand of the double-stranded region of the interfering RNA. Preferably, uridine and/or guanosine nucleotides in the interfering RNA are modified with 2'OMe nucleotides. In certain instances, the interfering RNA contains 2'OMe nucleotides in both the sense and antisense strands and comprises at least one 2'OMe-uridine nucleotide and at least one 2'OMe-guanosine nucleotide in the double-stranded region. In some embodiments, the sense and/or antisense strand of the interfering RNA may further comprise modified (e.g., 2'OMe-modified) adenosine and/or modified (e.g., 2'OMe-modified) cytosine nucleotides, e.g., in the double-stranded region of the interfering RNA.

In some embodiments, the sense and/or antisense strand sequences may comprise at least one, two, three, four, five, six, seven, eight, nine, ten, or more modified nucleotides such as 2'OMe nucleotides. In certain embodiments, the sense and/or antisense strand sequences may each independently comprise or consist of a modified (e.g., 2'OMe) and/or unmodified 3' overhang of 1, 2, 3, or 4 nucleotides, or one or both ends of the double-stranded molecule may be blunt-ended.

One of skill in the art will understand that unmodified sense and/or antisense strand sequences can be modified in accordance with the selective modification patterns described herein (e.g., at selective uridine and/or guanosine nucleotides, and optionally at adenosine and/or cytosine nucleotides, within the RNA duplex), and screened for RNAi activity as well as immune stimulation, such that the degree of chemical modifications introduced into the interfering RNA molecule strikes a balance between reduction or abrogation of the immunostimulatory properties of the interfering RNA and retention of RNAi activity.

In particular embodiments, the interfering RNA (e.g., siRNA) molecules of the present invention comprise a 3' overhang of 1, 2, 3, or 4 nucleotides in one or both strands. In certain instances, the interfering RNA may contain at least one blunt end. In particular embodiments, the 3' overhangs in one or both strands of the interfering RNA may each independently comprise 1, 2, 3, or 4 modified and/or unmodified deoxythymidine ("t" or "dT") nucleotides, 1, 2, 3, or 4 modified (e.g., 2'OMe) and/or unmodified uridine ("U") ribonucleotides, or 1, 2, 3, or 4 modified (e.g., 2'OMe) and/or unmodified ribonucleotides or deoxyribonucleotides having complementarity to the target sequence or the complementary strand thereof.

In another embodiment, the present invention provides a composition comprising a cocktail (e.g., at least 2, 3, 4, 5, 6, 7, 8, 9, 10, 11, 12, 13, 14, 15, 16, 17, 18, 19, 20, or more) of unmodified and/or modified interfering RNA (e.g., siRNA) sequences that target APOB, APOC3, PCSK9, DGAT1, and/or DGAT2 expression. The cocktail of interfering RNA (e.g., siRNA) may comprise sequences which are directed to the same region or domain (e.g., a "hot spot") and/or to different regions or domains of one or more target genes. In particular embodiments, at least 1, 2, 3, 4, 5, 6, 7, 8, 9, 10, 11, 12, 13, 14, 15, 16, 17, 18, 19, 20, or more (e.g., all) of these sequences are chemically modified (e.g., 2'OMe-modified) as described herein.

In certain embodiments, the sense strand comprises or consists of a sequence that is at least about 80%, 85%, 86%, 87%, 88%, 89%, 90%, 91%, 92%, 93%, 94%, 95%, 96%, 97%, 98%, 99%, or 100% identical to the target sequence or a portion thereof. In certain other embodiments, the sense strand comprises or consists of at least about 15 contiguous nucleotides (e.g., at least about 15, 16, 17, 18, or 19 contiguous nucleotides) of a sequence that is identical to the target sequence or a portion thereof. In preferred embodiments, the interfering RNA (e.g., siRNA) comprising such a sense strand sequence is capable of mediating target-specific RNAi.

In some embodiments, the antisense strand comprises or consists of a sequence that is at least about 80%, 85%, 86%, 87%, 88%, 89%, 90%, 91%, 92%, 93%, 94%, 95%, 96%, 97%, 98%, 99%, or 100% complementary to the target sequence or a portion thereof. In other embodiments, the antisense strand comprises or consists of at least about 15 contiguous nucleotides (e.g., at least about 15, 16, 17, 18, or 19 contiguous nucleotides) of a sequence that is complementary to the target sequence or a portion thereof. In further embodiments, the antisense strand comprises or consists of a sequence that specifically hybridizes to the target sequence or a portion thereof. In preferred embodiments, the interfering RNA (e.g., siRNA) comprising such an antisense strand sequence is capable of mediating target-specific RNAi.

In one preferred embodiment, the APOB siRNA comprises an antisense strand comprising the following sequence: 5'-UAUUCAGUGUGAUGACACU-3' (SEQ ID NO:14 In another preferred embodiment, the APOB siRNA further comprises a sense strand comprising the following sequence: 5'-AGUGUCAUCACACUGAAUA-3' (SEQ ID NO:14). In some embodiments, the APOB siRNA comprises at least one 2'OMe nucleotide, e.g., at least one 2'OMe-guanosine and/or 2'OMe-uridine nucleotide. In certain instances, the APOB siRNA comprises an antisense strand comprising at least one, at least two, at least three, at least four, at least five, at least six, at least seven, or more 2'OMe nucleotides, e.g., 2'OMe-guanosine and/or 2'OMe-uridine nucleotides. In certain other instances, the APOB siRNA comprises a sense strand comprising at least one, at least two, at least three, at least four, at least five, at least six, at least seven, or more 2'OMe nucleotides, e.g., 2'OMe-guanosine and/or 2'OMe-uridine nucleotides.

In particular embodiments, from about 20%-40%, 25%-40%, 30%-40%, 20%-35%, 25%-35%, 20%-30%, 25%-30%, 26%-34%, 27%-33%, 28%-32%, or about 25%, 26%, 27%, 28%, 29%, 30%, 31%, 32%, 33%, 34%, 35%, 36%, 37%, 38%, 39%, or 40% of the nucleotides in the double-stranded region of the siRNA comprise modified nucleotides such as, e.g., 2'OMe nucleotides (e.g., 2'OMe-guanosine and/or 2'OMe-uridine nucleotides).

In some embodiments, the APOB siRNA of the invention comprises a 3' overhang in one or both strands of the siRNA. In one particular embodiment, the antisense strand comprises a 5'-UC-3' overhang and the sense strand comprises a 5'-CC-3' overhang. In certain instances, the 3' overhangs on one or both strands of the siRNA comprise at least one 2'OMe nucleotide, e.g., at least one 2'OMe-guanosine and/or 2'OMe-uridine nucleotide. In other embodiments, the 3' overhangs on one or both strands of the siRNA molecule comprise 1-4 deoxythymidine (dT) nucleotides, 1-4 modified and/or unmodified uridine (U) ribonucleotides, or 1-2 additional ribonucleotides having complementarity to the target sequence or the complementary strand thereof.

In a first embodiment, the APOB siRNA comprises the following sense strand sequence: 5'-AGU<u>G</u>UCA<u>U</u>CACAC<u>U</u>GAAUACC-3' ("S-1"; SEQ ID NO:1), wherein the bolded and underlined nucleotides are 2'OMe nucleotides. In a second embodiment, the APOB siRNA comprises the following sense strand sequence: 5'-AGU<u>G</u>UC<u>A</u>UCACAC<u>U</u>GAA<u>U</u>ACC-3' ("S-2"; SEQ ID NO:3), wherein the bolded and underlined nucleotides are 2'OMe nucleotides. In a third embodiment, the APOB siRNA comprises the following sense strand sequence: 5'-AGU<u>G</u>UC<u>A</u>UCACAC<u>U</u>GA<u>A</u><u>U</u>ACC-3' ("S-3"; SEQ ID NO:4), wherein the bolded and underlined nucleotides are 2'OMe nucleotides. In a fourth embodiment, the APOB siRNA comprises the following sense strand sequence: 5'-AGU<u>G</u>UC<u>A</u>UCACAC<u>U</u>GA<u>A</u><u>U</u>ACC-3' ("S-4"; SEQ ID NO:5), wherein the bolded and underlined nucleotides are 2'OMe nucleotides. In a fifth embodiment, the APOB siRNA comprises the following sense strand sequence: 5'-AGU<u>G</u>UC<u>A</u>UCACAC<u>U</u>GAA<u>U</u>ACC-3' ("S-5"; SEQ ID NO:6), wherein the bolded and underlined nucleotides are 2'OMe nucleotides. In a sixth embodiment, the APOB siRNA comprises the following sense strand sequence: 5'-AGUGUCAUCACACUGAAU**ACC-3' ("S-6"; SEQ ID NO:7), wherein the bolded and underlined nucleotides are 2'OMe nucleotides.

In a first embodiment, the APOB siRNA comprises the following antisense strand sequence: 5'-UAUUCAGUGUGAUGACACUUG-3' ("AS-1"; SEQ ID NO:2), wherein the bolded and underlined nucleotides are 2'OMe nucleotides. In a second embodiment, the APOB siRNA comprises the following antisense strand sequence: 5'-UAUUCAGUGUGAUGACACUUG-3' ("AS-2"; SEQ ID NO:8), wherein the bolded and underlined nucleotides are 2'OMe nucleotides. In a third embodiment, the APOB siRNA comprises the following antisense strand sequence: 5'-UAUUCAGUGUGAUGACACUUG-3' ("AS-3"; SEQ ID NO:9), wherein the bolded and underlined nucleotides are 2'OMe nucleotides. In a fourth embodiment, the APOB siRNA comprises the following antisense strand sequence: 5'-UAUUCAGUGUGAUGACACUUG-3' ("AS-4"; SEQ ID NO:10), wherein the bolded and underlined nucleotides are 2'OMe nucleotides. In a fifth embodiment, the APOB siRNA comprises the following antisense strand sequence: 5'-UAUUCAGUGUGAUGA-CACUUG-3' ("AS-5"; SEQ ID NO:11), wherein the bolded and underlined nucleotides are 2'OMe nucleotides. In a sixth embodiment, the APOB siRNA comprises the following antisense strand sequence: 5'-UAUUCAGUGUGAUGACACUUG-3' ("AS-6"; SEQ ID NO:12), wherein the bolded and underlined nucleotides are 2'OMe nucleotides.

In one preferred embodiment, the APOB siRNA comprises: an antisense strand comprising the sequence 5'-UA-UUCAGUGUGAUGACACU-3' (SEQ ID NO:13) and at least one, two, three, four, five, six, or more 2'OMe nucleotides, e.g., at least one, two, three, four, five, six, or more 2'OMe-guanosine and/or 2'OMe-uridine nucleotides; and a sense strand comprising the sequence 5'-AGUGUCAUCA-CACUGAAUA-3' (SEQ ID NO:14) and at least one, two, three, four, five, six, or more 2'OMe nucleotides, e.g., at least one, two, three, four, five, six, or more 2'OMe-guanosine and/or 2'OMe-uridine nucleotides. In another preferred embodiment, the APOB siRNA of the invention comprises: a sense strand comprising nucleotides 1-19 of S-1, S-2, S-3, S-4, S-5, or S-6; and an antisense strand comprising nucleotides 1-19 of AS-1, AS-2, AS-3, AS-4, AS-5, or AS-6. In a particularly preferred embodiment, the APOB siRNA consists of: a sense strand selected from S-1, S-2, S-3, S-4, S-5, and S-6; and an antisense strand selected from AS-1, AS-2, AS-3, AS-4, AS-5, and AS-6.

In one particular embodiment, the APOB siRNA consists of the following sense and antisense strand sequences:

```
5'-AGUGUCAUCACACUGAAUACC-3'      (SEQ ID NO: 1)
3'-GUUCACAGUAGUGUGACUUAU-5',     (SEQ ID NO: 2)
```

("S-1+AS-1", "1/1", or "ApoB-8"), wherein the bolded and underlined nucleotides are 2'OMe nucleotides.

In another particular embodiment, the APOB siRNA consists of the following sense and antisense strand sequences:

```
5'-AGUGUCAUCACACUGAAUACC-3'      (SEQ ID NO: 3)
3'-GUUCACAGUAGUGUGACUUAU-5',     (SEQ ID NO: 8)
```

("S-2+AS-2" or "2/2"), wherein the bolded and underlined nucleotides are 2'OMe nucleotides.

In yet another particular embodiment, the APOB siRNA consists of the following sense and antisense strand sequences:

```
5'-AGUGUCAUCACACUGAAUACC-3'      (SEQ ID NO: 3)
3'-GUUCACAGUAGUGUGACUUAU-5',     (SEQ ID NO: 9)
```

("S-2+AS-3" or "2/3"), wherein the bolded and underlined nucleotides are 2'OMe nucleotides.

In still yet another particular embodiment, the APOB siRNA consists of the following sense and antisense strand sequences:

```
5'-AGUGUCAUCACACUGAAUACC-3'      (SEQ ID NO: 4)
3'-GUUCACAGUAGUGUGACUUAU-5',     (SEQ ID NO: 8)
```

("S-3+AS-2" or "3/2"), wherein the bolded and underlined nucleotides are 2'OMe nucleotides.

In another particular embodiment, the APOB siRNA consists of the following sense and antisense strand sequences:

```
5'-AGUGUCAUCACACUGAAUACC-3'      (SEQ ID NO: 4)
3'-GUUCACAGUAGUGUGACUUAU-5',     (SEQ ID NO: 9)
```

("S-3+AS-3" or "3/3"), wherein the bolded and underlined nucleotides are 2'OMe nucleotides.

In yet another particular embodiment, the APOB siRNA consists of the following sense and antisense strand sequences:

```
5'-AGUGUCAUCACACUGAAUACC-3'      (SEQ ID NO: 5)
3'-GUUCACAGUAGUGUGACUUAU-5',     (SEQ ID NO: 8)
```

("S-4+AS-2" or "4/2"), wherein the bolded and underlined nucleotides are 2'OMe nucleotides.

In still yet another particular embodiment, the APOB siRNA consists of the following sense and antisense strand sequences:

```
5'-AGUGUCAUCACACUGAAUACC-3'      (SEQ ID NO: 5)
3'-GUUCACAGUAGUGUGACUUAU-5',     (SEQ ID NO: 9)
```

("S-4+AS-3" or "4/3"), wherein the bolded and underlined nucleotides are 2'OMe nucleotides.

In another particular embodiment, the APOB siRNA consists of the following sense and antisense strand sequences:

```
5'-AGUGUCAUCACACUGAAUACC-3'      (SEQ ID NO: 6)
3'-GUUCACAGUAGUGUGACUUAU-5',     (SEQ ID NO: 8)
```

("S-5+AS-2" or "5/2"), wherein the bolded and underlined nucleotides are 2'OMe nucleotides.

In yet another particular embodiment, the APOB siRNA consists of the following sense and antisense strand sequences:

```
5'-AGUGUCAUCACACUGAAUACC-3'      (SEQ ID NO: 6)
3'-GUUCACAGUAGUGUGACUUAU-5',     (SEQ ID NO: 9)
```

("S-5+AS-3" or "⅝"), wherein the bolded and underlined nucleotides are 2'OMe nucleotides.

In still yet another particular embodiment, the APOB siRNA consists of the following sense and antisense strand sequences:

```
5'-AGGUCAUCACACUGAAUACC-3'      (SEQ ID NO: 7)

3'-GUUCACAGUAGUGUGACUUAU-5', (SEQ ID NO: 8)
```

("S-6+AS-2" or "6/2"), wherein the bolded and underlined nucleotides are 2'OMe nucleotides.

In another particular embodiment, the APOB siRNA consists of the following sense and antisense strand sequences:

```
5'-AGGUCAUCACACUGAAUACC-3'      (SEQ ID NO: 7)

3'-GUUCACAGUAGUGUGACUUAU-5',    (SEQ ID NO: 9)
```

("S-6+AS-3" or "6/3"), wherein the bolded and underlined nucleotides are 2'OMe nucleotides.

In yet another particular embodiment, the APOB siRNA consists of the following sense and antisense strand sequences:

```
5'-AGUGCAUCACACUGAAUACC-3'      (SEQ ID NO: 3)

3'-GUUCACAGUAGUGUGACUUAU-5',         (SEQ ID NO: 10)
```

("S-2+AS-4" or "2/4"), wherein the bolded and underlined nucleotides are 2'OMe nucleotides.

In still yet another particular embodiment, the APOB siRNA consists of the following sense and antisense strand sequences:

```
                                                 (SEQ ID NO: 3)
5'-AGUGCAUCACACUGAAUACC-3'

(SEQ ID NO: 11)
3'-GUUCACAGUAGUGUGACUUAU-5',
```

("S-2+AS-5" or "2/5"), wherein the bolded and underlined nucleotides are 2'OMe nucleotides.

In another particular embodiment, the APOB siRNA consists of the following sense and antisense strand sequences:

```
                                                 (SEQ ID NO: 3)
5'-AGUGCAUCACACUGAAUACC-3'

(SEQ ID NO: 12)
3'-GUUCACAGUAGUGUGACUUAU-5',
```

("S-2+AS-6" or "2/6"), wherein the bolded and underlined nucleotides are 2'OMe nucleotides.

In yet another particular embodiment, the APOB siRNA consists of the following sense and antisense strand sequences:

```
                                                 (SEQ ID NO: 4)
5'-AGUGUCAUCACACUGAAUACC-3'

(SEQ ID NO: 10)
3'-GUUCACAGUAGUGUGACUUAU-5',
```

("S-3+AS-4", or "3/4"), wherein the bolded and underlined nucleotides are 2'OMe nucleotides.

In still yet another particular embodiment, the APOB siRNA consists of the following sense and antisense strand sequences:

```
                                                 (SEQ ID NO: 4)
5'-AGUGUCAUCACACUGAAUACC-3'

(SEQ ID NO: 11)
3'-GUUCACAGUAGUGUGACUUAU-5',
```

("S-3+AS-5", "3/5", or "ApoB-10"), wherein the bolded and underlined nucleotides are 2'OMe nucleotides.

In another particular embodiment, the APOB siRNA consists of the following sense and antisense strand sequences:

```
                                                 (SEQ ID NO: 4)
5'-AGUGUCAUCACACUGAAUACC-3'

(SEQ ID NO: 12)
3'-GUUCACAGUAGUGUGACUUAU-5',
```

("S-3+AS-6" or "3/6"), wherein the bolded and underlined nucleotides are 2'OMe nucleotides.

In yet another particular embodiment, the APOB siRNA consists of the following sense and antisense strand sequences:

```
                                                 (SEQ ID NO: 5)
5'-AGUGUCAUCACACUGAAUACC-3'

(SEQ ID NO: 10)
3'-GUUCACAGUAGUGUGACUUAU-5',
```

("S-4+AS-4" or "4/4"), wherein the bolded and underlined nucleotides are 2'OMe nucleotides.

In still yet another particular embodiment, the APOB siRNA consists of the following sense and antisense strand sequences:

```
                                                 (SEQ ID NO: 5)
5'-AGUGUCAUCACACUGAAUACC-3'

(SEQ ID NO: 11)
3'-GUUCACAGUAGUGUGACUUAU-5',
```

("S-4+AS-5" or "4/5"), wherein the bolded and underlined nucleotides are 2'OMe nucleotides.

In another particular embodiment, the APOB siRNA consists of the following sense and antisense strand sequences:

```
                                                 (SEQ ID NO: 5)
5'-AGUGUCAUCACACUGAAUACC-3'

(SEQ ID NO: 12)
3'-GUUCACAGUAGUGUGACUUAU-5',
```

("S-4+AS-6" or "4/6"), wherein the bolded and underlined nucleotides are 2'OMe nucleotides.

In yet another particular embodiment, the APOB siRNA consists of the following sense and antisense strand sequences:

```
                                            (SEQ ID NO: 6)
          5'-AGUGUCAUCACACUGAAUACC-3'

(SEQ ID NO: 10)
          3'-GUUCACAGUAGUGUGACUUAU-5',
```

("S-5+AS-4" or "5/4"), wherein the bolded and underlined nucleotides are 2'OMe nucleotides.

In still yet another particular embodiment, the APOB siRNA consists of the following sense and antisense strand sequences:

```
                                            (SEQ ID NO: 6)
          5'-AGUGUCAUCACACUGAAUACC-3'

(SEQ ID NO: 11)
          3'-GUUCACAGUAGUGUGACUUAU-5',
```

("S-5+AS-5" or "5/5"), wherein the bolded and underlined nucleotides are 2'OMe nucleotides.

In another particular embodiment, the APOB siRNA consists of the following sense and antisense strand sequences:

```
                                            (SEQ ID NO: 6)
          5'-AGUGUCAUCACACUGAAUACC-3'

(SEQ ID NO: 12)
          3'-GUUCACAGUAGUGUGACUUAU-5',
```

("S-5+AS-6" or "5/6"), wherein the bolded and underlined nucleotides are 2'OMe nucleotides.

In yet another particular embodiment, the APOB siRNA consists of the following sense and antisense strand sequences:

```
                                            (SEQ ID NO: 7)
          5'-AGUGUCAUCACACUGAAUACC-3'

(SEQ ID NO: 10)
          3'-GUUCACAGUAGUGUGACUUAU-5',
```

("S-6+AS-4" or "6/4"), wherein the bolded and underlined nucleotides are 2'OMe nucleotides.

In still yet another particular embodiment, the APOB siRNA consists of the following sense and antisense strand sequences:

```
                                            (SEQ ID NO: 7)
          5'-AGUGUCAUCACACUGAAUACC-3'

(SEQ ID NO: 11)
          3'-GUUCACAGUAGUGUGACUUAU-5',
```

("S-6+AS-5" or "6/5"), wherein the bolded and underlined nucleotides are 2'OMe nucleotides.

In another particular embodiment, the APOB siRNA consists of the following sense and antisense strand sequences:

```
                                            (SEQ ID NO: 7)
          5'-AGUGUCAUCACACUGAAUACC-3'

(SEQ ID NO: 12)
          3'-GUUCACAGUAGUGUGACUUAU-5',
```

("S-6+AS-6" or "6/6"), wherein the bolded and underlined nucleotides are 2'OMe nucleotides.

In a further embodiment, the APOB siRNA consists of the following sense and antisense strand sequences:

```
                                           (SEQ ID NO: 17)
          5'-GUCAUCACACUGAAUACCAAU-3'

(SEQ ID NO: 18)
          3'-CACAGUAGUGUGACUUAUGGUUA-5'.
```

It will be readily apparent to those of skill in the art that the foregoing APOB siRNA can also be chemically modified, if desired, to reduce its immunostimulatory properties, while maintaining its silencing activities.

The nucleic acid-lipid particles (e.g., SNALP) typically comprise one or more (e.g., a cocktail) of the interfering RNAs described herein, a cationic lipid, and a non-cationic lipid. In certain instances, the nucleic acid-lipid particles (e.g., SNALP) further comprise a conjugated lipid that inhibits aggregation of particles. Preferably, the nucleic acid-lipid particles (e.g., SNALP) comprise one or more (e.g., a cocktail) of the interfering RNAs described herein, a cationic lipid, a non-cationic lipid, and a conjugated lipid that inhibits aggregation of particles. In particular embodiments, the nucleic acid-lipid particles (e.g., SNALP) of the invention comprise 1, 2, 3, 4, 5, 6, 7, 8, or more unmodified and/or modified interfering RNAs that silence 1, 2, 3, 4, 5, 6, 7, 8, or more different genes associated with liver diseases or disorders, a cationic lipid, a non-cationic lipid, and a conjugated lipid that inhibits aggregation of particles.

In some embodiments, the interfering RNAs (e.g., siRNAs) are fully encapsulated in the nucleic acid-lipid particle (e.g., SNALP). With respect to formulations comprising an interfering RNA cocktail, the different types of interfering RNA species present in the cocktail (e.g., interfering RNA compounds with different sequences) may be co-encapsulated in the same particle, or each type of interfering RNA species present in the cocktail may be encapsulated in a separate particle. The interfering RNA cocktail may be formulated in the particles described herein using a mixture of two or more individual interfering RNAs (each having a unique sequence) at identical, similar, or different concentrations or molar ratios. In one embodiment, a cocktail of interfering RNAs (corresponding to a plurality of interfering RNAs with different sequences) is formulated using identical, similar, or different concentrations or molar ratios of each interfering RNA species, and the different types of interfering RNAs are co-encapsulated in the same particle. In another embodiment, each type of interfering RNA species present in the cocktail is encapsulated in different particles at identical, similar, or different interfering RNA concentrations or molar ratios, and the particles thus formed (each containing a different interfering RNA payload) are administered separately (e.g., at different times in accordance with a therapeutic regimen), or are combined and administered together as a single unit dose (e.g., with a pharmaceutically acceptable carrier). The particles described herein are serum-stable, are resistant to nuclease degradation, and are substantially non-toxic to mammals such as humans.

The cationic lipid in the nucleic acid-lipid particles of the invention (e.g., SNALP) may comprise, e.g., one or more cationic lipids of Formulas I-III described herein and/or any other cationic lipid species. In one particular embodiment, the cationic lipid is selected from the group consisting of Compound 1, 4, 5, 8, 9, 10, 11, 12, 13, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 51, 56, 57, 58, 59, 60, 62, 63, 64, 65, or combinations thereof.

The non-cationic lipid in the nucleic acid-lipid particles of the present invention (e.g., SNALP) may comprise, e.g., one or more anionic lipids and/or neutral lipids. In some embodiments, the non-cationic lipid comprises one of the following neutral lipid components: (1) a mixture of a phospholipid and cholesterol or a derivative thereof; (2) cholesterol or a derivative thereof; or (3) a phospholipid. In certain preferred embodiments, the phospholipid comprises dipalmitoylphosphatidylcholine (DPPC), distearoylphosphatidylcholine (DSPC), or a mixture thereof. In a particularly preferred embodiment, the non-cationic lipid is a mixture of DPPC and cholesterol.

The lipid conjugate in the nucleic acid-lipid particles of the invention (e.g., SNALP) inhibits aggregation of particles and may comprise, e.g., one or more of the lipid conjugates described herein. In one particular embodiment, the lipid conjugate comprises a PEG-lipid conjugate. Examples of PEG-lipid conjugates include, but are not limited to, PEG-DAG conjugates, PEG-DAA conjugates, and mixtures thereof. In certain embodiments, the PEG-DAA conjugate in the lipid particle may comprise a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, a PEG-distearyloxypropyl ($C_{18}$) conjugate, or mixtures thereof. In another embodiment, the lipid conjugate comprises a POZ-lipid conjugate such as a POZ-DAA conjugate.

In exemplary aspects of these embodiments, the cationic lipid comprises one or more cationic lipids of Formulas I-III (e.g., Compound 1, 4, 5, 8, 9, 10, 11, 12, 13, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 51, 56, 57, 58, 59, 60, 62, 63, 64, 65, or combinations thereof), the non-cationic lipid comprises a mixture of a phospholipid (e.g., DPPC) and cholesterol (and/or a derivative thereof), and the PEG-lipid conjugate comprises a PEG-DAA conjugate such as a PEG2000-DMA conjugate and/or a PEG750-DMA conjugate. In a particularly preferred embodiment, the APOB siRNA is APOB siRNA ⅗ ("ApoB-10"), the cationic lipid comprises one or more cationic lipids of Formulas I-III (e.g., Compound 1, 4, 5, 8, 9, 10, 11, 12, 13, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 51, 56, 57, 58, 59, 60, 62, 63, 64, 65, or combinations thereof), the non-cationic lipid comprises a mixture of a phospholipid (e.g., DPPC) and cholesterol (and/or a derivative thereof), and the PEG-lipid conjugate comprises a PEG-DMA conjugate such as PEG2000-C-DMA.

In some embodiments, the present invention provides nucleic acid-lipid particles (e.g., SNALP) comprising: (a) one or more interfering RNA molecules that target APOB expression and/or the expression of other liver target genes such as APOC3, PCSK9, DGAT1, DGAT2, or combinations thereof; (b) one or more cationic lipids of Formulas I-III or salts thereof comprising from about 50 mol % to about 85 mol % of the total lipid present in the particle; (c) one or more non-cationic lipids comprising from about 13 mol % to about 49.5 mol % of the total lipid present in the particle; and (d) one or more conjugated lipids that inhibit aggregation of particles comprising from about 0.5 mol % to about 2 mol % of the total lipid present in the particle.

In one aspect of this embodiment, the nucleic acid-lipid particle comprises: (a) one or more interfering RNA molecules that target APOB expression and/or the expression of other liver target genes such as APOC3, PCSK9, DGAT1, DGAT2, or combinations thereof; (b) one or more cationic lipids of Formulas I-III or salts thereof comprising from about 50 mol % to about 65 mol % of the total lipid present in the particle; (c) one or more non-cationic lipids comprising a mixture of one or more phospholipids and cholesterol or a derivative thereof, wherein the one or more phospholipids comprises from about 4 mol % to about 10 mol % of the total lipid present in the particle and the cholesterol or derivative thereof comprises from about 30 mol % to about 40 mol % of the total lipid present in the particle; and (d) one or more PEG-lipid conjugates comprising from about 0.5 mol % to about 2 mol % of the total lipid present in the particle. This embodiment of nucleic acid-lipid particle is generally referred to herein as the "1:57" formulation.

In certain instances, the 1:57 formulation comprises: (a) one or more interfering RNA molecules that target APOB expression and/or the expression of other liver target genes such as APOC3, PCSK9, DGAT1, DGAT2, or combinations thereof; (b) one or more cationic lipids of Formulas I-III or salts thereof comprising from about 52 mol % to about 62 mol % of the total lipid present in the particle; (c) a mixture of one or more phospholipids and cholesterol or a derivative thereof comprising from about 36 mol % to about 47 mol % of the total lipid present in the particle; and (d) one or more PEG-lipid conjugates comprising from about 1 mol % to about 2 mol % of the total lipid present in the particle. In one particular embodiment, the 1:57 formulation is a four-component system comprising about 1.4 mol % PEG-lipid conjugate (e.g., PEG2000-C-DMA), about 57.1 mol % cationic lipid of Formulas I-III or a salt thereof, about 7.1 mol % DPPC (or DSPC), and about 34.3 mol % cholesterol (or derivative thereof).

In another aspect of this embodiment, the nucleic acid-lipid particle comprises: (a) one or more interfering RNA molecules that target APOB expression and/or the expression of other liver target genes such as APOC3, PCSK9, DGAT1, DGAT2, or combinations thereof; (b) one or more cationic lipids of Formulas I-III or salts thereof comprising from about 56.5 mol % to about 66.5 mol % of the total lipid present in the particle; (c) cholesterol and/or one or more derivatives thereof comprising from about 31.5 mol % to about 42.5 mol % of the total lipid present in the particle; and (d) one or more PEG-lipid conjugates comprising from about 1 mol % to about 2 mol % of the total lipid present in the particle. This embodiment of nucleic acid-lipid particle is generally referred to herein as the "1:62" formulation. In one particular embodiment, the 1:62 formulation is a three-component system which is phospholipid-free and comprises about 1.5 mol % PEG-lipid conjugate (e.g., PEG2000-C-DMA), about 61.5 mol % cationic lipid of Formulas I-III or a salt thereof, and about 36.9 mol % cholesterol (or derivative thereof).

Additional embodiments related to the 1:57 and 1:62 formulations are described in PCT Publication No. WO 09/127,060 and U.S. Patent Publication No. 20110071208, the disclosures of which are herein incorporated by reference in their entirety for all purposes.

In other embodiments, the present invention provides nucleic acid-lipid particles (e.g., SNALP) comprising: (a) one or more interfering RNA molecules that target APOB expression and/or the expression of other liver target genes such as APOC3, PCSK9, DGAT1, DGAT2, or combinations thereof; (b) one or more cationic lipids of Formulas I-III or salts thereof comprising from about 2 mol % to about 50 mol % of the total lipid present in the particle; (c) one or more non-cationic lipids comprising from about 5 mol % to about 90 mol % of the total lipid present in the particle; and (d) one or more conjugated lipids that inhibit aggregation of particles comprising from about 0.5 mol % to about 20 mol % of the total lipid present in the particle.

In one aspect of this embodiment, the nucleic acid-lipid particle comprises: (a) one or more interfering RNA molecules that target APOB expression and/or the expression of other liver target genes such as APOC3, PCSK9, DGAT1, DGAT2, or combinations thereof; (b) one or more cationic lipids of Formulas I-III or salts thereof comprising from about 30 mol % to about 50 mol % of the total lipid present in the particle; (c) a mixture of one or more phospholipids and cholesterol or a derivative thereof comprising from about 47 mol % to about 69 mol % of the total lipid present in the particle; and (d) one or more PEG-lipid conjugates comprising from about 1 mol % to about 3 mol % of the total lipid present in the particle. This embodiment of nucleic acid-lipid particle is generally referred to herein as the "2:40" formulation. In one particular embodiment, the 2:40 formulation is a four-component system which comprises about 2 mol % PEG-lipid conjugate (e.g., PEG2000-C-DMA), about 40 mol % cationic lipid of Formulas I-III or a salt thereof, about 10 mol % DPPC (or DSPC), and about 48 mol % cholesterol (or derivative thereof).

In further embodiments, the present invention provides nucleic acid-lipid particles (e.g., SNALP) comprising: (a) one or more interfering RNA molecules that target APOB expression and/or the expression of other liver target genes such as APOC3, PCSK9, DGAT1, DGAT2, or combinations thereof; (b) one or more cationic lipids of Formulas I-III or salts thereof comprising from about 50 mol % to about 65 mol % of the total lipid present in the particle; (c) one or more non-cationic lipids comprising from about 25 mol % to about 45 mol % of the total lipid present in the particle; and (d) one or more conjugated lipids that inhibit aggregation of particles comprising from about 5 mol % to about 10 mol % of the total lipid present in the particle.

In one aspect of this embodiment, the nucleic acid-lipid particle comprises: (a) one or more interfering RNA molecules that target APOB expression and/or the expression of other liver target genes such as APOC3, PCSK9, DGAT1, DGAT2, or combinations thereof; (b) one or more cationic lipids of Formulas I-III or salts thereof comprising from about 50 mol % to about 60 mol % of the total lipid present in the particle; (c) a mixture of one or more phospholipids and cholesterol or a derivative thereof comprising from about 35 mol % to about 45 mol % of the total lipid present in the particle; and (d) one or more PEG-lipid conjugates comprising from about 5 mol % to about 10 mol % of the total lipid present in the particle. This embodiment of nucleic acid-lipid particle is generally referred to herein as the "7:54" formulation. In certain instances, the non-cationic lipid mixture in the 7:54 formulation comprises: (i) a phospholipid of from about 5 mol % to about 10 mol % of the total lipid present in the particle; and (ii) cholesterol or a derivative thereof of from about 25 mol % to about 35 mol % of the total lipid present in the particle. In one particular embodiment, the 7:54 formulation is a four-component system which comprises about 7 mol % PEG-lipid conjugate (e.g., PEG750-C-DMA), about 54 mol % cationic lipid of Formulas I-III or a salt thereof, about 7 mol % DPPC (or DSPC), and about 32 mol % cholesterol (or derivative thereof).

In another aspect of this embodiment, the nucleic acid-lipid particle comprises: (a) one or more interfering RNA molecules that target APOB expression and/or the expression of other liver target genes such as APOC3, PCSK9, DGAT1, DGAT2, or combinations thereof; (b) one or more cationic lipids of Formulas or salts thereof comprising from about 55 mol % to about 65 mol % of the total lipid present in the particle; (c) cholesterol and/or one or more derivatives thereof comprising from about 30 mol % to about 40 mol % of the total lipid present in the particle; and (d) one or more PEG-lipid conjugates comprising from about 5 mol % to about 10 mol % of the total lipid present in the particle. This embodiment of nucleic acid-lipid particle is generally referred to herein as the "7:58" formulation. In one particular embodiment, the 7:58 formulation is a three-component system which is phospholipid-free and comprises about 7 mol % PEG-lipid conjugate (e.g., PEG750-C-DMA), about 58 mol % cationic lipid of Formulas I-III or a salt thereof, and about 35 mol % cholesterol (or derivative thereof).

Additional embodiments related to the 7:54 and 7:58 formulations are described in U.S. Patent Publication No. 20110076335, the disclosure of which is herein incorporated by reference in its entirety for all purposes.

The present invention also provides pharmaceutical compositions comprising a nucleic acid-lipid particle such as a SNALP and a pharmaceutically acceptable carrier.

The nucleic acid-lipid particles of the invention are useful for the therapeutic delivery of interfering RNA (e.g., siRNA) molecules that silence the expression of one or more genes associated with liver diseases or disorders (e.g., APOB, APOC3, PCSK9, DGAT1, and/or DGAT2). In some embodiments, a cocktail of siRNAs that target one or more genes expressed in the liver is formulated into the same or different nucleic acid-lipid particles, and the particles are administered to a mammal (e.g., a human) requiring such treatment. In certain instances, a therapeutically effective amount of the nucleic acid-lipid particles can be administered to the mammal, e.g., for treating, preventing, reducing the risk of developing, or delaying the onset of a lipid disorder such as dyslipidemia (e.g., elevated triglyceride and/or cholesterol levels) or atherosclerosis.

Non-limiting examples of lipid disorders suitable for prevention and/or treatment with the nucleic acid-lipid particles of the invention (e.g., SNALP) include dyslipidemia (e.g., hyperlipidemias such as elevated triglyceride levels (hypertriglyceridemia) and/or elevated cholesterol levels (hypercholesterolemia)), atherosclerosis, low HDL-cholesterol, high LDL-cholesterol, coronary heart disease, coronary artery disease, atherosclerotic cardiovascular disease (CVD), fatty liver disease (hepatic steatosis), abnormal lipid metabolism, abnormal cholesterol metabolism, pancreatitis (e.g., acute pancreatitis associated with severe hypertriglyceridemia), diabetes (including Type 2 diabetes), obesity, cardiovascular disease, and other disorders relating to abnormal metabolism.

As described in the Examples below, it has surprisingly been found that the SNALP formulations of the present invention containing at least one cationic lipid of Formulas I-III, either alone or in combination with other cationic lipids, show increased potency when targeting a gene of interest in the liver, such as APOB, when compared to other SNALP formulations. Thus, the present invention provides methods for treating a disease or disorder associated with overexpression of APOB in a mammal (e.g., human) in need thereof, the method comprising administering to the mammal a therapeutically effective amount of a lipid particle (e.g., SNALP) comprising one or more interfering RNAs that silence APOB expression. Diseases and disorders associated with overexpression of APOB are described herein and include, but are not limited to, atherosclerosis, angina pectoris, high blood pressure, diabetes, and hypothyroidism. In certain instances, the mammal (e.g., human) has a disease or disorder involving hypercholesterolemia and serum cholesterol levels are lowered when expression of APOB is silenced by the interfering RNA.

In some embodiments, the interfering RNA (e.g., siRNA) molecules described herein are used in methods for silencing APOB, APOC3, PCSK9, DGAT1, and/or DGAT2 gene expression, e.g., in a cell such as a liver cell. In particular, it is an object of the invention to provide methods for treating, preventing, reducing the risk of developing, or delaying the onset of a lipid disorder in a mammal by downregulating or silencing the transcription and/or translation of the APOB, APOC3, PCSK9, DGAT1, and/or DGAT2 gene. In certain embodiments, the present invention provides a method for introducing one or more interfering RNA (e.g., siRNA) molecules described herein into a cell by contacting the cell with a nucleic acid-lipid particle described herein (e.g., a SNALP formulation). In one particular embodiment, the cell is a liver cell such as, e.g., a hepatocyte present in the liver tissue of a mammal (e.g., a human). In another embodiment, the present invention provides a method for the in vivo delivery of one or more interfering RNA (e.g., siRNA) molecules described herein to a liver cell (e.g., hepatocyte) by administering to a mammal (e.g., human) a nucleic acid-lipid particle described herein (e.g., a SNALP formulation).

In some embodiments, the nucleic acid-lipid particles described herein (e.g., SNALP) are administered by one of the following routes of administration: oral, intranasal, intravenous, intraperitoneal, intramuscular, intra-articular, intralesional, intratracheal, subcutaneous, and intradermal. In particular embodiments, the nucleic acid-lipid particles are administered systemically, e.g., via enteral or parenteral routes of administration.

In particular embodiments, the nucleic acid-lipid particles of the invention (e.g., SNALP) can preferentially deliver a payload such as an interfering RNA (e.g., siRNA) to the liver as compared to other tissues, e.g., for the treatment of a liver disease or disorder such as dyslipidemia or atherosclerosis.

In certain aspects, the present invention provides methods for silencing APOB, APOC3, PCSK9, DGAT1, and/or DGAT2 gene expression in a mammal (e.g., human) in need thereof, the method comprising administering to the mammal a therapeutically effective amount of a nucleic acid-lipid particle (e.g., a SNALP formulation) comprising one or more interfering RNAs (e.g., siRNAs) described herein (e.g., one or more siRNAs targeting the APOB, APOC3, PCSK9, DGAT1, and/or DGAT2 gene). In some embodiments, administration of nucleic acid-lipid particles comprising one or more siRNAs described herein reduces liver mRNA levels of the target gene (e.g., in a human or in an animal model such as a mouse model or monkey model) by at least about 5%, 10%, 15%, 20%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% (or any range therein) relative to liver mRNA levels of the target gene detected in the absence of the siRNA (e.g., buffer control or irrelevant siRNA control). In other embodiments, administration of nucleic acid-lipid particles comprising one or more siRNAs described herein reduces liver mRNA levels of the target gene (e.g., in a human or in an animal model such as a mouse model or monkey model) for at least about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 days or more (or any range therein) relative to a negative control such as, e.g., a buffer control or an irrelevant siRNA control.

In certain other aspects, the present invention provides methods for treating, preventing, reducing the risk or likelihood of developing (e.g., reducing the susceptibility to), delaying the onset of, and/or ameliorating one or more symptoms associated with a lipid disorder in a mammal (e.g., human) in need thereof, the method comprising administering to the mammal a therapeutically effective amount of a nucleic acid-lipid particle (e.g., a SNALP formulation) comprising one or more interfering RNA molecules (e.g., siRNAs) described herein (e.g., one or more siRNAs targeting the APOB, APOC3, PCSK9, DGAT1, and/or DGAT2 gene). Non-limiting examples of lipid disorders are described above and include dyslipidemia and atherosclerosis.

In a related aspect, the present invention provides a method for treating and/or ameliorating one or more symptoms associated with atherosclerosis or a dyslipidemia such as hyperlipidemia (e.g., elevated levels of triglycerides and/or cholesterol) in a mammal (e.g., human) in need thereof (e.g., a mammal with atheromatous plaques, elevated triglyceride levels, and/or elevated cholesterol levels), the method comprising administering to the mammal a therapeutically effective amount of a nucleic acid-lipid particle (e.g., a SNALP formulation) comprising one or more interfering RNAs (e.g., siRNAs) described herein (e.g., one or more siRNAs targeting the APOB, APOC3, PCSK9, DGAT1, and/or DGAT2 gene). In some embodiments, administration of nucleic acid-lipid particles comprising one or more siRNA molecules described herein reduces the level of atherosclerosis (e.g., decreases the size and/or number of atheromatous plaques or lesions) or blood (e.g., serum and/or plasma) triglyceride and/or cholesterol levels (e.g., in a human or in an animal model such as a mouse model or monkey model) by at least about 5%, 10%, 15%, 20%, 25%, 30%, 35%, 40%, 45%, 50%, 55%, 60%, 65%, 70%, 75%, 80%, 85%, 90%, 95%, or 100% (or any range therein) relative to the level of atherosclerosis, blood triglyceride levels, or blood cholesterol levels detected in the absence of the siRNA (e.g., buffer control or irrelevant siRNA control).

In another related aspect, the present invention provides a method for reducing the risk or likelihood of developing (e.g., reducing the susceptibility to) atherosclerosis or a dyslipidemia such as hyperlipidemia (e.g., elevated levels of triglycerides and/or cholesterol) in a mammal (e.g., human) at risk of developing atherosclerosis or dyslipidemia, the method comprising administering to the mammal a therapeutically effective amount of a nucleic acid-lipid particle (e.g., a SNALP formulation) comprising one or more interfering RNAs (e.g., siRNAs) described herein (e.g., one or more siRNAs targeting the APOB, APOC3, PCSK9, DGAT1, and/or DGAT2 gene). In some embodiments, administration of nucleic acid-lipid particles comprising one or more siRNA molecules described herein reduces the risk or likelihood of developing atherosclerosis or dyslipidemia (e.g., in a human or in an animal model such as a mouse model or monkey model) by at least about 5%, 10%, 15%, 20%, 25%, 30%, 35%, 40%, 45%, 50%, 55%, 60%, 65%, 70%, 75%, 80%, 85%, 90%, 95%, or 100% (or any range therein) relative to the risk or likelihood of developing atherosclerosis or dyslipidemia in the absence of the siRNA (e.g., buffer control or irrelevant siRNA control).

In yet another related aspect, the present invention provides a method for preventing or delaying the onset of atherosclerosis or a dyslipidemia such as hyperlipidemia (e.g., elevated levels of triglycerides and/or cholesterol) in a mammal (e.g., human) at risk of developing atherosclerosis or dyslipidemia, the method comprising administering to the mammal a therapeutically effective amount of a nucleic acid-lipid particle (e.g., a SNALP formulation) comprising one or more interfering RNAs (e.g., siRNAs) described herein (e.g., one or more siRNAs targeting the APOB, APOC3, PCSK9, DGAT1, and/or DGAT2 gene).

In a further related aspect, the present invention provides a method for lowering or reducing cholesterol levels in a mammal (e.g., human) in need thereof (e.g., a mammal with elevated blood cholesterol levels), the method comprising administering to the mammal a therapeutically effective amount of a nucleic acid-lipid particle (e.g., a SNALP formulation) comprising one or more interfering RNAs (e.g., siRNAs) described herein (e.g., one or more siRNAs targeting the APOB, APOC3, PCSK9, DGAT1, and/or DGAT2 gene). In particular embodiments, administration of nucleic acid-lipid particles (e.g., SNALP) comprising one or more siRNA molecules described herein lowers or reduces blood (e.g., serum and/or plasma) cholesterol levels. In some embodiments, administration of nucleic acid-lipid particles (e.g., SNALP) comprising one or more siRNAs described herein reduces blood cholesterol levels (e.g., in a human or in an animal model such as a mouse model or monkey model) by at least about 5%, 10%, 15%, 20%, 25%, 30%, 35%, 40%, 45%, 50%, 55%, 60%, 65%, 70%, 75%, 80%, 85%, 90%, 95%, or 100% (or any range therein) relative to blood cholesterol levels detected in the absence of the siRNA (e.g., buffer control or irrelevant siRNA control). In certain instances, administration of nucleic acid-lipid particles (e.g., SNALP) comprising one or more siRNA molecules described herein elevates HDL-cholesterol levels and/or reduces LDL-cholesterol levels.

In another related aspect, the present invention provides a method for lowering or reducing triglyceride levels in a mammal (e.g., human) in need thereof (e.g., a mammal with elevated blood triglyceride levels), the method comprising administering to the mammal a therapeutically effective amount of a nucleic acid-lipid particle (e.g., a SNALP formulation) comprising one or more interfering RNAs (e.g., siRNAs) described herein (e.g., one or more siRNAs targeting the APOB, APOC3, PCSK9, DGAT1, and/or DGAT2 gene). In particular embodiments, administration of nucleic acid-lipid particles (e.g., SNALP) comprising one or more siRNA molecules described herein lowers or reduces blood (e.g., serum and/or plasma) triglyceride levels. In certain embodiments, administration of nucleic acid-lipid particles comprising one or more siRNA molecules described herein reduces blood triglyceride levels (e.g., in a human or in an animal model such as a mouse model or monkey model) by at least about 5%, 10%, 15%, 20%, 25%, 30%, 35%, 40%, 45%, 50%, 55%, 60%, 65%, 70%, 75%, 80%, 85%, 90%, 95%, or 100% (or any range therein) relative to blood triglyceride levels detected in the absence of the siRNA (e.g., buffer control or irrelevant siRNA control). In other embodiments, administration of nucleic acid-lipid particles of the invention lowers or reduces hepatic (i.e., liver) triglyceride levels.

In an additional related aspect, the present invention provides a method for lowering or reducing glucose levels in a mammal (e.g., human) in need thereof (e.g., a mammal with elevated blood glucose levels), the method comprising administering to the mammal a therapeutically effective amount of a nucleic acid-lipid particle (e.g., a SNALP formulation) comprising one or more interfering RNAs (e.g., siRNAs) described herein (e.g., one or more siRNAs targeting the APOB, APOC3, PCSK9, DGAT1, and/or DGAT2 gene). In particular embodiments, administration of nucleic acid-lipid particles (e.g., SNALP) comprising one or more siRNAs described herein lowers or reduces blood (e.g., serum and/or plasma) glucose levels. In some embodiments, administration of nucleic acid-lipid particles comprising one or more siRNAs described herein reduces blood glucose levels (e.g., in a human or in an animal model such as a mouse model or monkey model) by at least about 5%, 10%, 15%, 20%, 25%, 30%, 35%, 40%, 45%, 50%, 55%, 60%, 65%, 70%, 75%, 80%, 85%, 90%, 95%, or 100% (or any range therein) relative to blood glucose levels detected in the absence of the siRNA (e.g., buffer control or irrelevant siRNA control).

Lipid Particles

The present invention provides lipid particles comprising one or more of the cationic (amino) lipids of Formulas I-III as described herein. In some embodiments, the lipid particles of the invention further comprise one or more non-cationic lipids. In other embodiments, the lipid particles further comprise one or more conjugated lipids capable of reducing or inhibiting particle aggregation. In additional embodiments, the lipid particles further comprise one or more therapeutic nucleic acids (e.g., interfering RNA such as siRNA).

Lipid particles include, but are not limited to, lipid vesicles such as liposomes. As used herein, a lipid vesicle includes a structure having lipid-containing membranes enclosing an aqueous interior. In particular embodiments, lipid vesicles comprising one or more of the cationic lipids described herein are used to encapsulate nucleic acids within the lipid vesicles. In other embodiments, lipid vesicles comprising one or more of the cationic lipids described herein are complexed with nucleic acids to form lipoplexes.

The lipid particles of the present invention preferably comprise an active agent or therapeutic agent such as a therapeutic nucleic acid (e.g., an interfering RNA such as siRNA), a cationic lipid of Formulas a non-cationic lipid, and a conjugated lipid that inhibits aggregation of particles. In some embodiments, the therapeutic nucleic acid is fully encapsulated within the lipid portion of the lipid particle such that the therapeutic nucleic acid in the lipid particle is resistant in aqueous solution to enzymatic degradation, e.g., by a nuclease or protease. In other embodiments, the lipid particles described herein are substantially non-toxic to mammals such as humans. The lipid particles of the invention typically have a mean diameter of from about 30 nm to about 150 nm, from about 40 nm to about 150 nm, from about 50 nm to about 150 nm, from about 60 nm to about 130 nm, from about 70 nm to about 110 nm, or from about 70 to about 90 nm. The lipid particles of the invention also typically have a lipid:therapeutic agent (e.g., lipid:nucleic acid) ratio (mass/mass ratio) of from about 1:1 to about 100:1, from about 1:1 to about 50:1, from about 2:1 to about 25:1, from about 3:1 to about 20:1, from about 5:1 to about 15:1, or from about 5:1 to about 10:1.

In preferred embodiments, the lipid particles of the invention are serum-stable nucleic acid-lipid particles (SNALP) which comprise an interfering RNA (e.g., dsRNA such as siRNA, Dicer-substrate dsRNA, shRNA, aiRNA, and/or miRNA), a cationic lipid (e.g., one or more cationic lipids of Formulas I-III or salts thereof as set forth herein), a non-cationic lipid (e.g., mixtures of one or more phospholipids and cholesterol), and a conjugated lipid that inhibits aggregation of the particles (e.g., one or more PEG-lipid conjugates). The SNALP may comprise at least 1, 2, 3, 4, 5, 6, 7, 8, 9, 10, or more unmodified and/or modified interfering RNA (e.g., siRNA) that target one or more of the genes described herein. Nucleic acid-lipid particles and their method of preparation are described in, e.g., U.S. Pat. Nos. 5,753,613; 5,785,992; 5,705,385; 5,976,567; 5,981,501; 6,110,745; and 6,320,017; and PCT Publication No. WO 96/40964, the disclosures of which are each herein incorporated by reference in their entirety for all purposes.

In the nucleic acid-lipid particles of the invention, the nucleic acid may be fully encapsulated within the lipid portion of the particle, thereby protecting the nucleic acid from nuclease degradation. In preferred embodiments, a SNALP comprising a nucleic acid such as an interfering RNA is fully encapsulated within the lipid portion of the particle, thereby protecting the nucleic acid from nuclease degradation. In certain instances, the nucleic acid in the SNALP is not substantially degraded after exposure of the particle to a nuclease at 37° C. for at least about 20, 30, 45, or 60 minutes. In certain other instances, the nucleic acid in the SNALP is not substantially degraded after incubation of the particle in serum at 37° C. for at least about 30, 45, or 60 minutes or at least about 2, 3, 4, 5, 6, 7, 8, 9, 10, 12, 14, 16, 18, 20, 22, 24, 26, 28, 30, 32, 34, or 36 hours. In other embodiments, the nucleic acid is complexed with the lipid portion of the particle. One of the benefits of the formulations of the present invention is that the nucleic acid-lipid particle compositions are substantially non-toxic to mammals such as humans.

The term "fully encapsulated" indicates that the nucleic acid in the nucleic acid-lipid particle is not significantly degraded after exposure to serum or a nuclease assay that would significantly degrade free DNA or RNA. In a fully encapsulated system, preferably less than about 25% of the nucleic acid in the particle is degraded in a treatment that would normally degrade 100% of free nucleic acid, more preferably less than about 10%, and most preferably less than about 5% of the nucleic acid in the particle is degraded. "Fully encapsulated" also indicates that the nucleic acid-lipid particles are serum-stable, that is, that they do not rapidly decompose into their component parts upon in vivo administration.

In the context of nucleic acids, full encapsulation may be determined by performing a membrane-impermeable fluorescent dye exclusion assay, which uses a dye that has enhanced fluorescence when associated with nucleic acid. Specific dyes such as OliGreen® and RiboGreen® (Invitrogen Corp.; Carlsbad, Calif.) are available for the quantitative determination of plasmid DNA, single-stranded deoxyribonucleotides, and/or single- or double-stranded ribonucleotides. Encapsulation is determined by adding the dye to a liposomal formulation, measuring the resulting fluorescence, and comparing it to the fluorescence observed upon addition of a small amount of nonionic detergent. Detergent-mediated disruption of the liposomal bilayer releases the encapsulated nucleic acid, allowing it to interact with the membrane-impermeable dye. Nucleic acid encapsulation may be calculated as $E=(I_o-I)/I_o$, where I and $I_o$ refer to the fluorescence intensities before and after the addition of detergent (see, Wheeler et al., Gene Ther., 6:271-281 (1999)).

In other embodiments, the present invention provides a nucleic acid-lipid particle (e.g., SNALP) composition comprising a plurality of nucleic acid-lipid particles.

In some instances, the SNALP composition comprises nucleic acid that is fully encapsulated within the lipid portion of the particles, such that from about 30% to about 100%, from about 40% to about 100%, from about 50% to about 100%, from about 60% to about 100%, from about 70% to about 100%, from about 80% to about 100%, from about 90% to about 100%, from about 30% to about 95%, from about 40% to about 95%, from about 50% to about 95%, from about 60% to about 95%, from about 70% to about 95%, from about 80% to about 95%, from about 85% to about 95%, from about 90% to about 95%, from about 30% to about 90%, from about 40% to about 90%, from about 50% to about 90%, from about 60% to about 90%, from about 70% to about 90%, from about 80% to about 90%, or at least about 30%, 35%, 40%, 45%, 50%, 55%, 60%, 65%, 70%, 75%, 80%, 85%, 90%, 91%, 92%, 93%, 94%, 95%, 96%, 97%, 98%, or 99% (or any fraction thereof or range therein) of the particles have the nucleic acid encapsulated therein.

In other instances, the SNALP composition comprises nucleic acid that is fully encapsulated within the lipid portion of the particles, such that from about 30% to about 100%, from about 40% to about 100%, from about 50% to about 100%, from about 60% to about 100%, from about 70% to about 100%, from about 80% to about 100%, from about 90% to about 100%, from about 30% to about 95%, from about 40% to about 95%, from about 50% to about 95%, from about 60% to about 95%, from about 70% to about 95%, from about 80% to about 95%, from about 85% to about 95%, from about 90% to about 95%, from about 30% to about 90%, from about 40% to about 90%, from about 50% to about 90%, from about 60% to about 90%, from about 70% to about 90%, from about 80% to about 90%, or at least about 30%, 35%, 40%, 45%, 50%, 55%, 60%, 65%, 70%, 75%, 80%, 85%, 90%, 91%, 92%, 93%, 94%, 95%, 96%, 97%, 98%, or 99% (or any fraction thereof or range therein) of the input nucleic acid is encapsulated in the particles.

Depending on the intended use of the lipid particles of the invention, the proportions of the components can be varied and the delivery efficiency of a particular formulation can be measured using, e.g., an endosomal release parameter (ERP) assay.

In particular embodiments, the present invention provides a lipid particle (e.g., SNALP) composition comprising a plurality of lipid particles described herein and an antioxidant. In certain instances, the antioxidant in the lipid particle composition reduces, prevents, and/or inhibits the degradation of a cationic lipid (e.g., a polyunsaturated cationic lipid) present in the lipid particle. In instances wherein the active agent is a therapeutic nucleic acid such as an interfering RNA (e.g., siRNA), the antioxidant in the lipid particle composition reduces, prevents, and/or inhibits the degradation of the nucleic acid payload, e.g., by reducing, preventing, and/or inhibiting the oxidation of the cationic lipid, by reducing, preventing, and/or inhibiting the degradation of the nucleic acid payload, by reducing, preventing, and/or inhibiting the desulfurization of a phosphorothioate (PS)-modified nucleic acid payload, and/or by stabilizing both the lipid and nucleic acid components.

Examples of antioxidants include, but are not limited to, metal chelators (e.g., ethylenediaminetetraacetic acid (EDTA), citrate, and the like), primary antioxidants (e.g., vitamin E isomers such as α-tocopherol or a salt thereof, butylated hydroxyanisole (BHA), butylhydroxytoluene (BHT), tert-butylhydroquinone (TBHQ), and the like), secondary antioxidants (e.g., ascorbic acid, ascorbyl palmitate, cysteine, glutathione, α-lipoic acid, and the like), salts thereof, and mixtures thereof. If needed, the antioxidant is typically present in an amount sufficient to prevent, inhibit, and/or reduce the degradation of the cationic lipid and/or active agent present in the lipid particle. In particular embodiments, the antioxidant comprises EDTA or a salt thereof (e.g., from about 20 mM to about 100 mM), alone or in combination with a primary antioxidant such as α-tocopherol or a salt thereof (e.g., from about 0.02 mol % to about 0.5 mol %) and/or secondary antioxidant such as ascorbyl palmitate or a salt thereof (e.g., from about 0.02 mol % to about 5.0 mol %). An antioxidant such as EDTA may be included at any step or at multiple steps in the lipid particle formation process described in Section V (e.g., prior to, during, and/or after lipid particle formation).

Additional embodiments related to methods of preventing the degradation of cationic lipids and/or active agents (e.g., therapeutic nucleic acids) present in lipid particles, compositions comprising lipid particles stabilized by these methods, methods of making these lipid particles, and methods of delivering and/or administering these lipid particles are described in PCT Application No. PCT/CA2010/001919, filed Dec. 1, 2010, the disclosure of which is herein incorporated by reference in its entirety for all purposes.

In one aspect, the lipid particles of the invention may include a targeting lipid. In some embodiments, the targeting lipid comprises a GalNAc moiety (i.e., an N-galactosamine moiety). As a non-limiting example, a targeting lipid comprising a GalNAc moiety can include those described in U.S. application Ser. No. 12/328,669, filed Dec. 4, 2008, the disclosure of which is herein incorporated by reference in its entirety for all purposes. A targeting lipid can also include any other lipid (e.g., targeting lipid) known in the art, for example, as described in U.S. application Ser. No. 12/328,669 or PCT Publication No. WO 2008/042973, the contents of each of which are incorporated herein by reference in their entirety for all purposes. In some embodiments, the targeting lipid includes a plurality of GalNAc moieties, e.g., two or three GalNAc moieties. In some embodiments, the targeting lipid contains a plurality, e.g., two or three N-acetylgalactosamine (GalNAc) moieties. In some embodiments, the lipid in the targeting lipid is 1,2-Di-O-hexadecyl-sn-glyceride (i.e., DSG). In some embodiments, the targeting lipid includes a PEG moiety (e.g., a PEG moiety having a molecular weight of at least about 500 Da, such as about 1000 Da, 1500 Da, 2000 Da or greater), for example, the targeting moiety is connected to the lipid via a PEG moiety. Examples of GalNAc targeting lipids include, but are not limited to, (GalNAc)$_3$-PEG-DSG, (GalNAc)$_3$-PEG-LCO, and mixtures thereof.

In some embodiments, the targeting lipid includes a folate moiety. For example, a targeting lipid comprising a folate moiety can include those described in U.S. application Ser. No. 12/328,669, the disclosure of which is herein incorporated by reference in its entirety for all purposes. Examples of folate targeting lipids include, but are not limited to, 1,2-distearoyl-sn-glycero-3-phosphoethanolamine-N-[folate (polyethylene glycol)-2000] (ammonium salt) (Folate-PEG-DSPE), Folate-PEG2000-DSG, Folate-PEG3400-DSG, and mixtures thereof.

In another aspect, the lipid particles of the invention may further comprise one or more apolipoproteins. As used herein, the term "apolipoprotein" or "lipoprotein" refers to apolipoproteins known to those of skill in the art and variants and fragments thereof and to apolipoprotein agonists, analogues, or fragments thereof described in, e.g., PCT Publication No. WO 2010/0088537, the disclosure of which is herein incorporated by reference in its entirety for all purposes. Suitable apolipoproteins include, but are not limited to, ApoA-I, ApoA-II, ApoA-IV, ApoA-V, and ApoE (e.g., ApoE2, ApoE3, etc.), and active polymorphic forms, isoforms, variants, and mutants as well as fragments or truncated forms thereof. Isolated ApoE and/or active fragments and polypeptide analogues thereof, including recombinantly produced forms thereof, are described in U.S. Pat. Nos. 5,672,685; 5,525,472; 5,473,039; 5,182,364; 5,177,189; 5,168,045; and 5,116,739, the disclosures of which are herein incorporated by reference in their entirety for all purposes.

A. Therapeutic Nucleic Acids

The lipid particles of the present invention are associated with a nucleic acid, resulting in a nucleic acid-lipid particle (e.g., SNALP). In some embodiments, the nucleic acid is fully encapsulated in the lipid particle. As used herein, the term "nucleic acid" includes any oligonucleotide or polynucleotide, with fragments containing up to 60 nucleotides generally termed oligonucleotides, and longer fragments termed polynucleotides. In particular embodiments, oligonucleotides of the invention are from about 15 to about 60 nucleotides in length. Nucleic acid may be administered alone in the lipid particles of the invention, or in combination (e.g., co-administered) with lipid particles of the invention comprising peptides, polypeptides, or small molecules such as conventional drugs. Similarly, when used to diseases and disorders involving hypercholesterolemia, the nucleic acid, such as the interfering RNA, can be administered alone or co-administered (i.e., concurrently or consecutively) with conventional agents used to treat, e.g., a disease or disorder involving hypercholesterolemia. Such agents include statins such as, e.g., Lipitor®, Mevacor®, Zocor®, Lescol®, Crestor®, and Advicor®.

In the context of this invention, the terms "polynucleotide" and "oligonucleotide" refer to a polymer or oligomer of nucleotide or nucleoside monomers consisting of naturally-occurring bases, sugars and intersugar (backbone) linkages. The terms "polynucleotide" and "oligonucleotide" also include polymers or oligomers comprising non-naturally occurring monomers, or portions thereof, which function similarly. Such modified or substituted oligonucleotides are often preferred over native forms because of properties such as, for example, enhanced cellular uptake, reduced immunogenicity, and increased stability in the presence of nucleases.

Oligonucleotides are generally classified as deoxyribooligonucleotides or ribooligonucleotides. A deoxyribooligonucleotide consists of a 5-carbon sugar called deoxyribose joined covalently to phosphate at the 5' and 3' carbons of this sugar to form an alternating, unbranched polymer. A ribooligonucleotide consists of a similar repeating structure where the 5-carbon sugar is ribose.

The nucleic acid that is present in a nucleic acid-lipid particle according to this invention includes any form of nucleic acid that is known. The nucleic acids used herein can be single-stranded DNA or RNA, or double-stranded DNA or RNA, or DNA-RNA hybrids. In preferred embodiments, the nucleic acids are double-stranded RNA. Examples of double-stranded RNA are described herein and include, e.g., siRNA and other RNAi agents such as Dicer-substrate dsRNA, shRNA, aiRNA, and pre-miRNA. In other preferred embodiments, the nucleic acids are single-stranded nucleic acids. Single-stranded nucleic acids include, e.g., antisense oligonucleotides, ribozymes, mature miRNA, and triplex-forming oligonucleotides.

Nucleic acids of the invention may be of various lengths, generally dependent upon the particular form of nucleic acid. For example, in particular embodiments, plasmids or genes may be from about 1,000 to about 100,000 nucleotide residues in length. In particular embodiments, oligonucleotides may range from about 10 to about 100 nucleotides in length. In various related embodiments, oligonucleotides, both single-stranded, double-stranded, and triple-stranded, may range in length from about 10 to about 60 nucleotides, from about 15 to about 60 nucleotides, from about 20 to about 50 nucleotides, from about 15 to about 30 nucleotides, or from about 20 to about 30 nucleotides in length.

In particular embodiments, an oligonucleotide (or a strand thereof) of the invention specifically hybridizes to or is complementary to a target polynucleotide sequence. The terms "specifically hybridizable" and "complementary" as used herein indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. In preferred embodiments, an oligonucleotide is specifically hybridizable when binding of the oligonucleotide to the target sequence interferes with the normal function of the target sequence to cause a loss of utility or expression there from, and there is a sufficient degree of complementarity to avoid non-specific binding of the oligonucleotide to non-target sequences under conditions in which specific binding is desired, i.e., under physiological conditions in the case of in vivo assays or therapeutic treatment, or, in the case of in vitro assays, under conditions in which the assays are conducted. Thus, the oligonucleotide may include 1, 2, 3, or more base substitutions as compared to the region of a gene or mRNA sequence that it is targeting or to which it specifically hybridizes.

a) siRNA

The siRNA component of the nucleic acid-lipid particles of the present invention is capable of silencing the expression of a target gene of interest, such as APOB, APOC3, PCSK9, DGAT1, DGAT2, or combinations thereof. Each strand of the siRNA duplex is typically about 15 to about 60 nucleotides in length, preferably about 15 to about 30 nucleotides in length. In certain embodiments, the siRNA comprises at least one modified nucleotide. The modified siRNA is generally less immunostimulatory than a corresponding unmodified siRNA sequence and retains RNAi activity against the target gene of interest. In some embodiments, the modified siRNA contains at least one 2'OMe purine or pyrimidine nucleotide such as a 2'OMe-guanosine, 2'OMe-uridine, 2'OMe-adenosine, and/or 2'OMe-cytosine nucleotide. The modified nucleotides can be present in one strand (i.e., sense or antisense) or both strands of the siRNA. In some preferred embodiments, one or more of the uridine and/or guanosine nucleotides are modified (e.g., 2'OMe-modified) in one strand (i.e., sense or antisense) or both strands of the siRNA. In these embodiments, the modified siRNA can further comprise one or more modified (e.g., 2'OMe-modified) adenosine and/or modified (e.g., 2'OMe-modified) cytosine nucleotides. In other preferred embodiments, only uridine and/or guanosine nucleotides are modified (e.g., 2'OMe-modified) in one strand (i.e., sense or antisense) or both strands of the siRNA. The siRNA sequences may have overhangs (e.g., 3' or 5' overhangs as described in Elbashir et al., *Genes Dev.*, 15:188 (2001) or Nykanen et al., *Cell*, 107:309 (2001)), or may lack overhangs (i.e., have blunt ends).

In particular embodiments, the selective incorporation of modified nucleotides such as 2'OMe uridine and/or guanosine nucleotides into the double-stranded region of either or both strands of the siRNA reduces or completely abrogates the immune response to that siRNA molecule. In certain instances, the immunostimulatory properties of specific siRNA sequences and their ability to silence gene expression can be balanced or optimized by the introduction of minimal and selective 2'OMe modifications within the double-stranded region of the siRNA duplex. This can be achieved at therapeutically viable siRNA doses without cytokine induction, toxicity, and off-target effects associated with the use of unmodified siRNA.

The modified siRNA generally comprises from about 1% to about 100% (e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, or 100%) modified nucleotides in the double-stranded region of the siRNA duplex. In certain embodiments, one, two, three, four, five, six, seven, eight, nine, ten, or more of the nucleotides in the double-stranded region of the siRNA comprise modified nucleotides. In certain other embodiments, some or all of the modified nucleotides in the double-stranded region of the siRNA are 1, 2, 3, 4, 5, 6, 7, 8, 9, 10, or more nucleotides apart from each other. In one preferred embodiment, none of the modified nucleotides in the double-stranded region of the siRNA are adjacent to each other (e.g., there is a gap of at least 1, 2, 3, 4, 5, 6, 7, 8, 9, or 10 unmodified nucleotides between each modified nucleotide).

In some embodiments, less than about 50% (e.g., less than about 49%, 48%, 47%, 46%, 45%, 44%, 43%, 42%, 41%, 40%, 39%, 38%, 37%, or 36%, preferably less than about 35%, 34%, 33%, 32%, 31%, or 30%) of the nucleotides in the double-stranded region of the siRNA comprise modified (e.g., 2'OMe) nucleotides. In one aspect of these embodiments, less than about 50% of the uridine and/or guanosine nucleotides in the double-stranded region of one or both strands of the siRNA are selectively (e.g., only) modified. In another aspect of these embodiments, less than about 50% of the nucleotides in the double-stranded region of the siRNA comprise 2'OMe nucleotides, wherein the siRNA comprises 2'OMe nucleotides in both strands of the siRNA, wherein the siRNA comprises at least one 2'OMe-guanosine nucleotide and at least one 2'OMe-uridine nucleotide, and wherein 2'OMe-guanosine nucleotides and 2'OMe-uridine nucleotides are the only 2'OMe nucleotides present in the double-stranded region. In yet another aspect of these embodiments, less than about 50% of the nucleotides in the double-stranded region of the siRNA comprise 2'OMe nucleotides, wherein the siRNA comprises 2'OMe nucleotides in both strands of the modified siRNA, wherein the siRNA comprises 2'OMe nucleotides selected from the group consisting of 2'OMe-guanosine nucleotides, 2'OMe-uridine nucleotides, 2'OMe-adenosine nucleotides, and mixtures thereof, and wherein the siRNA does not comprise 2'OMe-cytosine nucleotides in the double-stranded region. In a further aspect of these embodiments, less than about 50% of the nucleotides in the double-stranded region of the siRNA comprise 2'OMe nucleotides, wherein the siRNA comprises 2'OMe nucleotides in both strands of the siRNA, wherein the siRNA comprises at least one 2'OMe-guanosine nucleotide and at least one 2'OMe-uridine nucleotide, and wherein the siRNA does not comprise 2'OMe-cytosine nucleotides in the double-stranded region. In another aspect of these embodiments, less than about 50% of the nucleotides in the double-stranded region of the siRNA comprise 2' OMe nucleotides, wherein the siRNA comprises 2'OMe nucleotides in both strands of the modified siRNA, wherein the siRNA comprises 2'OMe nucleotides selected from the group consisting of 2'OMe-guanosine nucleotides, 2'OMe-uridine nucleotides, 2'OMe-adenosine nucleotides, and mixtures thereof, and wherein the 2'OMe nucleotides in the double-stranded region are not adjacent to each other.

In other embodiments, from about 1% to about 50% (e.g., from about 5%-50%, 10%-50%, 15%-50%, 20%-50%, 25%-50%, 30%-50%, 35%-50%, 40%-50%, 45%-50%, 5%-45%, 10%-45%, 15%-45%, 20%-45%, 25%-45%, 30%-45%, 35%-45%, 40%-45%, 5%-40%, 10%-40%, 15%-40%, 20%-40%, 25%-40%, 25%-39%, 25%-38%, 25%-37%, 25%-36%, 26%-39%, 26%-38%, 26%-37%, 26%-36%, 27%-39%, 27%-38%, 27%-37%, 27%-36%, 28%-39%, 28%-38%, 28%-37%, 28%-36%, 29%-39%, 29%-38%, 29%-37%, 29%-36%, 30%-40%, 30%-39%, 30%-38%, 30%-37%, 30%-36%, 31%-39%, 31%-38%, 31%-37%, 31%-36%, 32%-39%, 32%-38%, 32%-37%, 32%-36%, 33%-39%, 33%-38%, 33%-37%, 33%-36%, 34%-39%, 34%-38%, 34%-37%, 34%-36%, 35%-40%, 5%-35%, 10%-35%, 15%-35%, 20%-35%, 21%-35%, 22%-35%, 23%-35%, 24%-35%, 25%-35%, 26%-35%, 27%-35%, 28%-35%, 29%-35%, 30%-35%, 31%-35%, 32%-35%, 33%-35%, 34%-35%, 30%-34%, 31%-34%, 32%-34%, 33%-34%, 30%-33%, 31%-33%, 32%-33%, 30%-32%, 31%-32%, 25%-34%, 25%-33%, 25%-32%, 25%-31%, 26%-34%, 26%-33%, 26%-32%, 26%-31%, 27%-34%, 27%-33%, 27%-32%, 27%-31%, 28%-34%, 28%-33%, 28%-32%, 28%-31%, 29%-34%, 29%-33%, 29%-32%, 29%-31%, 5%-30%, 10%-30%, 15%-30%, 20%-34%, 20%-33%, 20%-32%, 20%-31%, 20%-30%, 21%-30%, 22%-30%, 23%-30%, 24%-30%, 25%-30%, 25%-29%, 25%-28%, 25%-27%, 25%-26%, 26%-30%, 26%-29%, 26%-28%, 26%-27%, 27%-30%, 27%-29%, 27%-28%, 28%-30%, 28%-29%, 29%-30%, 5%-25%, 10%-25%, 15%-25%, 20%-29%, 20%-28%, 20%-27%, 20%-26%, 20%-25%, 5%-20%, 10%-20%, 15%-20%, 5%-15%, 10%-15%, or 5%-10%) of the nucleotides in the double-stranded region of the siRNA comprise modified nucleotides. In one aspect of these embodiments, from about 1% to about 50% of the uridine and/or guanosine nucleotides in the double-stranded region of one or both strands of the siRNA are selectively (e.g., only) modified. In another aspect of these embodiments, from about 1% to about 50% of the nucleotides in the double-stranded region of the siRNA comprise 2'OMe nucleotides, wherein the siRNA comprises 2'OMe nucleotides in both strands of the siRNA, wherein the siRNA comprises at least one 2'OMe-guanosine nucleotide and at least one 2'OMe-uridine nucleotide, and wherein 2'OMe-guanosine nucleotides and 2'OMe-uridine nucleotides are the only 2'OMe nucleotides present in the double-stranded region. In yet another aspect of these embodiments, from about 1% to about 50% of the nucleotides in the double-stranded region of the siRNA comprise 2'OMe nucleotides, wherein the siRNA comprises 2'OMe nucleotides in both strands of the modified siRNA, wherein the siRNA comprises 2'OMe nucleotides selected from the group consisting of 2'OMe-guanosine nucleotides, 2'OMe-uridine nucleotides, 2'OMe-adenosine nucleotides, and mixtures thereof, and wherein the siRNA does not comprise 2'OMe-cytosine nucleotides in the double-stranded region. In a further aspect of these embodiments, from about 1% to about 50% of the nucleotides in the double-stranded region of the siRNA comprise 2'OMe nucleotides, wherein the siRNA comprises 2'OMe nucleotides in both strands of the siRNA, wherein the siRNA comprises at least one 2'OMe-guanosine nucleotide and at least one 2'OMe-uridine nucleotide, and wherein the siRNA does not comprise 2'OMe-cytosine nucleotides in the double-stranded region. In another aspect of these embodiments, from about 1% to about 50% of the nucleotides in the double-stranded region of the siRNA comprise 2'OMe nucleotides, wherein the siRNA comprises 2'OMe nucleotides in both strands of the modified siRNA, wherein the siRNA comprises 2'OMe nucleotides selected from the group consisting of 2'OMe-guanosine nucleotides, 2'OMe-uridine nucleotides, 2'OMe-adenosine nucleotides, and mixtures thereof, and wherein the 2'OMe nucleotides in the double-stranded region are not adjacent to each other.

Additional ranges, percentages, and patterns of modifications that may be introduced into siRNA are described in U.S. Patent Publication No. 20070135372, the disclosure of which is herein incorporated by reference in its entirety for all purposes.

Selection of siRNA Sequences

Suitable siRNA sequences can be identified using any means known in the art. Typically, the methods described in Elbashir et al., *Nature*, 411:494-498 (2001) and Elbashir et al., *EMBO J.*, 20:6877-6888 (2001) are combined with rational design rules set forth in Reynolds et al., *Nature Biotech.*, 22(3):326-330 (2004).

As a non-limiting example, the nucleotide sequence 3' of the AUG start codon of a transcript from the target gene of interest may be scanned for dinucleotide sequences (e.g., AA, NA, CC, GG, or UU, wherein N=C, G, Or U) (see, e.g., Elbashir et al., *EMBO J.*, 20:6877-6888 (2001)). The nucleotides immediately 3' to the dinucleotide sequences are identified as potential siRNA sequences (i.e., a target sequence or a sense strand sequence). Typically, the 19, 21, 23, 25, 27, 29, 31, 33, 35, or more nucleotides immediately 3' to the dinucleotide sequences are identified as potential siRNA sequences. In some embodiments, the dinucleotide sequence is an AA or NA sequence and the 19 nucleotides immediately 3' to the AA or NA dinucleotide are identified as potential siRNA sequences. siRNA sequences are usually spaced at different positions along the length of the target gene. To further enhance silencing efficiency of the siRNA sequences, potential siRNA sequences may be analyzed to identify sites that do not contain regions of homology to other coding sequences, e.g., in the target cell or organism. For example, a suitable siRNA sequence of about 21 base pairs typically will not have more than 16-17 contiguous base pairs of homology to coding sequences in the target cell or organism. If the siRNA sequences are to be expressed from an RNA Pol III promoter, siRNA sequences lacking more than 4 contiguous A's or T's are selected.

Once a potential siRNA sequence has been identified, a complementary sequence (i.e., an antisense strand sequence) can be designed. A potential siRNA sequence can also be analyzed using a variety of criteria known in the art. For example, to enhance their silencing efficiency, the siRNA sequences may be analyzed by a rational design algorithm to identify sequences that have one or more of the following features: (1) G/C content of about 25% to about 60% G/C; (2) at least 3 A/Us at positions 15-19 of the sense strand; (3) no internal repeats; (4) an A at position 19 of the sense strand; (5) an A at position 3 of the sense strand; (6) a U at position 10 of the sense strand; (7) no G/C at position 19 of the sense strand; and (8) no G at position 13 of the sense strand. siRNA design tools that incorporate algorithms that assign suitable values of each of these features and are useful for selection of siRNA can be found at, e.g., http://ihome.ust.hk/~bokcmho/siRNA/siRNA.html. One of skill in the art will appreciate that sequences with one or more of the foregoing characteristics may be selected for further analysis and testing as potential siRNA sequences.

Additionally, potential siRNA sequences with one or more of the following criteria can often be eliminated as siRNA: (1) sequences comprising a stretch of 4 or more of the same base in a row; (2) sequences comprising homopolymers of Gs (i.e., to reduce possible non-specific effects due to structural characteristics of these polymers; (3) sequences comprising triple base motifs (e.g., GGG, CCC, AAA, or TTT); (4) sequences comprising stretches of 7 or more G/Cs in a row; and (5) sequences comprising direct repeats of 4 or more bases within the candidates resulting in internal fold-back structures. However, one of skill in the art will appreciate that sequences with one or more of the foregoing characteristics may still be selected for further analysis and testing as potential siRNA sequences.

In some embodiments, potential siRNA sequences may be further analyzed based on siRNA duplex asymmetry as described in, e.g., Khvorova et al., *Cell*, 115:209-216 (2003); and Schwarz et al., *Cell*, 115:199-208 (2003). In other embodiments, potential siRNA sequences may be further analyzed based on secondary structure at the target site as described in, e.g., Luo et al., *Biophys. Res. Commun.*, 318: 303-310 (2004). For example, secondary structure at the target site can be modeled using the Mfold algorithm (available at http://mfoldburnet.edu.au/rna_form) to select siRNA sequences which favor accessibility at the target site where less secondary structure in the form of base-pairing and stem-loops is present.

Once a potential siRNA sequence has been identified, the sequence can be analyzed for the presence of any immunostimulatory properties, e.g., using an in vitro cytokine assay or an in vivo animal model. Motifs in the sense and/or antisense strand of the siRNA sequence such as GU-rich motifs (e.g., 5'-GU-3',5'-UGU-3',5'-GUGU-3',5'-UGUGU-3', etc.) can also provide an indication of whether the sequence may be immunostimulatory. Once an siRNA molecule is found to be immunostimulatory, it can then be modified to decrease its immunostimulatory properties as described herein. As a non-limiting example, an siRNA sequence can be contacted with a mammalian responder cell under conditions such that the cell produces a detectable immune response to determine whether the siRNA is an immunostimulatory or a non-immunostimulatory siRNA. The mammalian responder cell may be from a naïve mammal (i.e., a mammal that has not previously been in contact with the gene product of the siRNA sequence). The mammalian responder cell may be, e.g., a peripheral blood mononuclear cell (PBMC), a macrophage, and the like. The detectable immune response may comprise production of a cytokine or growth factor such as, e.g., TNF-α, IFN-α, IFN-γ, IL-6, IL-12, or a combination thereof. An siRNA molecule identified as being immunostimulatory can then be modified to decrease its immunostimulatory properties by replacing at least one of the nucleotides on the sense and/or antisense strand with modified nucleotides. For example, less than about 30% (e.g., less than about 30%, 25%, 20%, 15%, 10%, or 5%) of the nucleotides in the double-stranded region of the siRNA duplex can be replaced with modified nucleotides such as 2'OMe nucleotides. The modified siRNA can then be contacted with a mammalian responder cell as described above to confirm that its immunostimulatory properties have been reduced or abrogated.

Suitable in vitro assays for detecting an immune response include, but are not limited to, the double monoclonal antibody sandwich immunoassay technique of David et al. (U.S. Pat. No. 4,376,110); monoclonal-polyclonal antibody sandwich assays (Wide et al., in Kirkham and Hunter, eds., *Radioimmunoassay Methods*, E. and S. Livingstone, Edinburgh (1970)); the "Western blot" method of Gordon et al. (U.S. Pat. No. 4,452,901); immunoprecipitation of labeled ligand (Brown et al., *J. Biol. Chem.*, 255:4980-4983 (1980)); enzyme-linked immunosorbent assays (ELISA) as described, for example, by Raines et al., *J. Biol. Chem.*, 257:5154-5160 (1982); immunocytochemical techniques, including the use of fluorochromes (Brooks et al., *Clin. Exp. Immunol.*, 39:477 (1980)); and neutralization of activity (Bowen-Pope et al., *Proc. Natl. Acad. Sci. USA*, 81:2396-2400 (1984)). In addition to the immunoassays described above, a number of other immunoassays are available, including those described in U.S. Pat. Nos. 3,817,827; 3,850,752; 3,901,654; 3,935,074; 3,984,533; 3,996,345; 4,034,074; and 4,098,876. The disclosures of these references are herein incorporated by reference in their entirety for all purposes.

A non-limiting example of an in vivo model for detecting an immune response includes an in vivo mouse cytokine induction assay as described in, e.g., Judge et al., *Mol. Ther.*, 13:494-505 (2006). In certain embodiments, the assay that can be performed as follows: (1) siRNA can be administered by standard intravenous injection in the lateral tail vein; (2) blood can be collected by cardiac puncture about 6 hours after administration and processed as plasma for cytokine analysis; and (3) cytokines can be quantified using sandwich ELISA kits according to the manufacturer's instructions (e.g., mouse and human IFN-α (PBL Biomedical; Piscataway, N.J.); human IL-6 and TNF-α (eBioscience; San Diego, Calif.); and mouse IL-6, TNF-α, and IFN-γ (BD Biosciences; San Diego, Calif.)).

Monoclonal antibodies that specifically bind cytokines and growth factors are commercially available from multiple sources and can be generated using methods known in the art (see, e.g., Kohler et al., *Nature*, 256: 495-497 (1975) and Harlow and Lane, ANTIBODIES, A LABORATORY MANUAL, Cold Spring Harbor Publication, New York (1999)). Generation of monoclonal antibodies has been previously described and can be accomplished by any means known in the art (Buhring et al., in Hybridoma, Vol. 10, No. 1, pp. 77-78 (1991)). In some methods, the monoclonal antibody is labeled (e.g., with any composition detectable by spectroscopic, photochemical, biochemical, electrical, optical, or chemical means) to facilitate detection.

Generating siRNA Molecules siRNA can be provided in several forms including, e.g., as one or more isolated small-interfering RNA (siRNA) duplexes, as longer double-stranded RNA (dsRNA), or as siRNA or dsRNA transcribed from a transcriptional cassette in a DNA plasmid. In some embodiments, siRNA may be produced enzymatically or by partial/total organic synthesis, and modified ribonucleotides can be introduced by in vitro enzymatic or organic synthesis. In certain instances, each strand is prepared chemically. Methods of synthesizing RNA molecules are known in the art, e.g., the chemical synthesis methods as described in Verma and Eckstein (1998) or as described herein.

An RNA population can be used to provide long precursor RNAs, or long precursor RNAs that have substantial or complete identity to a selected target sequence can be used to make the siRNA. The RNAs can be isolated from cells or tissue, synthesized, and/or cloned according to methods well known to those of skill in the art. The RNA can be a mixed population (obtained from cells or tissue, transcribed from cDNA, subtracted, selected, etc.), or can represent a single target sequence. RNA can be naturally occurring (e.g., isolated from tissue or cell samples), synthesized in vitro (e.g., using T7 or SP6 polymerase and PCR products or a cloned cDNA), or chemically synthesized.

To form a long dsRNA, for synthetic RNAs, the complement is also transcribed in vitro and hybridized to form a dsRNA. If a naturally molting RNA population is used, the RNA complements are also provided (e.g., to form dsRNA for digestion by *E. coli* RNase III or Dicer), e.g., by transcribing cDNAs corresponding to the RNA population, or by using RNA polymerases. The precursor RNAs are then hybridized to form double stranded RNAs for digestion. The dsRNAs can be directly administered to a subject or can be digested in vitro prior to administration.

Methods for isolating RNA, synthesizing RNA, hybridizing nucleic acids, making and screening cDNA libraries, and performing PCR are well known in the art (see, e.g., Gubler and Hoffman, *Gene*, 25:263-269 (1983); Sambrook et al., supra; Ausubel et al., supra), as are PCR methods (see, U.S. Pat. Nos. 4,683,195 and 4,683,202; *PCR Protocols: A Guide to Methods and Applications* (Innis et al., eds, 1990)). Expression libraries are also well known to those of skill in the art.

Additional basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994). The disclosures of these references are herein incorporated by reference in their entirety for all purposes.

Preferably, siRNA are chemically synthesized. The oligonucleotides that comprise the siRNA molecules of the invention can be synthesized using any of a variety of techniques known in the art, such as those described in Usman et al., *J. Am. Chem. Soc.*, 109:7845 (1987); Scaringe et al., *Nucl. Acids Res.*, 18:5433 (1990); Wincott et al., *Nucl. Acids Res.*, 23:2677-2684 (1995); and Wincott et al., *Methods Mol. Bio.*, 74:59 (1997). The synthesis of oligonucleotides makes use of common nucleic acid protecting and coupling groups, such as dimethoxytrityl at the 5'-end and phosphoramidites at the 3'-end. As a non-limiting example, small scale syntheses can be conducted on an Applied Biosystems synthesizer using a 0.2 µmol scale protocol. Alternatively, syntheses at the 0.2 µmol scale can be performed on a 96-well plate synthesizer from Protogene (Palo Alto, Calif.). However, a larger or smaller scale of synthesis is also within the scope of this invention. Suitable reagents for oligonucleotide synthesis, methods for RNA deprotection, and methods for RNA purification are known to those of skill in the art.

siRNA molecules can also be synthesized via a tandem synthesis technique, wherein both strands are synthesized as a single continuous oligonucleotide fragment or strand separated by a cleavable linker that is subsequently cleaved to provide separate fragments or strands that hybridize to form the siRNA duplex. The linker can be a polynucleotide linker or a non-nucleotide linker. The tandem synthesis of siRNA can be readily adapted to both multiwell/multiplate synthesis platforms as well as large scale synthesis platforms employing batch reactors, synthesis columns, and the like. Alternatively, siRNA molecules can be assembled from two distinct oligonucleotides, wherein one oligonucleotide comprises the sense strand and the other comprises the antisense strand of the siRNA. For example, each strand can be synthesized separately and joined together by hybridization or ligation following synthesis and/or deprotection. In certain other instances, siRNA molecules can be synthesized as a single continuous oligonucleotide fragment, where the self-complementary sense and antisense regions hybridize to form an siRNA duplex having hairpin secondary structure.

Modifying siRNA Sequences

In certain aspects, siRNA molecules comprise a duplex having two strands and at least one modified nucleotide in the double-stranded region, wherein each strand is about 15 to about 60 nucleotides in length. Advantageously, the modified siRNA is less immunostimulatory than a corresponding unmodified siRNA sequence, but retains the capability of silencing the expression of a target sequence. In preferred embodiments, the degree of chemical modifications introduced into the siRNA molecule strikes a balance between reduction or abrogation of the immunostimulatory properties of the siRNA and retention of RNAi activity. As a non-limiting example, an siRNA molecule that targets a gene of interest can be minimally modified (e.g., less than about 30%, 25%, 20%, 15%, 10%, or 5% modified) at selective uridine and/or guanosine nucleotides within the siRNA duplex to eliminate the immune response generated by the siRNA while retaining its capability to silence target gene expression.

Examples of modified nucleotides suitable for use in the invention include, but are not limited to, ribonucleotides having a 2'-O-methyl (2'OMe), 2'-deoxy-2'-fluoro (2'F), 2'-deoxy, 5-C-methyl, 2'-O-(2-methoxyethyl) (MOE), 4'-thio, 2'-amino, or 2'-C-allyl group. Modified nucleotides having a Northern conformation such as those described in, e.g., Saenger, *Principles of Nucleic Acid Structure*, Springer-Verlag Ed. (1984), are also suitable for use in siRNA molecules. Such modified nucleotides include, without limitation, locked nucleic acid (LNA) nucleotides (e.g., 2'-O, 4'-C-methylene-(D-ribofuranosyl) nucleotides), 2'-O-(2-methoxyethyl) (MOE) nucleotides, 2'-methyl-thio-ethyl nucleotides, 2'-deoxy-2'-fluoro (2'F) nucleotides, 2'-deoxy-2'-chloro (2'Cl) nucleotides, and 2'-azido nucleotides. In certain instances, the siRNA molecules described herein include one or more G-clamp nucleotides. A G-clamp nucleotide refers to a modified cytosine analog wherein the modifications confer the ability to hydrogen bond both Watson-Crick and Hoogsteen faces of a complementary guanine nucleotide within a duplex (see, e.g., Lin et al., *J. Am. Chem. Soc.*, 120:8531-8532 (1998)). In addition, nucleotides having a nucleotide base analog such as, for example, C-phenyl, C-naphthyl, other aromatic derivatives, inosine, azole carboxamides, and nitroazole derivatives such as 3-nitropyrrole, 4-nitroindole, 5-nitroindole, and 6-nitroindole (see, e.g., Loakes, *Nucl. Acids Res.*, 29:2437-2447 (2001)) can be incorporated into siRNA molecules.

In certain embodiments, siRNA molecules may further comprise one or more chemical modifications such as terminal cap moieties, phosphate backbone modifications, and the like. Examples of terminal cap moieties include, without limitation, inverted deoxy abasic residues, glyceryl modifications, 4',5'-methylene nucleotides, 1-(β3-D-erythrofuranosyl) nucleotides, 4'-thio nucleotides, carbocyclic nucleotides, 1,5-anhydrohexitol nucleotides, L-nucleotides, α-nucleotides, modified base nucleotides, threo-pentofuranosyl nucleotides, acyclic 3',4'-seco nucleotides, acyclic 3,4-dihydroxybutyl nucleotides, acyclic 3,5-dihydroxypentyl nucleotides, 3'-3'-inverted nucleotide moieties, 3'-3'-inverted abasic moieties, 3'-2'-inverted nucleotide moieties, 3'-2'-inverted abasic moieties, 5'-5'-inverted nucleotide moieties, 5'-5'-inverted abasic moieties, 3'-5'-inverted deoxy abasic moieties, 5'-amino-alkyl phosphate, 1,3-diamino-2-propyl phosphate, 3-aminopropyl phosphate, 6-aminohexyl phosphate, 1,2-aminododecyl phosphate, hydroxypropyl phosphate, 1,4-butanediol phosphate, 3'-phosphoramidate, 5'-phosphoramidate, hexylphosphate, aminohexyl phosphate, 3'-phosphate, 5'-amino, 3'-phosphorothioate, 5'-phosphorothioate, phosphorodithioate, and bridging or non-bridging methylphosphonate or 5'-mercapto moieties (see, e.g., U.S. Pat. No. 5,998,203; Beaucage et al., *Tetrahedron* 49:1925 (1993)). Non-limiting examples of phosphate backbone modifications (i.e., resulting in modified internucleotide linkages) include phosphorothioate, phosphorodithioate, methylphosphonate, phosphotriester, morpholino, amidate, carbamate, carboxymethyl, acetamidate, polyamide, sulfonate, sulfonamide, sulfamate, formacetal, thioformacetal, and alkylsilyl substitutions (see, e.g., Hunziker et al., *Nucleic Acid Analogues: Synthesis and Properties*, in *Modern Synthetic Methods*, VCH, 331-417 (1995); Mesmaeker et al., *Novel Backbone Replacements for Oligonucleotides*, in *Carbohydrate Modifications in Antisense Research*, ACS, 24-39 (1994)). Such chemical modifications can occur at the 5'-end and/or 3'-end of the sense strand, antisense strand, or both strands of the siRNA. The disclosures of these references are herein incorporated by reference in their entirety for all purposes.

In some embodiments, the sense and/or antisense strand of the siRNA molecule can further comprise a 3'-terminal overhang having about 1 to about 4 (e.g., 1, 2, 3, or 4) 2'-deoxyribonucleotides, modified (e.g., 2'OMe) and/or unmodified uridine ribonucleotides, and/or any other combination of modified (e.g., 2'OMe) and unmodified nucleotides.

Additional examples of modified nucleotides and types of chemical modifications that can be introduced into siRNA molecules are described, e.g., in UK Patent No. GB 2,397,818 B and U.S. Patent Publication Nos. 20040192626, 20050282188, and 20070135372, the disclosures of which are herein incorporated by reference in their entirety for all purposes.

The siRNA molecules described herein can optionally comprise one or more non-nucleotides in one or both strands of the siRNA. As used herein, the term "non-nucleotide" refers to any group or compound that can be incorporated into a nucleic acid chain in the place of one or more nucleotide units, including sugar and/or phosphate substitutions, and allows the remaining bases to exhibit their activity. The group or compound is abasic in that it does not contain a commonly recognized nucleotide base such as adenosine, guanine, cytosine, uracil, or thymine and therefore lacks a base at the 1'-position.

In other embodiments, chemical modification of the siRNA comprises attaching a conjugate to the siRNA molecule. The conjugate can be attached at the 5' and/or 3'-end of the sense and/or antisense strand of the siRNA via a covalent attachment such as, e.g., a biodegradable linker. The conjugate can also be attached to the siRNA, e.g., through a carbamate group or other linking group (see, e.g., U.S. Patent Publication Nos. 20050074771, 20050043219, and 20050158727). In certain instances, the conjugate is a molecule that facilitates the delivery of the siRNA into a cell. Examples of conjugate molecules suitable for attachment to siRNA include, without limitation, steroids such as cholesterol, glycols such as polyethylene glycol (PEG), human serum albumin (HSA), fatty acids, carotenoids, terpenes, bile acids, folates (e.g., folk acid, folate analogs and derivatives thereof), sugars (e.g., galactose, galactosamine, N-acetyl galactosamine, glucose, mannose, fructose, fucose, etc.), phospholipids, peptides, ligands for cellular receptors capable of mediating cellular uptake, and combinations thereof (see, e.g., U.S. Patent Publication Nos. 20030130186, 20040110296, and 20040249178; U.S. Pat. No. 6,753,423). Other examples include the lipophilic moiety, vitamin, polymer, peptide, protein, nucleic acid, small molecule, oligosaccharide, carbohydrate cluster, intercalator, minor groove binder, cleaving agent, and cross-linking agent conjugate molecules described in U.S. Patent Publication Nos. 20050119470 and 20050107325. Yet other examples include the 2'-O-alkyl amine, 2'-O-alkoxyalkyl amine, polyamine, C5-cationic modified pyrimidine, cationic peptide, guanidinium group, amidininium group, cationic amino acid conjugate molecules described in U.S. Patent Publication No. 20050153337. Additional examples include the hydrophobic group, membrane active compound, cell penetrating compound, cell targeting signal, interaction modifier, and steric stabilizer conjugate molecules described in U.S. Patent Publication No. 20040167090. Further examples include the conjugate molecules described in U.S. Patent Publication No. 20050239739. The type of conjugate used and the extent of conjugation to the siRNA molecule can be evaluated for improved pharmacokinetic profiles, bioavailability, and/or stability of the siRNA while retaining RNAi activity. As such, one skilled in the art can screen siRNA molecules having various conjugates attached thereto to identify ones having improved properties and full RNAi activity using any of a variety of well-known in vitro cell culture or in vivo animal models. The disclosures of the above-described patent documents are herein incorporated by reference in their entirety for all purposes.

Target Genes

The siRNA component of the nucleic acid-lipid particles of the present invention (e.g., SNALP) can be used to downregulate or silence the translation (i.e., expression) of a gene of interest. As previously mentioned, the present invention is based, in part, on the discovery that the use of certain cationic (amino) lipids in nucleic acid-lipid particles provide advantages when the particles are used for the in vivo delivery of therapeutic nucleic acids, such as siRNA, into the liver of a mammal. In particular, it has been unexpectedly found that the nucleic acid-lipid particles of the present invention (i.e., SNALP formulations) containing at least one cationic lipid of Formulas I-III and at least one interfering RNA as disclosed herein show increased potency (i.e., increased silencing) and/or increased tolerability (e.g., decreased toxicity) when targeting a gene of interest in the liver, such as APOB, when compared to other nucleic acid-lipid particle compositions previously described. As such, genes of interest include, but are not limited to, genes associated with metabolic diseases and disorders (e.g., liver diseases and disorders).

Genes associated with metabolic diseases and disorders (e.g., disorders in which the liver is the target and liver diseases and disorders) include, but are not limited to, genes expressed in dyslipidemia, such as, e.g., apolipoprotein B (APOB) (Genbank Accession No. NM_000384), apolipoprotein CIII (APOC3) (Genbank Accession Nos. NM_000040 and NG_008949 REGION: 5001.8164), apolipoprotein E (APOE) (Genbank Accession Nos. NM_000041 and NG_007084 REGION: 5001.8612), proprotein convertase subtilisin/kexin type 9 (PCSK9) (Genbank Accession No. NM_174936), diacylglycerol O-acyltransferase type 1 (DGAT1) (Genbank Accession No. NM_012079), diacylglyerol O-acyltransferase type 2 (DGAT2) (Genbank Accession No. NM_032564), liver X receptors such as LXRα and LXRβ (Genbank Accession No. NM_007121), farnesoid X receptors (FXR) (Genbank Accession No. NM_005123), sterol-regulatory element binding protein (SREBP), site-1 protease (S1P), 3-hydroxy-3-methylglutaryl coenzyme-A reductase (HMG coenzyme-A reductase); and genes expressed in diabetes, such as, e.g., glucose 6-phosphatase (see, e.g., Forman et al., *Cell*, 81:687 (1995); Seol et al., *Mol. Endocrinol.*, 9:72 (1995), Zavacki et al., *Proc. Natl. Acad. Sci. USA*, 94:7909 (1997); Sakai et al., *Cell*, 85:1037-1046 (1996); Duncan et al., *J. Biol. Chem.*, 272:12778-12785 (1997); Willy et al., *Genes Dev.*, 9:1033-1045 (1995); Lehmann et al, *J. Biol. Chem.*, 272:3137-3140 (1997); Janowski et al., *Nature*, 383:728-731 (1996); and Peet et al., *Cell*, 93:693-704 (1998)).

One of skill in the art will appreciate that genes associated with metabolic diseases and disorders (e.g., diseases and disorders in which the liver is a target and liver diseases and disorders) include genes that are expressed in the liver itself as well as and genes expressed in other organs and tissues. Silencing of sequences that encode genes associated with metabolic diseases and disorders can conveniently be used in combination with the administration of conventional agents used to treat the disease or disorder.

In a presently preferred embodiment, the SNALP formulations of the present invention are used to deliver to the liver an siRNA molecule that silences APOB gene expression.

Non-limiting examples of siRNA molecules targeting the APOB gene include, but are not limited to, those described in U.S. Patent Publication Nos. 20060134189, 20060105976, and 20070135372, and PCT Publication No. WO 04/091515, the disclosures of which are herein incorporated by reference in their entirety for all purposes. In another preferred embodiment, the SNALP formulations of the present invention are used to deliver to the liver an siRNA molecules that silences APOC3 gene expression. Non-limiting examples of siRNA molecules targeting the APOC3 gene include, but are not limited to, those described in PCT Application No. PCT/CA2010/000120, filed Jan. 26, 2010, the disclosure of which is herein incorporated by reference in its entirety for all purposes. In yet another preferred embodiment, the SNALP formulations of the present invention are used to deliver to the liver an siRNA molecule that silences PCSK9 gene expression. Non-limiting examples of siRNA molecules targeting the PCSK9 gene include those described in U.S. Patent Publication Nos. 20070173473, 20080113930, and 20080306015, the disclosures of which are herein incorporated by reference in their entirety for all purposes. In still another preferred embodiment, the SNALP formulations of the present invention are used to deliver to the liver siRNA molecules that silence DGAT1 and/or DGAT2 gene expression. Exemplary siRNA molecules targeting the DGAT1 gene may be designed using the antisense compounds described in U.S. Patent Publication No. 20040185559, the disclosure of which is herein incorporated by reference in its entirety for all purposes. Exemplary siRNA molecules targeting the DGAT2 gene may be designed using the antisense compounds described in U.S. Patent Publication No. 20050043524, the disclosure of which is herein incorporated by reference in its entirety for all purposes.

In addition to being particularly useful for silencing any of APOB, APOC3, PCSK9, DGAT1 and DGAT2, either alone or in various combinations, the SNALP formulations of the present invention are also useful for treating hepatitis. Exemplary hepatitis virus nucleic acid sequences that can be silenced include, but are not limited to, nucleic acid sequences involved in transcription and translation (e.g., En1, En2, X, P) and nucleic acid sequences encoding structural proteins (e.g., core proteins including C and C-related proteins, capsid and envelope proteins including S, M, and/or L proteins, or fragments thereof) (see, e.g., FIELDS VIROLOGY, supra). Exemplary Hepatitis C virus (HCV) nucleic acid sequences that can be silenced include, but are not limited to, the 5'-untranslated region (5'-UTR), the 3'-untranslated region (3'-UTR), the polyprotein translation initiation codon region, the internal ribosome entry site (IRES) sequence, and/or nucleic acid sequences encoding the core protein, the E1 protein, the E2 protein, the p7 protein, the NS2 protein, the NS3 protease/helicase, the NS4A protein, the NS4B protein, the NS5A protein, and/or the NS5B RNA-dependent RNA polymerase. HCV genome sequences are set forth in, e.g., Genbank Accession Nos. NC_004102 (HCV genotype 1a), AJ238799 (HCV genotype 1b), NC_009823 (HCV genotype 2), NC_009824 (HCV genotype 3), NC_009825 (HCV genotype 4), NC_009826 (HCV genotype 5), and NC_009827 (HCV genotype 6). Hepatitis A virus nucleic acid sequences are set forth in, e.g., Genbank Accession No. NC_001489; Hepatitis B virus nucleic acid sequences are set forth in, e.g., Genbank Accession No. NC_003977; Hepatitis D virus nucleic acid sequence are set forth in, e.g., Genbank Accession No. NC_001653; Hepatitis E virus nucleic acid sequences are set forth in, e.g., Genbank Accession No. NC_001434; and Hepatitis G virus nucleic acid sequences are set forth in, e.g., Genbank Accession No. NC_001710.

Silencing of sequences that encode genes associated with viral infection and survival can conveniently be used in combination with the administration of conventional agents used to treat the viral condition. Non-limiting examples of siRNA molecules targeting hepatitis virus nucleic acid sequences include, but are not limited to, those described in U.S. Patent Publication Nos. 20060281175, 20050058982, and 20070149470; U.S. Pat. No. 7,348,314; and PCT Application No. PCT/CA2010/000444, entitled "Compositions and Methods for Silencing Hepatitis C Virus Expression," filed Mar. 19, 2010, the disclosures of which are herein incorporated by reference in their entirety for all purposes.

In addition to its utility in silencing the expression of any of the above-described genes for therapeutic purposes, the siRNA described herein are also useful in research and development applications as well as diagnostic, prophylactic, prognostic, clinical, and other healthcare applications. As a non-limiting example, the siRNA can be used in target validation studies directed at testing whether a gene of interest has the potential to be a therapeutic target. The siRNA can also be used in target identification studies aimed at discovering genes as potential therapeutic targets.

Exemplary siRNA Embodiments

In some embodiments, each strand of the siRNA molecule comprises from about 15 to about 60 nucleotides in length (e.g., about 15-60, 15-50, 15-40, 15-30, 15-25, or 19-25 nucleotides in length, or 15, 16, 17, 18, 19, 20, 21, 22, 23, 24, or 25 nucleotides in length). In one particular embodiment, the siRNA is chemically synthesized. The siRNA molecules of the invention are capable of silencing the expression of a target sequence in vitro and/or in vivo.

In other embodiments, the siRNA comprises at least one modified nucleotide. In certain embodiments, the siRNA comprises one, two, three, four, five, six, seven, eight, nine, ten, or more modified nucleotides in the double-stranded region. In particular embodiments, less than about 50% (e.g., less than about 50%, 45%, 40%, 35%, 30%, 25%, 20%, 15%, 10%, or 5%) of the nucleotides in the double-stranded region of the siRNA comprise modified nucleotides. In preferred embodiments, from about 1% to about 50% (e.g., from about 5%-50%, 10%-50%, 15%-50%, 20%-50%, 25%-50%, 30%-50%, 35%-50%, 40%-50%, 45%-50%, 5%-45%, 10%-45%, 15%-45%, 20%-45%, 25%-45%, 30%-45%, 35%-45%, 40%-45%, 5%-40%, 10%-40%, 15%-40%, 20%-40%, 25%-40%, 30%-40%, 35%-40%, 5%-35%, 10%-35%, 15%-35%, 20%-35%, 25%-35%, 30%-35%, 5%-30%, 10%-30%, 15%-30%, 20%-30%, 25%-30%, 5%-25%, 10%-25%, 15%-25%, 20%-25%, 5%-20%, 10%-20%, 15%-20%, 5%-15%, 10%45%, or 5%-10%) of the nucleotides in the double-stranded region of the siRNA comprise modified nucleotides.

In further embodiments, the siRNA comprises modified nucleotides including, but not limited to, 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, locked nucleic acid (LNA) nucleotides, and mixtures thereof. In preferred embodiments, the siRNA comprises 2'OMe nucleotides (e.g., 2'OMe purine and/or pyrimidine nucleotides) such as, e.g., 2'OMe-guanosine nucleotides, 2'OMe-uridine nucleotides, 2'OMe-adenosine nucleotides, 2'OMe-cytosine nucleotides, or mixtures thereof. In one particular embodiment, the siRNA comprises at least one 2'OMe-guanosine nucleotide, 2'OMe-uridine nucleotide, or mixtures thereof. In certain instances, the siRNA does not comprise 2'OMe-cytosine nucleotides. In other embodiments, the siRNA comprises a hairpin loop structure.

In certain embodiments, the siRNA comprises modified nucleotides in one strand (i.e., sense or antisense) or both strands of the double-stranded region of the siRNA molecule. Preferably, uridine and/or guanosine nucleotides are modified at selective positions in the double-stranded region of the siRNA duplex. With regard to uridine nucleotide modifications, at least one, two, three, four, five, six, or more of the uridine nucleotides in the sense and/or antisense strand can be a modified uridine nucleotide such as a 2'OMe-uridine nucleotide. In some embodiments, every uridine nucleotide in the sense and/or antisense strand is a 2'OMe-uridine nucleotide. With regard to guanosine nucleotide modifications, at least one, two, three, four, five, six, or more of the guanosine nucleotides in the sense and/or antisense strand can be a modified guanosine nucleotide such as a 2'OMe-guanosine nucleotide. In some embodiments, every guanosine nucleotide in the sense and/or antisense strand is a 2'OMe-guanosine nucleotide.

In certain embodiments, at least one, two, three, four, five, six, seven, or more 5'-GU-3' motifs in an siRNA sequence may be modified, e.g., by introducing mismatches to eliminate the 5'-GU-3' motifs and/or by introducing modified nucleotides such as 2'OMe nucleotides. The 5'-GU-3' motif can be in the sense strand, the antisense strand, or both strands of the siRNA sequence. The 5'-GU-3' motifs may be adjacent to each other or, alternatively, they may be separated by 1, 2, 3, 4, 5, 6, 7, 8, 9, 10, 11, 12, or more nucleotides.

In some embodiments, a modified siRNA molecule is less immunostimulatory than a corresponding unmodified siRNA sequence. In such embodiments, the modified siRNA molecule with reduced immunostimulatory properties advantageously retains RNAi activity against the target sequence. In another embodiment, the immunostimulatory properties of the modified siRNA molecule and its ability to silence target gene expression can be balanced or optimized by the introduction of minimal and selective 2'OMe modifications within the siRNA sequence such as, e.g., within the double-stranded region of the siRNA duplex. In certain instances, the modified siRNA is at least about 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% less immunostimulatory than the corresponding unmodified siRNA. It will be readily apparent to those of skill in the art that the immunostimulatory properties of the modified siRNA molecule and the corresponding unmodified siRNA molecule can be determined by, for example, measuring INF-α and/or IL-6 levels from about two to about twelve hours after systemic administration in a mammal or transfection of a mammalian responder cell using an appropriate lipid-based delivery system (such as the SNALP delivery system disclosed herein).

In other embodiments, a modified siRNA molecule has an $IC_{50}$ (i.e., half-maximal inhibitory concentration) less than or equal to ten-fold that of the corresponding unmodified siRNA (i.e., the modified siRNA has an $IC_{50}$ that is less than or equal to ten-times the $IC_{50}$ of the corresponding unmodified siRNA). In other embodiments, the modified siRNA has an $IC_{50}$ less than or equal to three-fold that of the corresponding unmodified siRNA sequence. In yet other embodiments, the modified siRNA has an $IC_{50}$ less than or equal to two-fold that of the corresponding unmodified siRNA. It will be readily apparent to those of skill in the art that a dose-response curve can be generated and the $IC_{50}$ values for the modified siRNA and the corresponding unmodified siRNA can be readily determined using methods known to those of skill in the art.

In another embodiment, an unmodified or modified siRNA molecule is capable of silencing at least about 5%, 10%, 15%, 20%, 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the expression of the target sequence relative to a negative control (e.g., buffer only, an siRNA sequence that targets a different gene, a scrambled siRNA sequence, etc.).

In yet another embodiment, a modified siRNA molecule is capable of silencing at least about 5%, 10%, 15%, 20%, 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the expression of the target sequence relative to the corresponding unmodified siRNA sequence.

In some embodiments, the siRNA molecule does not comprise phosphate backbone modifications, e.g., in the sense and/or antisense strand of the double-stranded region. In other embodiments, the siRNA comprises one, two, three, four, or more phosphate backbone modifications, e.g., in the sense and/or antisense strand of the double-stranded region. In preferred embodiments, the siRNA does not comprise phosphate backbone modifications.

In further embodiments, the siRNA does not comprise 2'-deoxy nucleotides, e.g., in the sense and/or antisense strand of the double-stranded region. In yet further embodiments, the siRNA comprises one, two, three, four, or more 2'-deoxy nucleotides, e.g., in the sense and/or antisense strand of the double-stranded region. In preferred embodiments, the siRNA does not comprise 2'-deoxy nucleotides.

In certain instances, the nucleotide at the 3'-end of the double-stranded region in the sense and/or antisense strand is not a modified nucleotide. In certain other instances, the nucleotides near the 3'-end (e.g., within one, two, three, or four nucleotides of the 3'-end) of the double-stranded region in the sense and/or antisense strand are not modified nucleotides.

The siRNA molecules described herein may have 3' overhangs of one, two, three, four, or more nucleotides on one or both sides of the double-stranded region, or may lack overhangs (i.e., have blunt ends) on one or both sides of the double-stranded region. In certain embodiments, the 3' overhang on the sense and/or antisense strand independently comprises one, two, three, four, or more modified nucleotides such as 2'OMe nucleotides and/or any other modified nucleotide described herein or known in the art.

In particular embodiments, siRNAs are administered using a carrier system such as a nucleic acid-lipid particle. In a preferred embodiment, the nucleic acid-lipid particle comprises: (a) one or more siRNA molecules targeting APOB, APOC3, PCSK9, DGAT1 and/or DGAT2 gene expression; (b) a cationic lipid of Formulas I-III or a salt thereof; and (c) a non-cationic lipid (e.g., DPPC, DSPC, DSPE, and/or cholesterol). In certain instances, the nucleic acid-lipid particle may further comprise a conjugated lipid that prevents aggregation of particles (e.g., PEG-DAA and/or POZ-DAA).

b) Dicer-Substrate dsRNA

As used herein, the term "Dicer-substrate dsRNA" or "precursor RNAi molecule" is intended to include any precursor molecule that is processed in vivo by Dicer to produce an active siRNA which is incorporated into the RISC complex for RNA interference of a target gene, such as APOB, APOC3, PCSK9, DGAT1, DGAT2, or combinations thereof.

In one embodiment, the Dicer-substrate dsRNA has a length sufficient such that it is processed by Dicer to produce an siRNA. According to this embodiment, the Dicer-substrate dsRNA comprises (i) a first oligonucleotide sequence (also termed the sense strand) that is between about 25 and about 60 nucleotides in length (e.g., about 25-60, 25-55, 25-50, 25-45, 25-40, 25-35, or 25-30 nucleotides in length), preferably between about 25 and about 30 nucleotides in length (e.g., 25, 26, 27, 28, 29, or 30 nucleotides in length), and (ii) a second oligonucleotide sequence (also termed the antisense strand) that anneals to the first sequence under biological conditions, such as the conditions found in the cytoplasm of a cell. The second oligonucleotide sequence may be between about 25 and about 60 nucleotides in length (e.g., about 25-60, 25-55, 25-50, 25-45, 25-40, 25-35, or 25-30 nucleotides in length), and is preferably between about 25 and about 30 nucleotides in length (e.g., 25, 26, 27, 28, 29, or 30 nucleotides in length). In addition, a region of one of the sequences, particularly of the antisense strand, of the Dicer-substrate dsRNA has a sequence length of at least about 19 nucleotides, for example, from about 19 to about 60 nucleotides (e.g., about 19-60, 19-55, 19-50, 19-45, 19-40, 19-35, 19-30, or 19-25 nucleotides), preferably from about 19 to about 23 nucleotides (e.g., 19, 20, 21, 22, or 23 nucleotides) that are sufficiently complementary to a nucleotide sequence of the RNA produced from the target gene to trigger an RNAi response.

In a second embodiment, the Dicer-substrate dsRNA has several properties which enhance its processing by Dicer. According to this embodiment, the dsRNA has a length sufficient such that it is processed by Dicer to produce an siRNA and has at least one of the following properties: (i) the dsRNA is asymmetric, e.g., has a 3'-overhang on the antisense strand; and/or (ii) the dsRNA has a modified 3'-end on the sense strand to direct orientation of Dicer binding and processing of the dsRNA to an active siRNA. According to this latter embodiment, the sense strand comprises from about 22 to about 28 nucleotides and the antisense strand comprises from about 24 to about 30 nucleotides.

In one embodiment, the Dicer-substrate dsRNA has an overhang on the 3'-end of the antisense strand. In another embodiment, the sense strand is modified for Dicer binding and processing by suitable modifiers located at the 3'-end of the sense strand. Suitable modifiers include nucleotides such as deoxyribonucleotides, acyclonucleotides, and the like, and sterically hindered molecules such as fluorescent molecules and the like. When nucleotide modifiers are used, they replace ribonucleotides in the dsRNA such that the length of the dsRNA does not change. In another embodiment, the Dicer-substrate dsRNA has an overhang on the 3'-end of the antisense strand and the sense strand is modified for Dicer processing. In another embodiment, the 5'-end of the sense strand has a phosphate. In another embodiment, the 5'-end of the antisense strand has a phosphate. In another embodiment, the antisense strand or the sense strand or both strands have one or more 2'-O-methyl (2'OMe) modified nucleotides. In another embodiment, the antisense strand contains 2'OMe modified nucleotides. In another embodiment, the antisense stand contains a 3'-overhang that is comprised of 2'OMe modified nucleotides. The antisense strand could also include additional 2'OMe modified nucleotides. The sense and antisense strands anneal under biological conditions, such as the conditions found in the cytoplasm of a cell. In addition, a region of one of the sequences, particularly of the antisense strand, of the Dicer-substrate dsRNA has a sequence length of at least about 19 nucleotides, wherein these nucleotides are in the 21-nucleotide region adjacent to the 3'-end of the antisense strand and are sufficiently complementary to a nucleotide sequence of the RNA produced from the target gene, such as APOB. Further, in accordance with this embodiment, the Dicer-substrate dsRNA may also have one or more of the following additional properties: (a) the antisense strand has a right shift from the typical 21-mer (i.e., the antisense strand includes nucleotides on the right side of the molecule when compared to the typical 21-mer); (b) the strands may not be completely complementary, i.e., the strands may contain simple mismatch pairings; and (c) base modifications such as locked nucleic acid(s) may be included in the 5'-end of the sense strand.

In a third embodiment, the sense strand comprises from about 25 to about 28 nucleotides (e.g., 25, 26, 27, or 28 nucleotides), wherein the 2 nucleotides on the 3'-end of the sense strand are deoxyribonucleotides. The sense strand contains a phosphate at the 5'-end. The antisense strand comprises from about 26 to about 30 nucleotides (e.g., 26, 27, 28, 29, or 30 nucleotides) and contains a 3'-overhang of 1-4 nucleotides. The nucleotides comprising the 3'-overhang are modified with 2'OMe modified ribonucleotides. The antisense strand contains alternating 2'OMe modified nucleotides beginning at the first monomer of the antisense strand adjacent to the 3'-overhang, and extending 15-19 nucleotides from the first monomer adjacent to the 3'-overhang. For example, for a 27-nucleotide antisense strand and counting the first base at the 5'-end of the antisense strand as position number 1, 2'OMe modifications would be placed at bases 9, 11, 13, 15, 17, 19, 21, 23, 25, 26, and 27. In one embodiment, the Dicer-substrate dsRNA has the following structure:

```
5'-pXXXXXXXXXXXXXXXXXXXXXXXDD-3'

3'-YXXXXXXXXXXXXXXXXXXXXXXXXXp-5'
``` wherein "X"=RNA, "p"=a phosphate group, "X̲"=2'OMe RNA, "Y" is an overhang domain comprised of 1, 2, 3, or 4 RNA monomers that are optionally 2'OMe RNA monomers, and "D"=DNA. The top strand is the sense strand, and the bottom strand is the antisense strand.

In a fourth embodiment, the Dicer-substrate dsRNA has several properties which enhance its processing by Dicer. According to this embodiment, the dsRNA has a length sufficient such that it is processed by Dicer to produce an siRNA and at least one of the following properties: (i) the dsRNA is asymmetric, e.g., has a 3'-overhang on the sense strand; and (ii) the dsRNA has a modified 3'-end on the antisense strand to direct orientation of Dicer binding and processing of the dsRNA to an active siRNA. According to this embodiment, the sense strand comprises from about 24 to about 30 nucleotides (e.g., 24, 25, 26, 27, 28, 29, or 30 nucleotides) and the antisense strand comprises from about 22 to about 28 nucleotides (e.g., 22, 23, 24, 25, 26, 27, or 28 nucleotides). In one embodiment, the Dicer-substrate dsRNA has an overhang on the 3'-end of the sense strand. In another embodiment, the antisense strand is modified for Dicer binding and processing by suitable modifiers located at the 3'-end of the antisense strand. Suitable modifiers include nucleotides such as deoxyribonucleotides, acyclonucleotides, and the like, and sterically hindered molecules such as fluorescent molecules and the like. When nucleotide modifiers are used, they replace ribonucleotides in the dsRNA such that the length of the dsRNA does not change. In another embodiment, the dsRNA has an overhang on the 3'-end of the sense strand and the antisense strand is modified for Dicer processing. In one embodiment, the antisense strand has a 5'-phosphate. The sense and antisense strands anneal under biological conditions, such as the conditions found in the cytoplasm of a cell. In addition, a region of one of the sequences, particularly of the antisense strand, of the dsRNA has a sequence length of at least 19 nucleotides, wherein these nucleotides are adjacent to the 3'-end of antisense strand and are sufficiently complementary to a nucleotide sequence of the RNA produced from the target gene, such as APOB. Further, in accordance with this embodiment, the Dicer-substrate dsRNA may also have one or more of the following additional properties: (a) the antisense strand has a left shift from the typical 21-mer (i.e., the antisense strand includes nucleotides on the left side of the molecule when compared to the typical 21-mer); and (b) the strands may not be completely complementary, i.e., the strands may contain simple mismatch pairings.

In a preferred embodiment, the Dicer-substrate dsRNA has an asymmetric structure, with the sense strand having a 25-base pair length, and the antisense strand having a 27-base pair length with a 2 base 3'-overhang. In certain instances, this dsRNA having an asymmetric structure further contains 2 deoxynucleotides at the 3'-end of the sense strand in place of two of the ribonucleotides. In certain other instances, this dsRNA having an asymmetric structure further contains 2'OMe modifications at positions 9, 11, 13, 15, 17, 19, 21, 23, and 25 of the antisense strand (wherein the first base at the 5'-end of the antisense strand is position 1). In certain additional instances, this dsRNA having an asymmetric structure further contains a 3'-overhang on the antisense strand comprising 1, 2, 3, or 4 2'OMe nucleotides (e.g., a 3'-overhang of 2'OMe nucleotides at positions 26 and 27 on the antisense strand).

In another embodiment, Dicer-substrate dsRNAs may be designed by first selecting an antisense strand siRNA sequence having a length of at least 19 nucleotides. In some instances, the antisense siRNA is modified to include about 5 to about 11 ribonucleotides on the 5'-end to provide a length of about 24 to about 30 nucleotides. When the antisense strand has a length of 21 nucleotides, 3-9, preferably 4-7, or more preferably 6 nucleotides may be added on the 5'-end. Although the added ribonucleotides may be complementary to the target gene sequence, full complementarity between the target sequence and the antisense siRNA is not required. That is, the resultant antisense siRNA is sufficiently complementary with the target sequence. A sense strand is then produced that has about 22 to about 28 nucleotides. The sense strand is substantially complementary with the antisense strand to anneal to the antisense strand under biological conditions. In one embodiment, the sense strand is synthesized to contain a modified 3'-end to direct Dicer processing of the antisense strand. In another embodiment, the antisense strand of the dsRNA has a 3'-overhang. In a further embodiment, the sense strand is synthesized to contain a modified 3'-end for Dicer binding and processing and the antisense strand of the dsRNA has a 3'-overhang.

In a related embodiment, the antisense siRNA may be modified to include about 1 to about 9 ribonucleotides on the 5'-end to provide a length of about 22 to about 28 nucleotides. When the antisense strand has a length of 21 nucleotides, 1-7, preferably 2-5, or more preferably 4 ribonucleotides may be added on the 3'-end. The added ribonucleotides may have any sequence. Although the added ribonucleotides may be complementary to the target gene sequence, full complementarity between the target sequence and the antisense siRNA is not required. That is, the resultant antisense siRNA is sufficiently complementary with the target sequence. A sense strand is then produced that has about 24 to about 30 nucleotides. The sense strand is substantially complementary with the antisense strand to anneal to the antisense strand under biological conditions. In one embodiment, the antisense strand is synthesized to contain a modified 3'-end to direct Dicer processing. In another embodiment, the sense strand of the dsRNA has a 3'-overhang. In a further embodiment, the antisense strand is synthesized to contain a modified 3'-end for Dicer binding and processing and the sense strand of the dsRNA has a 3'-overhang.

Suitable Dicer-substrate dsRNA sequences can be identified, synthesized, and modified using any means known in the art for designing, synthesizing, and modifying siRNA sequences. In particular embodiments, Dicer-substrate dsRNAs are administered using a carrier system such as a nucleic acid-lipid particle. In a preferred embodiment, the nucleic acid-lipid particle comprises: (a) one or more Dicer-substrate dsRNA molecules targeting APOB, APOC3, PCSK9, DGAT1 and/or DGAT2 gene expression; (b) a cationic lipid of Formulas I-III or a salt thereof; and (c) a non-cationic lipid (e.g., DPPC, DSPC, DSPE, and/or cholesterol). In certain instances, the nucleic acid-lipid particle may further comprise a conjugated lipid that prevents aggregation of particles (e.g., PEG-DAA and/or POZ-DAA).

Additional embodiments related to the Dicer-substrate dsRNAs of the invention, as well as methods of designing and synthesizing such dsRNAs, are described in U.S. Patent Publication Nos. 20050244858, 20050277610, 20070265220, and 20110071208, the disclosures of which are herein incorporated by reference in their entirety for all purposes.

c) Small Hairpin RNA (shRNA)

A "small hairpin RNA" or "short hairpin RNA" or "shRNA" includes a short RNA sequence that makes a tight hairpin turn that can be used to silence gene expression via RNA interference. The shRNAs of the invention may be chemically synthesized or transcribed from a transcriptional cassette in a DNA plasmid. The shRNA hairpin structure is cleaved by the cellular machinery into siRNA, which is then bound to the RNA-induced silencing complex (RISC).

The shRNAs of the invention are typically about 15-60, 15-50, or 15-40 (duplex) nucleotides in length, more typically about 15-30, 15-25, or 19-25 (duplex) nucleotides in length, and are preferably about 20-24, 21-22, or 21-23 (duplex) nucleotides in length (e.g., each complementary sequence of the double-stranded shRNA is 15-60, 15-50, 15-40, 15-30, 15-25, or 19-25 nucleotides in length, preferably about 20-24, 21-22, or 21-23 nucleotides in length, and the double-stranded shRNA is about 15-60, 15-50, 15-40, 15-30, 15-25, or 19-25 base pairs in length, preferably about 18-22, 19-20, or 19-21 base pairs in length). shRNA duplexes may comprise 3' overhangs of about 1 to about 4 nucleotides or about 2 to about 3 nucleotides on the antisense strand and/or 5'-phosphate termini on the sense strand. In some embodiments, the shRNA comprises a sense strand and/or antisense strand sequence of from about 15 to about 60 nucleotides in length (e.g., about 15-60, 15-55, 15-50, 15-45, 15-40, 15-35, 15-30, or 15-25 nucleotides in length), preferably from about 19 to about 40 nucleotides in length (e.g., about 19-40, 19-35, 19-30, or 19-25 nucleotides in length), more preferably from about 19 to about 23 nucleotides in length (e.g., 19, 20, 21, 22, or 23 nucleotides in length).

Non-limiting examples of shRNA include a double-stranded polynucleotide molecule assembled from a single-stranded molecule, where the sense and antisense regions are linked by a nucleic acid-based or non-nucleic acid-based linker; and a double-stranded polynucleotide molecule with a hairpin secondary structure having self-complementary sense and antisense regions. In preferred embodiments, the sense and antisense strands of the shRNA are linked by a loop structure comprising from about 1 to about 25 nucleotides, from about 2 to about 20 nucleotides, from about 4 to about 15 nucleotides, from about 5 to about 12 nucleotides, or 1, 2, 3, 4, 5, 6, 7, 8, 9, 10, 11, 12, 13, 14, 15, 16, 17, 18, 19, 20, 21, 22, 23, 24, 25, or more nucleotides.

Suitable shRNA sequences can be identified, synthesized, and modified using any means known in the art for designing, synthesizing, and modifying siRNA sequences. In particular embodiments, shRNAs are administered using a carrier system such as a nucleic acid-lipid particle. In a preferred embodiment, the nucleic acid-lipid particle comprises: (a) one or more shRNA molecules targeting APOB, APOC3, PCSK9, DGAT1 and/or DGAT2 gene expression; (b) a cationic lipid of Formulas I-III or a salt thereof; and (c) a non-cationic lipid (e.g., DPPC, DSPC, DSPE, and/or cholesterol). In certain instances, the nucleic acid-lipid particle may further comprise a conjugated lipid that prevents aggregation of particles (e.g., PEG-DAA and/or POZ-DAA).

Additional embodiments related to the shRNAs of the invention, as well as methods of designing and synthesizing such shRNAs, are described in U.S. Publication No. 20110071208, the disclosure of which is herein incorporated by reference in its entirety for all purposes.

d) aiRNA

Like siRNA, asymmetrical interfering RNA (aiRNA) can recruit the RNA-induced silencing complex (RISC) and lead to effective silencing of a variety of genes in mammalian cells by mediating sequence-specific cleavage of the target sequence between nucleotide 10 and 11 relative to the 5' end of the antisense strand (Sun et al., *Nat. Biotech.*, 26:1379-1382 (2008)). Typically, an aiRNA molecule comprises a short RNA duplex having a sense strand and an antisense strand, wherein the duplex contains overhangs at the 3' and 5' ends of the antisense strand. The aiRNA is generally asymmetric because the sense strand is shorter on both ends when compared to the complementary antisense strand. In some aspects, aiRNA molecules may be designed, synthesized, and annealed under conditions similar to those used for siRNA molecules. As a non-limiting example, aiRNA sequences may be selected and generated using the methods described above for selecting siRNA sequences.

In another embodiment, aiRNA duplexes of various lengths (e.g., about 10-25, 12-20, 12-19, 12-18, 13-17, or 14-17 base pairs, more typically 12, 13, 14, 15, 16, 17, 18, 19, or 20 base pairs) may be designed with overhangs at the 3' and 5' ends of the antisense strand to target an mRNA of interest. In certain instances, the sense strand of the aiRNA molecule is about 10-25, 12-20, 12-19, 12-18, 13-17, or 14-17 nucleotides in length, more typically 12, 13, 14, 15, 16, 17, 18, 19, or 20 nucleotides in length. In certain other instances, the antisense strand of the aiRNA molecule is about 15-60, 15-50, or 15-40 nucleotides in length, more typically about 15-30, 15-25, or 19-25 nucleotides in length, and is preferably about 20-24, 21-22, or 21-23 nucleotides in length.

In some embodiments, the 5' antisense overhang contains one, two, three, four, or more nontargeting nucleotides (e.g., "AA", "UU", "dTdT", etc.). In other embodiments, the 3' antisense overhang contains one, two, three, four, or more nontargeting nucleotides (e.g., "AA", "UU", "dTdT", etc.). In certain aspects, the aiRNA molecules described herein may comprise one or more modified nucleotides, e.g., in the double-stranded (duplex) region and/or in the antisense overhangs. As a non-limiting example, aiRNA sequences may comprise one or more of the modified nucleotides described above for siRNA sequences. In a preferred embodiment, the aiRNA molecule comprises 2'OMe nucleotides such as, for example, 2'OMe-guanosine nucleotides, 2'OMe-uridine nucleotides, or mixtures thereof.

In certain embodiments, aiRNA molecules may comprise an antisense strand which corresponds to the antisense strand of an siRNA molecule, e.g., one of the siRNA molecules described herein. In particular embodiments, aiRNAs are administered using a carrier system such as a nucleic acid-lipid particle. In a preferred embodiment, the nucleic acid-lipid particle comprises: (a) one or more aiRNA molecules targeting APOB, APOC3, PCSK9, DGAT1 and/or DGAT2 gene expression; (b) a cationic lipid of Formulas I-III or a salt thereof; and (c) a non-cationic lipid (e.g., DPPC, DSPC, DSPE, and/or cholesterol). In certain instances, the nucleic acid-lipid particle may further comprise a conjugated lipid that prevents aggregation of particles (e.g., PEG-DAA and/or POZ-DAA).

Suitable aiRNA sequences can be identified, synthesized, and modified using any means known in the art for designing, synthesizing, and modifying siRNA sequences. Additional embodiments related to the aiRNA molecules of the invention are described in U.S. Patent Publication No. 20090291131 and PCT Publication No. WO 09/127,060, the disclosures of which are herein incorporated by reference in their entirety for all purposes.

e) miRNA

Generally, microRNAs (miRNA) are single-stranded RNA molecules of about 21-23 nucleotides in length which regulate gene expression. miRNAs are encoded by genes from whose DNA they are transcribed, but miRNAs are not translated into protein (non-coding RNA); instead, each primary transcript (a pri-miRNA) is processed into a short stem-loop structure called a pre-miRNA and finally into a functional mature miRNA. Mature miRNA molecules are either partially or completely complementary to one or more messenger RNA (mRNA) molecules, and their main function is to down-regulate gene expression. The identification of miRNA molecules is described, e.g., in Lagos-Quintana et al., *Science*, 294:853-858; Lau et al., *Science*, 294:858-862; and Lee et al., *Science*, 294:862-864.

The genes encoding miRNA are much longer than the processed mature miRNA molecule. miRNA are first transcribed as primary transcripts or pri-miRNA with a cap and poly-A tail and processed to short, ~70-nucleotide stem-loop structures known as pre-miRNA in the cell nucleus. This processing is performed in animals by a protein complex known as the Microprocessor complex, consisting of the nuclease Drosha and the double-stranded RNA binding protein Pasha (Denli et al., *Nature*, 432:231-235 (2004)). These pre-miRNA are then processed to mature miRNA in the cytoplasm by interaction with the endonuclease Dicer, which also initiates the formation of the RNA-induced silencing complex (RISC) (Bernstein et al., *Nature*, 409:363-366 (2001). Either the sense strand or antisense strand of DNA can function as templates to give rise to miRNA.

When Dicer cleaves the pre-miRNA stem-loop, two complementary short RNA molecules are formed, but only one is integrated into the RISC complex. This strand is known as the guide strand and is selected by the argonaute protein, the catalytically active RNase in the RISC complex, on the basis of the stability of the 5' end (Preall et al., *Curr. Biol.*, 16:530-535 (2006)). The remaining strand, known as the anti-guide or passenger strand, is degraded as a RISC complex substrate (Gregory et al., *Cell*, 123:631-640 (2005)). After integration into the active RISC complex, miRNAs base pair with their complementary mRNA molecules and induce target mRNA degradation and/or translational silencing.

Mammalian miRNA molecules are usually complementary to a site in the 3' UTR of the target mRNA sequence. In certain instances, the annealing of the miRNA to the target mRNA inhibits protein translation by blocking the protein translation machinery. In certain other instances, the annealing of the miRNA to the target mRNA facilitates the cleavage and degradation of the target mRNA through a process similar to RNA interference (RNAi). miRNA may also target methylation of genomic sites which correspond to targeted mRNA. Generally, miRNA function in association with a complement of proteins collectively termed the miRNP.

In certain aspects, the miRNA molecules described herein are about 15-100, 15-90, 15-80, 15-75, 15-70, 15-60, 15-50, or 15-40 nucleotides in length, more typically about 15-30, 15-25, or 19-25 nucleotides in length, and are preferably about 20-24, 21-22, or 21-23 nucleotides in length. In certain other aspects, miRNA molecules may comprise one or more modified nucleotides. As a non-limiting example, miRNA sequences may comprise one or more of the modified nucleotides described above for siRNA sequences. In a preferred embodiment, the miRNA molecule comprises 2'OMe nucleotides such as, for example, 2'OMe-guanosine nucleotides, 2'OMe-uridine nucleotides, or mixtures thereof.

In particular embodiments, miRNAs are administered using a carrier system such as a nucleic acid-lipid particle. In a preferred embodiment, the nucleic acid-lipid particle comprises: (a) one or more miRNA molecules targeting APOB, APOC3, PCSK9, DGAT1 and/or DGAT2 gene expression; (b) a cationic lipid of Formulas I-III or a salt thereof; and (c) a non-cationic lipid (e.g., DPPC, DSPC, DSPE, and/or cholesterol). In certain instances, the nucleic acid-lipid particle may further comprise a conjugated lipid that prevents aggregation of particles (e.g., PEG-DAA and/or POZ-DAA).

In other embodiments, one or more agents that block the activity of an miRNA targeting APOB, APOC3, PCSK9, DGAT1 and/or DGAT2 mRNA are administered using a lipid particle of the invention (e.g., a nucleic acid-lipid particle such as SNALP). Examples of blocking agents include, but are not limited to, steric blocking oligonucleotides, locked nucleic acid oligonucleotides, and Morpholino oligonucleotides. Such blocking agents may bind directly to the miRNA or to the miRNA binding site on the target mRNA.

Additional embodiments related to the miRNA molecules of the invention are described in U.S. Patent Publication No. 20090291131 and PCT Publication No. WO 09/127,060, the disclosures of which are herein incorporated by reference in their entirety for all purposes.

B. Cationic Lipids

Any of the cationic lipids of Formulas I-III or salts thereof as set forth herein may be used in the lipid particles of the present invention (e.g., SNALP), either alone or in combination with one or more other cationic lipid species or non-cationic lipid species. The cationic lipids include the (R) and/or (S) enantiomers thereof.

In some embodiments, the cationic lipid comprises a racemic mixture. In other embodiments, the cationic lipid comprises a mixture of one or more diastereomers. In certain embodiments, the cationic lipid is enriched in one enantiomer, such that the cationic lipid comprises at least about 55%, 60%, 65%, 70%, 75%, 80%, 85%, 90%, or 95% enantiomeric excess. In certain other embodiments, the cationic lipid is enriched in one diastereomer, such that the cationic lipid comprises at least about 55%, 60%, 65%, 70%, 75%, 80%, 85%, 90%, or 95% diastereomeric excess. In certain additional embodiments, the cationic lipid is chirally pure (e.g., comprises a single optical isomer). In further embodiments, the cationic lipid is enriched in one optical isomer (e.g., an optically active isomer), such that the cationic lipid comprises at least about 55%, 60%, 65%, 70%, 75%, 80%, 85%, 90%, or 95% isomeric excess. The present invention provides the synthesis of the cationic lipids of Formulas I-III as a racemic mixture or in optically pure form.

The terms "cationic lipid" and "amino lipid" are used interchangeably herein to include those lipids and salts thereof having one, two, three, or more fatty acid or fatty alkyl chains and a pH-titratable amino head group (e.g., an alkylamino or dialkylamino head group). The cationic lipid is typically protonated (i.e., positively charged) at a pH below the $pK_a$ of the cationic lipid and is substantially neutral at a pH above the $pK_a$. The cationic lipids of the invention may also be termed titratable cationic lipids.

The term "salts" includes any anionic and cationic complex, such as the complex formed between a cationic lipid disclosed herein and one or more anions. Non-limiting examples of anions include inorganic and organic anions, e.g., hydride, fluoride, chloride, bromide, iodide, oxalate (e.g., hemioxalate), phosphate, phosphonate, hydrogen phosphate, dihydrogen phosphate, oxide, carbonate, bicarbonate, nitrate, nitrite, nitride, bisulfite, sulfide, sulfite, bisulfate, sulfate, thiosulfate, hydrogen sulfate, borate, formate, acetate, benzoate, citrate, tartrate, lactate, acrylate, polyacrylate, fumarate, maleate, itaconate, glycolate, gluconate, malate, mandelate, tiglate, ascorbate, salicylate, polymethacrylate, perchlorate, chlorate, chlorite, hypochlorite, bromate, hypobromite, iodate, an alkylsulfonate, an arylsulfonate, arsenate, arsenite, chromate, dichromate, cyanide, cyanate, thiocyanate, hydroxide, peroxide, permanganate, and mixtures thereof. In particular embodiments, the salts of the cationic lipids disclosed herein are crystalline salts.

The term "alkyl" includes a straight chain or branched, noncyclic or cyclic, saturated aliphatic hydrocarbon containing from 1 to 24 carbon atoms. Representative saturated straight chain alkyls include, but are not limited to, methyl, ethyl, n-propyl, n-butyl, n-pentyl, n-hexyl, and the like, while saturated branched alkyls include, without limitation, isopropyl, sec-butyl, isobutyl, tert-butyl, isopentyl, and the like. Representative saturated cyclic alkyls include, but are not limited to, the $C_{3-8}$ cycloalkyls described herein, while unsaturated cyclic alkyls include, without limitation, the $C_{3-8}$ cycloalkenyls described herein.

The term "heteroalkyl," includes a straight chain or branched, noncyclic or cyclic, saturated aliphatic hydrocarbon as defined above having from about 1 to about 5 heteroatoms (i.e., 1, 2, 3, 4, or 5 heteroatoms) such as, for example, O, N, Si, and/or S, wherein the nitrogen and sulfur atoms may optionally be oxidized and the nitrogen heteroatom may optionally be quaternized. The heteroalkyl group can be attached to the remainder of the molecule through a carbon atom or a heteroatom.

The term "cyclic alkyl" includes any of the substituted or unsubstituted cycloalkyl, heterocycloalkyl, cycloalkenyl, and heterocycloalkenyl groups described below.

The term "cycloalkyl" includes a substituted or unsubstituted cyclic alkyl group having from about 3 to about 8 carbon atoms (i.e., 3, 4, 5, 6, 7, or 8 carbon atoms) as ring vertices. Preferred cycloalkyl groups include those having from about 3 to about 6 carbon atoms as ring vertices. Examples of $C_{3-8}$ cycloalkyl groups include, but are not limited to, cyclopropyl, methyl-cyclopropyl, dimethyl-cyclopropyl, cyclobutyl, methyl-cyclobutyl, cyclopentyl, methyl-cyclopentyl, cyclohexyl, methyl-cyclohexyl, dimethyl-cyclohexyl, cycloheptyl, and cyclooctyl, as well as other substituted $C_{3-8}$ cycloalkyl groups.

The term "heterocycloalkyl" includes a substituted or unsubstituted cyclic alkyl group as defined above having from about 1 to about 3 heteroatoms as ring members selected from the group consisting of O, N, Si and S, wherein the nitrogen and sulfur atoms may optionally be oxidized and the nitrogen heteroatom may optionally be quaternized. The heterocycloalkyl group can be attached to the remainder of the molecule through a carbon atom or a heteroatom.

The term "cycloalkenyl" includes a substituted or unsubstituted cyclic alkenyl group having from about 3 to about 8 carbon atoms (i.e., 3, 4, 5, 6, 7, or 8 carbon atoms) as ring vertices. Preferred cycloalkenyl groups are those having from about 3 to about 6 carbon atoms as ring vertices. Examples of $C_{3-8}$ cycloalkenyl groups include, but are not limited to, cyclopropenyl, methyl-cyclopropenyl, dimethyl-cyclopropenyl, cyclobutenyl, cyclopentenyl, cyclohexenyl, cycloheptenyl, and cyclooctenyl, as well as other substituted $C_{3-8}$ cycloalkenyl groups.

The term "heterocycloalkenyl" includes a substituted or unsubstituted cyclic alkenyl group as defined above having from about 1 to about 3 heteroatoms as ring members selected from the group consisting of O, N, Si and S, wherein the nitrogen and sulfur atoms may optionally be oxidized and the nitrogen heteroatom may optionally be quaternized. The heterocycloalkenyl group can be attached to the remainder of the molecule through a carbon atom or a heteroatom.

The term "alkoxy" includes a group of the formula alkyl-O—, wherein "alkyl" has the previously given definition. Non-limiting examples of alkoxy groups include methoxy, ethoxy, n-propoxy, iso-propoxy, n-butoxy, iso-butoxy, sec-butoxy and tert-butoxy.

The term "alkenyl" includes an alkyl, as defined above, containing at least one double bond between adjacent carbon atoms. Alkenyls include both cis and trans isomers. Representative straight chain and branched alkenyls include, but are not limited to, ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like. Representative cyclic alkenyls are described above.

The term "alkynyl" includes any alkyl or alkenyl, as defined above, which additionally contains at least one triple bond between adjacent carbons. Representative straight chain and branched alkynyls include, without limitation, acetylenyl, propynyl, 1-butynyl, 2-butynyl, 1-pentynyl, 2-pentynyl, 3-methyl-1 butynyl, and the like.

The term "aryl" includes a polyunsaturated, typically aromatic, hydrocarbon group which can be a single ring or multiple rings (up to three rings) which are fused together or linked covalently, and which optionally carries one or more substituents, such as, for example, halogen, trifluoromethyl, amino, alkyl, alkoxy, alkylcarbonyl, cyano, carbamoyl, alkoxycarbamoyl, methylendioxy, carboxy, alkoxycarbonyl, aminocarbonyl, alkylaminocarbonyl, dialkylaminocarbonyl, hydroxy, nitro, and the like. Non-limiting examples of unsubstituted aryl groups include phenyl, naphthyl, and biphenyl. Examples of substituted aryl groups include, but are not limited to, phenyl, chlorophenyl, trifluoromethylphenyl, chlorofluorophenyl, and aminophenyl.

The terms "alkylthio," "alkylsulfonyl," "alkylsulfinyl," and "arylsulfonyl" include groups having the formula —S—$R^i$, —S(O)$_2$—$R^i$, —S(O)—$R^i$ and —S(O)$_2R^j$, respectively, wherein $R^i$ is an alkyl group as previously defined and $R^j$ is an aryl group as previously defined.

The terms "alkenyloxy" and "alkynyloxy" include groups having the formula —O—$R^i$, wherein $R^i$ is an alkenyl or alkynyl group, respectively.

The terms "alkenylthio" and "alkynylthio" include groups having the formula —S—$R^k$, wherein $R^k$ is an alkenyl or alkynyl group, respectively.

The term "alkoxycarbonyl" includes a group having the formula —C(O)O—$R^i$, wherein $R^i$ is an alkyl group as defined above and wherein the total number of carbon atoms refers to the combined alkyl and carbonyl moieties.

The term "acyl" includes any alkyl, alkenyl, or alkynyl wherein the carbon at the point of attachment is substituted with an oxo group, as defined below. The following are non-limiting examples of acyl groups: —C(=O)alkyl, —C(=O)alkenyl, and —C(=O)alkynyl.

The term "heterocycle" includes a 5- to 7-membered monocyclic, or 7- to 10-membered bicyclic, heterocyclic ring which is either saturated, unsaturated, or aromatic, and which contains one, two, three, or more heteroatoms independently selected from nitrogen (N), oxygen (O), and sulfur (S), and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include, but are not limited to, heteroaryls as defined below, as well as morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The term "heteroaryl" includes an aromatic 5- to 10-membered heterocycle which contains one, two, three, or more heteroatoms selected from nitrogen (N), oxygen (O), and sulfur (S). The heteroaryl can be substituted on one or more carbon atoms with substituents such as, for example, halogen, alkyl, alkoxy, cyano, haloalkyl (e.g., trifluoromethyl), heterocyclyl (e.g., morpholinyl or pyrrolidinyl), and the like. Non-limiting examples of heteroaryls include pyridinyl and furanyl.

The term "halogen" includes fluoro, chloro, bromo, and iodo.

The terms "optionally substituted alkyl," "optionally substituted cyclic alkyl," "optionally substituted alkenyl," "optionally substituted alkynyl," "optionally substituted acyl," and "optionally substituted heterocycle" mean that, when substituted, at least one hydrogen atom is replaced with a substituent. In the case of an "oxo" substituent (=O), two hydrogen atoms are replaced. Non-limiting examples of substituents include oxo, halogen, heterocycle, —CN, —OR$^x$, —NR$^x$R$^y$, —Nr$^x$C(=O)R$^y$, —Nr$^x$SO$_2$R$^y$, —C(=O)R$^x$, —C(=O)OR$^x$, —C(=O)N$^x$R$^y$, —SO$_n$R$^x$, and —SO$_n$N$^x$R$^y$, wherein n is 0, 1, or 2, R$^x$ and R$^y$ are the same or different and are independently hydrogen, alkyl, or heterocycle, and each of the alkyl and heterocycle substituents may be further substituted with one or more of oxo, halogen, —OH, —CN, alkyl, —OR$^x$, heterocycle, —NR$^x$R$^y$, —Nr$^x$C(=O)R$^y$, —Nr$^x$SO$_2$R$^y$, —C(=O)R$^x$, —C(=O)OR$^x$, —C(=O)N$^x$R$^y$, —SO$_n$R$^x$, and —SO$_n$N$^x$R$^y$. The term "optionally substituted," when used before a list of substituents, means that each of the substituents in the list may be optionally substituted as described herein.

In one aspect, cationic lipids of Formula I having the following structure (or salts thereof) are useful in the present invention:

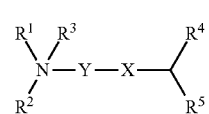

(I)

or salts thereof, wherein:

R$^1$ and R$^2$ are either the same or different and are independently hydrogen (H) or an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring;

$R^3$ is either absent or is hydrogen (H) or a $C_1$-$C_6$ alkyl to provide a quaternary amine;

$R^4$ and $R^5$ are either the same or different and are independently an optionally substituted $C_{10}$-$C_{24}$ alkyl, $C_{10}$-$C_{24}$ alkenyl, $C_{10}$-$C_{24}$ alkynyl, or $C_{10}$-$C_{24}$ acyl;

X is O, S, N($R^6$), C(O), C(O)O, OC(O), C(O)N($R^6$), N($R^6$)C(O), OC(O)N($R^6$), N($R^6$)C(O)O, C(O)S, C(S)O, S(O), S(O)(O), C(S), or an optionally substituted heterocyclic ring, wherein $R^6$ is hydrogen (H) or an optionally substituted $C_1$-$C_{10}$ alkyl, $C_2$-$C_{10}$ alkenyl, or $C_2$-$C_{10}$ alkynyl; and Y is either absent or is an optionally substituted $C_1$-$C_6$ alkyl, $C_2$-$C_6$ alkenyl, or $C_2$-$C_6$ alkynyl.

In some embodiments, $R^1$ and $R^2$ are each independently hydrogen (H) or an optionally substituted $C_1$-$C_2$ alkyl, $C_1$-$C_3$ alkyl, $C_1$-$C_4$ alkyl, $C_1$-$C_5$ alkyl, $C_2$-$C_3$ alkyl, $C_2$-$C_4$ alkyl, $C_2$-$C_5$ alkyl, $C_2$-$C_6$ alkyl, $C_3$-$C_4$ alkyl, $C_3$-$C_5$ alkyl, $C_3$-$C_6$ alkyl, $C_4$-$C_5$ alkyl, $C_4$-$C_6$ alkyl, $C_5$-$C_6$ alkyl, $C_2$-$C_3$ alkenyl, $C_2$-$C_4$ alkenyl, $C_2$-$C_5$ alkenyl, $C_2$-$C_6$ alkenyl, $C_3$-$C_4$ alkenyl, $C_3$-$C_5$ alkenyl, $C_3$-$C_6$ alkenyl, $C_4$-$C_5$ alkenyl, $C_4$-$C_6$ alkenyl, $C_5$-$C_6$ alkenyl, $C_2$-$C_3$ alkynyl, $C_2$-$C_4$ alkynyl, $C_2$-$C_5$ alkynyl, $C_2$-$C_6$ alkynyl, $C_3$-$C_4$ alkynyl, $C_3$-$C_5$ alkynyl, $C_3$-$C_6$ alkynyl, $C_4$-$C_5$ alkynyl, $C_4$-$C_6$ alkynyl, or $C_5$-$C_6$ alkynyl. In particular embodiments, $R^1$ and $R^2$ are both methyl groups, both ethyl groups, or a combination of one methyl group and one ethyl group. In certain instances, $R^3$ is absent when the pH is above the p$K_a$ of the cationic lipid and $R^3$ is hydrogen (H) when the pH is below the p$K_a$ of the cationic lipid such that the amino head group is protonated. In certain other instances, $R^3$ is an optionally substituted $C_1$-$C_2$ alkyl, $C_1$-$C_3$ alkyl, $C_1$-$C_4$ alkyl, $C_1$-$C_5$ alkyl, $C_2$-$C_3$ alkyl, $C_2$-$C_4$ alkyl, $C_2$-$C_5$ alkyl, $C_2$-$C_6$ alkyl, $C_3$-$C_4$ alkyl, $C_3$-$C_5$ alkyl, $C_3$-$C_6$ alkyl, $C_4$-$C_5$ alkyl, $C_4$-$C_6$ alkyl, or $C_5$-$C_6$ alkyl to provide a quaternary amine.

In certain embodiments, $R^1$ and $R^2$ are joined to form an optionally substituted heterocyclic ring comprising 1, 2, 3, 4, 5, 6, or more carbon atoms and 1, 2, 3, 4, or more heteroatoms such as nitrogen (N), oxygen (O), sulfur (S), and mixtures thereof. In some embodiments, the optionally substituted heterocyclic ring comprises from 2 to 5 carbon atoms and from 1 to 3 heteroatoms such as nitrogen (N), oxygen (O), and/or sulfur (S). In certain embodiments, the heterocyclic ring comprises an optionally substituted imidazole, triazole (e.g., 1,2,3-triazole, 1,2,4-triazole), pyrazole, thiazole, pyrrole, furan, oxazole, isoxazole, oxazoline, oxazolidine, oxadiazole, tetrazole, and the like. In some instances, the optionally substituted heterocyclic ring comprises 5 carbon atoms and 1 nitrogen atom, wherein the heterocyclic ring can be substituted with a substituent such as a hydroxyl (—OH) group at the ortho, meta, and/or para positions. In certain instances, the heterocyclic ring comprises an optionally substituted imidazole group.

In other embodiments, $R^6$ is hydrogen (H) or an optionally substituted $C_1$-$C_2$ alkyl, $C_1$-$C_3$ alkyl, $C_1$-$C_4$ alkyl, $C_1$-$C_5$ alkyl, $C_1$-$C_6$ alkyl, $C_1$-$C_7$ alkyl, $C_1$-$C_8$ alkyl, $C_1$-$C_9$ alkyl, $C_2$-$C_3$ alkyl, $C_2$-$C_4$ alkyl, $C_2$-$C_5$ alkyl, $C_2$-$C_6$ alkyl, $C_2$-$C_7$ alkyl, $C_2$-$C_8$ alkyl, $C_2$-$C_9$ alkyl, $C_2$-$C_{10}$ alkyl, $C_3$-$C_4$ alkyl, $C_3$-$C_5$ alkyl, $C_3$-$C_6$ alkyl, $C_3$-$C_7$ alkyl, $C_3$-$C_8$ alkyl, $C_3$-$C_9$ alkyl, $C_3$-$C_{10}$ alkyl, $C_4$-$C_5$ alkyl, $C_4$-$C_6$ alkyl, $C_4$-$C_7$ alkyl, $C_4$-$C_8$ alkyl, $C_4$-$C_9$ alkyl, $C_4$-$C_{10}$ alkyl, $C_5$-$C_6$ alkyl, $C_5$-$C_7$ alkyl, $C_5$-$C_8$ alkyl, $C_5$-$C_9$ alkyl, $C_5$-$C_{10}$ alkyl, $C_6$-$C_7$ alkyl, $C_6$-$C_8$ alkyl, $C_6$-$C_9$ alkyl, $C_6$-$C_{10}$ alkyl, $C_7$-$C_8$ alkyl, $C_7$-$C_9$ alkyl, $C_7$-$C_{10}$ alkyl, $C_8$-$C_9$ alkyl, $C_8$-$C_{10}$ alkyl, $C_9$-$C_{10}$ alkyl, $C_2$-$C_3$ alkenyl, $C_2$-$C_4$ alkenyl, $C_2$-$C_5$ alkenyl, $C_2$-$C_6$ alkenyl, $C_2$-$C_7$ alkenyl, $C_2$-$C_8$ alkenyl, $C_2$-$C_9$ alkenyl, $C_2$-$C_{10}$ alkenyl, $C_3$-$C_4$ alkenyl, $C_3$-$C_5$ alkenyl, $C_3$-$C_6$ alkenyl, $C_3$-$C_7$ alkenyl, $C_3$-$C_8$ alkenyl, $C_3$-$C_9$ alkenyl, $C_3$-$C_{10}$ alkenyl, $C_4$-$C_5$ alkenyl, $C_4$-$C_6$ alkenyl, $C_4$-$C_7$ alkenyl, $C_4$-$C_8$ alkenyl, $C_4$-$C_9$ alkenyl, $C_4$-$C_{10}$ alkenyl, $C_5$-$C_6$ alkenyl, $C_5$-$C_7$ alkenyl, $C_5$-$C_8$ alkenyl, $C_5$-$C_9$ alkenyl, $C_5$-$C_{10}$ alkenyl, $C_6$-$C_7$ alkenyl, $C_6$-$C_8$ alkenyl, $C_6$-$C_9$ alkenyl, $C_6$-$C_{10}$ alkenyl, $C_7$-$C_8$ alkenyl, $C_7$-$C_9$ alkenyl, $C_7$-$C_{10}$ alkenyl, $C_8$-$C_9$ alkenyl, $C_8$-$C_{10}$ alkenyl, $C_9$-$C_{10}$ alkenyl, $C_2$-$C_3$ alkynyl, $C_2$-$C_4$ alkynyl, $C_2$-$C_5$ alkynyl, $C_2$-$C_6$ alkynyl, $C_2$-$C_7$ alkynyl, $C_2$-$C_8$ alkynyl, $C_2$-$C_9$ alkynyl, $C_3$-$C_4$ alkynyl, $C_3$-$C_5$ alkynyl, $C_3$-$C_6$ alkynyl, $C_3$-$C_7$ alkynyl, $C_3$-$C_8$ alkynyl, $C_3$-$C_9$ alkynyl, $C_3$-$C_{10}$ alkynyl, $C_4$-$C_5$ alkynyl, $C_4$-$C_6$ alkynyl, $C_4$-$C_7$ alkynyl, $C_4$-$C_8$ alkynyl, $C_4$-$C_9$ alkynyl, $C_4$-$C_{10}$ alkynyl, $C_5$-$C_6$ alkynyl, $C_5$-$C_7$ alkynyl, $C_5$-$C_8$ alkynyl, $C_5$-$C_9$ alkynyl, $C_5$-$C_{10}$ alkynyl, $C_6$-$C_7$ alkynyl, $C_6$-$C_8$ alkynyl, $C_6$-$C_9$ alkynyl, $C_6$-$C_{10}$ alkynyl, $C_7$-$C_8$ alkynyl, $C_7$-$C_9$ alkynyl, $C_7$-$C_{10}$ alkynyl, $C_8$-$C_9$ alkynyl, $C_8$-$C_{10}$ alkynyl, or $C_9$-$C_{10}$ alkynyl. In one particular embodiment, $R^6$ is selected from the group consisting of hydrogen (H), a $C_1$ alkyl (methyl) group, and a $C_2$, $C_3$, $C_4$, $C_5$, $C_6$, $C_7$, $C_8$, $C_9$, and $C_{10}$ alkyl, alkenyl, and alkynyl group.

In one particular embodiment, X is C(O)O. In another particular embodiment, X is O. In certain embodiments, X is C(O)N($R^6$), N($R^6$)C(O)O, or C(O)S. In one particular embodiment, X is N($R^6$)C(O)O and $R^6$ is hydrogen (H), a methyl group, or a $C_2$, $C_3$, $C_4$, $C_5$, $C_6$, $C_7$, $C_8$, $C_9$, or $C_{10}$ alkyl, alkenyl, or alkynyl group. In certain other embodiments, X is an optionally substituted heterocyclic ring. In particular embodiments, the heterocyclic ring comprises 1, 2, 3, 4, 5, 6, or more carbon atoms and 1, 2, 3, 4, or more heteroatoms such as nitrogen (N), oxygen (O), sulfur (S), and mixtures thereof. In some embodiments, the optionally substituted heterocyclic ring comprises from 2 to 5 carbon atoms and from 1 to 3 heteroatoms such as nitrogen (N), oxygen (O), and/or sulfur (S). In certain embodiments, the heterocyclic ring comprises an optionally substituted imidazole, triazole (e.g., 1,2,3-triazole, 1,2,4-triazole), pyrazole, thiazole, pyrrole, furan, oxazole, isoxazole, oxazoline, oxazolidine, oxadiazole, tetrazole, and the like. In certain instances, $R^1$ and $R^2$ are not both methyl groups when X is C(O)O, Y is $(CH_2)_2$ or $(CH_2)_3$, and $R^4$ and $R^5$ are both linoleyl moieties.

In certain embodiments, at least one or both $R^4$ and $R^5$ independently comprises an optionally substituted $C_{12}$-$C_{24}$, $C_{12}$-$C_{22}$, $C_{12}$-$C_{20}$, $C_{14}$-$C_{24}$, $C_{14}$-$C_{22}$, $C_{14}$-$C_{20}$, $C_{16}$-$C_{24}$, $C_{16}$-$C_{22}$, or $C_{16}$-$C_{20}$ alkyl, alkenyl, alkynyl, or acyl group (i.e., $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, or $C_{24}$ alkyl, alkenyl, alkynyl, or acyl group). In other embodiments, at least one or both $R^4$ and $R^5$ independently comprises at least 1, 2, 3, 4, 5, or 6 sites of unsaturation (e.g., 1-2, 1-3, 1-4, 1-5, 1-6, 2-3, 2-4, 2-5, or 2-6 sites of unsaturation) or a substituted alkyl or acyl group. In certain instances, the unsaturated side-chain comprises a dodecenyl moiety, a tetradecenyl (e.g., myristoleyl) moiety, a hexadecenyl (e.g., palmitoleyl) moiety, an octadecenyl (e.g., oleyl) moiety, an icosenyl moiety, a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, or an acyl derivative thereof (e.g., oleoyl, linoleoyl, linolenoyl, γ-linolenoyl, etc.). In some instances, the octadecadienyl moiety is a linoleyl moiety. In particular embodiments, $R^4$ and $R^5$ are both linoleyl moieties. In other instances, the octadecatrienyl moiety is a linolenyl moiety or a γ-linolenyl moiety. In particular embodiments, $R^4$ and $R^5$ are both linolenyl moieties or γ-linolenyl moieties. In embodiments where one or both $R^4$ and $R^5$ independently comprises a branched alkyl or acyl group (e.g., a substituted alkyl or acyl group), the branched alkyl or acyl group may comprise a $C_{12}$-$C_{24}$ alkyl or acyl having at least 1-6 (e.g., 1, 2, 3, 4, 5, 6, or more) $C_1$-$C_6$ alkyl substituents. In particular embodiments, the branched alkyl or acyl group comprises a $C_{12}$-$C_{20}$ or $C_{14}$-$C_{22}$ alkyl or acyl with 1-6 (e.g., 1, 2, 3, 4, 5, 6) $C_1$-$C_4$ alkyl (e.g., methyl, ethyl, propyl, or butyl) substituents. In some embodiments, the branched alkyl group comprises a phytanyl (3,7,11,15-tetramethyl-hexadecanyl) moiety and the branched acyl group comprises a phytanoyl (3,7,11,15-tetramethyl-hexadecanoyl) moiety. In particular embodiments, $R^4$ and $R^5$ are both phytanyl moieties. In further embodiments, at least one or both $R^4$ and $R^5$ are independently substituted with one, two, three, four, or more substituents such as oxo (=O) substituents, substituents, and combinations thereof, wherein each $R^x$ is independently hydrogen or an alkyl group. In certain instances, an oxo (=O) or —$OR^x$ (e.g., —OH) substituent is present in one or both $R^4$ and $R^5$ at the carbon which attaches $R^4$ or $R^5$ to the remainder of the compound.

In some embodiments, the 1, 2, 3, 4, 5, 6, or more sites of unsaturation present in one or both $R^4$ and $R^5$ correspond to, in each instance, cis double bonds, trans double bonds, or combinations thereof, at specific positions in one or both of the unsaturated side-chains. For those unsaturated side-chains where a double bond is located between hydrogen atoms and alkyl or alkylene chains, the chemical notation "E" refers to the trans double bond configuration and the chemical notation "Z" refers to the cis double bond configuration. As non-limiting examples, one or both $R^4$ and $R^5$ are $C_{18}$ alkyl groups containing any combination of double bonds in the cis and/or trans configuration at one or more positions in the side-chain (e.g., cis and/or trans double bonds at position 9, at positions 6 and 9, at positions 3, 6, and 9, at positions 6, 9, and 12, or at positions 7 and 9 of a $C_{18}$ alkyl group). Similarly, as non-limiting examples, one or both $R^4$ and $R^5$ are $C_{18}$ alkyl groups containing any combination of double bonds which can be characterized by either the "E" chemical notation and/or the "Z" chemical notation at one or more positions in the side-chain (e.g., "Z" and/or "E" double bonds at position 9, at positions 6 and 9, at positions 3, 6, and 9, at positions 6, 9, and 12, or at positions 7 and 9 of a $C_{18}$ alkyl group).

In other embodiments, at least one or both $R^4$ and $R^5$ independently comprises at least 1, 2, 3, 4, 5, 6, or more optionally substituted cyclic alkyl groups (e.g., 1-2, 1-3, 1-4, 1-5, 1-6, 2-3, 2-4, 2-5, or 2-6 optionally substituted cyclic alkyl groups). In certain other embodiments, $R^4$ and $R^5$ are independently an optionally substituted $C_{12}$-$C_{24}$, $C_{12}$-$C_{22}$, $C_{12}$-$C_{20}$, $C_{14}$-$C_{24}$, $C_{14}$-$C_{22}$, $C_{14}$-$C_{20}$, $C_{16}$-$C_{24}$, $C_{16}$-$C_{22}$, or $C_{16}$-$C_{20}$ alkyl, alkenyl, alkynyl, or acyl group (i.e., a $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, or $C_{24}$ alkyl, alkenyl, alkynyl, or acyl group), wherein at least one or more of (e.g., both) $R^4$ and $R^5$ independently comprises at least 1, 2, 3, 4, 5, or 6 optionally substituted cyclic alkyl groups (e.g., 1-2, 1-3, 1-4, 1-5, 1-6, 2-3, 2-4, 2-5, or 2-6 optionally substituted cyclic alkyl groups). In particular embodiments, the at least 1, 2, 3, 4, 5, or 6 optionally substituted cyclic alkyl groups present in $R^4$ and/or $R^5$ are independently selected from the group consisting of an optionally substituted saturated cyclic alkyl group, an optionally substituted unsaturated cyclic alkyl group, and combinations thereof. In certain instances, the optionally substituted saturated cyclic alkyl group comprises an optionally substituted $C_{3-8}$ cycloalkyl group (e.g., cyclopropyl, cyclobutyl, cyclopentyl, cyclohexyl, cycloheptyl, cyclooctyl, etc.). In preferred embodiments, the optionally substituted saturated cyclic alkyl group comprises a cyclopropyl group, optionally containing one or more substituents and/or heteroatoms. In other instances, the optionally substituted unsaturated cyclic alkyl group comprises an optionally substituted $C_{3-8}$ cycloalkenyl group (e.g., cyclopropenyl, cyclobutenyl, cyclopentenyl, cyclohexenyl, cycloheptenyl, cyclooctenyl, etc.). In particular embodiments, $R^4$ and $R^5$ are the same length (e.g., $C_{12}$-$C_{20}$ or $C_{18}$ alkyl chains) and contain the same number and type of cyclic alkyl group (e.g., one, two, or three $C_{3-8}$ cycloalkyl groups such as one, two, or three cyclopropyl groups on each of $R^4$ and $R^5$).

In certain other embodiments, one of $R^4$ or $R^5$ comprises at least 1, 2, 3, 4, 5, or 6 sites of unsaturation (e.g., 1-2, 1-3, 1-4, 1-5, 1-6, 2-3, 2-4, 2-5, or 2-6 sites of unsaturation) or a substituted alkyl or acyl group, and the other side-chain comprises at least 1, 2, 3, 4, 5, or 6 optionally substituted cyclic alkyl groups (e.g., 1-2, 1-3, 1-4, 1-5, 1-6, 2-3, 2-4, 2-5, or 2-6 optionally substituted cyclic alkyl groups). In embodiments where one of $R^4$ or $R^5$ comprises at least 1, 2, 3, 4, 5, or 6 sites of unsaturation, the unsaturated side-chain may comprise a dodecenyl moiety, a tetradecenyl (e.g., myristoleyl) moiety, a hexadecenyl (e.g., palmitoleyl) moiety, an octadecenyl (e.g., oleyl) moiety, an icosenyl moiety, a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, or an acyl derivative thereof (e.g., oleoyl, linoleoyl, linolenoyl, γ-linolenoyl, etc.). In some instances, the octadecadienyl moiety is a linoleyl moiety. In other instances, the octadecatrienyl moiety is a linolenyl moiety or a γ-linolenyl moiety. In embodiments where one of $R^4$ or $R^5$ comprises a branched alkyl or acyl group (e.g., a substituted alkyl or acyl group), the branched alkyl or acyl group may comprise a $C_{12}$-$C_{24}$ alkyl or acyl having at least 1-6 (e.g., 1, 2, 3, 4, 5, 6, or more) $C_1$-$C_6$ alkyl substituents. In particular embodiments, the branched alkyl or acyl group comprises a $C_{12}$-$C_{20}$ or $C_{14}$-$C_{22}$ alkyl or acyl with 1-6 (e.g., 1, 2, 3, 4, 5, 6) $C_1$-$C_4$ alkyl (e.g., methyl, ethyl, propyl, or butyl) substituents. In some embodiments, the branched alkyl group comprises a phytanyl (3,7,11,15-tetramethyl-hexadecanyl) moiety and the branched acyl group comprises a phytanoyl (3,7,11,15-tetramethyl-hexadecanoyl) moiety.

In particular embodiments, $R^4$ and $R^5$ are both independently selected $C_{12}$-$C_{20}$ alkyl groups (i.e., $C_{12}$, $C_{13}$, $C_{14}$, $C_{15}$, $C_{16}$, $C_{17}$, $C_{18}$, $C_{19}$, or $C_{20}$ alkyl groups) having at least 1, 2, 3, 4, 5, or 6 optionally substituted cyclic alkyl groups (e.g., 1-2, 1-3, 1-4, 1-5, 1-6, 2-3, 2-4, 2-5, or 2-6 optionally substituted cyclic alkyl groups). In preferred embodiments, $R^4$ and $R^5$ are both $C_{18}$ alkyl groups having at least one, two, three, or more optionally substituted cyclic alkyl groups such as, for example, an optionally substituted $C_{3-8}$ cycloalkyl group (e.g., a cyclopropyl group, optionally containing one or more substituents and/or heteroatoms). In certain embodiments, each of the optionally substituted cyclic alkyl groups is independently selected and can be the same cyclic alkyl group (e.g., all cyclopropyl groups) or different cyclic alkyl groups (e.g., cyclopropyl and other cycloalkyl, heterocycloalkyl, cycloalkenyl, and/or heterocycloalkenyl groups).

In preferred embodiments, the optionally substituted cyclic alkyl groups present in $R^4$ and/or $R^5$ are located at the site(s) of unsaturation in the corresponding unsaturated side-chain. As a non-limiting example, one or both of $R^4$ and $R^5$ are $C_{18}$ alkyl groups having 1, 2, or 3 optionally substituted cyclic alkyl groups, wherein the optionally substituted cyclic alkyl groups (e.g., independently selected cyclopropyl groups) are located at one or more (e.g., all) of the sites of unsaturation present in a corresponding linoleyl moiety, linolenyl moiety, or γ-linolenyl moiety.

In alternative embodiments to the cationic lipid of Formula I, $R^4$ and $R^5$ are different and are independently an optionally substituted $C_1$-$C_{24}$ alkyl, $C_2$-$C_{24}$ alkenyl, $C_2$-$C_{24}$ alkynyl, or $C_1$-$C_{24}$ acyl. In particular embodiments, one of $R^4$ or $R^5$ comprises at least 1, 2, 3, 4, 5, or 6 optionally substituted cyclic alkyl groups (e.g., 1-2, 1-3, 1-4, 1-5, 1-6, 2-3, 2-4, 2-5, or 2-6 optionally substituted cyclic alkyl groups). In certain embodiments, $R^4$ and $R^5$ are different and are independently an optionally substituted $C_4$-$C_{20}$ alkyl, $C_4$-$C_{20}$ alkenyl, $C_4$-$C_{20}$ alkynyl, or $C_4$-$C_{20}$ acyl. In some instances, $R^4$ is an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl, and $R^5$ is an optionally substituted $C_4$-$C_{10}$ alkyl, $C_4$-$C_{10}$ alkenyl, $C_4$-$C_{10}$ alkynyl, or $C_4$-$C_{10}$ acyl. In other instances, $R^4$ is an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl, and $R^5$ is an optionally substituted $C_4$-$C_8$ or $C_6$ alkyl, $C_4$-$C_8$ or $C_6$ alkenyl, $C_4$-$C_8$ or $C_6$ alkynyl, or $C_4$-$C_8$ or $C_6$ acyl. In certain instances, $R^4$ is an optionally substituted $C_4$-$C_{10}$ alkyl, $C_4$-$C_{10}$ alkenyl, $C_4$-$C_{10}$ alkynyl, or $C_4$-$C_{10}$ acyl, and $R^5$ is an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl. In certain other instances, $R^4$ is an optionally substituted $C_4$-$C_8$ or $C_6$ alkyl, $C_4$-$C_8$ or $C_6$ alkenyl, $C_4$-$C_8$ or $C_6$ alkynyl, or $C_4$-$C_8$ or $C_6$ acyl, and $R^5$ is an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl. In particular embodiments, one or more of the optionally substituted cyclic alkyl groups, when present in one of $R^4$ or $R^5$, are as described above.

In some groups of embodiments to the cationic lipid of Formula I, $R^4$ and $R^5$ are either the same or different and are independently selected from the group consisting of:

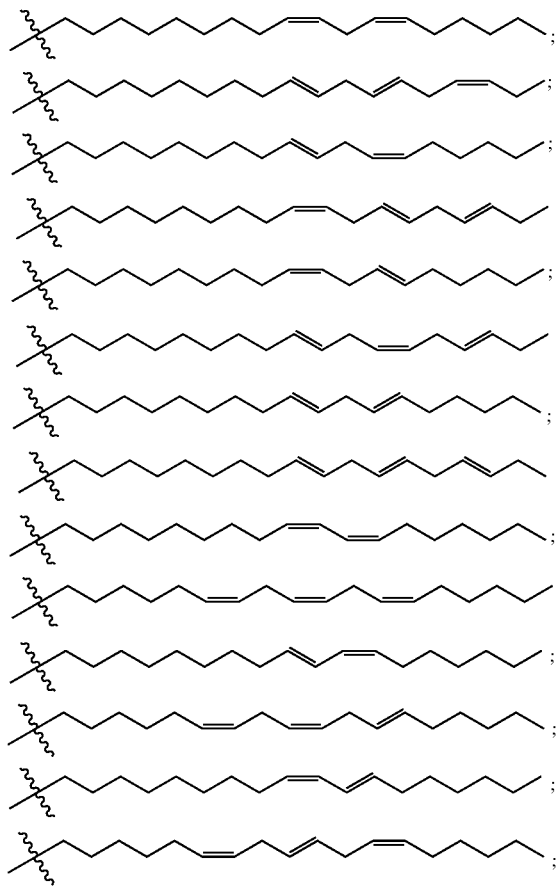

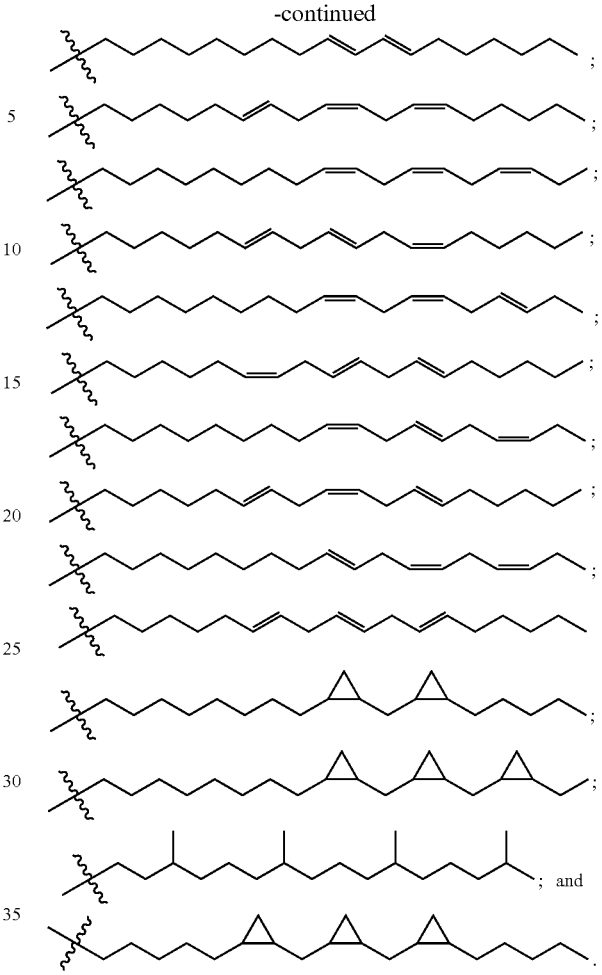

In certain embodiments, Y is an optionally substituted $C_1$-$C_2$ alkyl, $C_1$-$C_3$ alkyl, $C_1$-$C_4$ alkyl, $C_1$-$C_5$ alkyl, $C_2$-$C_3$ alkyl, $C_2$-$C_4$ alkyl, $C_2$-$C_5$ alkyl, $C_2$-$C_6$ alkyl, $C_3$-$C_4$ alkyl, $C_3$-$C_5$ alkyl, $C_3$-$C_6$ alkyl, $C_4$-$C_5$ alkyl, $C_4$-$C_6$ alkyl, $C_5$-$C_6$ alkyl, $C_2$-$C_3$ alkenyl, $C_2$-$C_4$ alkenyl, $C_2$-$C_5$ alkenyl, $C_2$-$C_6$ alkenyl, $C_3$-$C_4$ alkenyl, $C_3$-$C_5$ alkenyl, $C_3$-$C_6$ alkenyl, $C_4$-$C_5$ alkenyl, $C_4$-$C_6$ alkenyl, $C_5$-$C_6$ alkenyl, $C_2$-$C_3$ alkynyl, $C_2$-$C_4$ alkynyl, $C_2$-$C_5$ alkynyl, $C_2$-$C_6$ alkynyl, $C_3$-$C_4$ alkynyl, $C_3$-$C_5$ alkynyl, $C_3$-$C_6$ alkynyl, $C_4$-$C_5$ alkynyl, $C_4$-$C_6$ alkynyl, or $C_5$-$C_6$ alkynyl. In one particular embodiment, Y is $(CH_2)_n$ and n is 0, 1, 2, 3, 4, 5, or 6 (e.g., 1-2, 1-3, 1-4, 1-5, 1-6, 2-3, 2-4, 2-5, or 2-6). In a preferred embodiment, n is 2, 3, or 4.

In particular embodiments, the cationic lipid of Formula I has the following structure:

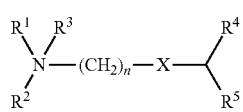

or salts thereof, wherein $R^1$, $R^2$, $R^3$, $R^4$, $R^5$, X, and n are the same as described above.

In some embodiments, the cationic lipid of Formula I forms a salt (preferably a crystalline salt) with one or more anions. In one particular embodiment, the cationic lipid of Formula I is the oxalate (e.g., hemioxalate) salt thereof, which is preferably a crystalline salt.

In particularly preferred embodiments, the cationic lipid of Formula I has one of the following structures:
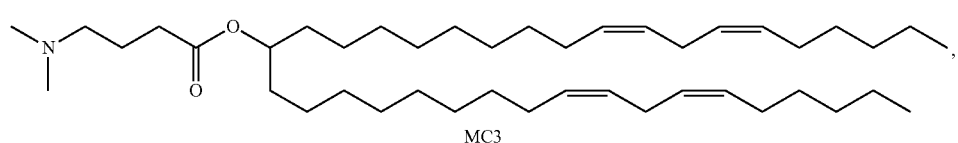
MC3 (Compound 1)
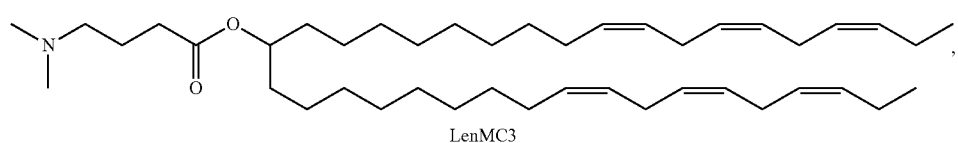
LenMC3 (Compound 4)
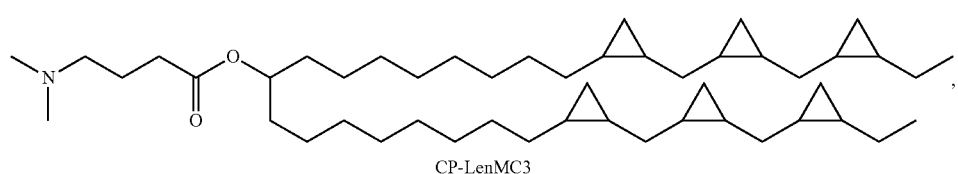
CP-LenMC3 (Compound 5)
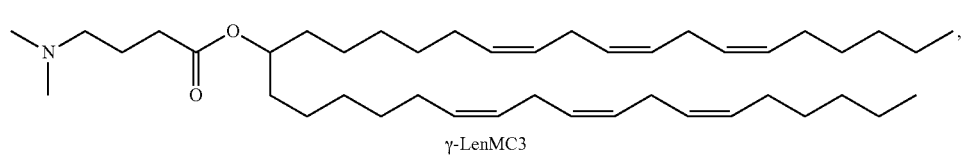
γ-LenMC3 (Compound 8)
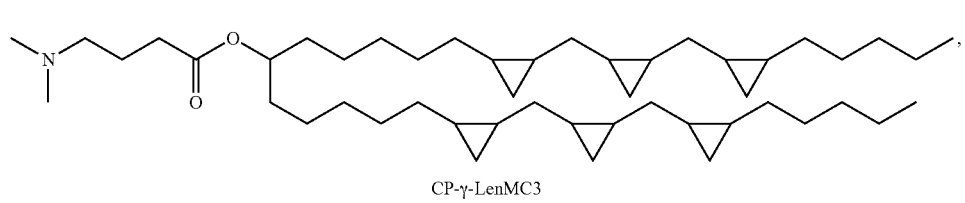
CP-γ-LenMC3 (Compound 9)
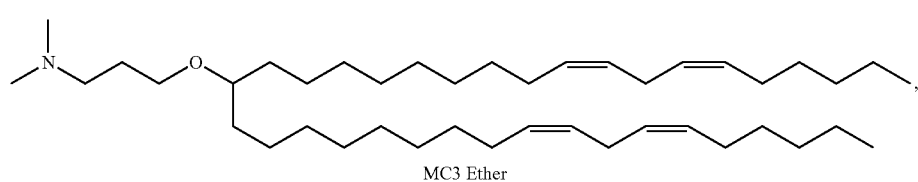
MC3 Ether (Compound 13)
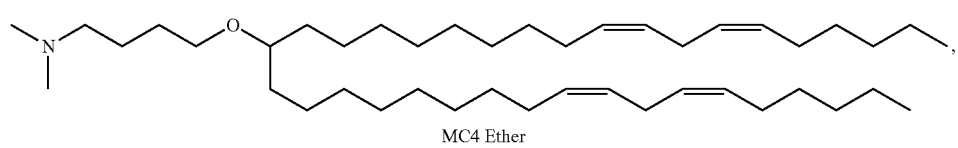
MC4 Ether (Compound 15)
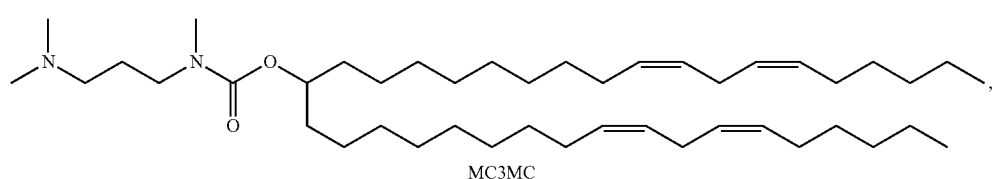
MC3MC (Compound 10)
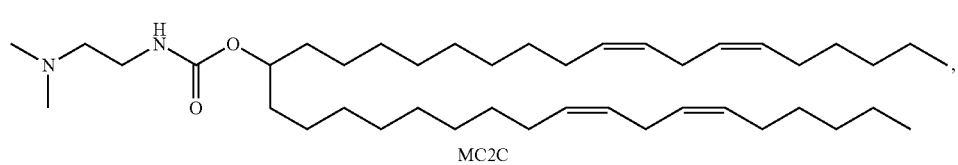
MC2C (Compound 12)

(Compound 11)
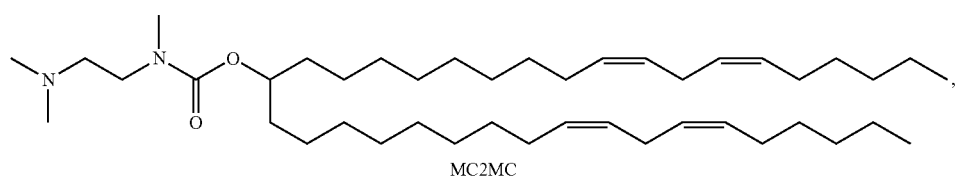
MC2MC
(Compound 20)
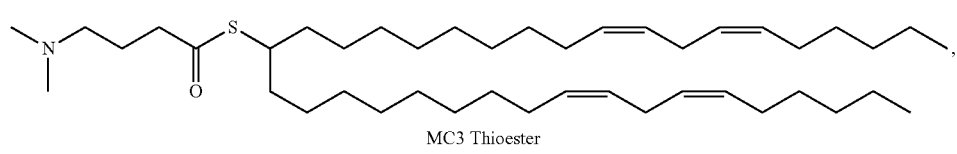
MC3 Thioester
(Compound 63)
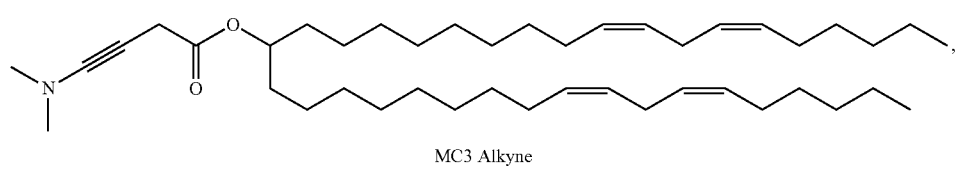
MC3 Alkyne
(Compound 16)
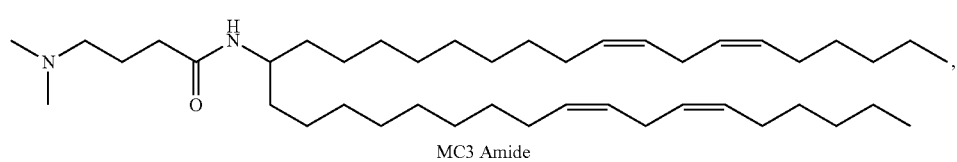
MC3 Amide
(Compound 17)
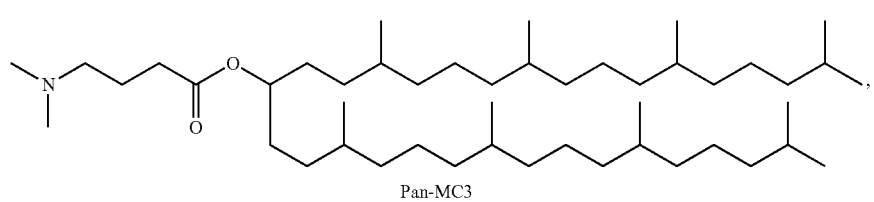
Pan-MC3
(Compound 18)
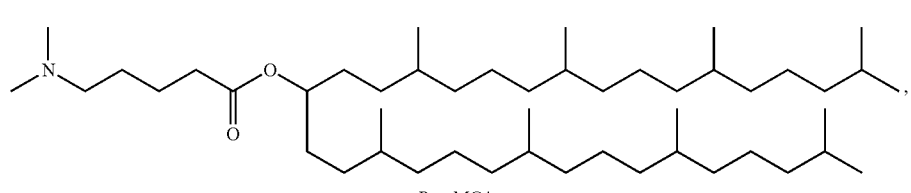
Pan-MC4
(Compound 19)
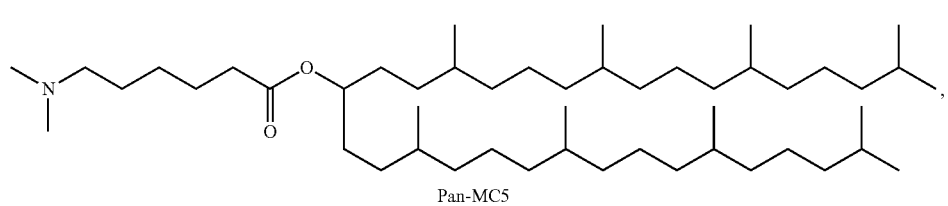
Pan-MC5
Compound 21
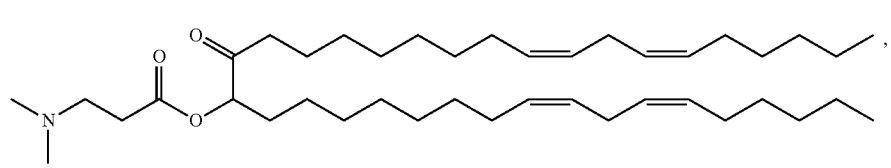
Compound 22
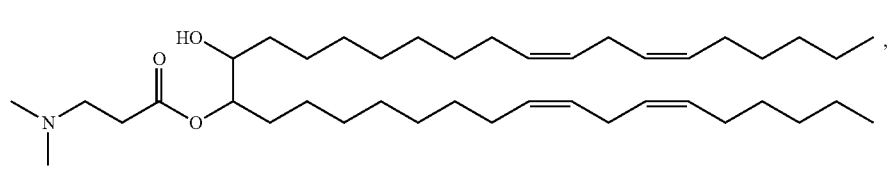

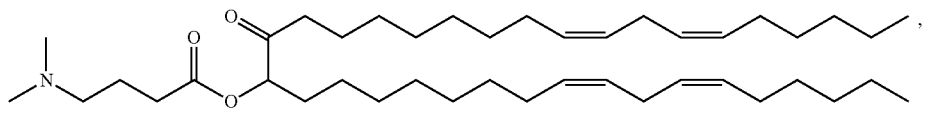
Compound 23
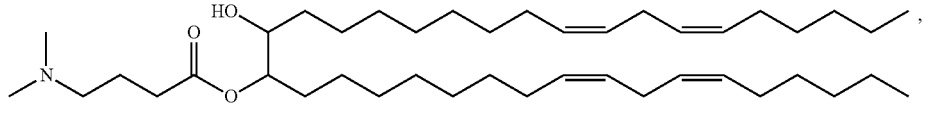
Compound 24
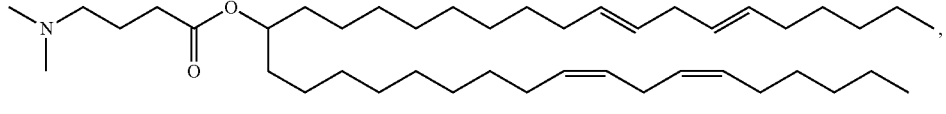
Compound 25
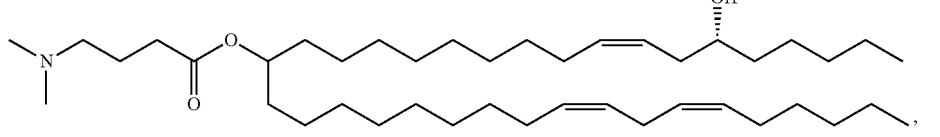
Compound 26
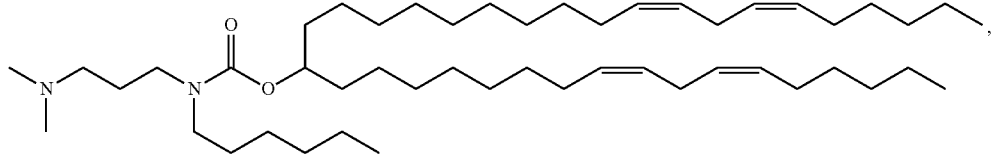
Compound 27
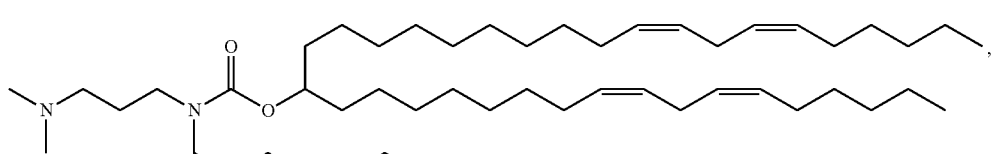
Compound 28
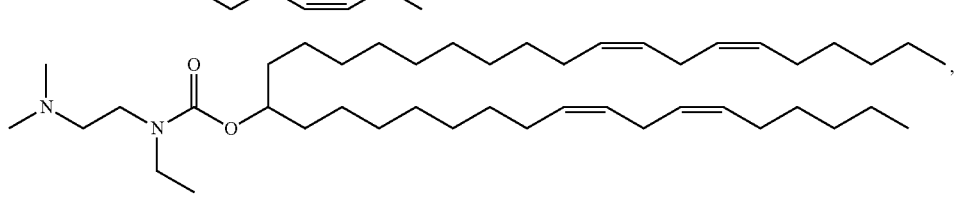
Compound 29
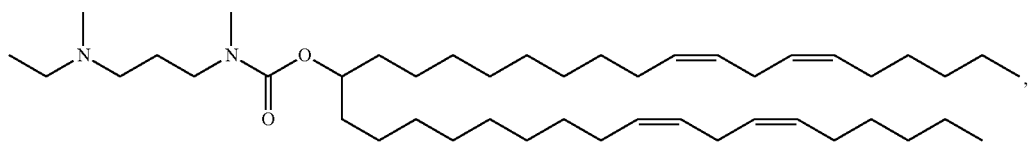
Compound 30
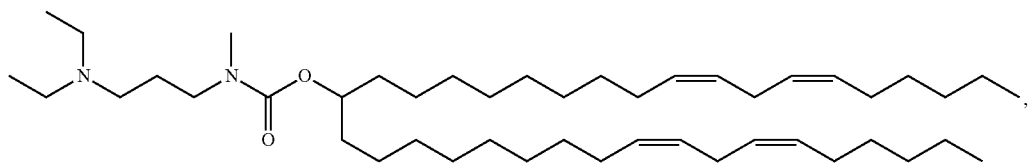
Compound 31
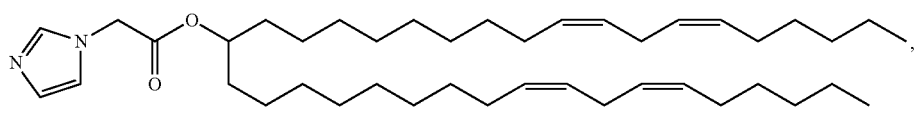
Compound 32
Compound 33

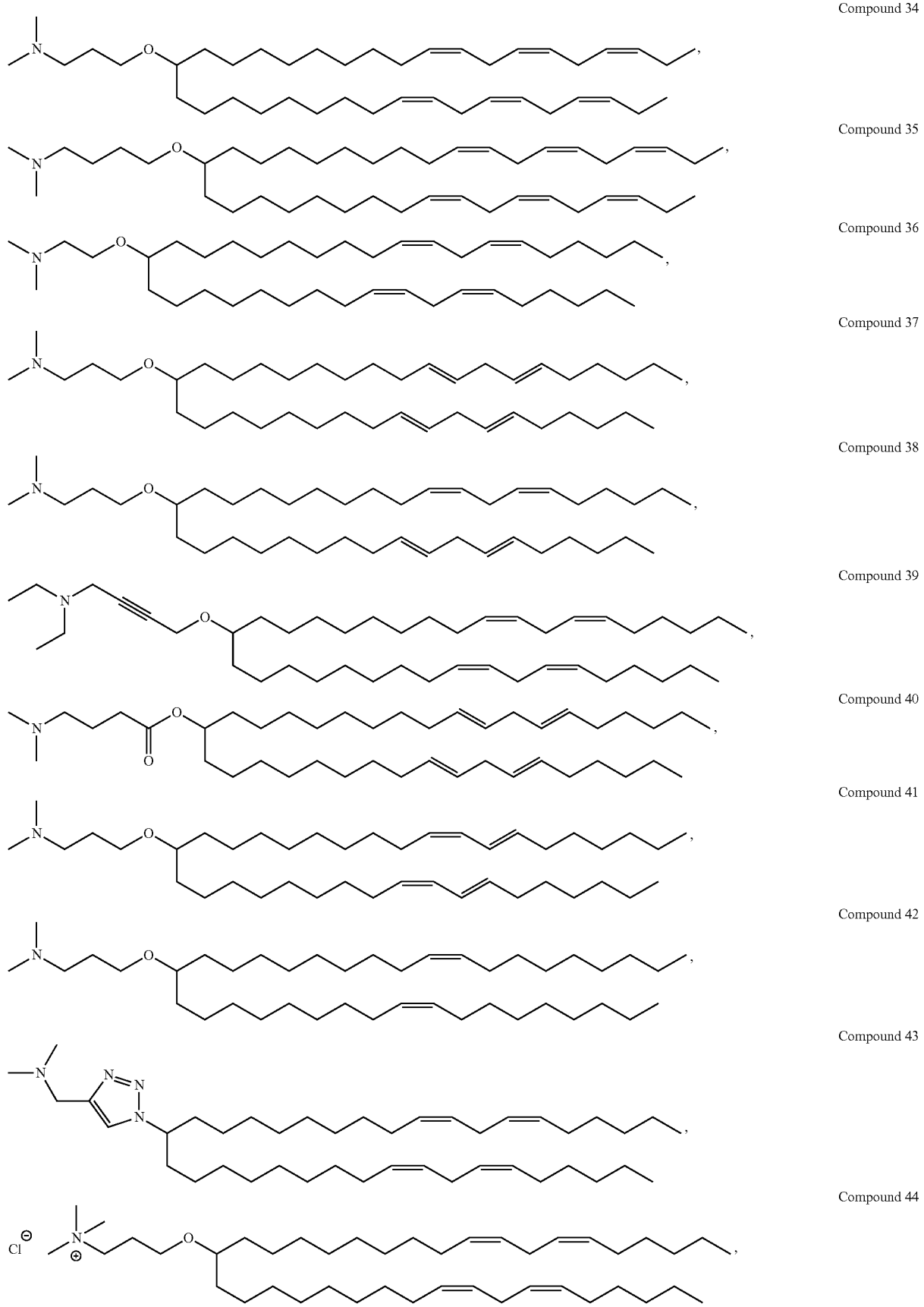

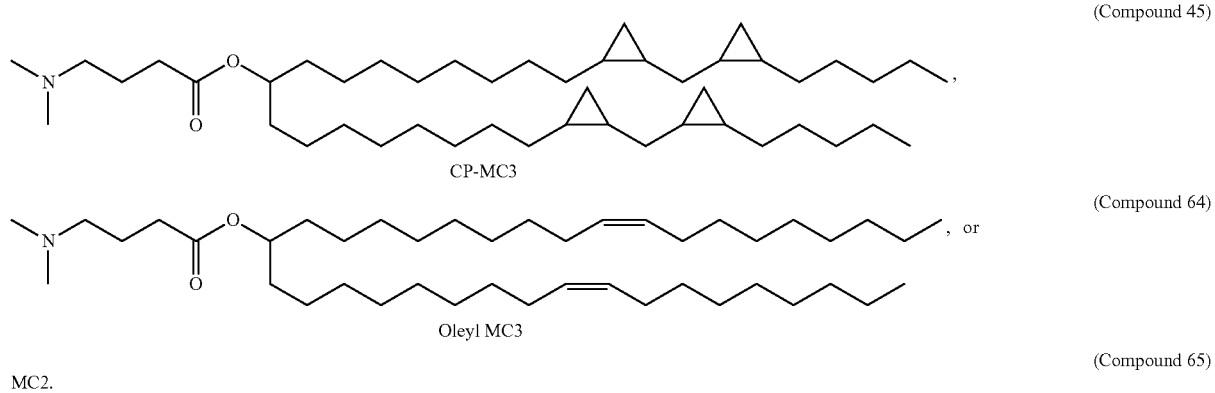

(Compound 45) CP-MC3

(Compound 64) Oleyl MC3

(Compound 65) MC2.

The synthesis of Compounds 1, 4, 5, 8, 9, 10, 11, 12, 13, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, and 45 is described herein. The synthesis of oleyl MC3 (Compound 64) is described in PCT Publication Nos. WO 2010/054401 and WO 2010/054405, the disclosures of which are herein incorporated by reference in their entirety for all purposes. The synthesis of MC2 (Compound 65) (dilinoleylmethyl-3-dimethylaminopropionate, also known as DLin-M-C2-DMA, DLin-M-K-DMA, or DLin-M-DMA) is described in PCT Publication No. WO 2010/042877, the disclosure of which is incorporated herein by reference in its entirety for all purposes.

In another aspect, cationic lipids of Formula II having the following structure (or salts thereof) are useful in the present invention:

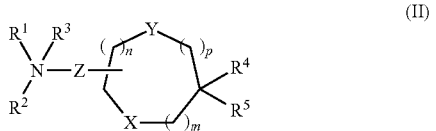

(II)

or salts thereof, wherein:

$R^1$ and $R^2$ are either the same or different and are independently an optionally substituted $C_1$-$C_6$ alkyl, $C_2$-$C_6$ alkenyl, or $C_2$-$C_6$ alkenyl, or $R^1$ and $R^2$ may join to form an optionally substituted heterocyclic ring;

$R^3$ is either absent or is hydrogen (H) or a $C_1$-$C_6$ alkyl to provide a quaternary amine;

$R^4$ and $R^5$ are either the same or different and are independently an optionally substituted $C_{10}$-$C_{24}$ alkyl, $C_{10}$-$C_{24}$ alkenyl, $C_{10}$-$C_{24}$ alkynyl, or $C_{10}$-$C_{24}$ acyl, wherein at least one of $R^4$ and $R^5$ comprises at least 1, 2, 3, 4, 5, 6, or more optionally substituted cyclic alkyl groups (e.g., 1-2, 1-3, 1-4, 1-5, 1-6, 2-3, 2-4, 2-5, or 2-6 optionally substituted cyclic alkyl groups);

m, n, and p are either the same or different and are independently either 0, 1, or 2, with the proviso that in, n, and p are not simultaneously 0;

X and Y are either the same or different and are independently O, S, N($R^6$), C(O), C(O)O, OC(O), C(O)N($R^6$), N($R^6$)C(O), OC(O)N($R^6$), N($R^6$)C(O)O, C(O)S, C(S)O, S(O), S(O)(O), or C(S), wherein $R^6$ is hydrogen (H) or an optionally substituted $C_1$-$C_{10}$ alkyl, $C_2$-$C_{10}$ alkenyl, or $C_2$-$C_{10}$ alkynyl; and Z is either absent or is an optionally substituted $C_1$-$C_6$ alkyl, $C_2$-$C_6$ alkenyl, or $C_2$-$C_6$ alkynyl.

In some embodiments, $R^1$ and $R^2$ are each independently hydrogen (H) or an optionally substituted $C_1$-$C_2$ alkyl, $C_1$-$C_3$ alkyl, $C_1$-$C_4$ alkyl, $C_1$-$C_5$ alkyl, $C_2$-$C_3$ alkyl, $C_2$-$C_4$ alkyl, $C_2$-$C_5$ alkyl, $C_2$-$C_6$ alkyl, $C_3$-$C_4$ alkyl, $C_3$-$C_5$ alkyl, $C_3$-$C_6$ alkyl, $C_4$-$C_5$ alkyl, $C_4$-$C_6$ alkyl, $C_5$-$C_6$ alkyl, $C_2$-$C_3$ alkenyl, $C_2$-$C_4$ alkenyl, $C_2$-$C_5$ alkenyl, $C_2$-$C_6$ alkenyl, $C_3$-$C_4$ alkenyl, $C_3$-$C_5$ alkenyl, $C_3$-$C_6$ alkenyl, $C_4$-$C_5$ alkenyl, $C_4$-$C_6$ alkenyl, $C_5$-$C_6$ alkenyl, $C_2$-$C_3$ alkynyl, $C_2$-$C_4$ alkynyl, $C_2$-$C_5$ alkynyl, $C_2$-$C_6$ alkynyl, $C_3$-$C_4$ alkynyl, $C_3$-$C_5$ alkynyl, $C_3$-$C_6$ alkynyl, $C_4$-$C_5$ alkynyl, $C_4$-$C_6$ alkynyl, or $C_5$-$C_6$ alkynyl. In particular embodiments, $R^1$ and $R^2$ are both methyl groups, both ethyl groups, or a combination of one methyl group and one ethyl group. In certain instances, $R^3$ is absent when the pH is above the $pK_a$ of the cationic lipid and $R^3$ is hydrogen (H) when the pH is below the $pK_a$ of the cationic lipid such that the amino head group is protonated. In certain other instances, $R^3$ is an optionally substituted $C_1$-$C_2$ alkyl, $C_1$-$C_3$ alkyl, $C_1$-$C_4$ alkyl, $C_1$-$C_5$ alkyl, $C_2$-$C_3$ alkyl, $C_2$-$C_4$ alkyl, $C_2$-$C_5$ alkyl, $C_2$-$C_6$ alkyl, $C_3$-$C_4$ alkyl, $C_3$-$C_5$ alkyl, $C_3$-$C_6$ alkyl, $C_4$-$C_5$ alkyl, $C_4$-$C_6$ alkyl, or $C_5$-$C_6$ alkyl to provide a quaternary amine.

In certain embodiments, $R^1$ and $R^2$ are joined to form an optionally substituted heterocyclic ring comprising 1, 2, 3, 4, 5, 6, or more carbon atoms and 1, 2, 3, 4, or more heteroatoms such as nitrogen (N), oxygen (O), sulfur (S), and mixtures thereof. In some embodiments, the optionally substituted heterocyclic ring comprises from 2 to 5 carbon atoms and from 1 to 3 heteroatoms such as nitrogen (N), oxygen (O), and/or sulfur (S). In certain embodiments, the heterocyclic ring comprises an optionally substituted imidazole, triazole (e.g., 1,2,3-triazole, 1,2,4-triazole), pyrazole, thiazole, pyrrole, furan, oxazole, isoxazole, oxazoline, oxazolidine, oxadiazole, tetrazole, and the like. In some instances, the optionally substituted heterocyclic ring comprises 5 carbon atoms and 1 nitrogen atom, wherein the heterocyclic ring can be substituted with a substituent such as a hydroxyl (—OH) group at the ortho, meta, and/or para positions. In certain instances, the heterocyclic ring comprises an optionally substituted imidazole group.

In other embodiments, $R^6$ is hydrogen (H) or an optionally substituted $C_1$-$C_2$ alkyl, $C_1$-$C_3$ alkyl, $C_1$-$C_4$ alkyl, $C_1$-$C_5$ alkyl, $C_1$-$C_6$ alkyl, $C_1$-$C_7$ alkyl, $C_1$-$C_8$ alkyl, $C_1$-$C_9$ alkyl, $C_2$-$C_3$ alkyl, $C_2$-$C_4$ alkyl, $C_2$-$C_5$ alkyl, $C_2$-$C_6$ alkyl, $C_2$-$C_7$ alkyl, $C_2$-$C_8$ alkyl, $C_2$-$C_9$ alkyl, $C_2$-$C_{10}$ alkyl, $C_3$-$C_4$ alkyl, $C_3$-$C_5$ alkyl, $C_3$-$C_6$ alkyl, $C_3$-$C_7$ alkyl, $C_3$-$C_8$ alkyl, $C_3$-$C_9$ alkyl, $C_3$-$C_{10}$ alkyl, $C_4$-$C_5$ alkyl, $C_4$-$C_6$ alkyl, $C_4$-$C_7$ alkyl, $C_4$-$C_8$ alkyl, $C_4$-$C_9$ alkyl, $C_4$-$C_{10}$ alkyl, $C_5$-$C_6$ alkyl, $C_5$-$C_7$ alkyl, $C_5$-$C_8$ alkyl, $C_5$-$C_9$ alkyl, $C_5$-$C_{10}$ alkyl, $C_6$-$C_7$ alkyl, $C_6$-$C_8$ alkyl, $C_6$-$C_9$ alkyl, $C_6$-$C_{10}$ alkyl, $C_7$-$C_8$ alkyl, $C_7$-$C_9$ alkyl, $C_7$-$C_{10}$ alkyl, $C_8$-$C_9$ alkyl, $C_8$-$C_{10}$ alkyl, $C_9$-$C_{10}$ alkyl, $C_2$-$C_3$ alkenyl, $C_2$-$C_4$ alkenyl, $C_2$-$C_5$ alkenyl, $C_2$-$C_6$ alkenyl, $C_2$-$C_7$ alkenyl, $C_2$-$C_8$ alkenyl, $C_2$-$C_9$ alkenyl, $C_3$-$C_4$ alkenyl, $C_3$-$C_5$ alkenyl, $C_3$-$C_6$ alkenyl, $C_3$-$C_7$ alkenyl, $C_3$-$C_8$ alkenyl, $C_3$-$C_9$ alkenyl, $C_3$-$C_{10}$ alkenyl, $C_4$-$C_5$ alkenyl, $C_4$-$C_6$ alkenyl, $C_4$-$C_7$ alkenyl, $C_4$-$C_8$ alkenyl, $C_4$-$C_9$ alkenyl, $C_4$-$C_{10}$ alkenyl, $C_5$-$C_6$ alkenyl, $C_5$-$C_7$ alkenyl, $C_5$-$C_8$ alkenyl, $C_5$-$C_9$ alkenyl, $C_5$-$C_{10}$ alkenyl, $C_6$-$C_7$ alkenyl, $C_6$-$C_8$ alkenyl, $C_6$-$C_9$ alkenyl, $C_6$-$C_{10}$ alkenyl, $C_7$-$C_8$ alkenyl, $C_7$-$C_9$ alkenyl, $C_7$-$C_{10}$ alkenyl, $C_8$-$C_9$ alkenyl, $C_8$-$C_{10}$ alkenyl, $C_9$-$C_{10}$ alkenyl, $C_2$-$C_3$ alkynyl, $C_2$-$C_4$ alkynyl, $C_2$-$C_5$ alkynyl, $C_2$-$C_6$ alkynyl, $C_2$-$C_7$ alkynyl, $C_2$-$C_8$ alkynyl, $C_2$-$C_9$ alkynyl, $C_3$-$C_4$ alkynyl, $C_3$-$C_5$ alkynyl, $C_3$-$C_6$ alkynyl, $C_3$-$C_7$ alkynyl, $C_3$-$C_8$ alkynyl, $C_3$-$C_9$ alkynyl, $C_3$-$C_{10}$ alkynyl, $C_4$-$C_5$ alkynyl, $C_4$-$C_6$ alkynyl, $C_4$-$C_7$ alkynyl, $C_4$-$C_8$ alkynyl, $C_4$-$C_9$ alkynyl, $C_4$-$C_{10}$ alkynyl, $C_5$-$C_6$ alkynyl, $C_5$-$C_7$ alkynyl, $C_5$-$C_8$ alkynyl, $C_5$-$C_9$ alkynyl, $C_5$-$C_{10}$ alkynyl, $C_6$-$C_7$ alkynyl, $C_6$-$C_8$ alkynyl, $C_6$-$C_9$ alkynyl, $C_6$-$C_{10}$ alkynyl, $C_7$-$C_8$ alkynyl, $C_7$-$C_9$ alkynyl, $C_7$-$C_{10}$ alkynyl, $C_8$-$C_9$ alkynyl, $C_8$-$C_{10}$ alkynyl, or $C_9$-$C_{10}$ alkynyl. In one particular embodiment, $R^6$ is selected from the group consisting of hydrogen (H), a $C_1$ alkyl (methyl) group, and a $C_2$, $C_3$, $C_4$, $C_5$, $C_6$, $C_7$, $C_8$, $C_9$, and $C_{10}$ alkyl, alkenyl, and alkynyl group.

In one embodiment, X and Y are independently selected from the group consisting of O, C(O)O, C(O)N($R^6$), N($R^6$)C(O)O, and C(O)S. In one particular embodiment, X and Y are both oxygen (O). In another particular embodiment, at least one of (e.g., both) X and Y is N($R^6$)C(O)O and each $R^6$ is independently hydrogen (H), a methyl group, or a $C_2$, $C_3$, $C_4$, $C_5$, $C_6$, $C_7$, $C_8$, $C_9$, or $C_{10}$ alkyl, alkenyl, or alkynyl group.

In certain embodiments, $R^4$ and $R^5$ are independently an optionally substituted $C_{12}$-$C_{24}$, $C_{12}$-$C_{22}$, $C_{12}$-$C_{20}$, $C_{14}$-$C_{24}$, $C_{14}$-$C_{22}$, $C_{14}$-$C_{20}$, $C_{16}$-$C_{24}$, $C_{16}$-$C_{22}$, or $C_{16}$-$C_{20}$ alkyl, alkenyl, alkynyl, or acyl group (i.e., a $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, or $C_{24}$ alkyl, alkenyl, alkynyl, or acyl group), wherein at least one or more of (e.g., both) $R^4$ and $R^5$ independently comprises at least 1, 2, 3, 4, 5, or 6 optionally substituted cyclic alkyl groups (e.g., 1-2, 1-3, 1-4, 1-5, 1-6, 2-3, 2-4, 2-5, or 2-6 optionally substituted cyclic alkyl groups). In particular embodiments, the at least 1, 2, 3, 4, 5, or 6 optionally substituted cyclic alkyl groups present in $R^4$ and/or $R^5$ are independently selected from the group consisting of an optionally substituted saturated cyclic alkyl group, an optionally substituted unsaturated cyclic alkyl group, and combinations thereof. In certain instances, the optionally substituted saturated cyclic alkyl group comprises an optionally substituted $C_{3-8}$ cycloalkyl group (e.g., cyclopropyl, cyclobutyl, cyclopentyl, cyclohexyl, cycloheptyl, cyclooctyl, etc.). In preferred embodiments, the optionally substituted saturated cyclic alkyl group comprises a cyclopropyl group, optionally containing one or more substituents and/or heteroatoms. In other instances, the optionally substituted unsaturated cyclic alkyl group comprises an optionally substituted $C_{3-8}$ cycloalkenyl group (e.g., cyclopropenyl, cyclobutenyl, cyclopentenyl, cyclohexenyl, cycloheptenyl, cyclooctenyl, etc.). In particular embodiments, $R^4$ and $R^5$ are the same length (e.g., $C_{12}$-$C_{20}$ or $C_{18}$ alkyl chains) and contain the same number and type of cyclic alkyl group (e.g., one, two, or three $C_{3-4}$ cycloalkyl groups such as one, two, or three cyclopropyl groups on each of $R^4$ and $R^5$).

In certain other embodiments, one of $R^4$ or $R^5$ comprises at least 1, 2, 3, 4, 5, or 6 sites of unsaturation (e.g., 1-2, 1-3, 1-4, 1-5, 1-6, 2-3, 2-4, 2-5, or 2-6 sites of unsaturation) or a substituted alkyl or acyl group, and the other side-chain comprises at least 1, 2, 3, 4, 5, or 6 optionally substituted cyclic alkyl groups (e.g., 1-2, 1-3, 1-4, 1-5, 1-6, 2-3, 2-4, 2-5, or 2-6 optionally substituted cyclic alkyl groups). In embodiments where one of $R^4$ or $R^5$ comprises at least 1, 2, 3, 4, 5, or 6 sites of unsaturation, the unsaturated side-chain may comprise a dodecenyl moiety, a tetradecenyl (e.g., myristoleyl) moiety, a hexadecenyl (e.g., palmitoleyl) moiety, an octadecenyl (e.g., oleyl) moiety, an icosenyl moiety, a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, or an acyl derivative thereof (e.g., oleoyl, linoleoyl, linolenoyl, γ-linolenoyl, etc.). In some instances, the octadecadienyl moiety is a linoleyl moiety. In other instances, the octadecatrienyl moiety is a linolenyl moiety or a γ-linolenyl moiety. In embodiments where one of $R^4$ or $R^5$ comprises a branched alkyl or acyl group (e.g., a substituted alkyl or acyl group), the branched alkyl or acyl group may comprise a $C_{12}$-$C_{24}$ alkyl or acyl having at least 1-6 (e.g., 1, 2, 3, 4, 5, 6, or more) $C_1$-$C_6$ alkyl substituents. In particular embodiments, the branched alkyl or acyl group comprises a $C_{12}$-$C_{20}$ or $C_{14}$-$C_{22}$ alkyl or acyl with 1-6 (e.g., 1, 2, 3, 4, 5, 6) $C_1$-$C_4$ alkyl (e.g., methyl, ethyl, propyl, or butyl) substituents. In some embodiments, the branched alkyl group comprises a phytanyl (3,7,11,15-tetramethyl-hexadecanyl) moiety and the branched acyl group comprises a phytanoyl (3,7,11,15-tetramethyl-hexadecanoyl) moiety.

In particular embodiments, $R^4$ and $R^5$ are both independently selected $C_{12}$-$C_{20}$ alkyl groups (i.e., $C_{12}$, $C_{13}$, $C_{14}$, $C_{15}$, $C_{16}$, $C_{17}$, $C_{18}$, $C_{19}$, or $C_{20}$ alkyl groups) having at least 1, 2, 3, 4, 5, or 6 optionally substituted cyclic alkyl groups (e.g., 1-2, 1-3, 1-4, 1-5, 1-6, 2-3, 2-4, 2-5, or 2-6 optionally substituted cyclic alkyl groups). In preferred embodiments, $R^4$ and $R^5$ are both $C_{18}$ alkyl groups having at least one, two, three, or more optionally substituted cyclic alkyl groups such as, for example, an optionally substituted $C_{3-8}$ cycloalkyl group (e.g., a cyclopropyl group, optionally containing one or more substituents and/or heteroatoms). In certain embodiments, each of the optionally substituted cyclic alkyl groups is independently selected and can be the same cyclic alkyl group (e.g., all cyclopropyl groups) or different cyclic alkyl groups (e.g., cyclopropyl and other cycloalkyl, heterocycloalkyl, cycloalkenyl, and/or heterocycloalkenyl groups).

In preferred embodiments, the optionally substituted cyclic alkyl groups present in $R^4$ and/or $R^5$ are located at the site(s) of unsaturation in the corresponding unsaturated side-chain. As a non-limiting example, one or both of $R^4$ and $R^5$ are $C_{18}$ alkyl groups having 1, 2, or 3 optionally substituted cyclic alkyl groups, wherein the optionally substituted cyclic alkyl groups (e.g., independently selected cyclopropyl groups) are located at one or more (e.g., all) of the sites of unsaturation present in a corresponding linoleyl moiety, linolenyl moiety, or γ-linolenyl moiety.

In alternative embodiments to the cationic lipid of Formula II, $R^4$ and $R^5$ are different and are independently an optionally substituted $C_1$-$C_{24}$ alkyl, $C_2$-$C_{24}$ alkenyl, $C_2$-$C_{24}$ alkynyl, or $C_1$-$C_{24}$ acyl, wherein at least one of $R^4$ and $R^5$ comprises at least one optionally substituted cyclic alkyl group. In certain embodiments, $R^4$ and $R^5$ are different and are independently an optionally substituted $C_4$-$C_{20}$ alkyl, $C_4$-$C_{20}$ alkenyl, $C_4$-$C_{20}$ alkynyl, or $C_4$-$C_{20}$ acyl. In some instances, $R^4$ is an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl, and $R^5$ is an optionally substituted $C_4$-$C_{10}$ alkyl, $C_4$-$C_{10}$ alkenyl, $C_4$-$C_{10}$ alkynyl, or $C_4$-$C_{10}$ acyl. In other instances, $R^4$ is an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl, and $R^5$ is an optionally substituted $C_4$-$C_8$ or $C_6$ alkyl, $C_4$-$C_8$ or $C_6$ alkenyl, $C_4$-$C_8$ or $C_6$ alkynyl, or $C_4$-$C_8$ or $C_6$ acyl. In certain instances, $R^4$ is an optionally substituted $C_4$-$C_{10}$ alkyl, $C_4$-$C_{10}$ alkenyl, $C_4$-$C_{10}$ alkynyl, or $C_4$-$C_{10}$ acyl, and $R^5$ is an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl. In certain other instances, $R^4$ is an optionally substituted $C_4$-$C_8$ or $C_6$ alkyl, $C_4$-$C_8$ or $C_6$ alkenyl, $C_4$-$C_8$ or $C_6$ alkynyl, or $C_4$-$C_8$ or $C_6$ acyl, and $R^5$ is an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl. In particular embodiments, one or more of the optionally substituted cyclic alkyl groups present in $R^4$ and/or $R^5$ are as described above.

In some groups of embodiments to the cationic lipid of Formula II, $R^4$ and $R^5$ are either the same or different and are independently selected from the group consisting of:

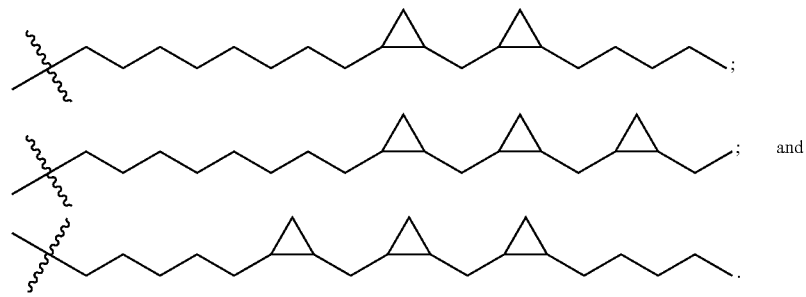

In other groups of embodiments to the cationic lipid of Formula II, one of $R^4$ or $R^5$ is selected from the group consisting of:

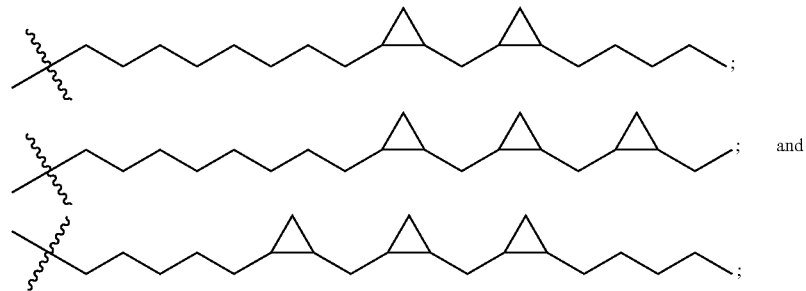

and the other of $R^4$ or $R^5$ is selected from the group consisting of:

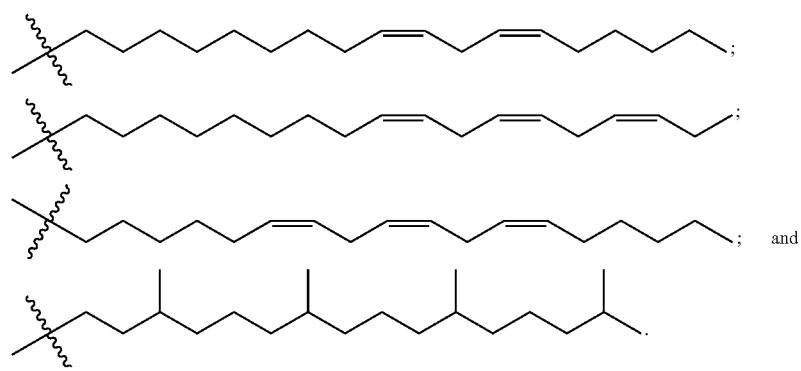

In certain embodiments, Z is an optionally substituted $C_1$-$C_2$ alkyl, $C_1$-$C_3$ alkyl, $C_1$-$C_4$ alkyl, $C_1$-$C_5$ alkyl, $C_2$-$C_3$ alkyl, $C_2$-$C_4$ alkyl, $C_2$-$C_5$ alkyl, $C_2$-$C_6$ alkyl, $C_3$-$C_4$ alkyl, $C_3$-$C_5$ alkyl, $C_3$-$C_6$ alkyl, $C_4$-$C_5$ alkyl, $C_4$-$C_6$ alkyl, $C_5$-$C_6$ alkyl, $C_2$-$C_3$ alkenyl, $C_2$-$C_4$ alkenyl, $C_2$-$C_5$ alkenyl, $C_2$-$C_6$ alkenyl, $C_3$-$C_4$ alkenyl, $C_3$-$C_5$ alkenyl, $C_3$-$C_6$ alkenyl, $C_4$-$C_5$ alkenyl, $C_4$-$C_6$ alkenyl, $C_5$-$C_6$ alkenyl, $C_2$-$C_3$ alkynyl, $C_2$-$C_4$ alkynyl, $C_2$-$C_5$ alkynyl, $C_2$-$C_6$ alkynyl, $C_3$-$C_4$ alkynyl, $C_3$-$C_5$ alkynyl, $C_3$-$C_6$ alkynyl, $C_4$-$C_5$ alkynyl, $C_4$-$C_6$ alkynyl, or $C_5$-$C_6$ alkynyl. In one particular embodiment, Z is $(CH_2)_q$ and q is 0, 1, 2, 3, 4, 5, or 6 (e.g., 1-2, 1-3, 1-4, 1-5, 1-6, 2-3, 2-4, 2-5, or 2-6). In a preferred embodiment, q is 2. In certain other embodiments, q is 1 or 3.

In particular embodiments, the cationic lipid of Formula II has the following structure:

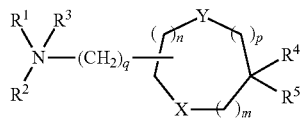

or salts thereof, wherein $R^1$, $R^2$, $R^3$, $R^4$, $R^5$, X, Y, m, n, p, and q are the same as described above.

In some embodiments, the cationic lipid of Formula II forms a salt (preferably a crystalline salt) with one or more anions. In one particular embodiment, the cationic lipid of Formula II is the oxalate (e.g., hemioxalate) salt thereof, which is preferably a crystalline salt.

In particularly preferred embodiments, the cationic lipid of Formula II has one of the following structures:

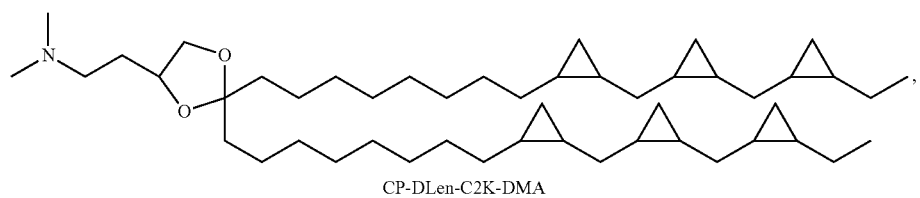

CP-DLen-C2K-DMA (Compound 46)

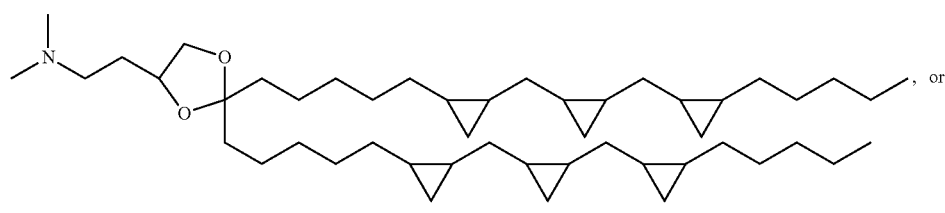

CP-γDLen-C2K-DMA (Compound 51)

, or

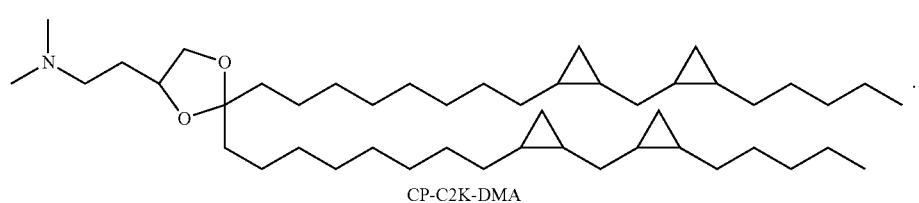

CP-C2K-DMA (Compound 56)

The synthesis of Compounds 46, 51, and 56 is described herein.

In another aspect, cationic lipids of Formula III having the following structure (or salts thereof) are useful in the present invention:

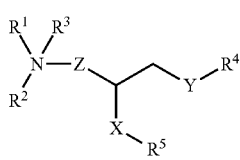

(III)

or salts thereof, wherein:

$R^1$ and $R^2$ are either the same or different and are independently hydrogen (H) or an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring;

$R^3$ is either absent or is hydrogen (H) or a $C_1$-$C_6$ alkyl to provide a quaternary amine;

$R^4$ and $R^5$ are either the same or different and are independently an optionally substituted $C_{10}$-$C_{24}$ alkyl, $C_{10}$-$C_{24}$ alkenyl, $C_{10}$-$C_{24}$ alkynyl, or $C_{10}$-$C_{24}$ acyl, wherein at least one of $R^4$ and $R^5$ comprises at least 1, 2, 3, 4, 5, 6, or more optionally substituted cyclic alkyl groups (e.g., 1-2, 1-3, 1-4, 1-5, 1-6, 2-3, 2-4, 2-5, or 2-6 optionally substituted cyclic alkyl groups);

X and Y are either the same or different and are independently O, S, N($R^6$), C(O), C(O)O, OC(O), C(O)N($R^6$), N($R^6$)C(O), OC(O)N($R^6$), N($R^6$)C(O)O, C(O)S, C(S)O, S(O), S(O)(O), C(S), or an optionally substituted heterocyclic ring, wherein $R^6$ is hydrogen (H) or an optionally substituted $C_1$-$C_{10}$ alkyl, $C_2$-$C_{10}$ alkenyl, or $C_2$-$C_{10}$ alkynyl; and Z is either absent or is an optionally substituted $C_1$-$C_6$ alkyl, $C_2$-$C_6$ alkenyl, or $C_2$-$C_6$ alkynyl.

In some embodiments, $R^1$ and $R^2$ are each independently hydrogen (H) or an optionally substituted $C_1$-$C_2$ alkyl, $C_1$-$C_3$ alkyl, $C_1$-$C_4$ alkyl, $C_1$-$C_5$ alkyl, $C_2$-$C_3$ alkyl, $C_2$-$C_4$ alkyl, $C_2$-$C_5$ alkyl, $C_2$-$C_6$ alkyl, $C_3$-$C_4$ alkyl, $C_3$-$C_5$ alkyl, $C_3$-$C_6$ alkyl, $C_4$-$C_5$ alkyl, $C_4$-$C_6$ alkyl, $C_5$-$C_6$ alkyl, $C_2$-$C_3$ alkenyl, $C_2$-$C_4$ alkenyl, $C_2$-$C_5$ alkenyl, $C_2$-$C_6$ alkenyl, $C_3$-$C_4$ alkenyl, $C_3$-$C_5$ alkenyl, $C_3$-$C_6$ alkenyl, $C_4$-$C_5$ alkenyl, $C_4$-$C_6$ alkenyl, $C_5$-$C_6$ alkenyl, $C_2$-$C_3$ alkynyl, $C_2$-$C_4$ alkynyl, $C_2$-$C_5$ alkynyl, $C_2$-$C_6$ alkynyl, $C_3$-$C_4$ alkynyl, $C_3$-$C_5$ alkynyl, $C_3$-$C_6$ alkynyl, $C_4$-$C_5$ alkynyl, $C_4$-$C_6$ alkynyl, or $C_5$-$C_6$ alkynyl. In particular embodiments, $R^1$ and $R^2$ are both methyl groups, both ethyl groups, or a combination of one methyl group and one ethyl group. In certain instances, $R^3$ is absent when the pH is above the $pK_a$ of the cationic lipid and $R^3$ is hydrogen (H) when the pH is below the $pK_a$ of the cationic lipid such that the amino head group is protonated. In certain other instances, $R^3$ is an optionally substituted $C_1$-$C_2$ alkyl, $C_1$-$C_3$ alkyl, $C_1$-$C_4$ alkyl, $C_1$-$C_5$ alkyl, $C_2$-$C_3$ alkyl, $C_2$-$C_4$ alkyl, $C_2$-$C_5$ alkyl, $C_2$-$C_6$ alkyl, $C_3$-$C_4$ alkyl, $C_3$-$C_5$ alkyl, $C_3$-$C_6$ alkyl, $C_4$-$C_5$ alkyl, $C_4$-$C_6$ alkyl, or $C_5$-$C_6$ alkyl to provide a quaternary amine.

In certain embodiments, $R^1$ and $R^2$ are joined to form an optionally substituted heterocyclic ring comprising 1, 2, 3, 4, 5, 6, or more carbon atoms and 1, 2, 3, 4, or more heteroatoms such as nitrogen (N), oxygen (O), sulfur (S), and mixtures thereof. In some embodiments, the optionally substituted heterocyclic ring comprises from 2 to 5 carbon atoms and from 1 to 3 heteroatoms such as nitrogen (N), oxygen (O), and/or sulfur (S). In certain embodiments, the heterocyclic ring comprises an optionally substituted imidazole, triazole (e.g., 1,2,3-triazole, 1,2,4-triazole), pyrazole, thiazole, pyrrole, furan, oxazole, isoxazole, oxazoline, oxazolidine, oxadiazole, tetrazole, and the like. In some instances, the optionally substituted heterocyclic ring comprises 5 carbon atoms and 1 nitrogen atom, wherein the heterocyclic ring can be substituted with a substituent such as a hydroxyl (—OH) group at the ortho, meta, and/or para positions. In certain instances, the heterocyclic ring comprises an optionally substituted imidazole group.

In other embodiments, $R^6$ is hydrogen (H) or an optionally substituted $C_1$-$C_2$ alkyl, $C_1$-$C_3$ alkyl, $C_1$-$C_4$ alkyl, $C_1$-$C_5$ alkyl, $C_1$-$C_6$ alkyl, $C_1$-$C_7$ alkyl, $C_1$-$C_8$ alkyl, $C_1$-$C_9$ alkyl, $C_2$-$C_3$ alkyl, $C_2$-$C_4$ alkyl, $C_2$-$C_5$ alkyl, $C_2$-$C_6$ alkyl, $C_2$-$C_7$ alkyl, $C_2$-$C_8$ alkyl, $C_2$-$C_9$ alkyl, $C_2$-$C_{10}$ alkyl, $C_3$-$C_4$ alkyl, $C_3$-$C_5$ alkyl, $C_3$-$C_6$ alkyl, $C_3$-$C_7$ alkyl, $C_3$-$C_8$ alkyl, $C_3$-$C_9$ alkyl, $C_3$-$C_{10}$ alkyl, $C_4$-$C_5$ alkyl, $C_4$-$C_6$ alkyl, $C_4$-$C_7$ alkyl, $C_4$-$C_8$ alkyl, $C_4$-$C_9$ alkyl, $C_4$-$C_{10}$ alkyl, $C_5$-$C_6$ alkyl, $C_5$-$C_7$ alkyl, $C_5$-$C_8$ alkyl, $C_5$-$C_9$ alkyl, $C_5$-$C_{10}$ alkyl, $C_6$-$C_7$ alkyl, $C_6$-$C_8$ alkyl, $C_6$-$C_9$ alkyl, $C_6$-$C_{10}$ alkyl, $C_7$-$C_8$ alkyl, $C_7$-$C_9$ alkyl, $C_7$-$C_{10}$ alkyl, $C_8$-$C_9$ alkyl, $C_8$-$C_{10}$ alkyl, $C_9$-$C_{10}$ alkyl, $C_2$-$C_3$ alkenyl, $C_2$-$C_4$ alkenyl, $C_2$-$C_5$ alkenyl, $C_2$-$C_6$ alkenyl, $C_2$-$C_7$ alkenyl, $C_2$-$C_8$ alkenyl, $C_2$-$C_9$ alkenyl, $C_3$-$C_4$ alkenyl, $C_3$-$C_5$ alkenyl, $C_3$-$C_6$ alkenyl, $C_3$-$C_7$ alkenyl, $C_3$-$C_8$ alkenyl, $C_3$-$C_9$ alkenyl, $C_3$-$C_{10}$ alkenyl, $C_4$-$C_5$ alkenyl, $C_4$-$C_6$ alkenyl, $C_4$-$C_7$ alkenyl, $C_4$-$C_8$ alkenyl, $C_4$-$C_9$ alkenyl, $C_4$-$C_{10}$ alkenyl, $C_5$-$C_6$ alkenyl, $C_5$-$C_7$ alkenyl, $C_5$-$C_8$ alkenyl, $C_5$-$C_9$ alkenyl, $C_5$-$C_{10}$ alkenyl, $C_6$-$C_7$ alkenyl, $C_6$-$C_8$ alkenyl, $C_6$-$C_9$ alkenyl, $C_6$-$C_{10}$ alkenyl, $C_7$-$C_8$ alkenyl, $C_7$-$C_9$ alkenyl, $C_7$-$C_{10}$ alkenyl, $C_8$-$C_9$ alkenyl, $C_8$-$C_{10}$ alkenyl, $C_9$-$C_{10}$ alkenyl, $C_2$-$C_3$ alkynyl, $C_2$-$C_4$ alkynyl, $C_2$-$C_5$ alkynyl, $C_2$-$C_6$ alkynyl, $C_2$-$C_7$ alkynyl, $C_2$-$C_8$ alkynyl, $C_2$-$C_9$ alkynyl, $C_3$-$C_4$ alkynyl, $C_3$-$C_5$ alkynyl, $C_3$-$C_6$ alkynyl, $C_3$-$C_7$ alkynyl, $C_3$-$C_8$ alkynyl, $C_3$-$C_9$ alkynyl, $C_3$-$C_{10}$ alkynyl, $C_4$-$C_5$ alkynyl, $C_4$-$C_6$ alkynyl, $C_4$-$C_7$ alkynyl, $C_4$-$C_8$ alkynyl, $C_4$-$C_9$ alkynyl, $C_4$-$C_{10}$ alkynyl, $C_5$-$C_6$ alkynyl, $C_5$-$C_7$ alkynyl, $C_5$-$C_8$ alkynyl, $C_5$-$C_9$ alkynyl, $C_5$-$C_{10}$ alkynyl, $C_6$-$C_7$ alkynyl, $C_6$-$C_8$ alkynyl, $C_6$-$C_9$ alkynyl, $C_6$-$C_{10}$ alkynyl, $C_7$-$C_8$ alkynyl, $C_7$-$C_9$ alkynyl, $C_7$-$C_{10}$ alkynyl, $C_8$-$C_9$ alkynyl, $C_8$-$C_{10}$ alkynyl, or $C_9$-$C_{10}$ alkynyl. In one particular embodiment, $R^6$ is selected from the group consisting of hydrogen (H), a $C_1$ alkyl (methyl) group, and a $C_2$, $C_3$, $C_4$, $C_5$, $C_6$, $C_7$, $C_8$, $C_9$, and $C_{10}$ alkyl, alkenyl, and alkynyl group.

In one embodiment, X and Y are independently selected from the group consisting of O, C(O)O, C(O)N($R^6$), N($R^6$)C(O)O, and C(O)S. In one particular embodiment, X and Y are both oxygen (O). In another particular embodiment, at least one of (e.g., both) X and Y is N($R^6$)C(O)O and each $R^6$ is independently hydrogen (H), a methyl group, or a $C_2$, $C_3$, $C_4$, $C_5$, $C_6$, $C_7$, $C_8$, $C_9$, or $C_{10}$ alkyl, alkenyl, or alkynyl group. In certain other embodiments, at least one of (e.g., both) X and Y is an independently selected optionally substituted heterocyclic ring. In particular embodiments, the heterocyclic ring comprises 1, 2, 3, 4, 5, 6, or more carbon atoms and 1, 2, 3, 4, or more heteroatoms such as nitrogen (N), oxygen (O), sulfur (S), and mixtures thereof. In some embodiments, the optionally substituted heterocyclic ring comprises from 2 to 5 carbon atoms and from 1 to 3 heteroatoms such as nitrogen (N), oxygen (O), and/or sulfur (S). In certain embodiments, the heterocyclic ring comprises an optionally substituted imidazole, triazole (e.g., 1,2,3-triazole, 1,2,4-triazole), pyrazole, thiazole, pyrrole, furan, oxazole, isoxazole, oxazoline, oxazolidine, oxadiazole, tetrazole, and the like.

In certain embodiments, $R^4$ and $R^5$ are independently an optionally substituted $C_{12}$-$C_{24}$, $C_{12}$-$C_{22}$, $C_{12}$-$C_{20}$, $C_{14}$-$C_{24}$, $C_{14}$-$C_{22}$, $C_{14}$-$C_{20}$, $C_{16}$-$C_{24}$, $C_{16}$-$C_{22}$, or $C_{16}$-$C_{20}$ alkyl, alkenyl, alkynyl, or acyl group (i.e., a $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, or $C_{24}$ alkyl, alkenyl, alkynyl, or acyl group), wherein at least one or more of (e.g., both) $R^4$ and $R^5$ independently comprises at least 1, 2, 3, 4, 5, or 6 optionally substituted cyclic alkyl groups (e.g., 1-2, 1-3, 1-4, 1-5, 1-6, 2-3, 2-4, 2-5, or 2-6 optionally substituted cyclic alkyl groups). In particular embodiments, the at least 1, 2, 3, 4, 5, or 6 optionally substituted cyclic alkyl groups present in $R^4$ and/or $R^5$ are independently selected from the group consisting of an optionally substituted saturated cyclic alkyl group, an optionally substituted unsaturated cyclic alkyl group, and combinations thereof. In certain instances, the optionally substituted saturated cyclic alkyl group comprises an optionally substituted $C_{3-8}$ cycloalkyl group (e.g., cyclopropyl, cyclobutyl, cyclopentyl, cyclohexyl, cycloheptyl, cyclooctyl, etc.). In preferred embodiments, the optionally substituted saturated cyclic alkyl group comprises a cyclopropyl group, optionally containing one or more substituents and/or heteroatoms. In other instances, the optionally substituted unsaturated cyclic alkyl group comprises an optionally substituted $C_{3-8}$ cycloalkenyl group (e.g., cyclopropenyl, cyclobutenyl, cyclopentenyl, cyclohexenyl, cycloheptenyl, cyclooctenyl, etc.). In particular embodiments, $R^4$ and $R^5$ are the same length (e.g., $C_{12}$-$C_{20}$ or $C_{18}$ alkyl chains) and contain the same number and type of cyclic alkyl group (e.g., one, two, or three $C_{3-8}$ cycloalkyl groups such as one, two, or three cyclopropyl groups on each of $R^4$ and $R^5$).

In certain other embodiments, one of $R^4$ or $R^5$ comprises at least 1, 2, 3, 4, 5, or 6 sites of unsaturation (e.g., 1-2, 1-3, 1-4, 1-5, 1-6, 2-3, 2-4, 2-5, or 2-6 sites of unsaturation) or a substituted alkyl or acyl group, and the other side-chain comprises at least 1, 2, 3, 4, 5, or 6 optionally substituted cyclic alkyl groups (e.g., 1-2, 1-3, 1-4, 1-5, 1-6, 2-3, 2-4, 2-5, or 2-6 optionally substituted cyclic alkyl groups). In embodiments where one of $R^4$ or $R^5$ comprises at least 1, 2, 3, 4, 5, or 6 sites of unsaturation, the unsaturated side-chain may comprise a dodecenyl moiety, a tetradecenyl (e.g., myristoleyl) moiety, a hexadecenyl (e.g., palmitoleyl) moiety, an octadecenyl (e.g., oleyl) moiety, an icosenyl moiety, a dodecadienyl moiety, a tetradecadienyl moiety, a hexadecadienyl moiety, an octadecadienyl moiety, an icosadienyl moiety, a dodecatrienyl moiety, a tetradectrienyl moiety, a hexadecatrienyl moiety, an octadecatrienyl moiety, an icosatrienyl moiety, or an acyl derivative thereof (e.g., oleoyl, linoleoyl, linolenoyl, γ-linolenoyl, etc.). In some instances, the octadecadienyl moiety is a linoleyl moiety. In other instances, the octadecatrienyl moiety is a linolenyl moiety or a γ-linolenyl moiety. In embodiments where one of $R^4$ or $R^5$ comprises a branched alkyl or acyl group (e.g., a substituted alkyl or acyl group), the branched alkyl or acyl group may comprise a $C_{12}$-$C_{24}$ alkyl or acyl having at least 1-6 (e.g., 1, 2, 3, 4, 5, 6, or more) $C_1$-$C_6$ alkyl substituents. In particular embodiments, the branched alkyl or acyl group comprises a $C_{12}$-$C_{20}$ or $C_{14}$-$C_{22}$ alkyl or acyl with 1-6 (e.g., 1, 2, 3, 4, 5, 6) $C_1$-$C_4$ alkyl (e.g., methyl, ethyl, propyl, or butyl) substituents. In some embodiments, the branched alkyl group comprises a phytanyl (3,7,11,15- tetramethyl-hexadecanyl) moiety and the branched acyl group comprises a phytanoyl (3,7,11,15-tetramethyl-hexadecanoyl) moiety.

In particular embodiments, $R^4$ and $R^5$ are both independently selected $C_{12}$-$C_{20}$ alkyl groups (i.e., $C_{12}$, $C_{13}$, $C_{14}$, $C_{15}$, $C_{16}$, $C_{17}$, $C_{18}$, $C_{19}$, or $C_{20}$ alkyl groups) having at least 1, 2, 3, 4, 5, or 6 optionally substituted cyclic alkyl groups (e.g., 1-2, 1-3, 1-4, 1-5, 1-6, 2-3, 2-4, 2-5, or 2-6 optionally substituted cyclic alkyl groups). In preferred embodiments, $R^4$ and $R^5$ are both $C_{18}$ alkyl groups having at least one, two, three, or more optionally substituted cyclic alkyl groups such as, for example, an optionally substituted $C_{3-8}$ cycloalkyl group (e.g., a cyclopropyl group, optionally containing one or more substituents and/or heteroatoms). In certain embodiments, each of the optionally substituted cyclic alkyl groups is independently selected and can be the same cyclic alkyl group (e.g., all cyclopropyl groups) or different cyclic alkyl groups (e.g., cyclopropyl and other cycloalkyl, heterocycloalkyl, cycloalkenyl, and/or heterocycloalkenyl groups).

In preferred embodiments, the optionally substituted cyclic alkyl groups present in $R^4$ and/or $R^5$ are located at the site(s) of unsaturation in the corresponding unsaturated sidechain. As a non-limiting example, one or both of $R^4$ and $R^5$ are $C_{18}$ alkyl groups having 1, 2, or 3 optionally substituted cyclic alkyl groups, wherein the optionally substituted cyclic alkyl groups (e.g., independently selected cyclopropyl groups) are located at one or more (e.g., all) of the sites of unsaturation present in a corresponding linoleyl moiety, linolenyl moiety, or γ-linolenyl moiety.

In alternative embodiments to the cationic lipid of Formula III, $R^4$ and $R^5$ are different and are independently an optionally substituted $C_1$-$C_{24}$ alkyl, $C_2$-$C_{24}$ alkenyl, $C_2$-$C_{24}$ alkynyl, or $C_1$-$C_{24}$ acyl, wherein at least one of $R^4$ and $R^5$ comprises at least one optionally substituted cyclic alkyl group. In certain embodiments, $R^4$ and $R^5$ are different and are independently an optionally substituted $C_4$-$C_{20}$ alkyl, $C_4$-$C_{20}$ alkenyl, $C_4$-$C_{20}$ alkynyl, or $C_4$-$C_{20}$ acyl. In some instances, $R^4$ is an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl, and $R^5$ is an optionally substituted $C_4$-$C_{10}$ alkyl, $C_4$-$C_{10}$ alkenyl, $C_4$-$C_{10}$ alkynyl, or $C_4$-$C_{10}$ acyl. In other instances, $R^4$ is an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl, and $R^5$ is an optionally substituted $C_4$-$C_8$ or $C_6$ alkyl, $C_4$-$C_8$ or $C_6$ alkenyl, $C_4$-$C_8$ or $C_6$ alkynyl, or $C_4$-$C_8$ or $C_6$ acyl. In certain instances, $R^4$ is an optionally substituted $C_4$-$C_{10}$ alkyl, $C_4$-$C_{10}$ alkenyl, $C_4$-$C_{10}$ alkynyl, or $C_4$-$C_{10}$ acyl, and $R^5$ is an optionally substituted $C_{12}$-$C_{24}$ alkyl, $C_{12}$-$C_{24}$ alkenyl, $C_{12}$-$C_{24}$ alkynyl, or $C_{12}$-$C_{24}$ acyl. In certain other instances, $R^4$ is an optionally substituted $C_4$-$C_8$ or $C_6$ alkyl, $C_4$-$C_8$ or $C_6$ alkenyl, $C_4$-$C_8$ or $C_6$ alkynyl, or $C_4$-$C_8$ or $C_6$ acyl, and $R^5$ is an optionally substituted $C_{12}$-$C_{20}$ or $C_{14}$-$C_{22}$ alkyl, $C_{12}$-$C_{20}$ or $C_{14}$-$C_{22}$ alkenyl, $C_{12}$-$C_{20}$ or $C_{14}$-$C_{22}$ alkynyl, or $C_{12}$-$C_{20}$ or $C_{14}$-$C_{22}$ acyl. In particular embodiments, one or more of the optionally substituted cyclic alkyl groups present in $R^4$ and/or $R^5$ are as described above.

In some groups of embodiments to the cationic lipid of Formula III, $R^4$ and $R^5$ are either the same or different and are independently selected from the group consisting of:

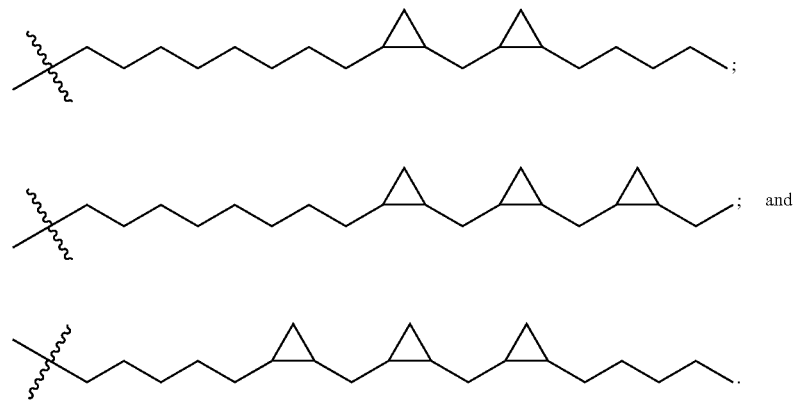

In other groups of embodiments to the cationic lipid of Formula III, one of $R^4$ or $R^5$ is selected from the group consisting of:

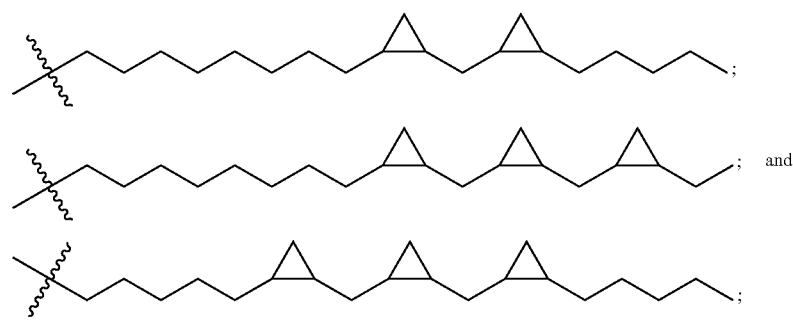

and the other of $R^4$ or $R^5$ is selected from the group consisting of:

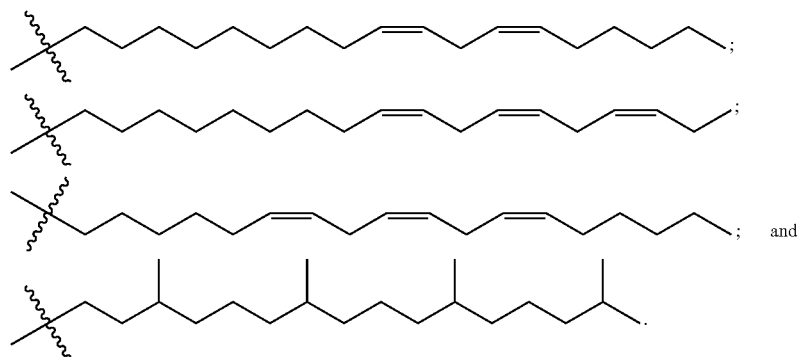

In certain embodiments, Z is an optionally substituted $C_1$-$C_2$ alkyl, $C_1$-$C_3$ alkyl, $C_1$-$C_4$ alkyl, $C_1$-$C_5$ alkyl, $C_2$-$C_3$ alkyl, $C_2$-$C_4$ alkyl, $C_2$-$C_5$ alkyl, $C_2$-$C_6$ alkyl, $C_3$-$C_4$ alkyl, $C_3$-$C_5$ alkyl, $C_3$-$C_6$ alkyl, $C_4$-$C_5$ alkyl, $C_4$-$C_6$ alkyl, $C_5$-$C_6$ alkyl, $C_2$-$C_3$ alkenyl, $C_2$-$C_4$ alkenyl, $C_2$-$C_5$ alkenyl, $C_2$-$C_6$ alkenyl, $C_3$-$C_4$ alkenyl, $C_3$-$C_5$ alkenyl, $C_3$-$C_6$ alkenyl, $C_4$-$C_5$ alkenyl, $C_4$-$C_6$ alkenyl, $C_5$-$C_6$ alkenyl, $C_2$-$C_3$ alkynyl, $C_2$-$C_4$ alkynyl, $C_2$-$C_5$ alkynyl, $C_2$-$C_6$ alkynyl, $C_3$-$C_4$ alkynyl, $C_3$-$C_5$ alkynyl, $C_3$-$C_6$ alkynyl, $C_4$-$C_5$ alkynyl, $C_4$-$C_6$ alkynyl, or $C_5$-$C_6$ alkynyl. In one particular embodiment, Z is $(CH_2)_n$ and n is 0, 1, 2, 3, 4, 5, or 6 (e.g., 1-2, 1-3, 1-4, 1-5, 1-6, 2-3, 2-4, 2-5, or 2-6). In a preferred embodiment, n is 1. In certain other embodiments, n is 2 or 3.

In particular embodiments, the cationic lipid of Formula III has the following structure:

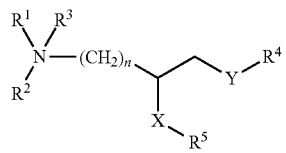

or salts thereof, wherein $R^1$, $R^2$, $R^3$, $R^4$, $R^5$, X, Y, and n are the same as described above.

In some embodiments, the cationic lipid of Formula III forms a salt (preferably a crystalline salt) with one or more anions. In one particular embodiment, the cationic lipid of Formula III is the oxalate (e.g., hemioxalate) salt thereof, which is preferably a crystalline salt.

In particularly preferred embodiments, the cationic lipid of Formula III has one of the following structures:

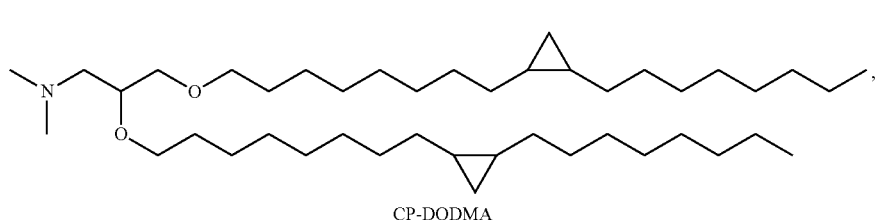
(Compound 57)
CP-DODMA

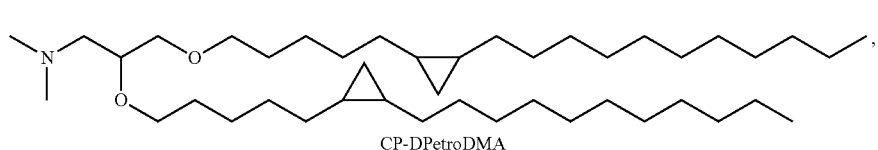
(Compound 58)
CP-DPetroDMA

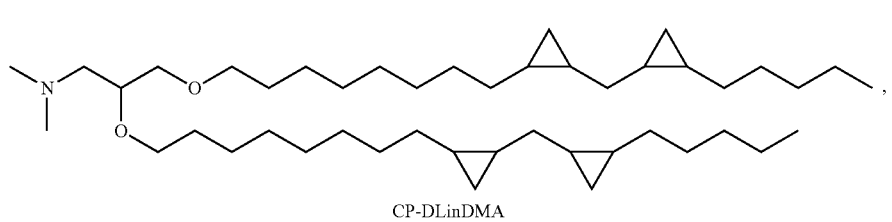
(Compound 59)
CP-DLinDMA

-continued

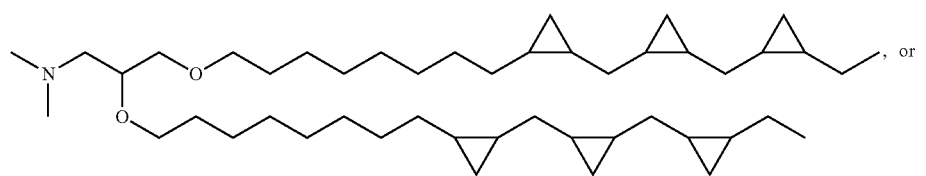

(Compound 60)

CP-DLenDMA

(Compound 62)

CP-γDLenDMA

The synthesis of Compounds 57, 58, 59, 60, and 62 is described herein.

The compounds of the invention may be prepared by known organic synthesis techniques, including the methods described in the Examples. In some embodiments, the synthesis of the cationic lipids of the invention may require the use of protecting groups. Protecting group methodology is well known to those skilled in the art (see, e.g., PROTECTIVE GROUPS IN ORGANIC SYNTHESIS, Green, T. W. et. al., Wiley-Interscience, New York City, 1999). Briefly, protecting groups within the context of this invention are any group that reduces or eliminates the unwanted reactivity of a functional group. A protecting group can be added to a functional group to mask its reactivity during certain reactions and then removed to reveal the original functional group. In certain instances, an "alcohol protecting group" is used. An "alcohol protecting group" is any group which decreases or eliminates the unwanted reactivity of an alcohol functional group. Protecting groups can be added and removed using techniques well known in the art.

In certain embodiments, the cationic lipids of the present invention have at least one protonatable or deprotonatable group, such that the lipid is positively charged at a pH at or below physiological pH (e.g., pH 7.4), and neutral at a second pH, preferably at or above physiological pH. It will be understood by one of ordinary skill in the art that the addition or removal of protons as a function of pH is an equilibrium process, and that the reference to a charged or a neutral lipid refers to the nature of the predominant species and does not require that all of the lipid be present in the charged or neutral form. Lipids that have more than one protonatable or deprotonatable group, or which are zwiterrionic, are not excluded from use in the invention.

In certain other embodiments, protonatable lipids according to the invention have a $pK_a$ of the protonatable group in the range of about 4 to about 11. Most preferred is a $pK_a$ of about 4 to about 7, because these lipids will be cationic at a lower pH formulation stage, while particles will be largely (though not completely) surface neutralized at physiological pH of around pH 7.4. One of the benefits of this $pK_a$ is that at least some nucleic acid associated with the outside surface of the particle will lose its electrostatic interaction at physiological pH and be removed by simple dialysis, thus greatly reducing the particle's susceptibility to clearance.

In some embodiments, a mixture of cationic lipids or salts thereof can be included in the lipid particles of the present invention. In these embodiments, the mixture of cationic lipids includes one or more cationic lipids of Formulas I-III together with one or more additional cationic lipids.

Other cationic lipids suitable for use in combination with the cationic lipids of Formulas I-III include, but are not limited to, one or more of the cationic lipids of Formulas I-XXII or salts thereof as described in U.S. application Ser. No. 13/077,856, filed Mar. 31, 2011, and/or one or more of the cationic lipids of Formulas I-XIX or salts thereof as described in PCT Application No. PCT/CA2010/001919, filed Dec. 1, 2010, the disclosures of which are herein incorporated by reference in their entirety for all purposes. Non-limiting examples of additional cationic lipids suitable for use in combination with the cationic lipids of Formulas I-III include 1,2-dilinoleyloxy-N,N-dimethylaminopropane (DLinDMA), 1,2-dilinolenyloxy-N,N-dimethylaminopropane (DLenDMA), 2,2-dilinoleyl-4-(2-dimethylaminoethyl)-[1,3]-dioxolane (DLin-K-C2-DMA; "XTC2" or "C2K"), 2,2-dilinoleyl-4-dimethylaminomethyl-[1,3]-dioxolane (DLin-K-DMA), 2,2-dilinoleyl-4-(3-dimethylaminopropyl)-[1,3]-dioxolane (DLin-K-C3-DMA; "C3K"), 2,2-dilinoleyl-4-(4-dimethylaminobutyl)[1,3]-dioxolane (DLin-K-C4-DMA; "C4K"), 2,2-dilinoleyl-5-dimethylaminomethyl-[1,3]-dioxane (DLin-K6-DMA), 2,2-dilinoleyl-4-N-methylpepiazino-[1,3]-dioxolane (DLin-K-MPZ), 2,2-dioleoyl-4-dimethylaminomethyl-[1,3]-dioxolane (DO-K-DMA), 2,2-distearoyl-4-dimethylaminomethyl-[1,3]-dioxolane (DS-K-DMA), 2,2-dilinoleyl-4-N-morpholino-[1,3]-dioxolane (DLin-K-MA), 2,2-Dilinoleyl-4-trimethylamino-[1,3]-dioxolane chloride (DLin-K-TMA.Cl), 2,2-dilinoleyl-4,5-bis(dimethylaminomethyl)-[1,3]-dioxolane (DLin-K²-DMA), 2,2-dilinoleyl-4-methylpiperzine-[1,3]-dioxolane (D-Lin-K-N-methylpiperzine), DLen-C2K-DMA, γ-DLen-C2K-DMA, DPan-C2K-DMA, DPan-C3K-DMA, DLen-C2K-DMA, γ-DLen-C2K-DMA, DPan-C2K-DMA, TLinDMA, C2-TLinDMA, C3-TLinDMA, 1,2-di-γ-linolenyloxy-N,N-dimethylaminopropane (γ-DLenDMA), 1,2-dilinoleyloxy-(N,N-dimethyl)-butyl-4-amine (C2-DLinDMA), 1,2-dilinoleoyloxy-(N,N-dimethyl)-butyl-4-amine (C2-DLinDAP), analogs thereof, salts thereof, and mixtures thereof.

Examples of yet additional cationic lipids include, but are not limited to, 1,2-dioeylcarbamoyloxy-3-dimethylaminopropane (DO-C-DAP), 1,2-dimyristoleoyl-3-dimethylaminopropane (DMDAP), 1,2-dioleoyl-3-trimethylaminopropane chloride (DOTAP.Cl), 1,2-dilinoleylcarbamoyloxy-3-dimethylaminopropane (DLin-C-DAP), 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleyltihio-3-dimethylaminopropane (DLin-S-DMA), 1-linoleoyl-2-linoleyloxy-3-dimethylaminopropane (DLin- 2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanedio (DOAP), 1,2-dilinoleyloxo-3-(2-N,N-dimethylamino)ethoxypropane (DLin-EG-DMA), 3-dimethylamino-2-(cholest-5-en-3-beta-oxybutan-4-oxy)-1-(cis,cis-9,12-octadecadienoxy)propane (CLinDMA), 2-[5'-(cholest-5-en-3-beta-oxy)-3'-oxapentoxy)-3-dimethyl-1-(cis,cis-9',1-2'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 1,2-N,N'-dilinoleylcarbamyl-3-dimethylaminopropane (DLincarbDAP), N,N-dioleyl-N,N-dimethylammonium chloride (DODAC), 1,2-dioleyloxy-N,N-dimethylaminopropane (DODMA), 1,2-distearyloxy-N,N-dimethylaminopropane (DSDMA), N-(1-(2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)-N,N,N-trimethylammonium chloride (DOTAP), 3-(N—(N',N'-dimethylaminoethane)-carbamoyl)cholesterol (DC-Chol), N-(1,2-dimyristyloxyprop-3-yl)-N,N-dimethyl-N-hydroxyethyl ammonium bromide (DMRIE), 2,3-dioleyloxy-N-[2(sperminecarboxamido)ethyl]-N,N-dimethyl-1-propanaminiumtrifluoroacetate (DOSPA), dioctadecylamidoglycyl spermine (DOGS), analogs thereof, salts thereof, and mixtures thereof.

In some embodiments, the additional cationic lipid forms a salt (preferably a crystalline salt) with one or more anions. In one particular embodiment, the additional cationic lipid is the oxalate (e.g., hemioxalate) salt thereof, which is preferably a crystalline salt.

The synthesis of cationic lipids such as DLinDMA and DLenDMA, as well as additional cationic lipids, is described in U.S. Patent Publication No. 20060083780, the disclosure of which is herein incorporated by reference in its entirety for all purposes.

The synthesis of cationic lipids such as DLin-K-C2-DMA, DLin-K-C3-DMA, DLin-K-C4-DMA, DLin-K6-DMA, DLin-K-MPZ, DO-K-DMA, DS-K-DMA, DLin-K-MA, DLin-K-TMA.Cl, DLin-K$^2$-DMA, D-Lin-K-N-methylpiperzine, DO-C-DAP, DMDAP, and DOTAP.Cl, as well as additional cationic lipids, is described in PCT Publication No. WO 2010/042877, the disclosure of which is incorporated herein by reference in its entirety for all purposes.

The synthesis of cationic lipids such as DLin-K-DMA, DLin-C-DAP, DLMDAC, DLinMA, DLinDAP, DLin-S-DMA, DLin-2-DMAP, DLinTMA.Cl, DLinTAP.Cl, DLin-MPZ, DLMAP, DOAP, and DLin-EG-DMA, as well as additional cationic lipids, is described in PCT Publication No. WO 09/086,558, the disclosure of which is herein incorporated by reference in its entirety for all purposes.

The synthesis of cationic lipids such as γ-DLenDMA, DLen-C2K-DMA, γ-DLen-C2K-DMA, DPan-C2K-DMA, DPan-C3K-DMA, DLen-C2K-DMA, γ-DLen-C2K-DMA, DPan-C2K-DMA, TLinDMA, C2-TLinDMA, C3-TLinDMA, C2-DLinDMA, and C2-DLinDAP, as well as additional cationic lipids, is described in PCT Publication No. WO 2011/000106, the disclosure of which is herein incorporated by reference in its entirety for all purposes.

The synthesis of cationic lipids such as CLinDMA, as well as additional cationic lipids, is described in U.S. Patent Publication No. 20060240554, the disclosure of which is herein incorporated by reference in its entirety for all purposes.

The synthesis of a number of other cationic lipids and related analogs has been described in U.S. Pat. Nos. 5,208,036; 5,264,618; 5,279,833; 5,283,185; 5,753,613; and 5,785,992; and PCT Publication No. WO 96/10390, the disclosures of which are each herein incorporated by reference in their entirety for all purposes. Additionally, a number of commercial preparations of cationic lipids can be used, such as, e.g., LIPOFECTIN® (including DOTMA and DOPE, available from GIBCO/BRL); LIPOFECTAMINE® (including DOSPA and DOPE, available from GIBCO/BRL); and TRANSFECTAM® (including DOGS, available from Promega Corp.).

The synthesis of additional cationic lipids suitable for use in the lipid particles of the present invention is described in PCT Publication Nos. WO 2010/054401, WO 2010/054405, WO 2010/054406, WO 2010/054384, and WO 2010/144740; U.S. Patent Publication No. 20090023673; and U.S. Provisional Application No. 61/287,995, entitled "Methods and Compositions for Delivery of Nucleic Acids," filed Dec. 18, 2009, the disclosures of which are herein incorporated by reference in their entirety for all purposes.

In some embodiments, the cationic lipid comprises from about 45 mol % to about 90 mol %, from about 45 mol % to about 85 mol %, from about 45 mol % to about 80 mol %, from about 45 mol % to about 75 mol %, from about 45 mol % to about 70 mol %, from about 45 mol % to about 65 mol %, from about 45 mol % to about 60 mol %, from about 45 mol % to about 55 mol %, from about 50 mol % to about 90 mol %, from about 50 mol % to about 85 mol %, from about 50 mol % to about 80 mol %, from about 50 mol % to about 75 mol %, from about 50 mol % to about 70 mol %, from about 50 mol % to about 65 mol %, from about 50 mol % to about 60 mol %, from about 55 mol % to about 65 mol % or from about 55 mol % to about 70 mol % (or any fraction thereof or range therein) of the total lipid present in the particle.

In certain preferred embodiments, the cationic lipid comprises from about 50 mol % to about 58 mol %, from about 51 mol % to about 59 mol %, from about 51 mol % to about 58 mol %, from about 51 mol % to about 57 mol %, from about 52 mol % to about 58 mol %, from about 52 mol % to about 57 mol %, from about 52 mol % to about 56 mol %, or from about 53 mol % to about 55 mol % (or any fraction thereof or range therein) of the total lipid present in the particle. In particular embodiments, the cationic lipid comprises about 50 mol %, 51 mol %, 52 mol %, 53 mol %, 54 mol %, 55 mol %, 56 mol %, 57 mol %, 58 mol %, 59 mol %, 60 mol %, 61 mol %, 62 mol %, 63 mol %, 64 mol %, or 65 mol % (or any fraction thereof or range therein) of the total lipid present in the particle. In other embodiments, the cationic lipid comprises (at least) about 66, 67, 68, 69, 70, 71, 72, 73, 74, 75, 76, 77, 78, 79, 80, 81, 82, 83, 84, 85, 86, 87, 88, 89, or 90 mol % (or any fraction thereof or range therein) of the total lipid present in the particle.

In additional embodiments, the cationic lipid comprises from about 2 mol % to about 60 mol %, from about 5 mol % to about 50 mol %, from about 10 mol % to about 50 mol %, from about 20 mol % to about 50 mol %, from about 20 mol % to about 40 mol %, from about 30 mol % to about 40 mol %, or about 40 mol % (or any fraction thereof or range therein) of the total lipid present in the particle.

Additional percentages and ranges of cationic lipids suitable for use in the lipid particles of the present invention are described in PCT Publication No. WO 09/127,060, U.S. Publication No. 20110071208, and U.S. Publication No. 20110076335, the disclosures of which are herein incorporated by reference in their entirety for all purposes.

It should be understood that the percentage of cationic lipid present in the lipid particles of the invention is a target amount, and that the actual amount of cationic lipid present in the formulation may vary, for example, by ±5 mol %. For example, in the 1:57 lipid particle (e.g., SNALP) formulation, the target amount of cationic lipid is 57.1 mol %, but the actual amount of cationic lipid may be ±5 mol %, ±4 mol %, ±3 mol %, ±2 mol %, ±1 mol %, ±0.75 mol %, ±0.5 mol %, ±0.25 mol %, or ±0.1 mol % of that target amount, with the balance of the formulation being made up of other lipid components (adding up to 100 mol % of total lipids present in the particle). Similarly, in the 7:54 lipid particle (e.g., SNALP) formulation, the target amount of cationic lipid is 54.06 mol %, but the actual amount of cationic lipid may be ±5 mol %, ±4 mol %, ±3 mol %, ±2 mol %, ±1 mol %, ±0.75 mol %, ±0.5 mol %, ±0.25 mol %, or ±0.1 mol % of that target amount, with the balance of the formulation being made up of other lipid components (adding up to 100 mol % of total lipids present in the particle).

C. Non-Cationic Lipids

The non-cationic lipids used in the lipid particles of the invention (e.g., SNALP) can be any of a variety of neutral uncharged, zwitterionic, or anionic lipids capable of producing a stable complex.

Non-limiting examples of non-cationic lipids include phospholipids such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleyl-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lysophosphatidylcholine, dilinoleoylphosphatidylcholine, and mixtures thereof. Other diacylphosphatidylcholine and diacylphosphatidylethanolamine phospholipids can also be used. The acyl groups in these lipids are preferably acyl groups derived from fatty acids having $C_{10}$-$C_{24}$ carbon chains, e.g., lauroyl, myristoyl, palmitoyl, stearoyl, or oleoyl.

Additional examples of non-cationic lipids include sterols such as cholesterol and derivatives thereof. Non-limiting examples of cholesterol derivatives include polar analogues such as 5α-cholestanol, 5β-coprostanol, cholesteryl-(2'-hydroxy)-ethyl ether, cholesteryl-(4'-hydroxy)-butyl ether, and 6-ketocholestanol; non-polar analogues such as 5α-cholestane, cholestenone, 5α-cholestanone, 5β-cholestanone, and cholesteryl decanoate; and mixtures thereof. In preferred embodiments, the cholesterol derivative is a polar analogue such as cholesteryl-(4'-hydroxy)-butyl ether. The synthesis of cholesteryl-(2'-hydroxy)-ethyl ether is described in PCT Publication No. WO 09/127,060, the disclosure of which is herein incorporated by reference in its entirety for all purposes.

In some embodiments, the non-cationic lipid present in the lipid particles (e.g., SNALP) comprises or consists of a mixture of one or more phospholipids and cholesterol or a derivative thereof. In other embodiments, the non-cationic lipid present in the lipid particles (e.g., SNALP) comprises or consists of one or more phospholipids, e.g., a cholesterol-free lipid particle formulation. In yet other embodiments, the non-cationic lipid present in the lipid particles (e.g., SNALP) comprises or consists of cholesterol or a derivative thereof, e.g., a phospholipid-free lipid particle formulation.

Other examples of non-cationic lipids suitable for use in the present invention include nonphosphorous containing lipids such as, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide, ceramide, sphingomyelin, and the like.

In some embodiments, the non-cationic lipid comprises from about 10 mol % to about 60 mol %, from about 20 mol % to about 55 mol %, from about 20 mol % to about 45 mol %, from about 20 mol % to about 40 mol %, from about 25 mol % to about 50 mol %, from about 25 mol % to about 45 mol %, from about 30 mol % to about 50 mol %, from about 30 mol % to about 45 mol %, from about 30 mol % to about 40 mol %, from about 35 mol % to about 45 mol %, from about 37 mol % to about 42 mol %, or about 35 mol %, 36 mol %, 37 mol %, 38 mol %, 39 mol %, 40 mol %, 41 mol %, 42 mol %, 43 mol %, 44 mol %, or 45 mol % (or any fraction thereof or range therein) of the total lipid present in the particle.

In embodiments where the lipid particles contain a mixture of phospholipid and cholesterol or a cholesterol derivative, the mixture may comprise up to about 40 mol %, 45 mol %, 50 mol %, 55 mol %, or 60 mol % of the total lipid present in the particle.

In some embodiments, the phospholipid component in the mixture may comprise from about 2 mol % to about 20 mol %, from about 2 mol % to about 15 mol %, from about 2 mol % to about 12 mol %, from about 4 mol % to about 15 mol %, or from about 4 mol % to about 10 mol % (or any fraction thereof or range therein) of the total lipid present in the particle. In certain preferred embodiments, the phospholipid component in the mixture comprises from about 5 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle. As a non-limiting example, a 1:57 lipid particle formulation comprising a mixture of phospholipid and cholesterol may comprise a phospholipid such as DPPC or DSPC at about 7 mol % (or any fraction thereof), e.g., in a mixture with cholesterol or a cholesterol derivative at about 34 mol % (or any fraction thereof) of the total lipid present in the particle. As another non-limiting example, a 7:54 lipid particle formulation comprising a mixture of phospholipid and cholesterol may comprise a phospholipid such as DPPC or DSPC at about 7 mol % (or any fraction thereof), e.g., in a mixture with cholesterol or a cholesterol derivative at about 32 mol % (or any fraction thereof) of the total lipid present in the particle.

In other embodiments, the cholesterol component in the mixture may comprise from about 25 mol % to about 45 mol %, from about 25 mol % to about 40 mol %, from about 30 mol % to about 45 mol %, from about 30 mol % to about 40 mol %, from about 27 mol % to about 37 mol %, from about 25 mol % to about 30 mol %, or from about 35 mol % to about 40 mol % (or any fraction thereof or range therein) of the total lipid present in the particle. In certain preferred embodiments, the cholesterol component in the mixture comprises from about 25 mol % to about 35 mol %, from about 27 mol % to about 35 mol %, from about 29 mol % to about 35 mol %, from about 30 mol % to about 35 mol %, from about 30 mol % to about 34 mol %, from about 31 mol % to about 33 mol %, or about 30 mol %, 31 mol %, 32 mol %, 33 mol %, 34 mol %, or 35 mol % (or any fraction thereof or range therein) of the total lipid present in the particle. In other embodiments, the cholesterol component in the mixture comprises about 36, 37, 38, 39, 40, 41, 42, 43, 44, or 45 mol % (or any fraction thereof or range therein) of the total lipid present in the particle. Typically, a 1:57 lipid particle formulation comprising a mixture of phospholipid and cholesterol may comprise cholesterol or a cholesterol derivative at about 34 mol % (or any fraction thereof), e.g., in a mixture with a phospholipid such as DPPC or DSPC at about 7 mol % (or any fraction thereof) of the total lipid present in the particle. Typically, a 7:54 lipid particle formulation comprising a mixture of phospholipid and cholesterol may comprise cholesterol or a cholesterol derivative at about 32 mol % (or any fraction thereof), e.g., in a mixture with a phospholipid such as DPPC or DSPC at about 7 mol % (or any fraction thereof) of the total lipid present in the particle.

In embodiments where the lipid particles are phospholipid-free, the cholesterol or derivative thereof may comprise up to about 25 mol %, 30 mol %, 35 mol %, 40 mol %, 45 mol %, 50 mol %, 55 mol %, or 60 mol % of the total lipid present in the particle.

In some embodiments, the cholesterol or derivative thereof in the phospholipid-free lipid particle formulation may comprise from about 25 mol % to about 45 mol %, from about 25 mol % to about 40 mol %, from about 30 mol % to about 45 mol %, from about 30 mol % to about 40 mol %, from about 31 mol % to about 39 mol %, from about 32 mol % to about 38 mol %, from about 33 mol % to about 37 mol %, from about 35 mol % to about 45 mol %, from about 30 mol % to about 35 mol %, from about 35 mol % to about 40 mol %, or about 30 mol %, 31 mol %, 32 mol %, 33 mol %, 34 mol %, 35 mol %, 36 mol %, 37 mol %, 38 mol %, 39 mol %, 40 mol %, 41 mol %, 42 mol %, 43 mol %, 44 mol %, or 45 mol % (or any fraction thereof or range therein) of the total lipid present in the particle. As a non-limiting example, a 1:62 lipid particle formulation may comprise cholesterol at about 37 mol % (or any fraction thereof) of the total lipid present in the particle. As another non-limiting example, a 7:58 lipid particle formulation may comprise cholesterol at about 35 mol % (or any fraction thereof) of the total lipid present in the particle.

In other embodiments, the non-cationic lipid comprises from about 5 mol % to about 90 mol %, from about 10 mol % to about 85 mol %, from about 20 mol % to about 80 mol %, about 10 mol % (e.g., phospholipid only), or about 60 mol % (e.g., phospholipid and cholesterol or derivative thereof) (or any fraction thereof or range therein) of the total lipid present in the particle.

Additional percentages and ranges of non-cationic lipids suitable for use in the lipid particles of the present invention are described in PCT Publication No. WO 09/127,060, U.S. Publication No. 20110071208, and U.S. Publication No. 20110076335, the disclosures of which are herein incorporated by reference in their entirety for all purposes.

It should be understood that the percentage of non-cationic lipid present in the lipid particles of the invention is a target amount, and that the actual amount of non-cationic lipid present in the formulation may vary, for example, by ±5 mol %. For example, in the 1:57 lipid particle (e.g., SNALP) formulation, the target amount of phospholipid is 7.1 mol % and the target amount of cholesterol is 34.3 mol %, but the actual amount of phospholipid may be ±2 mol %, ±1.5 mol %, ±1 mol %, ±0.75 mol %, ±0.5 mol %, ±0.25 mol %, or ±0.1 mol % of that target amount, and the actual amount of cholesterol may be ±3 mol %, ±2 mol %, ±1 mol %, ±0.75 mol %, ±0.5 mol %, ±0.25 mol %, or ±0.1 mol % of that target amount, with the balance of the formulation being made up of other lipid components (adding up to 100 mol % of total lipids present in the particle). Similarly, in the 7:54 lipid particle (e.g., SNALP) formulation, the target amount of phospholipid is 6.75 mol % and the target amount of cholesterol is 32.43 mol %, but the actual amount of phospholipid may be ±2 mol %, ±1.5 mol %, ±1 mol %, ±0.75 mol %, ±0.5 mol %, ±0.25 mol %, or ±0.1 mol % of that target amount, and the actual amount of cholesterol may be ±3 mol %, ±2 mol %, ±1 mol %, ±0.75 mol %, ±0.5 mol %, ±0.25 mol %, or ±0.1 mol % of that target amount, with the balance of the formulation being made up of other lipid components (adding up to 100 mol % of total lipids present in the particle).

D. Lipid Conjugates

In addition to cationic and non-cationic lipids, the lipid particles of the invention (e.g., SNALP) may further comprise a lipid conjugate. The conjugated lipid is useful in that it prevents the aggregation of particles. Suitable conjugated lipids include, but are not limited to, PEG-lipid conjugates, POZ-lipid conjugates, ATTA-lipid conjugates, cationic-polymer-lipid conjugates (CPLs), and mixtures thereof. In certain embodiments, the lipid particles comprise either a PEG-lipid conjugate or an ATTA-lipid conjugate together with a CPL. The term "ATTA" or "polyamide" includes, without limitation, compounds described in U.S. Pat. Nos. 6,320,017 and 6,586,559, the disclosures of which are herein incorporated by reference in their entirety for all purposes.

In a preferred embodiment, the lipid conjugate is a PEG-lipid. Examples of PEG-lipids include, but are not limited to, PEG coupled to dialkyloxypropyls (PEG-DAA) as described in, e.g., PCT Publication No. WO 05/026372, PEG coupled to diacylglycerol (PEG-DAG) as described in, e.g., U.S. Patent Publication Nos. 20030077829 and 2005008689, PEG coupled to phospholipids such as phosphatidylethanolamine (PEG-PE), PEG conjugated to ceramides as described in, e.g., U.S. Pat. No. 5,885,613, PEG conjugated to cholesterol or a derivative thereof, and mixtures thereof. The disclosures of these patent documents are herein incorporated by reference in their entirety for all purposes.

Additional PEG-lipids suitable for use in the invention include, without limitation, mPEG2000-1,2-di-O-alkyl-sn3-carbomoylglyceride (PEG-C-DOMG). The synthesis of PEG-C-DOMG is described in PCT Publication No. WO 09/086,558, the disclosure of which is herein incorporated by reference in its entirety for all purposes. Yet additional suitable PEG-lipid conjugates include, without limitation, 1-[8'-(1,2-dimyristoyl-3-propanoxy)-carboxamido-3',6'-dioxaoctanyl]carbamoyl-ω-methyl-poly(ethylene glycol) (2 KPEG-DMG). The synthesis of 2 KPEG-DMG is described in U.S. Pat. No. 7,404,969, the disclosure of which is herein incorporated by reference in its entirety for all purposes.

PEG is a linear, water-soluble polymer of ethylene PEG repeating units with two terminal hydroxyl groups. PEGs are classified by their molecular weights; for example, PEG 2000 has an average molecular weight of about 2,000 daltons, and PEG 5000 has an average molecular weight of about 5,000 daltons. PEGs are commercially available from Sigma Chemical Co. and other companies and include, but are not limited to, the following: monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-$NH_2$), monomethoxypolyethylene glycol-tresylate (MePEG-TRES), monomethoxypolyethylene glycol-imidazolyl-carbonyl (MePEG-IM), as well as such compounds containing a terminal hydroxyl group instead of a terminal methoxy group (e.g., HO-PEG-S, HO-PEG-S-NHS, HO-PEG-NH$_2$, etc.). Other PEGs such as those described in U.S. Pat. Nos. 6,774,180 and 7,053,150 (e.g., mPEG (20 KDa) amine) are also useful for preparing the PEG-lipid conjugates of the present invention. The disclosures of these patents are herein incorporated by reference in their entirety for all purposes. In addition, monomethoxypolyethyleneglycol-acetic acid (MePEG-CH$_2$COOH) is particularly useful for preparing PEG-lipid conjugates including, e.g., PEG-DAA conjugates.

The PEG moiety of the PEG-lipid conjugates described herein may comprise an average molecular weight ranging from about 550 daltons to about 10,000 daltons. In certain instances, the PEG moiety has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons, etc.). In other instances, the PEG moiety has an average molecular weight of from about 550 daltons to about 1000 daltons, from about 250 daltons to about 1000 daltons, from about 400 daltons to about 1000 daltons, from about 600 daltons to about 900 daltons, from about 700 daltons to about 800 daltons, or about 200, 250, 300, 350, 400, 450, 500, 550, 600, 650, 700, 750, 800, 850, 900, 950, or 1000 daltons. In preferred embodiments, the PEG moiety has an average molecular weight of about 2,000 daltons or about 750 daltons.

In certain instances, the PEG can be optionally substituted by an alkyl, alkoxy, acyl, or aryl group. The PEG can be conjugated directly to the lipid or may be linked to the lipid via a linker moiety. Any linker moiety suitable for coupling the PEG to a lipid can be used including, e.g., non-ester containing linker moieties and ester-containing linker moieties. In a preferred embodiment, the linker moiety is a non-ester containing linker moiety. As used herein, the term "non-ester containing linker moiety" refers to a linker moiety that does not contain a carboxylic ester bond (—OC(O)—). Suitable non-ester containing linker moieties include, but are not limited to, amido (—C(O)NH—), amino (—NR—), carbonyl (—C(O)—), carbamate (—NHC(O)O—), urea (—NHC(O)NH—), disulphide (—S—S—), ether (—O—), succinyl (—(O)CCH$_2$CH$_2$C(O)—), succinamidyl (—NHC(O)CH$_2$CH$_2$C(O)NH—), ether, disulphide, as well as combinations thereof (such as a linker containing both a carbamate linker moiety and an amido linker moiety). In a preferred embodiment, a carbamate linker is used to couple the PEG to the lipid.

In other embodiments, an ester containing linker moiety is used to couple the PEG to the lipid. Suitable ester containing linker moieties include, e.g., carbonate (—OC(O)O—), succinyl, phosphate esters (—O—(O)POH—O—), sulfonate esters, and combinations thereof.

Phosphatidylethanolamines having a variety of acyl chain groups of varying chain lengths and degrees of saturation can be conjugated to PEG to form the lipid conjugate. Such phosphatidylethanolamines are commercially available, or can be isolated or synthesized using conventional techniques known to those of skilled in the art. Phosphatidyl-ethanolamines containing saturated or unsaturated fatty acids with carbon chain lengths in the range of $C_{10}$ to $C_{20}$ are preferred. Phosphatidylethanolamines with mono- or diunsaturated fatty acids and mixtures of saturated and unsaturated fatty acids can also be used. Suitable phosphatidylethanolamines include, but are not limited to, dimyristoyl-phosphatidyletha-nolamine (DMPE), dipalmitoyl-phosphatidylethanolamine (DPPE), dioleoylphosphatidylethanolamine (DOPE), and distearoyl-phosphatidylethanolamine (DSPE).

The term "diacylglycerol" or "DAG" includes a compound having 2 fatty acyl chains, $R^1$ and $R^2$, both of which have independently between 2 and 30 carbons bonded to the 1- and 2-position of glycerol by ester linkages. The acyl groups can be saturated or have varying degrees of unsaturation. Suitable acyl groups include, but are not limited to, lauroyl ($C_{12}$), myristoyl ($C_{14}$), palmitoyl ($C_{16}$), stearoyl ($C_{18}$), and icosoyl ($C_{20}$). In preferred embodiments, $R^1$ and $R^2$ are the same, i.e., $R^1$ and $R^2$ are both myristoyl (i.e., dimyristoyl), $R^1$ and $R^2$ are both stearoyl (i.e., distearoyl), etc. Diacylglycerols have the following general formula:

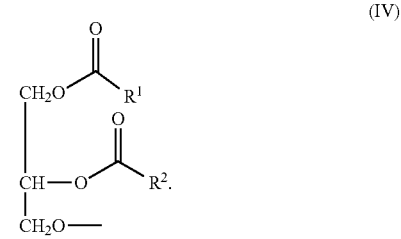

(IV)

The term "dialkyloxypropyl" or "DAA" includes a compound having 2 alkyl chains, $R^1$ and $R^2$, both of which have independently between 2 and 30 carbons. The alkyl groups can be saturated or have varying degrees of unsaturation. Dialkyloxypropyls have the following general formula:

(V)

In a preferred embodiment, the PEG-lipid is a PEG-DAA conjugate having the following formula:

(VI)

wherein $R^1$ and $R^2$ are independently selected and are long-chain alkyl groups having from about 10 to about 22 carbon atoms; PEG is a polyethyleneglycol; and L is a non-ester containing linker moiety or an ester containing linker moiety as described above. The long-chain alkyl groups can be saturated or unsaturated. Suitable alkyl groups include, but are not limited to, decyl ($C_{10}$), lauryl ($C_{12}$), myristyl ($C_{14}$), palmityl ($C_{16}$), stearyl ($C_{18}$), and icosyl ($C_{20}$). In preferred embodiments, $R^1$ and $R^2$ are the same, i.e., $R^1$ and $R^2$ are both myristyl (i.e., dimyristyl), $R^1$ and $R^2$ are both stearyl (i.e., distearyl), etc.

In Formula VI above, the PEG has an average molecular weight ranging from about 550 daltons to about 10,000 daltons. In certain instances, the PEG has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons, etc.). In other instances, the PEG moiety has an average molecular weight of from about 550 daltons to about 1000 daltons, from about 250 daltons to about 1000 daltons, from about 400 daltons to about 1000 daltons, from about 600 daltons to about 900 daltons, from about 700 daltons to about 800 daltons, or about 200, 250, 300, 350, 400, 450, 500, 550, 600, 650, 700, 750, 800, 850, 900, 950, or 1000 daltons. In preferred embodiments, the PEG has an average molecular weight of about 2,000 daltons or about 750 daltons. The PEG can be optionally substituted with alkyl, alkoxy, acyl, or aryl groups. In certain embodiments, the terminal hydroxyl group is substituted with a methoxy or methyl group.

In a preferred embodiment, "L" is a non-ester containing linker moiety. Suitable non-ester containing linkers include, but are not limited to, an amido linker moiety, an amino linker moiety, a carbonyl linker moiety, a carbamate linker moiety, a urea linker moiety, an ether linker moiety, a disulphide linker moiety, a succinamidyl linker moiety, and combinations thereof. In a preferred embodiment, the non-ester containing linker moiety is a carbamate linker moiety (i.e., a PEG-C-DAA conjugate). In another preferred embodiment, the non-ester containing linker moiety is an amido linker moiety (i.e., a PEG-A-DAA conjugate). In yet another preferred embodiment, the non-ester containing linker moiety is a succinamidyl linker moiety (i.e., a PEG-S-DAA conjugate).

In particular embodiments, the PEG-lipid conjugate is selected from:

PEG-dipalmityloxypropyl ($C_{16}$) conjugate, or a PEG-distearyloxypropyl ($C_{18}$) conjugate. In these embodiments, the PEG preferably has an average molecular weight of about 750 or about 2,000 daltons. In one particularly preferred embodiment, the PEG-lipid conjugate comprises PEG2000-C-DMA, wherein the "2000" denotes the average molecular weight of the PEG, the "C" denotes a carbamate linker moiety, and the "DMA" denotes dimyristyloxypropyl. In another particularly preferred embodiment, the PEG-lipid conjugate comprises PEG750-C-DMA, wherein the "750" denotes the average molecular weight of the PEG, the "C" denotes a carbamate linker moiety, and the "DMA" denotes dimyristyloxypropyl. In particular embodiments, the terminal hydroxyl group of the PEG is substituted with a methyl group. Those of skill in the art will readily appreciate that other dialkyloxypropyls can be used in the PEG-DAA conjugates of the present invention.

In addition to the foregoing, it will be readily apparent to those of skill in the art that other hydrophilic polymers can be used in place of PEG. Examples of suitable polymers that can be used in place of PEG include, but are not limited to, polyvinylpyrrolidone, polymethyloxazoline, polyethyloxazoline, polyhydroxypropyl methacrylamide, polymethacrylamide and polydimethylacrylamide, polylactic acid, polyglycolic acid, and derivatized celluloses such as hydroxymethylcellulose or hydroxyethylcellulose.

In addition to the foregoing components, the lipid particles (e.g., SNALP) of the present invention can further comprise cationic poly(ethylene glycol) (PEG) lipids or CPLs (see,

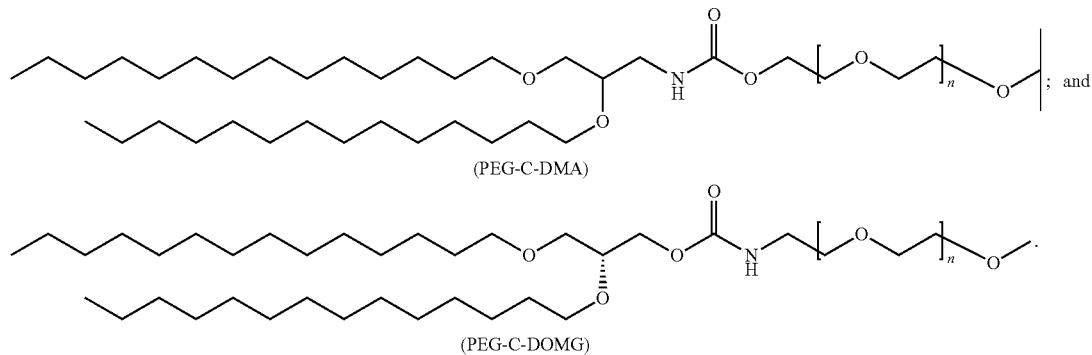

(PEG-C-DMA)

(PEG-C-DOMG)

The PEG-DAA conjugates are synthesized using standard techniques and reagents known to those of skill in the art. It will be recognized that the PEG-DAA conjugates will contain various amide, amine, ether, thio, carbamate, and urea linkages. Those of skill in the art will recognize that methods and reagents for forming these bonds are well known and readily available. See, e.g., March, ADVANCED ORGANIC CHEMISTRY (Wiley 1992); Larock, COMPREHENSIVE ORGANIC TRANSFORMATIONS (VCH 1989); and Furniss, VOGEL'S TEXTBOOK OF PRACTICAL ORGANIC CHEMISTRY, 5th ed. (Longman 1989). It will also be appreciated that any functional groups present may require protection and deprotection at different points in the synthesis of the PEG-DAA conjugates. Those of skill in the art will recognize that such techniques are well known. See, e.g., Green and Wuts, PROTECTIVE GROUPS IN ORGANIC SYNTHESIS (Wiley 1991).

Preferably, the PEG-DAA conjugate is a PEG-didecyloxypropyl ($C_{10}$) conjugate, a PEG-dilauryloxypropyl ($C_{12}$) conjugate, a PEG-dimyristyloxypropyl ($C_{14}$) conjugate, a e.g., Chen et al., *Bioconj. Chem.*, 11:433-437 (2000); U.S. Pat. No. 6,852,334; PCT Publication No. WO 00/62813, the disclosures of which are herein incorporated by reference in their entirety for all purposes).

In some embodiments, the lipid conjugate (e.g., PEG-lipid) comprises from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 0.9 mol % to about 1.6 mol %, from about 0.9 mol % to about 1.8 mol %, from about 1 mol % to about 1.8 mol %, from about 1 mol % to about 1.7 mol %, from about 1.2 mol % to about 1.8 mol %, from about 1.2 mol % to about 1.7 mol %, from about 1.3 mol % to about 1.6 mol %, from about 1.4 mol % to about 1.5 mol %, or about 1, 1.1, 1.2, 1.3, 1.4, 1.5, 1.6, 1.7, 1.8, 1.9, or 2 mol (or any fraction thereof or range therein) of the total lipid present in the particle.

In other embodiments, the lipid conjugate (e.g., PEG-lipid) comprises from about 0 mol % to about 20 mol %, from about 0.5 mol % to about 20 mol %, from about 2 mol % to about 20 mol %, from about 1.5 mol % to about 18 mol %, from about 2 mol % to about 15 mol %, from about 4 mol % to about 15 mol %, from about 2 mol % to about 12 mol %, from about 5 mol % to about 12 mol %, or about 2 mol % (or any fraction thereof or range therein) of the total lipid present in the particle.

In further embodiments, the lipid conjugate (e.g., PEG-lipid) comprises from about 4 mol % to about 10 mol %, from about 5 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle.

Additional examples, percentages, and/or ranges of lipid conjugates suitable for use in the lipid particles of the invention are described in PCT Publication No. WO 09/127,060, U.S. Publication No. 20110071208, U.S. Publication No. 20110076335, U.S. application Ser. No. 13/006,277, filed Jan. 13, 2011, and PCT Publication No. WO 2010/006282, the disclosures of which are herein incorporated by reference in their entirety for all purposes.

It should be understood that the percentage of lipid conjugate (e.g., PEG-lipid) present in the lipid particles of the invention is a target amount, and that the actual amount of lipid conjugate present in the formulation may vary, for example, by ±2 mol %. For example, in the 1:57 lipid particle (e.g., SNALP) formulation, the target amount of lipid conjugate is 1.4 mol %, but the actual amount of lipid conjugate may be ±0.5 mol %, ±0.4 mol %, ±0.3 mol %, ±0.2 mol %, ±0.1 mol %, or ±0.05 mol % of that target amount, with the balance of the formulation being made up of other lipid components (adding up to 100 mol % of total lipids present in the particle). Similarly, in the 7:54 lipid particle (e.g., SNALP) formulation, the target amount of lipid conjugate is 6.76 mol %, but the actual amount of lipid conjugate may be ±2 mol %, ±1.5 mol %, ±1 mol %, ±0.75 mol %, ±0.5 mol %, ±0.25 mol %, or ±0.1 mol % of that target amount, with the balance of the formulation being made up of other lipid components (adding up to 100 mol % of total lipids present in the particle).

One of ordinary skill in the art will appreciate that the concentration of the lipid conjugate can be varied depending on the lipid conjugate employed and the rate at which the lipid particle is to become fusogenic.

By controlling the composition and concentration of the lipid conjugate, one can control the rate at which the lipid conjugate exchanges out of the lipid particle and, in turn, the rate at which the lipid particle becomes fusogenic. For instance, when a PEG-DAA conjugate is used as the lipid conjugate, the rate at which the lipid particle becomes fusogenic can be varied, for example, by varying the concentration of the lipid conjugate, by varying the molecular weight of the PEG, or by varying the chain length and degree of saturation of the alkyl groups on the PEG-DAA conjugate. In addition, other variables including, for example, pH, temperature, ionic strength, etc. can be used to vary and/or control the rate at which the lipid particle becomes fusogenic. Other methods which can be used to control the rate at which the lipid particle becomes fusogenic will become apparent to those of skill in the art upon reading this disclosure. Also, by controlling the composition and concentration of the lipid conjugate, one can control the lipid particle (e.g., SNALP) size.

Preparation of Lipid Particles

The lipid particles of the present invention, e.g., SNALP, in which an active agent such as a nucleic acid (e.g., an interfering RNA such as an siRNA) is entrapped within the lipid portion of the particle and is protected from degradation, can be formed by any method known in the art including, but not limited to, a continuous mixing method, a direct dilution process, and an in-line dilution process. In certain embodiments, one or more antioxidants such as metal chelators (e.g., EDTA), primary antioxidants, and/or secondary antioxidants may be included at any step or at multiple steps in the process (e.g., prior to, during, and/or after lipid particle formation) as described in PCT Application No. PCT/CA2010/001919, the disclosure of which is herein incorporated by reference in its entirety for all purposes.

In particular embodiments, the cationic lipids may comprise at least one, two, three, four, five, or more cationic lipids such as those set forth in Formulas I-III or salts thereof, alone or in combination with other cationic lipid species. In other embodiments, the non-cationic lipids may comprise one, two, or more lipids including egg sphingomyelin (ESM), distearoylphosphatidylcholine (DSPC), dioleoylphosphatidylcholine (DOPC), 1-palmitoyl-2-oleoyl-phosphatidylcholine (POPC), dipalmitoyl-phosphatidylcholine (DPPC), monomethyl-phosphatidylethanolamine, dimethyl-phosphatidylethanolamine, 14:0 PE (1,2-dimyristoyl-phosphatidylethanolamine (DMPE)), 16:0 PE (1,2-dipalmitoyl-phosphatidylethanolamine (DPPE)), 18:0 PE (1,2-distearoyl-phosphatidylethanolamine (DSPE)), 18:1 PE (1,2-dioleoyl-phosphatidylethanolamine (DOPE)), 18:1 trans PE (1,2-dielaidoyl-phosphatidylethanolamine (DEPE)), 18:0-18:1 PE (1-stearoyl-2-oleoyl-phosphatidylethanolamine (SOPE)), 16:0-18:1 PE (1-palmitoyl-2-oleoyl-phosphatidylethanolamine (POPE)), polyethylene glycol-based polymers (e.g., PEG 2000, PEG 5000, PEG-modified diacylglycerols, or PEG-modified dialkyloxypropyls), cholesterol, derivatives thereof, or combinations thereof.

In certain embodiments, the present invention provides nucleic acid-lipid particles (e.g., SNALP) produced via a continuous mixing method, e.g., a process that includes providing an aqueous solution comprising a nucleic acid (e.g., interfering RNA) in a first reservoir, providing an organic lipid solution in a second reservoir (wherein the lipids present in the organic lipid solution are solubilized in an organic solvent, e.g., a lower alkanol such as ethanol), and mixing the aqueous solution with the organic lipid solution such that the organic lipid solution mixes with the aqueous solution so as to substantially instantaneously produce a lipid vesicle (e.g., liposome) encapsulating the nucleic acid within the lipid vesicle. This process and the apparatus for carrying out this process are described in detail in U.S. Patent Publication No. 20040142025, the disclosure of which is herein incorporated by reference in its entirety for all purposes.

The action of continuously introducing lipid and buffer solutions into a mixing environment, such as in a mixing chamber, causes a continuous dilution of the lipid solution with the buffer solution, thereby producing a lipid vesicle substantially instantaneously upon mixing. As used herein, the phrase "continuously diluting a lipid solution with a buffer solution" (and variations) generally means that the lipid solution is diluted sufficiently rapidly in a hydration process with sufficient force to effectuate vesicle generation. By mixing the aqueous solution comprising a nucleic acid with the organic lipid solution, the organic lipid solution undergoes a continuous stepwise dilution in the presence of the buffer solution (i.e., aqueous solution) to produce a nucleic acid-lipid particle.

The nucleic acid-lipid particles formed using the continuous mixing method typically have a size of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, less than about 120 nm, 110 nm, 100 nm, 90 nm, or 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm (or any fraction thereof or range therein). The particles thus formed do not aggregate and are optionally sized to achieve a uniform particle size.

In another embodiment, the present invention provides nucleic acid-lipid particles (e.g., SNALP) produced via a direct dilution process that includes forming a lipid vesicle (e.g., liposome) solution and immediately and directly introducing the lipid vesicle solution into a collection vessel containing a controlled amount of dilution buffer. In preferred aspects, the collection vessel includes one or more elements configured to stir the contents of the collection vessel to facilitate dilution. In one aspect, the amount of dilution buffer present in the collection vessel is substantially equal to the volume of lipid vesicle solution introduced thereto. As a non-limiting example, a lipid vesicle solution in 45% ethanol when introduced into the collection vessel containing an equal volume of dilution buffer will advantageously yield smaller particles.

In yet another embodiment, the present invention provides nucleic acid-lipid particles (e.g., SNALP) produced via an in-line dilution process in which a third reservoir containing dilution buffer is fluidly coupled to a second mixing region. In this embodiment, the lipid vesicle (e.g., liposome) solution formed in a first mixing region is immediately and directly mixed with dilution buffer in the second mixing region. In preferred aspects, the second mixing region includes a T-connector arranged so that the lipid vesicle solution and the dilution buffer flows meet as opposing 180° flows; however, connectors providing shallower angles can be used, e.g., from about 27° to about 180° (e.g., about 90°). A pump mechanism delivers a controllable flow of buffer to the second mixing region. In one aspect, the flow rate of dilution buffer provided to the second mixing region is controlled to be substantially equal to the flow rate of lipid vesicle solution introduced thereto from the first mixing region. This embodiment advantageously allows for more control of the flow of dilution buffer mixing with the lipid vesicle solution in the second mixing region, and therefore also the concentration of lipid vesicle solution in buffer throughout the second mixing process. Such control of the dilution buffer flow rate advantageously allows for small particle size formation at reduced concentrations.

These processes and the apparatuses for carrying out these direct dilution and in-line dilution processes are described in detail in U.S. Patent Publication No. 20070042031, the disclosure of which is herein incorporated by reference in its entirety for all purposes.

The nucleic acid-lipid particles formed using the direct dilution and in-line dilution processes typically have a size of from about 30 nm to about 150 nm, from about 40 nm to about 150 nm, from about 50 nm to about 150 nm, from about 60 nm to about 130 nm, from about 70 mm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, less than about 120 nm, 110 nm, 100 nm, 90 nm, or 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm (or any fraction thereof or range therein). The particles thus formed do not aggregate and are optionally sized to achieve a uniform particle size.

If needed, the lipid particles of the invention (e.g., SNALP) can be sized by any of the methods available for sizing liposomes. The sizing may be conducted in order to achieve a desired size range and relatively narrow distribution of particle sizes.

Several techniques are available for sizing the particles to a desired size. One sizing method, used for liposomes and equally applicable to the present particles, is described in U.S. Pat. No. 4,737,323, the disclosure of which is herein incorporated by reference in its entirety for all purposes. Sonicating a particle suspension either by bath or probe sonication produces a progressive size reduction down to particles of less than about 50 nm in size. Homogenization is another method which relies on shearing energy to fragment larger particles into smaller ones. In a typical homogenization procedure, particles are recirculated through a standard emulsion homogenizer until selected particle sizes, typically between about 60 and about 80 nm, are observed. In both methods, the particle size distribution can be monitored by conventional laser-beam particle size discrimination, or QELS.

Extrusion of the particles through a small-pore polycarbonate membrane or an asymmetric ceramic membrane is also an effective method for reducing particle sizes to a relatively well-defined size distribution. Typically, the suspension is cycled through the membrane one or more times until the desired particle size distribution is achieved. The particles may be extruded through successively smaller-pore membranes, to achieve a gradual reduction in size.

In some embodiments, the nucleic acids present in the particles are precondensed as described in, e.g., U.S. patent application Ser. No. 09/744,103, the disclosure of which is herein incorporated by reference in its entirety for all purposes.

In other embodiments, the methods may further comprise adding non-lipid polycations which are useful to effect the lipofection of cells using the present compositions. Examples of suitable non-lipid polycations include, hexadimethrine bromide (sold under the brand name POLYBRENE®, from Aldrich Chemical Co., Milwaukee, Wis., USA) or other salts of hexadimethrine. Other suitable polycations include, for example, salts of poly-L-ornithine, poly-L-arginine, poly-L-lysine, poly-D-lysine, polyallylamine, and polyethyleneimine. Addition of these salts is preferably after the particles have been formed.

In some embodiments, the nucleic acid to lipid ratios (mass/mass ratios) in a formed nucleic acid-lipid particle (e.g., SNALP) will range from about 0.01 to about 0.2, from about 0.05 to about 0.2, from about 0.02 to about 0.1, from about 0.03 to about 0.1, or from about 0.01 to about 0.08. The ratio of the starting materials (input) also falls within this range. In other embodiments, the particle preparation uses about 400 µg nucleic acid per 10 mg total lipid or a nucleic acid to lipid mass ratio of about 0.01 to about 0.08 and, more preferably, about 0.04, which corresponds to 1.25 mg of total lipid per 50 µg of nucleic acid. In other preferred embodiments, the particle has a nucleic acid:lipid mass ratio of about 0.08.

In other embodiments, the lipid to nucleic acid ratios (mass/mass ratios) in a formed nucleic acid-lipid particle (e.g., SNALP) will range from about 1 (1:1) to about 100 (100:1), from about 5 (5:1) to about 100 (100:1), from about 1 (1:1) to about 50 (50:1), from about 2 (2:1) to about 50

(50:1), from about 3 (3:1) to about 50 (50:1), from about 4 (4:1) to about 50 (50:1), from about 5 (5:1) to about 50 (50:1), from about 1 (1:1) to about 25 (25:1), from about 2 (2:1) to about 25 (25:1), from about 3 (3:1) to about 25 (25:1), from about 4 (4:1) to about 25 (25:1), from about 5 (5:1) to about 25 (25:1), from about 5 (5:1) to about 20 (20:1), from about 5 (5:1) to about 15 (15:1), from about 5 (5:1) to about 10 (10:1), or about 5 (5:1), 6 (6:1), 7 (7:1), 8 (8:1), 9 (9:1), 10 (10:1), 11 (11:1), 12 (12:1), 13 (13:1), 14 (14:1), 15 (15:1), 16 (16:1), 17 (17:1), 18 (18:1), 19 (19:1), 20 (20:1), 21 (21:1), 22 (22:1), 23 (23:1), 24 (24:1), or 25 (25:1), or any fraction thereof or range therein. The ratio of the starting materials (input) also falls within this range.

As previously discussed, the conjugated lipid may further include a CPL. A variety of general methods for making SNALP-CPLs (CPL-containing SNALP) are discussed herein. Two general techniques include the "post-insertion" technique, that is, insertion of a CPL into, for example, a pre-formed SNALP, and the "standard" technique, wherein the CPL is included in the lipid mixture during, for example, the SNALP formation steps. The post-insertion technique results in SNALP having CPLs mainly in the external face of the SNALP bilayer membrane, whereas standard techniques provide SNALP having CPLs on both internal and external faces. The method is especially useful for vesicles made from phospholipids (which can contain cholesterol) and also for vesicles containing PEG-lipids (such as PEG-DAAs and PEG-DAGs). Methods of making SNALP-CPLs are taught, for example, in U.S. Pat. Nos. 5,705,385; 6,586,410; 5,981, 501; 6,534,484; and 6,852,334; U.S. Patent Publication No. 20020072121; and PCT Publication No. WO 00/62813, the disclosures of which are herein incorporated by reference in their entirety for all purposes.

Kits

The present invention also provides lipid particles (e.g., SNALP) in kit form. In some embodiments, the kit comprises a container which is compartmentalized for holding the various elements of the lipid particles (e.g., the active agents or therapeutic agents such as nucleic acids and the individual lipid components of the particles). Preferably, the kit comprises a container (e.g., a vial or ampoule) which holds the lipid particles of the invention (e.g., SNALP), wherein the particles are produced by one of the processes set forth herein. In certain embodiments, the kit may further comprise an endosomal membrane destabilizer (e.g., calcium ions). The kit typically contains the particle compositions of the invention, either as a suspension in a pharmaceutically acceptable carrier or in dehydrated form, with instructions for their rehydration (if lyophilized) and administration.

As explained herein, it has surprisingly been found that the SNALP formulations of the present invention containing at least one cationic lipid of Formulas I-III, either alone or in combination with other cationic lipids, show increased potency and/or increased tolerability when targeting a gene of interest in the liver, such as, e.g., APOB, APOC3, PCSK9, DGAT1, and/or DGAT2, when compared to other SNALP formulations. For instance, as set forth in the Examples below, it has been found that a 1:57 lipid particle containing, e.g., DLin-M-C3-DMA (Compound 1), was unexpectedly more potent in silencing ApoB expression in vivo compared to SNALP formulations containing DLin-C2K-DMA (C2K) or DLinDMA. In addition, as set forth in the Examples below, it has been found that a 1:57 lipid particle containing, e.g., MC3 Ether (Compound 13) or MC2MC (Compound 11), displayed similar or greater potency in silencing ApoB expression in vivo compared to SNALP formulations containing C2K. Furthermore, as set forth in the Examples below, it has been found that a 1:57 lipid particle containing, e.g., CP-DLen-C2K-DMA (Compound 46), displayed considerable potency in silencing ApoB expression in vivo and displayed an unexpectedly more favorable toxicity profile in vivo compared to SNALP formulations containing C2K. Moreover, Table 6 in Example 46 illustrates that a SNALP formulation containing Compound 1, 4, 8, 13, 15, 27, 28, or 35 displayed unexpectedly improved ApoB silencing activity compared to a SNALP formulation containing the C2K benchmark cationic lipid when administered at the same dose. As such, in certain preferred embodiments, the kits of the invention comprise 1:57, 1:62, 7:54, and/or 7:58 lipid particles containing one or more cationic lipids of Formulas I-III, such as Compound 1, 4, 8, 11, 13, 15, 27, 28, 35, and/or 46. Those of skill in the art will appreciate that the lipid particles can be present in a container as a suspension or in dehydrated form.

In certain other instances, it may be desirable to have a targeting moiety attached to the surface of the lipid particle to further enhance the targeting of the particle. Methods of attaching targeting moieties (e.g., antibodies, proteins, etc.) to lipids (such as those used in the present particles) are known to those of skill in the art.

Administration of Lipid Particles

Once formed, the lipid particles of the invention (e.g., SNALP) are particularly useful for introducing an interfering RNA (e.g., an siRNA molecule) targeting a gene of interest (such as APOB, APOC3, PCSK9, DGAT1, DGAT2, or combinations thereof) into the liver. As noted, it has surprisingly been found that the SNALP formulations of the present invention containing a cationic lipid of Formulas I-III are unexpectedly more potent at silencing ApoB expression and/or display increased tolerability in vivo compared to SNALP formulations containing other cationic lipids such as DLin-C2K-DMA (C2K). Accordingly, the present invention also provides methods for introducing an interfering RNA (e.g., an siRNA molecule) into a liver cell. The methods are carried out in vitro or in vivo by first forming the particles as described above and then contacting the particles with the cells (e.g., cells of the liver, such as hepatocytes) for a period of time sufficient for delivery of the interfering RNA to the liver cells to occur.

The lipid particles of the invention (e.g., SNALP) can be adsorbed to almost any cell type with which they are mixed or contacted. Once adsorbed, the particles can either be endocytosed by a portion of the cells, exchange lipids with cell membranes, or fuse with the cells. Transfer or incorporation of the active agent or therapeutic agent (e.g., nucleic acid) portion of the particle can take place via any one of these pathways. In particular, when fusion takes place, the particle membrane is integrated into the cell membrane and the contents of the particle combine with the intracellular fluid.

The lipid particles of the invention (e.g., SNALP) can be administered either alone or in a mixture with a pharmaceutically acceptable carrier (e.g., physiological saline or phosphate buffer) selected in accordance with the route of administration and standard pharmaceutical practice. Generally, normal buffered saline (e.g., 135-150 mM NaCl) will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc. Additional suitable carriers are described in, e.g., REMINGTON'S PHARMACEUTICAL SCIENCES, Mack Publishing Company, Philadelphia, Pa., 17th ed. (1985). As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The phrase "pharmaceutically acceptable" refers to molecular entities and compositions that do not produce an allergic or similar untoward reaction when administered to a human.

The pharmaceutically acceptable carrier is generally added following lipid particle formation. Thus, after the lipid particle (e.g., SNALP) is formed, the particle can be diluted into pharmaceutically acceptable carriers such as normal buffered saline.

The concentration of particles in the pharmaceutical formulations can vary widely, i.e., from less than about 0.05%, usually at or at least about 2 to 5%, to as much as about 10 to 90% by weight, and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, particles composed of irritating lipids may be diluted to low concentrations to lessen inflammation at the site of administration.

The pharmaceutical compositions of the present invention may be sterilized by conventional, well-known sterilization techniques. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, and calcium chloride. Additionally, the particle suspension may include lipid-protective agents which protect lipids against free-radical and lipid-peroxidative damages on storage. Lipophilic free-radical quenchers, such as alphatocopherol, and water-soluble iron-specific chelators, such as ferrioxamine, are suitable.

In some embodiments, the lipid particles of the invention (e.g., SNALP) are particularly useful in methods for the therapeutic delivery of one or more nucleic acids comprising an interfering RNA sequence (e.g., siRNA). In particular, it is an object of this invention to provide in vitro and in vivo methods for treatment of a disease or disorder in a mammal (e.g., a rodent such as a mouse or a primate such as a human, chimpanzee, or monkey) by downregulating or silencing the transcription and/or translation of one or more target nucleic acid sequences or genes of interest (such as APOB, APOC3, PCSK9, DGAT1, DGAT2, or combinations thereof). As a non-limiting example, the methods of the invention are useful for in vivo delivery of interfering RNA (e.g., siRNA) to the liver of a mammalian subject for the treatment of metabolic diseases and disorders (e.g., diseases and disorders in which the liver is a target and liver diseases and disorders). In certain embodiments, the disease or disorder is associated with expression and/or overexpression of a gene and expression or overexpression of the gene is reduced by the interfering RNA (e.g., siRNA). In certain other embodiments, a therapeutically effective amount of the lipid particle may be administered to the mammal. In some instances, an interfering RNA (e.g., siRNA) is formulated into a SNALP containing a cationic lipid of Formulas I-III, and the particles are administered to patients requiring such treatment. In other instances, cells are removed from a patient, the interfering RNA is delivered in vitro (e.g., using a SNALP described herein), and the cells are reinjected into the patient.

E. In Vivo Administration

Systemic delivery for in vivo therapy, e.g., delivery of a therapeutic nucleic acid to a distal target cell via body systems such as the circulation, has been achieved using nucleic acid-lipid particles such as those described in PCT Publication Nos. WO 05/007196, WO 05/121348, WO 05/120152, and WO 04/002453, the disclosures of which are herein incorporated by reference in their entirety for all purposes. The present invention also provides fully encapsulated lipid particles that protect the nucleic acid from nuclease degradation in serum, are non-immunogenic, are small in size, and are suitable for repeat dosing.

For in vivo administration, administration can be in any manner known in the art, e.g., by injection, oral administration, inhalation (e.g., intransal or intratracheal), transdermal application, or rectal administration. Administration can be accomplished via single or divided doses. The pharmaceutical compositions can be administered parenterally, i.e., intraarticularly, intravenously, intraperitoneally, subcutaneously, or intramuscularly. In some embodiments, the pharmaceutical compositions are administered intravenously or intraperitoneally by a bolus injection (see, e.g., U.S. Pat. No. 5,286,634). Intracellular nucleic acid delivery has also been discussed in Straubringer et al., *Methods Enzymol.*, 101:512 (1983); Mannino et al., *Biotechniques*, 6:682 (1988); Nicolau et al., *Crit. Rev. Ther. Drug Carrier Syst.*, 6:239 (1989); and Behr, *Acc. Chem. Res.*, 26:274 (1993). Still other methods of administering lipid-based therapeutics are described in, for example, U.S. Pat. Nos. 3,993,754; 4,145,410; 4,235,871; 4,224,179; 4,522,803; and 4,588,578. The lipid particles can be administered by direct injection at the site of disease or by injection at a site distal from the site of disease (see, e.g., Culver, HUMAN GENE THERAPY, MaryAnn Liebert, Inc., Publishers, New York. pp. 70-71 (1994)). The disclosures of the above-described references are herein incorporated by reference in their entirety for all purposes.

In embodiments where the lipid particles of the present invention (e.g., SNALP) are administered intravenously, at least about 5%, 10%, 15%, 20%, or 25% of the total injected dose of the particles is present in plasma about 8, 12, 24, 36, or 48 hours after injection. In other embodiments, more than about 20%, 30%, 40% and as much as about 60%, 70% or 80% of the total injected dose of the lipid particles is present in plasma about 8, 12, 24, 36, or 48 hours after injection. In certain instances, more than about 10% of a plurality of the particles is present in the plasma of a mammal about 1 hour after administration. In certain other instances, the presence of the lipid particles is detectable at least about 1 hour after administration of the particle. In certain embodiments, the presence of a therapeutic agent such as a nucleic acid is detectable liver cells (e.g., hepatocytes) at about 8, 12, 24, 36, 48, 60, 72 or 96 hours after administration. In other embodiments, downregulation of expression of a target sequence, such as APOB, by an interfering RNA (e.g., siRNA) is detectable at about 8, 12, 24, 36, 48, 60, 72 or 96 hours after administration. In yet other embodiments, downregulation of expression of a target sequence, such as APOB, by an interfering RNA (e.g., siRNA) occurs preferentially in liver cells (e.g., hepatocytes). In further embodiments, the presence or effect of an interfering RNA (e.g., siRNA) in cells at a site proximal or distal to the site of administration or in liver cells (e.g., hepatocytes) is detectable at about 12, 24, 48, 72, or 96 hours, or at about 6, 8, 10, 12, 14, 16, 18, 19, 20, 22, 24, 26, or 28 days after administration. In additional embodiments, the lipid particles (e.g., SNALP) of the invention are administered parenterally or intraperitoneally.

The compositions of the present invention, either alone or in combination with other suitable components, can be made into aerosol formulations (i.e., they can be "nebulized") to be administered via inhalation (e.g., intranasally or intratracheally) (see, Brigham et al., *Am. Sci.,* 298:278 (1989)). Aerosol formulations can be placed into pressurized acceptable propellants, such as dichlorodifluoromethane, propane, nitrogen, and the like.

In certain embodiments, the pharmaceutical compositions may be delivered by intranasal sprays, inhalation, and/or other aerosol delivery vehicles. Methods for delivering nucleic acid compositions directly to the lungs via nasal aerosol sprays have been described, e.g., in U.S. Pat. Nos. 5,756,353 and 5,804,212. Likewise, the delivery of drugs using intranasal microparticle resins and lysophosphatidyl-glycerol compounds (U.S. Pat. No. 5,725,871) are also well-known in the pharmaceutical arts. Similarly, transmucosal drug delivery in the form of a polytetrafluoroetheylene support matrix is described in U.S. Pat. No. 5,780,045. The disclosures of the above-described patents are herein incorporated by reference in their entirety for all purposes.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions are preferably administered, for example, by intravenous infusion, orally, topically, intraperitoneally, intravesically, or intrathecally.

Generally, when administered intravenously, the lipid particle formulations are formulated with a suitable pharmaceutical carrier. Many pharmaceutically acceptable carriers may be employed in the compositions and methods of the present invention. Suitable formulations for use in the present invention are found, for example, in REMINGTON'S PHARMACEUTICAL SCIENCES, Mack Publishing Company, Philadelphia, Pa., 17th ed. (1985). A variety of aqueous carriers may be used, for example, water, buffered water, 0.4% saline, 0.3% glycine, and the like, and may include glycoproteins for enhanced stability, such as albumin, lipoprotein, globulin, etc. Generally, normal buffered saline (135-150 mM NaCl) will be employed as the pharmaceutically acceptable carrier, but other suitable carriers will suffice. These compositions can be sterilized by conventional liposomal sterilization techniques, such as filtration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. These compositions can be sterilized using the techniques referred to above or, alternatively, they can be produced under sterile conditions. The resulting aqueous solutions may be packaged for use or filtered under aseptic conditions and lyophilized, the lyophilized preparation being combined with a sterile aqueous solution prior to administration.

In certain applications, the lipid particles disclosed herein may be delivered via oral administration to the individual. The particles may be incorporated with excipients and used in the form of ingestible tablets, buccal tablets, troches, capsules, pills, lozenges, elixirs, mouthwash, suspensions, oral sprays, syrups, wafers, and the like (see, e.g., U.S. Pat. Nos. 5,641,515, 5,580,579, and 5,792,451, the disclosures of which are herein incorporated by reference in their entirety for all purposes). These oral dosage forms may also contain the following: binders, gelatin; excipients, lubricants, and/or flavoring agents. When the unit dosage form is a capsule, it may contain, in addition to the materials described above, a liquid carrier. Various other materials may be present as coatings or to otherwise modify the physical form of the dosage unit. Of course, any material used in preparing any unit dosage form should be pharmaceutically pure and substantially non-toxic in the amounts employed.

Typically, these oral formulations may contain at least about 0.1% of the lipid particles or more, although the percentage of the particles may, of course, be varied and may conveniently be between about 1% or 2% and about 60% or 70% or more of the weight or volume of the total formulation. Naturally, the amount of particles in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

Formulations suitable for oral administration can consist of: (a) liquid solutions, such as an effective amount of a packaged therapeutic agent such as nucleic acid (e.g., interfering RNA) suspended in diluents such as water, saline, or PEG 400; (b) capsules, sachets, or tablets, each containing a predetermined amount of a therapeutic agent such as nucleic acid (e.g., interfering RNA), as liquids, solids, granules, or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise a therapeutic agent such as nucleic acid (e.g., interfering RNA) in a flavor, e.g., sucrose, as well as pastilles comprising the therapeutic agent in an inert base, such as gelatin and glycerin or sucrose and acacia emulsions, gels, and the like containing, in addition to the therapeutic agent, carriers known in the art.

In another example of their use, lipid particles can be incorporated into a broad range of topical dosage forms. For instance, a suspension containing nucleic acid-lipid particles such as SNALP can be formulated and administered as gels, oils, emulsions, topical creams, pastes, ointments, lotions, foams, mousses, and the like.

When preparing pharmaceutical preparations of the lipid particles of the invention, it is preferable to use quantities of the particles which have been purified to reduce or eliminate empty particles or particles with therapeutic agents such as nucleic acid associated with the external surface.

The methods of the present invention may be practiced in a variety of hosts. Preferred hosts include mammalian species, such as primates (e.g., humans and chimpanzees as well as other nonhuman primates), canines, felines, equines, bovines, ovines, caprines, rodents (e.g., rats and mice), lagomorphs, and swine.

The amount of particles administered will depend upon the ratio of therapeutic agent (e.g., nucleic acid) to lipid, the particular therapeutic agent (e.g., nucleic acid) used, the disease or disorder being treated, the age, weight, and condition of the patient, and the judgment of the clinician, but will generally be between about 0.01 and about 50 mg per kilogram of body weight, preferably between about 0.1 and about 5 mg/kg of body weight, or about $10^8$-$10^{10}$ particles per administration (e.g., injection).

F. In Vitro Administration

For in vitro applications, the delivery of therapeutic agents such as nucleic acids (e.g., interfering RNA) can be to any cell grown in culture, whether of plant or animal origin, vertebrate or invertebrate, and of any tissue or type. In preferred embodiments, the cells are animal cells, more preferably mammalian cells, and most preferably human cells (e.g., liver cells, i.e., hepatocytes).

Contact between the cells and the lipid particles, when carried out in vitro, takes place in a biologically compatible medium. The concentration of particles varies widely depending on the particular application, but is generally between about 1 µmol and about 10 mmol. Treatment of the cells with the lipid particles is generally carried out at physiological temperatures (about 37° C.) for periods of time of from about 1 to 48 hours, preferably of from about 2 to 4 hours.

In one group of preferred embodiments, a lipid particle suspension is added to 60-80% confluent plated cells having a cell density of from about $10^3$ to about $10^5$ cells/ml, more preferably about $2\times10^4$ cells/ml. The concentration of the suspension added to the cells is preferably of from about 0.01 to 0.2 µg/ml, more preferably about 0.1 µg/ml.

To the extent that tissue culture of cells may be required, it is well-known in the art. For example, Freshney, Culture of Animal Cells, a Manual of Basic Technique, 3rd Ed., Wiley-Liss, New York (1994), Kuchler et al., Biochemical Methods in Cell Culture and Virology, Dowden, Hutchinson and Ross, Inc. (1977), and the references cited therein provide a general guide to the culture of cells. Cultured cell systems often will be in the form of monolayers of cells, although cell suspensions are also used.

Using an Endosomal Release Parameter (ERP) assay, the delivery efficiency of the SNALP or other lipid particle of the invention can be optimized. An ERP assay is described in detail in U.S. Patent Publication No. 20030077829, the disclosure of which is herein incorporated by reference in its entirety for all purposes. More particularly, the purpose of an ERP assay is to distinguish the effect of various cationic lipids and helper lipid components of SNALP or other lipid particle based on their relative effect on binding/uptake or fusion with/destabilization of the endosomal membrane. This assay allows one to determine quantitatively how each component of the SNALP or other lipid particle affects delivery efficiency, thereby optimizing the SNALP or other lipid particle. Usually, an ERP assay measures expression of a reporter protein (e.g., luciferase, β-galactosidase, green fluorescent protein (GFP), etc.), and in some instances, a SNALP formulation optimized for an expression plasmid will also be appropriate for encapsulating an interfering RNA. In other instances, an ERP assay can be adapted to measure downregulation of transcription or translation of a target sequence in the presence or absence of an interfering RNA (e.g., siRNA). By comparing the ERPs for each of the various SNALP or other lipid particles, one can readily determine the optimized system, e.g., the SNALP or other lipid particle that has the greatest uptake in the cell.

G. Cells for Delivery of Lipid Particles

The compositions and methods of the present invention are particularly well suited for treating metabolic diseases and disorders by targeting, e.g., APOB in vivo. In preferred embodiments, an interfering RNA (e.g., an siRNA) in a SNALP formulation containing a cationic lipid of Formulas I-III is delivered to liver cells (e.g., hepatocytes), which surprisingly results in increased silencing of the target gene of interest (e.g., APOB). The methods and compositions can be employed with liver cells (e.g., hepatocytes) of a wide variety of vertebrates, including mammals, such as, e.g., canines, felines, equines, bovines, ovines, caprines, rodents (e.g., mice, rats, and guinea pigs), lagomorphs, swine, and primates (e.g. monkeys, chimpanzees, and humans).

H. Detection of Lipid Particles

In some embodiments, the lipid particles of the present invention (e.g., SNALP) are detectable in the subject at about 1, 2, 3, 4, 5, 6, 7, 8 or more hours. In other embodiments, the lipid particles of the present invention (e.g., SNALP) are detectable in the subject at about 8, 12, 24, 48, 60, 72, or 96 hours, or about 6, 8, 10, 12, 14, 16, 18, 19, 22, 24, 25, or 28 days after administration of the particles. The presence of the particles can be detected in the cells, tissues, or other biological samples from the subject. The particles may be detected, e.g., by direct detection of the particles, detection of a therapeutic nucleic acid such as an interfering RNA (e.g., siRNA) sequence, detection of the target sequence of interest (i.e., by detecting expression or reduced expression of the sequence of interest), or a combination thereof.

1. Detection of Particles

Lipid particles of the invention such as SNALP can be detected using any method known in the art. For example, a label can be coupled directly or indirectly to a component of the lipid particle using methods well-known in the art. A wide variety of labels can be used, with the choice of label depending on sensitivity required, ease of conjugation with the lipid particle component, stability requirements, and available instrumentation and disposal provisions. Suitable labels include, but are not limited to, spectral labels such as fluorescent dyes (e.g., fluorescein and derivatives, such as fluorescein isothiocyanate (FITC) and Oregon Green™; rhodamine and derivatives such Texas red, tetrarhodimine isothiocynate (TRITC), etc., digoxigenin, biotin, phycoerythrin, AMCA, CyDyes™, and the like; radiolabels such as $^3$H, $^{125}$I, $^{35}$S, $^{14}$C, $^{32}$P, $^{33}$P, etc.; enzymes such as horse radish peroxidase, alkaline phosphatase, etc.; spectral colorimetric labels such as colloidal gold or colored glass or plastic beads such as polystyrene, polypropylene, latex, etc. The label can be detected using any means known in the art.

2. Detection of Nucleic Acids

Nucleic acids (e.g., interfering RNA) are detected and quantified herein by any of a number of means well-known to those of skill in the art. The detection of nucleic acids may proceed by well-known methods such as Southern analysis, Northern analysis, gel electrophoresis, PCR, radiolabeling, scintillation counting, and affinity chromatography. Additional analytic biochemical methods such as spectrophotometry, radiography, electrophoresis, capillary electrophoresis, high performance liquid chromatography (HPLC), thin layer chromatography (TLC), and hyperdiffusion chromatography may also be employed.

The selection of a nucleic acid hybridization format is not critical. A variety of nucleic acid hybridization formats are known to those skilled in the art. For example, common formats include sandwich assays and competition or displacement assays. Hybridization techniques are generally described in, e.g., "Nucleic Acid Hybridization, A Practical Approach," Eds. Hames and Higgins, IRL Press (1985).

The sensitivity of the hybridization assays may be enhanced through the use of a nucleic acid amplification system which multiplies the target nucleic acid being detected. In vitro amplification techniques suitable for amplifying sequences for use as molecular probes or for generating nucleic acid fragments for subsequent subcloning are known. Examples of techniques sufficient to direct persons of skill through such in vitro amplification methods, including the polymerase chain reaction (PCR), the ligase chain reaction (LCR), Qβ-replicase amplification, and other RNA polymerase mediated techniques (e.g., NASBA™) are found in Sambrook et al., *In Molecular Cloning: A Laboratory Manual*, Cold Spring Harbor Laboratory Press (2000); and Ausubel et al., SHORT PROTOCOLS IN MOLECULAR BIOLOGY, eds., Current Protocols, Greene Publishing Associates, Inc. and John Wiley & Sons, Inc. (2002); as well as U.S. Pat. No. 4,683,202; PCR Protocols, A Guide to Methods and Applications (Innis et al. eds.) Academic Press Inc. San Diego, Calif. (1990); Arnheim & Levinson (Oct. 1, 1990), *C&EN* 36; The *Journal Of NIH Research*, 3:81 (1991); Kwoh et al., *Proc. Natl. Acad. Sci. USA*, 86:1173 (1989); Guatelli et al., *Proc. Natl. Acad. Sci. USA*, 87:1874 (1990); Lomell et al., *J. Clin. Chem.*, 35:1826 (1989); Landegren et al., *Science*, 241: 1077 (1988); Van Brunt, *Biotechnology*, 8:291 (1990); Wu and Wallace, *Gene*, 4:560 (1989); Barringer et al., *Gene*, 89:117 (1990); and Sooknanan and Malek, *Biotechnology*, 13:563 (1995). Improved methods of cloning in vitro amplified nucleic acids are described in U.S. Pat. No. 5,426,039. Other methods described in the art are the nucleic acid sequence based amplification (NASBA™, Cangene, Mississauga, Ontario) and Qβ-replicase systems. These systems can be used to directly identify mutants where the PCR or LCR primers are designed to be extended or ligated only when a select sequence is present. Alternatively, the select sequences can be generally amplified using, for example, nonspecific PCR primers and the amplified target region later probed for a specific sequence indicative of a mutation. The disclosures of the above-described references are herein incorporated by reference in their entirety for all purposes.

Nucleic acids for use as probes, e.g., in in vitro amplification methods, for use as gene probes, or as inhibitor components are typically synthesized chemically according to the solid phase phosphoramidite triester method described by Beaucage et al., *Tetrahedron Letts.*, 22:1859 1862 (1981), e.g., using an automated synthesizer, as described in Needham VanDevanter et al., *Nucleic Acids Res.*, 12:6159 (1984). Purification of polynucleotides, where necessary, is typically performed by either native acrylamide gel electrophoresis or by anion exchange HPLC as described in Pearson et al., *J. Chrom.*, 255:137 149 (1983). The sequence of the synthetic polynucleotides can be verified using the chemical degradation method of Maxam and Gilbert (1980) in Grossman and Moldave (eds.) Academic Press, New York, *Methods in Enzymology*, 65:499.

An alternative means for determining the level of transcription is in situ hybridization. In situ hybridization assays are well-known and are generally described in Angerer et al., *Methods Enzymol.*, 152:649 (1987). In an in situ hybridization assay, cells are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters.

EXAMPLES

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1

Synthesis of MC3

MC3 (Compound 1) having the structure shown below was synthesized as described in Scheme 1 below.

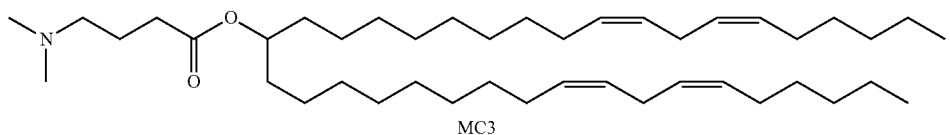 [SMILES: CCCCC/C=C\C/C=C\CCCCCCCCC(CCCCCCCC/C=C\C/C=C\CCCCC)OC(=O)CCCN(C)C]

MC3

Scheme 1

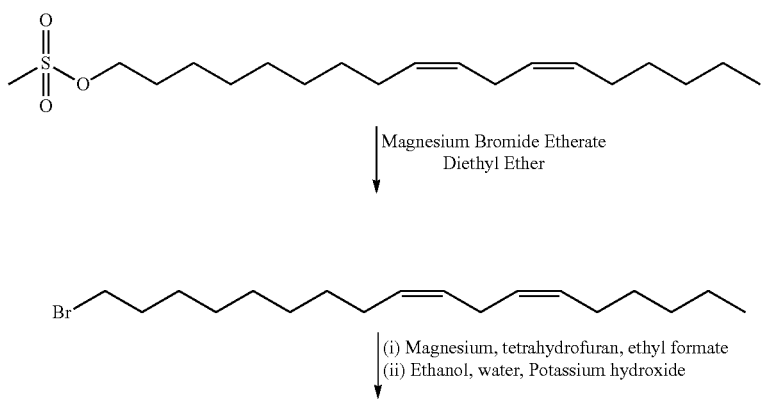

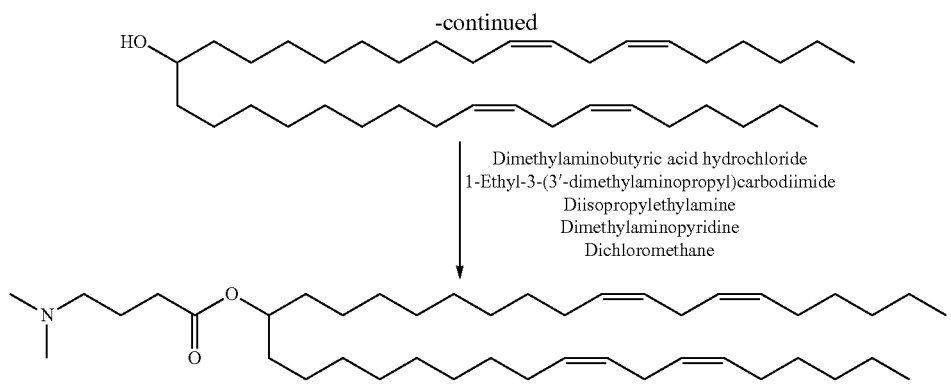

Step 1:

Magnesium bromide etherate (34 g, 110 mmol) and a stir bar were added to a 2000 mL round bottom flask. The flask was sealed and flushed with nitrogen. Anhydrous diethyl ether (400 mL) was added via canulla. A solution of linolenyl mesylate (20 g, 58 mmol) in anhydrous ether (300 mL) was then added, and the suspension stirred overnight. The suspension was poured into 500 mL of chilled water and transferred to a 2000-mL separating funnel. After shaking, the organic phase was separated. The aqueous phase was then extracted with ether (2×250 mL) and all ether phases combined. The ether phase was washed with water (2×250 mL), brine (250 mL) and dried over anhydrous $Mg_2SO_4$. The solution was filtered, concentrated and purified by flash chromatography. Final yield 18.9 g, 99%.

Step 2:

A 1 liter RBF was charged with magnesium turnings (11.1 g, 463 mmol), anhydrous THF (65 mL) and stir-bar and flushed with nitrogen. In a separate flask, a solution of linoleyl bromide (140 g, 425 mL) in anhydrous THF (150 mL) was prepared, and 20 mL of this solution added to the magnesium. When most of the heat had dissipated, the remainder of the bromide was added over a period of 15 minutes. Temperature was then maintained at 45° C. for 4 h. The reaction was then cooled (0° C.). Using a dropping funnel, a solution of ethyl formate (32.4 g, 438 mmol) in anhydrous THF (150 mL) was added over a 40 minute period. The reaction was stirred overnight at room temperature. The reaction was cooled to −15° C. and 5N HCl (185 mL) added slowly. The mixture was transferred to a 2 L separating funnel separated. Water (150 mL) and hexane (150 mL) were added, the mixture washed, and again the aqueous removed. The organic was washed a final time with water (150 mL) and then concentrated to a yellow oil. The yellow oil was stirred with a mixture of EtOH (210 mL), water (30 mL) and KOH (15.8 g) for 1.5 h at room temp. The EtOH was evaporated and the residue treated with hexane (50 mL). 5N HCl (200 mL) was added via dropping funnel. The organic was washed with water (2×50 mL) evaporated, dried and purified by chromatography (0-5% EtOAc in hexane, 91 g, 81%).

Step 3:

Dilinoleylmethanol (7.8 g, 14.9 mmol), dimethylaminobutyric acid hydrochloride (2.99 g, 17.8 mmol) and a stir bar were added to 500 mL RBF. The flask was flushed with nitrogen and anh. DCM (120 mL) added, followed by EDCI (3.6 g, 18.8 mmol), DIPEA (6.3 mL, 36.3 mmol) and DMAP (450 mg, 3.69 mmol). The reaction was stirred overnight. The reaction was diluted with DCM (300 mL) and washed with sat. $NaHCO_3$ (200 mL), water (300 mL) and sat. NaCL (200 mL). Each aq. wash was extracted once with DCM (50 mL). Organics were combined, dried ($MgSO_4$) and concentrated to yield a yellow oil with some crystalline matter. This was purified by chromatography (0-2% MeOH in $CHCl_3$) to yield Lin-MC3 as a pale yellow oil (9.0 g, 14.1 mmol, 95%).

Example 2

Synthesis of LenMC3 and CP-LenMC3

LenMC3 (Compound 4) and CP-LenMC3 (Compound 5) having the structures shown below were synthesized as described in Scheme 2 below. LenMC3 is also known as linolenyl-MC3 and DLen-MC3. CP-LenMC3 is also known as CP-linolenyl-MC3 and CP-DLen-MC3.

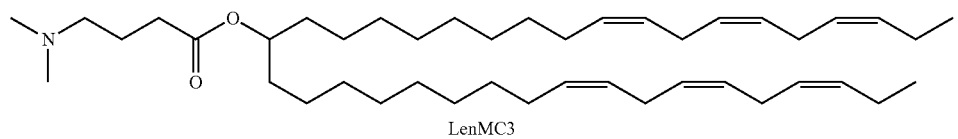

LenMC3

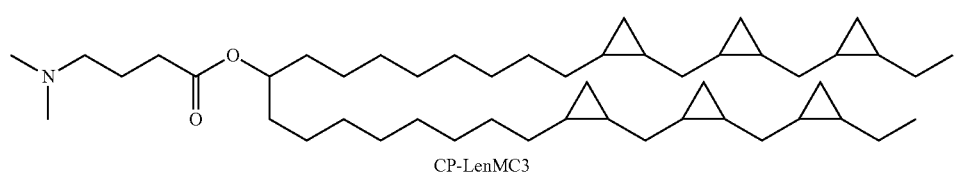

CP-LenMC3

Scheme 2

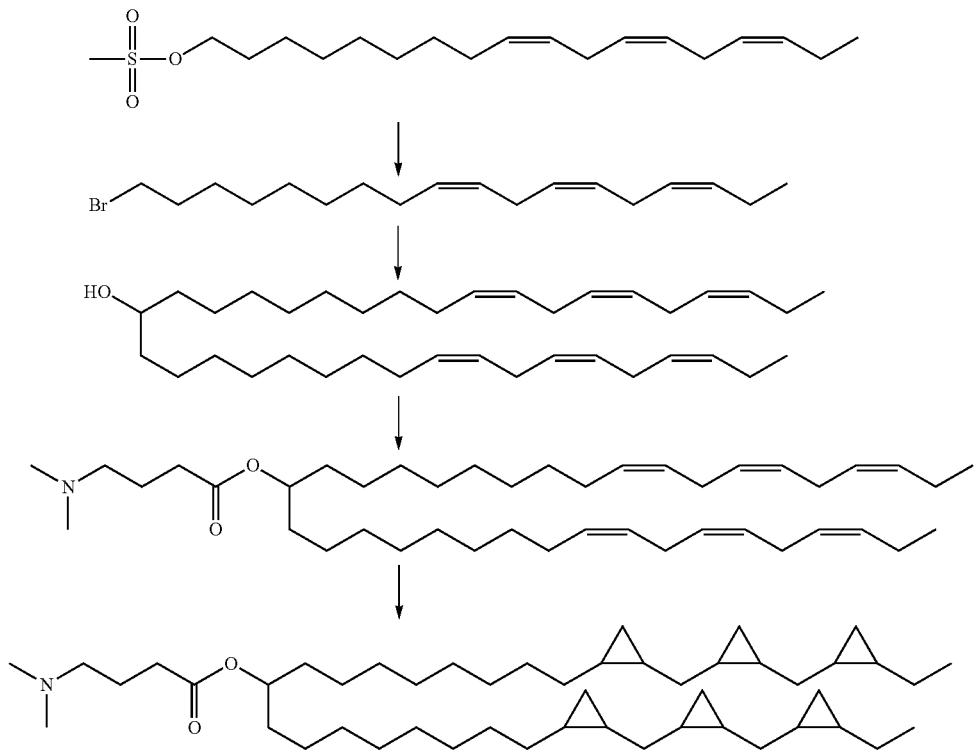

Synthesis of Linolenyl Bromide (Compound 2)

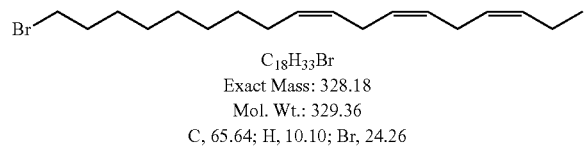 [SMILES: CC/C=C\C/C=C\C/C=C\CCCCCCCCBr]

$C_{18}H_{33}Br$
Exact Mass: 328.18
Mol. Wt.: 329.36
C, 65.64; H, 10.10; Br, 24.26

Magnesium bromide etherate (34 g, 110 mmol) and a stir bar were added to a 2000 mL round bottom flask. The flask was sealed and flushed with nitrogen. Anhydrous diethyl ether (400 mL) was added via canulla. A solution of linolenyl mesylate (20 g, 58 mmol) in anhydrous ether (300 mL) was then added, and the suspension stirred overnight. The suspension was poured into 500 mL of chilled water and transferred to a 2000-mL separating funnel. After shaking, the organic phase was separated. The aqueous phase was then extracted with ether (2×250 mL) and all ether phases combined. The ether phase was washed with water (2×250 mL), brine (250 mL) and dried over anhydrous $Mg_2SO_4$. The solution was filtered, concentrated and purified by flash chromatography. Final yield 19.1 g, 100%.

Synthesis of Dilinolenyl Methanol (Compound 3)

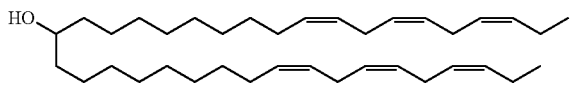

Magnesium turnings (2.1 g, 87 mmol), 5 crystals of iodine and a stirbar were added to a 1000 mL round-bottom flask. The flask was flushed with nitrogen and a solution of linolenyl bromide (Compound 2) (19.1 g, 58 mmol) in anhydrous diethyl ether (500 mL) added via cannula. The mixture turned cloudy and was refluxed overnight. The mixture was cooled to RT and ethyl formate (4.66 mL, 58 mmol) added via syringe. The addition was made dropwise, directly into the reaction mixture, and the cloudy suspension again stirred overnight. During this time the reaction turned bright yellow. The R.M. was transferred to a 2000-mL sep. funnel with ether (50 mL), and washed with 10% $H_2SO_4$ (200 mL), water (2×200 mL) and brine (200 mL). The organic was dried over anhydrous $MgSO_4$, filtered and concentrated. Crude yield was 14.5 g. TLC indicated that majority of product was the methyl formate, which was purified by column chromatography. The purified formate (9.3 g, 16.7 mmol) was transferred to a 1000 mL round bottom flask and EtOH (600 mL) and a stirbar added. With stirring, water (25 mL—forming ~5% aqueous solution) was slowly added, followed by KOH (2.0 g, 35.7 mmol). After 1 hour, the solution had turned pale yellow. TLC indicated reaction had gone to completion. The solution was concentrated by rotovap to 50% of its volume and then poured into 200 mL of 5% HCl. The aqueous phase was extracted with ether (3×200 mL). The ether fractions were combined and washed with water (3×200 mL), dried ($MgSO_4$) and concentrated to yield 8.9 g of dilinolenyl methanol (16.8 mmol, 58%).

Synthesis of Len-MC3 (Compound 4)

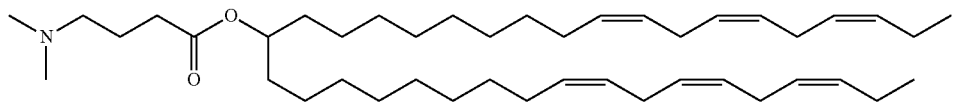 [SMILES: CC/C=C\C/C=C\C/C=C\CCCCCCCCC(CCCCCCCC/C=C\C/C=C\C/C=C\CC)OC(=O)CCCN(C)C]

Dilinolenyl methanol (Compound 3) (2.5 g, 4.76 mmol), dimethylaminobutyric acid hydrochloride (970 mg, 5.77 mmol) and a stir bar were added to 100 mL RBF. The flask was flushed with nitrogen and anhydrous DCM (40 mL) added, followed by EDCI (FW 191.7, 1.2 g, 6.26 mmol), DIPEA (2.1 mL, 12.1 mmol) and DMAP (150 mg, 1.23 mmol). The reaction was stirred overnight, whereupon TLC indicated >80% conversion. Reaction was diluted with DCM (100 mL) and washed with sat. NaHCO$_3$ (100 mL), water (200 mL) and sat. NaCL (100 mL). Aqueous washes were combined and extracted with DCM (2×50 mL). Organics were then combined, dried (MgSO$_4$) and concentrated to yield a yellow oil with some crystalline matter. This was purified by chromatography to yield Len-MC3 as a pale yellow oil (2.3 g, 3.6 mmol, 76%).

Synthesis of CP-LenMC3 (Compound 5)

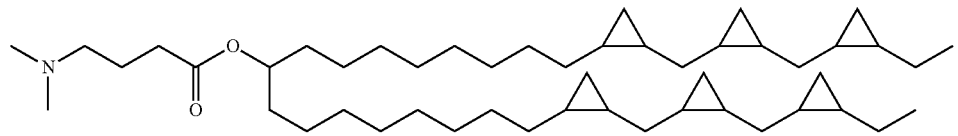

Chemical Formula: C$_{49}$H$_{87}$NO$_2$
Exact Mass: 721.7
Molecular Weight: 722.2
Elemental Analysis: C, 81.49; H, 12.14; N, 1.94; O, 4.43

To a 250 mL RBF was added Len-MC3 (Compound 4) (1.1 g, 1.72 mmol), a stirbar and anhydrous DCM (40 mL). The flask was flushed with N$_2$ and cooled to 0° C., then a 1M solution of diethylzinc in hexanes added (30 mL, 30 mmol). The solution was stirred for 1 hour at 0° C., then diiodomethane (2.4 mL 30 mmol) added and the reaction stirred overnight at RT. The reaction mixture was concentrated and then redissolved in EtOAc (50 mL). The EtOAc was washed successively with 5% HCl (2×50 mL), water (50 mL), NaHCO$_3$ (50 mL), water (50 mL), and brine (50 mL). The aqueous washes were combined and extracted with DCM (2×50 mL). All organics were combined, dried and concentrated to yield crude CP-Len-MC3. $^1$H-NMR indicated some olefins still to be present, so the compound was treated again, using the same procedures and amounts outlined above. This time, after chromatography, $^1$H-NMR indicated total conversion of the olefins. Final yield 1.0 g, 1.39 mmol, 81%.

Example 3

Synthesis of γ-LenMC3 and CP-γ-LenMC3

γ-LenMC3 (Compound 8) and CP-γ-LenMC3 (Compound 9) having the structures shown below were synthesized as described in Scheme 3 below. γ-LenMC3 is also known as γlinolenyl-MC3, γDLen-MC3, and D-γ-Len-MC3. CP-γ-LenMC3 is also known as CP-γlinolenyl-MC3, CP-γDLen-MC3, and CP-D-γ-Len-MC3.

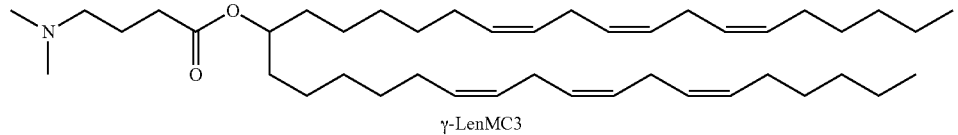

γ-LenMC3

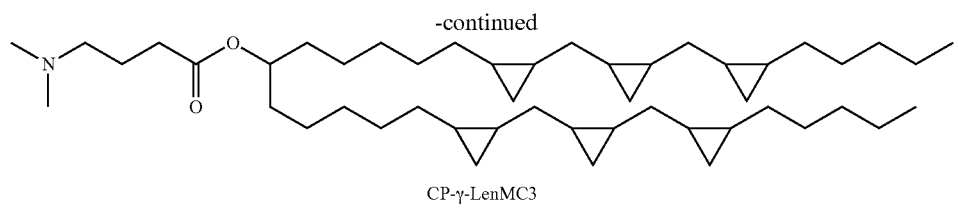

CP-γ-LenMC3

Scheme 3

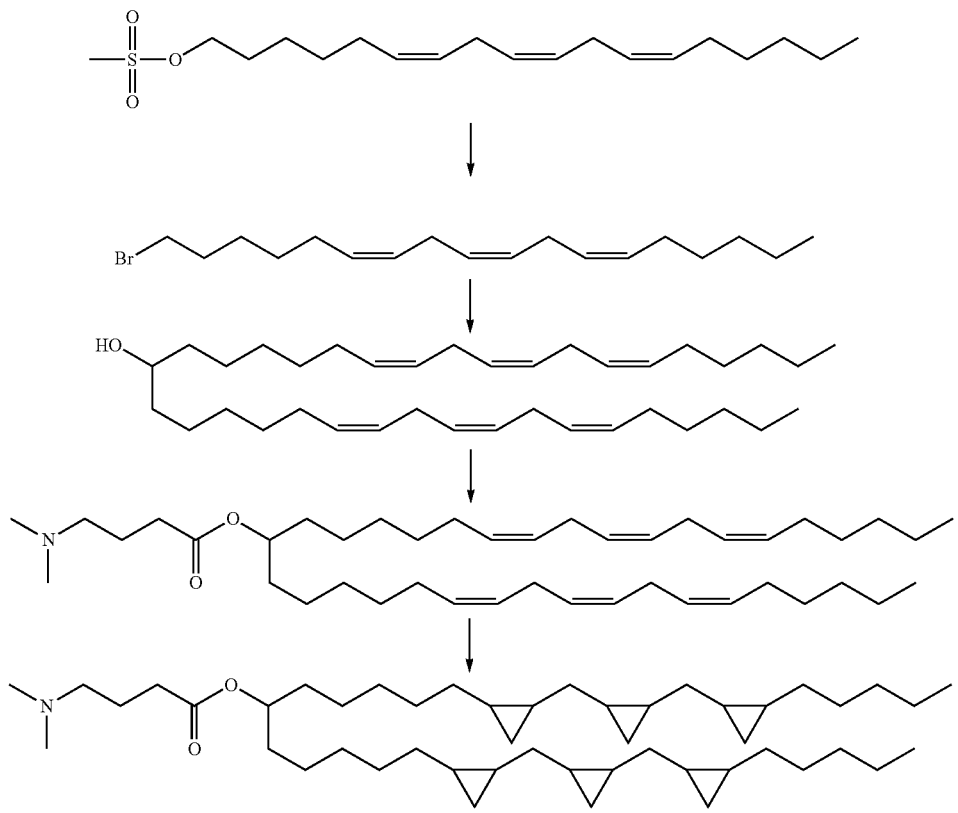

Synthesis of γ-Linolenyl Bromide (Compound 6)

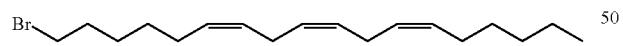

Magnesium bromide etherate (34 g, 110 mmol) and a stir bar were added to a 2000 mL round bottom flask. The flask was sealed and flushed with nitrogen. Anhydrous diethyl ether (400 mL) was added via canulla. A solution of γ-linolenyl mesylate (20 g, 58 mmol) in anhydrous ether (300 mL) was then added, and the suspension stirred overnight. The suspension was poured into 500 mL of chilled water and transferred to a 2000-mL separating funnel. After shaking, the organic phase was separated. The aqueous phase was then extracted with ether (2×250 mL) and all ether phases combined. The ether phase was washed with water (2×250 mL), brine (250 mL) and dried over anhydrous $Mg_2SO_4$. The solution was filtered, concentrated and purified by flash chromatography. Final yield 18.9 g, 99%.

Synthesis of Di-γ-Linolenyl Methanol (Compound 7)

Magnesium turnings (2.1 g, 87 mmol), 5 crystals of iodine and a stirbar were added to a 1000 mL round-bottom flask. The flask was flushed with nitrogen and a solution of γ-linolenyl bromide (Compound 6) (18.9 g, 57 mmol) in anhydrous diethyl ether (500 mL) added via cannula. The mixture turned cloudy and was refluxed overnight. The mixture was cooled to RT and ethyl formate (4.66 mL, 58 mmol) added dropwise. The suspension was stirred overnight, turning bright yellow. The R.M. was transferred to a 2000-mL sep. funnel with ether (50 mL), and washed with 10% sulphuric acid (200 mL), water (2×200 mL) and brine (200 mL). The organic was dried over anhydrous $MgSO_4$, filtered and concentrated. Crude yield was 14.5 g. TLC indicated that majority of product was the methyl formate, which was purified by column chromatography. The purified formate was transferred to a 1000 mL round bottom flask and EtOH (600 mL) and a stirbar added. With stirring, water (25 mL—forming ~5% aqueous solution) was slowly added, followed by KOH (2.0 g, 35.7 mmol). After 1 hour, solution had turned pale yellow. TLC indicated reaction had gone to completion. The solution was concentrated by rotovap to 50% of its volume and then poured into 200 mL of 5% HCl. The aqueous phase was extracted with ether (3×200 mL). The ether fractions were combined and washed with water (3×200 mL), dried (MgSO$_4$) and concentrated to yield 8.8 g of di-γ-linolenyl methanol (16.8 mmol, 58%).

Synthesis of γ-LenMC3 (Compound 8)

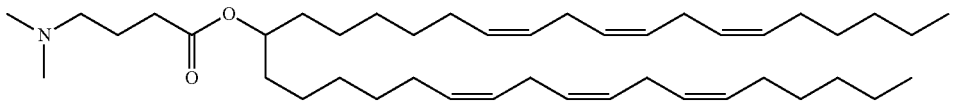 [SMILES: CCCCC/C=C\C/C=C\C/C=C\CCCCCC(CCCCC/C=C\C/C=C\C/C=C\CCCCC)OC(=O)CCCN(C)C]

Di-γ-linolenyl methanol (Compound 7) (2.5 g, 4.76 mmol), dimethylaminobutyric acid hydrochloride (970 mg, 5.77 mmol) and a stir bar were added to 100 mL RBF. The flask was flushed with nitrogen and anhydrous DCM (40 mL) added, followed by EDCI (1.2 g, 6.26 mmol), DIPEA (2.1 mL, 12.1 mmol) and DMAP (150 mg, 1.23 mmol). The reaction was stirred overnight. The reaction was diluted with DCM (100 mL) and washed with sat. NaHCO$_3$ (100 mL), water (200 mL) and sat. NaCL (100 mL). Aqueous washes were combined and extracted with DCM (2×50 mL). Organics were then combined, dried (MgSO$_4$) and concentrated to yield a yellow oil. This was purified by chromatography to yield γ-Len-MC3 as a pale yellow oil (2.6 g, 4.1 mmol, 86%).

Synthesis of CP-γ-LenMC3 (Compound 9)

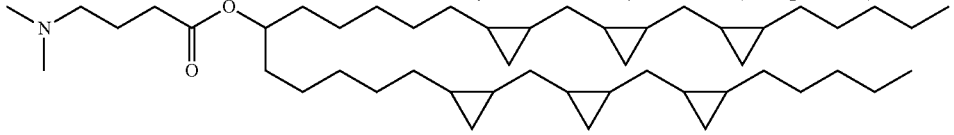 [SMILES: CCCCCC1CC1CC1CC1CC1CC1CCCCCC(CCCCCC1CC1CC1CC1CC1CC1CCCCC)OC(=O)CCCN(C)C]

To a 250 mL RBF was added γ-LenMC3 (Compound 8) (1.28 g, 2.0 mmol), a stirbar and anhydrous DCM (40 mL). The flask was flushed with N$_2$ and cooled to 0° C., then a 1M solution of diethylzinc in hexanes added (30 mL, 30 mmol, ~5 equivalents per olefin). The solution was stirred for 1 hour at 0° C., then diiodomethane (2.4 mL 50 mmol) added and the reaction stirred overnight at RT. The reaction mixture was concentrated and then redissolved in EtOAc (50 mL). The EtOAc was washed successively with 5% HCl (2×50 mL), water (50 mL), NaHCO$_3$ (50 mL), water (50 mL), and brine (50 mL). The aqueous washes were combined and extracted with DCM (2×50 mL). All organics were combined, dried and concentrated to yield crude CP-γ-LenMC3. $^1$H-NMR indicated some olefins still to be present, so the compound was treated again, using the same procedures and amounts outlined above. This time $^1$H-NMR indicated total conversion of the olefins. Final yield after chromatography was 1.3 g, 1.8 mmol, 90%.

Example 4

Synthesis of MC3MC

MC3MC (Compound 10) having the structure shown below was synthesized as described in Schemes 4 and 5 below.

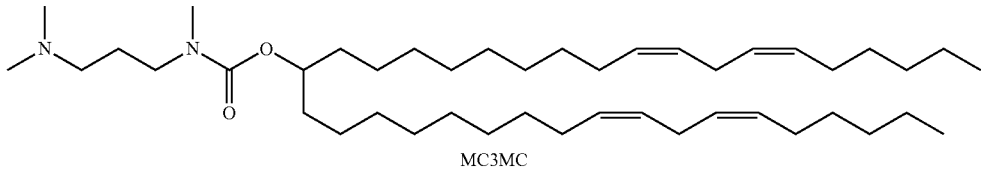 [SMILES: CCCCC/C=C\C/C=C\CCCCCCCCC(CCCCCCCC/C=C\C/C=C\CCCCC)OC(=O)N(C)CCCN(C)C]

MC3MC

Scheme 4

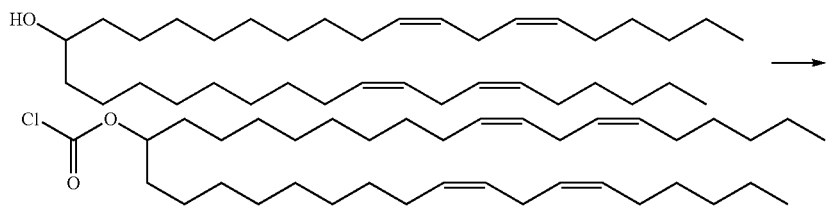

A 50 mL round bottom flask was charged with dilinoleyl methanol (3.06 g, 5.78 mmol) and a stir bar and flushed with nitrogen. Anhydrous DCM (30 mL) was added, followed by diphosgene (1.75 mL, 14.46 mmol, 2.5 eqv.). The reaction was stirred overnight and then concentrated by rotovap and purified by chromatography. This yielded the product as a colourless oil (2.6 g, 4.4 mmol, 76%).

Scheme 5

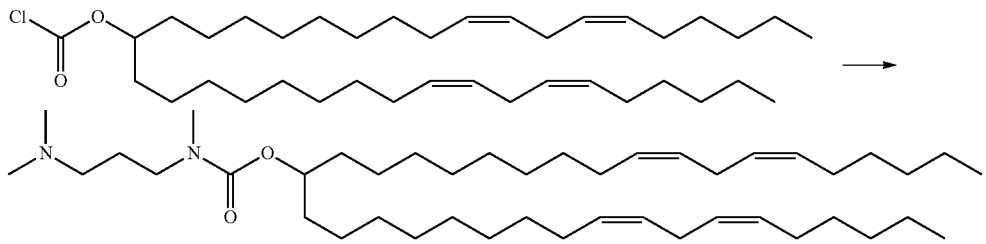

A 50 mL r.b.f. containing the chloroformate (350 mg, 0.59 mmol) and a stir bar was flushed with nitrogen and sealed. Anhydrous DCM (10 mL) and N,N,N'-trimethyl-1,3-propanediamine (580 mg, 5 mmol) were added and the reaction stirred for 4 h. TLC indicated the reaction to have gone to completion. The mixture was diluted to a volume of 40 mL with DCM and washed with sat. NaHCO$_3$ (30 mL), water (30 mL) and brine (30 mL). The aqueous phases were combined and extracted once with DCM (20 mL). Organics were then combined, dried over MgSO$_4$, and concentrated by rotovap. Purification yielded the product as a pale oil, 350 mg, 0.52 mmol, 89%.

Example 5

Synthesis of MC2MC

MC2MC (Compound 11) having the structure shown below was synthesized as described in Scheme 6 below.

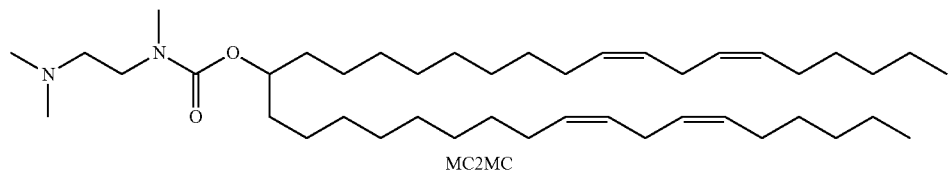 [SMILES: CCCCC/C=C\C/C=C\CCCCCCCCC(CCCCCCCC/C=C\C/C=C\CCCCC)OC(=O)N(C)CCN(C)C]

MC2MC

Scheme 6

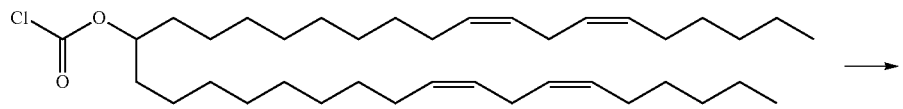

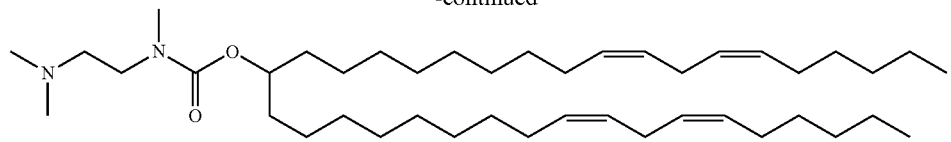

A 50 mL round bottom flask containing the chloroformate (400 mg, 0.68 mmol) and a stir bar was flushed with nitrogen and sealed. Anhydrous DCM (10 mL) and N,N,N'-trimethyl-1,2-ethanediamine (510 mg, 5 mmol) were added and the reaction stirred for overnight. TLC indicated the reaction to have gone to completion. The mixture was concentrated by rotovap and purified by column chromatography to yield the product as a pale oil (350 mg, 0.53 mmol, 78%).

Example 6

Synthesis of MC2C

MC2C (Compound 12) having the structure shown below was synthesized as described in Scheme 7 below.

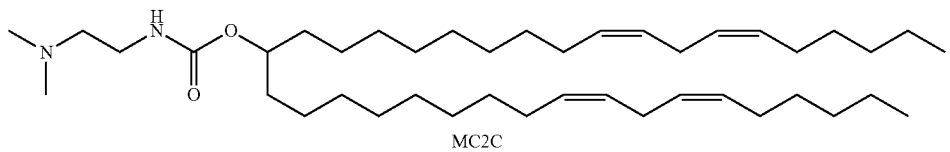 [SMILES: CCCCC/C=C\C/C=C\CCCCCCCCC(CCCCCCCC/C=C\C/C=C\CCCCC)OC(=O)NCCN(C)C]

MC2C

Scheme 7

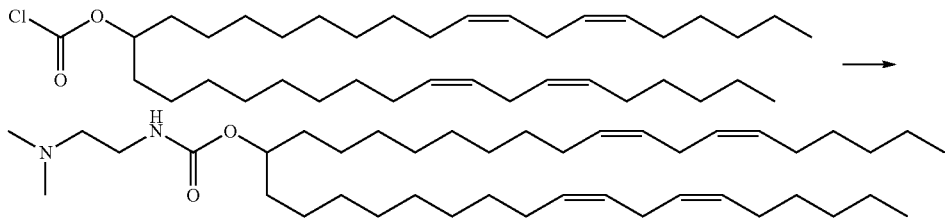

A 50 mL round bottom flask containing the chloroformate (400 mg, 0.68 mmol) and a stir bar was flushed with nitrogen and sealed. Anhydrous DCM (10 mL) and N,N,-dimethylethylenediamine (440 mg, 5 mmol) were added and the reaction stirred for overnight. TLC indicated the reaction to have gone to completion. The mixture was concentrated by rotovap and purified by column chromatography to yield the product as a pale yellow oil (350 mg, 0.54 mmol, 80%).

Example 7

Synthesis of MC3 Ether

MC3 Ether (Compound 13) having the structure shown below was synthesized as described in Scheme 8 below.

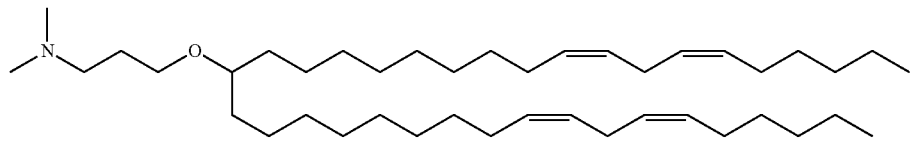

Chemical Formula: $C_{42}H_{79}NO$
Exact Mass: 613.6
Molecular Weight: 614.1
Elemental Analysis: C, 82.15; H, 12.97; N, 2.28; O, 2.61

MC3 Ether

Scheme 8

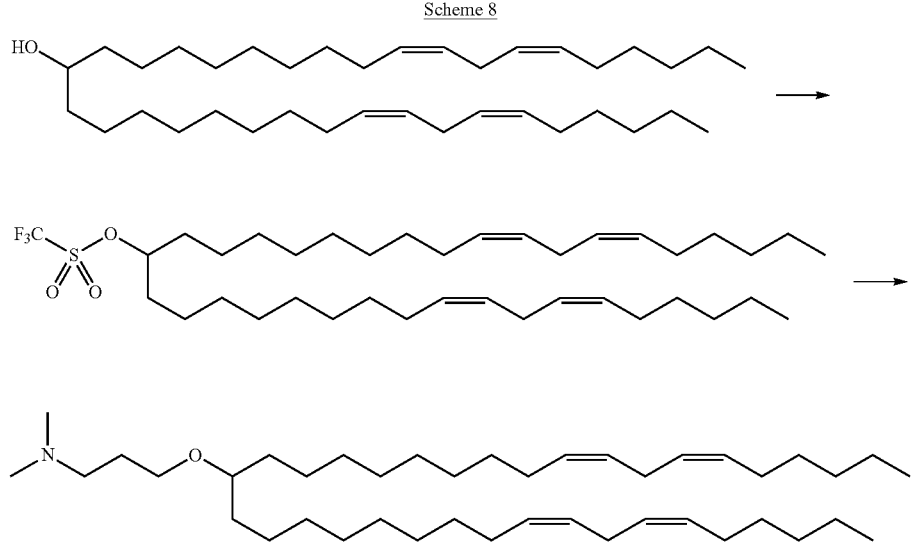

A 50 mL RBF with stir-bar was flushed with nitrogen and anhydrous DCM (4 mL). Triflic anhydride (0.7 g, 420 µL, 2.5 mmol) was added and the flask cooled to −15° C. Anhydrous pyridine (198 mg, 202 µL, 2.5 mmol) was slowly added, causing fuming and a white precipitate to form. A solution of dilinoleyl methanol (1.06 g, 2 mmol) in anhydrous DCM (2 mL) was added slowly over a period of 2 minutes. After stirring for 2 h at ~−15° C. the reaction was off-white in color. TLC showed triflate formation and water (2 mL) was added to quench the reaction. DCM (10 mL) was added and the mixture washed with water (2×20 mL), dried (MgSO$_4$), filtered and transferred to a 25 mL round bottom flask. Proton Sponge (1.07 g, 5 mmol, min 2.5 eqv.), dimethylaminopropanol (515 mg, 5 mmol, min. 2.5 eqv) and a stir bar added and the vessel flushed with nitrogen, fitted with a condenser and refluxed for 48 h. Water (10 mL) was added, and after stirring vigorously for several minutes, separated in a 30 mL sep funnel. The organic was washed again with water (10 mL), dried over MgSO$_4$, concentrated and purified by chromatography (MeOH/CHCl$_3$) to yield the product as a pale yellow oil (400 mg, 33%).

Alternatively, MC3 Ether (Compound 13) was synthesized starting from dilinoleyl methanol (DLinMeOH) as follows:

Synthesis of Compound 14

A 50 mL RBF with stir-bar was flushed with nitrogen, and DLinMeOH (1060 mg, 2 mmol), TEA (6 mmol, 834 µL) and anh. DCM (20 mL) added. Flask was cooled to 0° C. and either MsCl (6 mmol) added. Reaction was stirred overnight. Reaction was diluted to 70 mL with DCM, washed with sat. NaHCO$_3$ (2×50 mL) and sat. NaCl (50 mL), dried (MgSO$_4$), filtered, concentrated and purified by column chromatography (1-4% EtOAc in hexane). Yield 900 mg, 75%.

Synthesis of MC3 Ether

A 50 mL RBF with stir-bar were flushed with nitrogen, and NaH (220 mg, 9 mmol), dimethylaminopropanol (927 mg, 1.06 mL, 9 mmol) and anh. benzene (10 mL) added. After effervescence subsided, Compound 14 (440 mg, 0.75 mmol) was added and RM refluxed overnight at 90° C. TLC indicated 30-50% product formation. RM was refluxed a second night, but TLC did not appear to indicate further reaction. The reaction was diluted to 40 mL with benzene, and quenched with ethanol (25 mL). It was then washed with water (40 mL), dried and concentrated. The crude product was purified to yield product as a pale yellow oil, 157 mg, 33%.

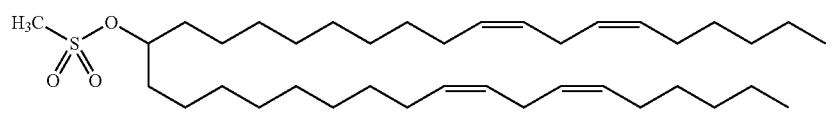

Chemical Formula: C$_{38}$H$_{70}$O$_3$S
Exact Mass: 606.5
Molecular Weight: 607.0
Elemental Analysis: C, 75.19; H, 11.62; O, 7.91; S, 5.28

Example 8

Synthesis of MC4 Ether

MC4 Ether (Compound 15) having the structure shown below was synthesized as described below.

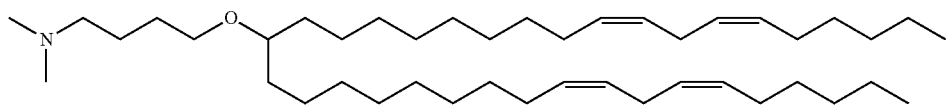

Chemical Formula: $C_{43}H_{81}NO$
Exact Mass: 627.6
Molecular Weight: 628.1
Elemental Analysis: C, 82.22; H, 13.00; N, 2.23; O, 2.55
MC4 Ether A 50 mL RBF with stir-bar were flushed with nitrogen, and NaH (220 mg, 9 mmol), dimethylaminobutanol (1.05 g, 9 mmol) and anh. benzene (10 mL) added. After effervescence subsided, Compound 14 (440 mg, 0.75 mmol) was added and RM refluxed overnight at 90° C. TLC indicated some product formation. The reaction was diluted to 40 mL with benzene, and quenched with ethanol (25 mL). It was then washed with water (40 mL), dried and concentrated. The crude product was purified to yield product as a pale yellow oil, 145 mg, 31%.

Example 9

Synthesis of MC3 Amide

MC3 Amide (Compound 16) having the structure shown below was synthesized as described in Schemes 9-11 below.

To a 500 mL RBF containing a solution of dilinoleyl methanol (10 g, 18.9 mmol) in DCM (200 mL) was added pyridinium chlorochromate (12.24 g, 56.7 mmol), anh. sodium carbonate (1.0 g, 9.5 mmol) and a stir bar. The resulting suspension was stirred under nitrogen at RT for 3 h, after which time TLC indicated all SM to have been consumed. Ether (300 mL) was then added to the mixture and the resulting brown suspension filtered through a pad of silica (300 mL), washing the pad with ether (3×100 mL). The ether phases were combined, concentrated and purified to yield 9.0 g (17.1 mmol, 90%) of ketone.

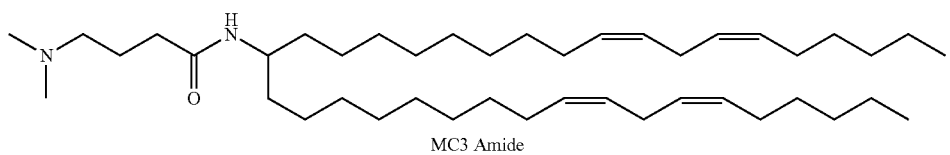 [SMILES: CCCCC/C=C\C/C=C\CCCCCCCCC(CCCCCCCC/C=C\C/C=C\CCCCC)NC(=O)CCCN(C)C]

MC3 Amide

Scheme 9

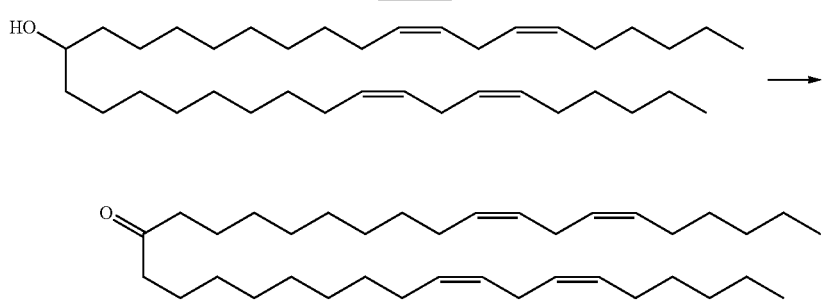

Scheme 10

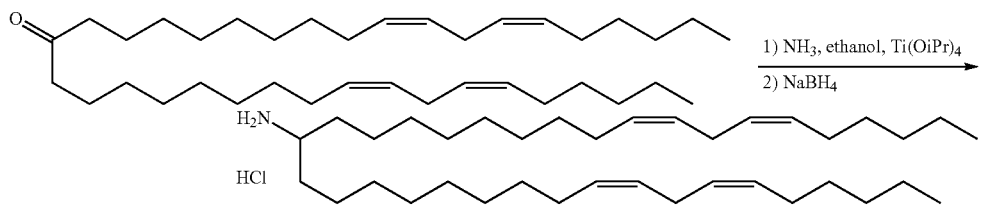

To a solution of dilinoleyl ketone (1.0 g, 1.9 mmol) in 2M ammonia in ethanol (5 mL) was added titanium(IV) isopropoxide (1.15 mL, 3.8 mmol). The solution was stirred under nitrogen at room temperature for 6 hours then sodium borohydride (110 mg, 3.8 mmol) was added. The solution effervesced for approximately 5 minutes, and then a colorless precipitate began to form. The solution was stirred for 16 hours at room temperature, quenched with 10% NH$_4$OH (25 mL) and diluted with ethyl acetate (50 mL). The inorganic solids were filtered and the aqueous phase was washed with ethyl acetate (2×75 mL). The combine ethyl acetate extracts were washed with 2M HCl (2×50 mL), dried on magnesium sulfate, filtered and concentrated to dryness to afford the product as a pale yellow HCl salt (1.1 g, quantitative).

Scheme 11

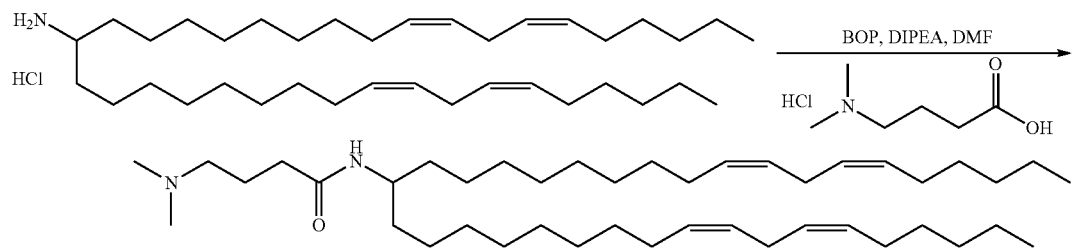

To a solution of dilinoleyl methylamine hydrochloride (1.1 g, 1.95 mmol), BOP (1.1 g, 2.4 mmol) and 4-(dimethylamino) butanoic acid hydrochloride (402 mg, 2.4 mmol) in anhydrous DMF (20 mL) was added diisopropylethylamine (1.4 mL, 7.8 mmol). The solution was stirred for 16 hours at room temperature. The solution was concentrated in vacuo to dryness and dissolved in ethyl acetate (100 mL). The ethyl acetate was washed with brine (3×50 mL), dried on magnesium sulfate, filtered and concentrated in vacuo to dryness. The residue was purified by column chromatography (1% to 2.5% MeOH in CHCl$_3$) to afford the product as an orange oil. Decolorization through a pad of silica gel (eluted with 50% hexanes ethyl acetate to 100% ethyl acetate) afforded the product as a pale yellow oil (151 mg, 12%).

Example 10

Synthesis of Pan-MC1

Phytanyl-MC3 ("Pan-MC3") (Compound 17) having the structure shown below was synthesized as described in Scheme 12 below.

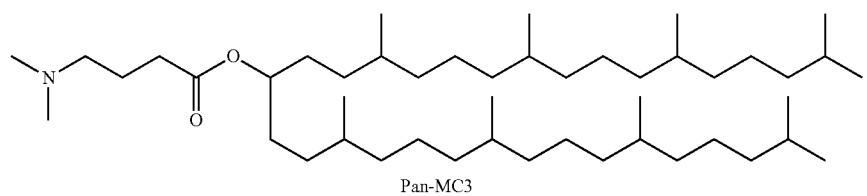 [SMILES: CC(C)CCCC(C)CCCC(C)CCCC(C)CCC(CCC(C)CCCC(C)CCCC(C)CCCC(C)C)OC(=O)CCCN(C)C]

Pan-MC3

Scheme 12

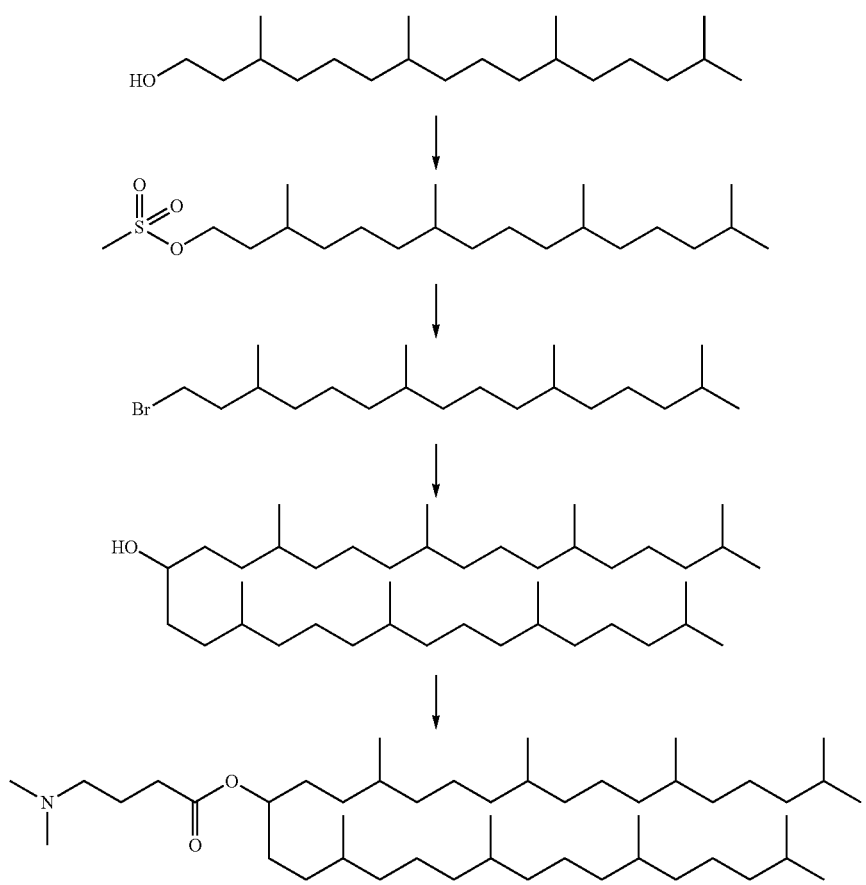

Synthesis of Phytanyl Mesylate

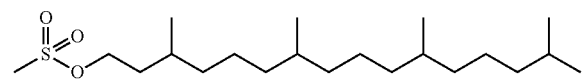 [SMILES: CC(C)CCCC(C)CCCC(C)CCCC(C)CCOS(C)(=O)=O]

To a solution of phytanol (14.98 g, 50.2 mmol) in anhydrous dichloromethane (150 mL) under nitrogen was added triethylamine (7.7 mL, 55.2 mmol). The solution was cooled to −10° C. and then a solution of methanesulfonyl chloride (11.51 g, 100.5 mmol) in anhydrous dichloromethane (100 mL) was added dropwise over 30 minutes. Upon completion, the solution was diluted to 500 mL using dichloromethane. The solution was washed twice with saturated NaHCO$_3$, dried over MgSO$_4$, filtered, and concentrated to dryness to afford the product as a colorless oil (18.9 g, 100%).

Synthesis of Phytanyl Bromide

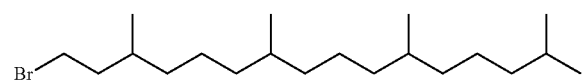 [SMILES: CC(C)CCCC(C)CCCC(C)CCCC(C)CCBr]

To a suspension of magnesium bromide diethyl etherate (25.9 g, 100.3 mmol) in anhydrous diethyl ether (250 mL) under nitrogen at room temperature was added a solution of phytanyl mesylate (18.9 g, 50.2 mmol) in anhydrous diethyl ether (200 mL) dropwise over 15 minutes. The resulting slurry was stirred for 72 hours at room temperature. Upon completion, the reaction mixture was cooled to 0° C. and ice cold water was added dropwise until all solid dissolved and bubbling stopped. Diethyl ether (300 mL) was added, and the organic and aqueous layers separated. The aqueous layer was back-extracted with diethyl ether (200 mL). The combined diethyl ether extracts were dried on MgSO$_4$, filtered, and concentrated. The resulting oil was purified by column chromatography (column 10"L×2"W; eluted with 100% hexanes) to afford the product as a pale yellow oil (16.3 g, 90%).

Synthesis of Diphytanyl Methanol

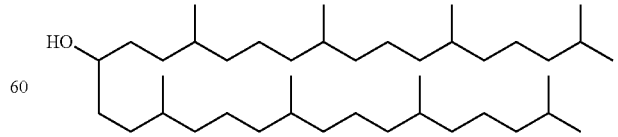

Magnesium turnings (1.18 g, 48.5 mmol) were heated at 250° C. in an oven for 1 hour and then stirred at room temperature under nitrogen for 2 hours. Anhydrous diethyl ether (300 mL) and a single crystal of iodine were added, followed by a solution of phytanyl bromide (15.2 g, 42.1 mmol) in anhydrous diethyl ether (30 mL). The resulting cloudy mixture was heated to reflux overnight. The solution was cooled (0° C.) and a solution of ethyl formate (3.9 mL, 48.5 mmol) in anhydrous diethyl ether (15 mL) was added dropwise over 25 minutes. The resulting yellow solution was again stirred overnight. The yellow solution was cooled (0° C.) and quenched using 5M HCl (15 mL), and then hexanes (100 mL) and water (150 mL) were added. The aqueous and organic layers were separated and the aqueous layer back-extracted twice with hexanes. The combined organics were washed with water, dried on MgSO$_4$, filtered, and concentrated in vacuo to dryness.

The resulting pale yellow oil was dissolved in ethanol (25 mL) and transferred to a flask containing a solution of potassium hydroxide (2.2 g, 39.2 mmol) in water (5 mL). The resulting biphasic solution was stirred at 10° C. for 2.5 hours. Ethanol was removed in vacuo and hexanes (25 mL) and 5M HCl (35 mL) were added. The organic and aqueous layers were separated and the organic layer washed twice with water. The combined organics were dried over MgSO$_4$, filtered, and concentrated. The resulting pale yellow oil was purified by column chromatography (column 12"L×2"W; eluted with a gradient of 100% hexanes→>2%→>4% ethyl ether in hexanes) to afford the product as a pale yellow oil (6.4 g, 49%).

Synthesis of Phytanyl-MC3

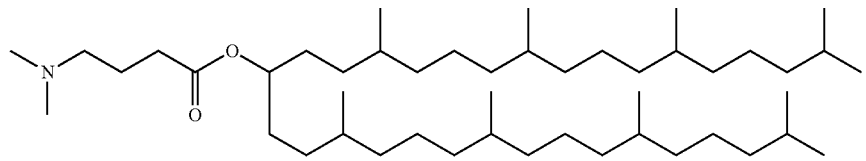 [SMILES: CC(C)CCCC(C)CCCC(C)CCCC(C)CCC(CCC(C)CCCC(C)CCCC(C)CCCC(C)C)OC(=O)CCCN(C)C]

To a solution of diphytanyl methanol (6.4 g, 10.3 mmol) and 4-(dimethylamino) butyric acid hydrochloride (2.25 g, 13.4 mmol) in anhydrous dichloromethane (60 mL) under nitrogen at room temperature was added EDC (2.77 g, 18.0 mmol), diisopropylethylamine (5.4 mL, 31.0 mmol), and 4-dimethylaminopyridine (45 mg, 0.37 mmol). After 16 hours the reaction mixture was diluted with dichloromethane (75 mL). The organic layer was washed with saturated NaHCO$_3$, water, and brine, and then dried on MgSO$_4$, filtered, and concentrated. The resulting yellow oil was purified by column chromatography (column 10"L×2"W; eluted with a gradient of 100% hexanes→10%→50% ethyl acetate in hexanes) to afford the product as a pale yellow oil (3.53 g, 49%) with recovery of some phytanyl methanol (2.81 g, 44%).

Example 11

Synthesis of Pan-MC4

Phytanyl-MC4 ("Pan-MC4") (Compound 18) having the structure shown below was synthesized as described in Scheme 13 below.

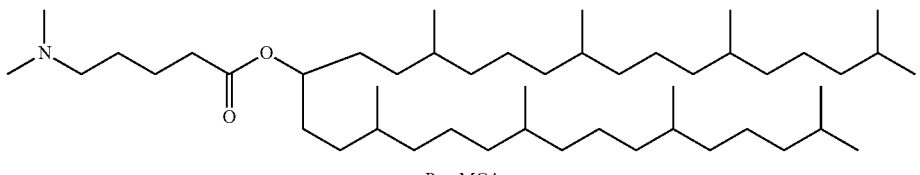

Pan-MC4

Scheme 13

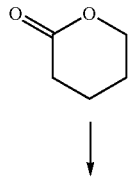

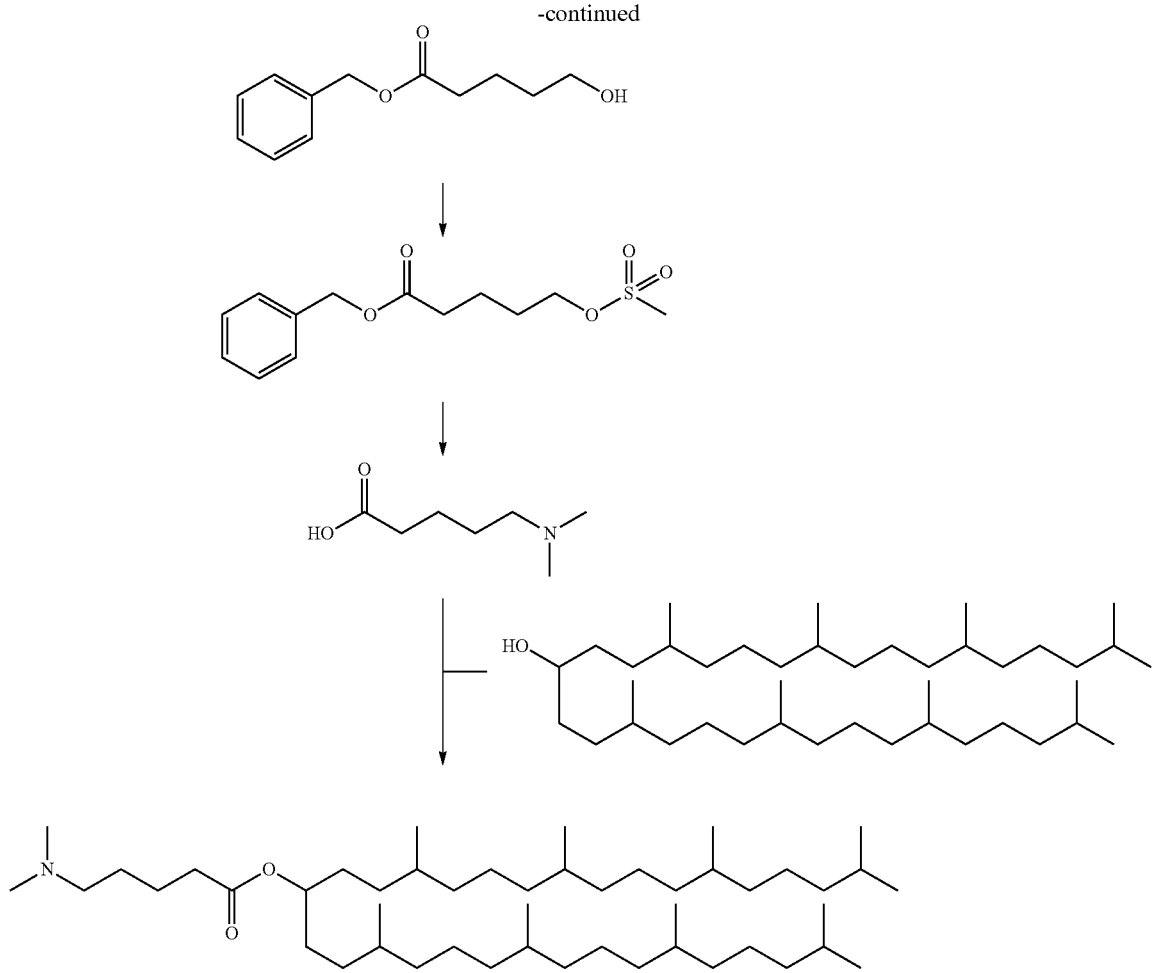

Synthesis of Benzyl 5-Hydroxypentanoate

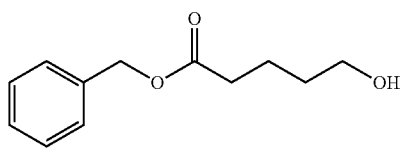 [SMILES: O=C(CCCCO)OCc1ccccc1]

A solution of δ-valerolactone (10 g, 100 mmol) in 1M aqueous sodium hydroxide (100 mL) was heated overnight with stirring at 65° C. The solution was concentrated in vacuo to dryness and any residual water removed under high vacuum at −190° C. The resulting white powder was broken up and suspended in acetone (40 mL). With stirring, benzyl bromide (17 g, 101.4 mmol) and tetrabutylammonium bromide (0.82 g, 2.539 mmol) were added. The mixture was heated at 45° C. with stirring for 72 hours, cooled, and concentrated. The resulting white oily powder was dissolved in ethyl acetate (300 mL) and washed twice each with saturated NaHCO₃ and brine. The organic portion was dried over anhydrous MgSO₄, filtered, and then concentrated. The result was a yellow oil, which was purified by column chromatography (column 10"L×2"W; eluted with a gradient of 100% hexanes→+30%→50% ethyl acetate in hexanes) to afford the product as a pale yellow oil (3.11 g, 15%).

Synthesis of Benzyl 5-(Methanesulfonyl)Pentanoate

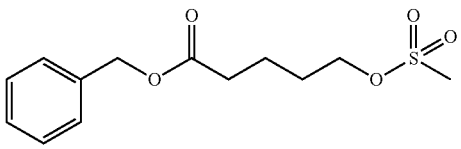 [SMILES: CS(=O)(=O)OCCCCC(=O)OCc1ccccc1]

To a solution of benzyl 5-hydroxypentanoate (2.01 g, 9.65 mmol) in anhydrous dichloromethane (30 mL) under nitrogen at −15° C. was added triethylamine (2.7 mL, 19.3 mmol) followed by a solution of methanesulfonyl chloride (1.5 mL, 19.3 mmol) dropwise over 20 minutes. The reaction was stirred at room temperature overnight and then diluted to 75 mL using dichloromethane. The organic layer was washed three times with saturated NaHCO₃ and the combined aqueous layers backextracted with dichloromethane. The combined organic phases were dried over MgSO₄, filtered, and concentrated. The resulting dark orange oil was purified by column chromatography (column 5"L×1"W; eluted with a gradient of 100% hexanes→10%→20%→25% diethyl ether in hexanes) to afford the product as a pale yellow oil (1.39 g, 50%).

Synthesis of Benzyl 5-(Dimethylamino)Pentanoate

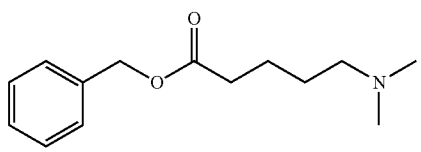 [SMILES: CN(C)CCCCC(=O)OCc1ccccc1]

Benzyl 5-(methanesulfonyl)pentanoate (1.39 g, 4.85 mmol) was allowed to react in a 5.6M solution of dimethylamine in ethanol (100 mL) for 20 hours. The solution was then concentrated in vacuo to dryness. The resulting brown oil was purified by column chromatography (column 10"L× 1"W; eluted with a gradient of 100% dichloromethane→2%/ 0.5%→4%/0.5% MeOH/NH$_4$OH in dichloromethane) to afford the product as a yellow oil (0.79 g, 69%).

Synthesis of 5-(Dimethylamino)Pentanoic Acid

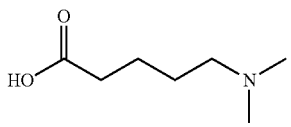

To a solution of 5-(dimethylamino)benzyl pentanoate (0.79 g, 33.6 mmol) in anhydrous ethyl acetate (20 mL) under nitrogen at room temperature was added 10% palladium on carbon (250 mg). The solution was stirred vigorously under a hydrogen atmosphere. After 16 hours additional palladium on carbon (100 mg) was added to encourage the reaction, and at 24 hours hydrogen gas was bubbled through the solution. At 40 hours the solution was filtered through celite and concentrated in vacuo to dryness to afford the product as a yellow oil (295 mg, 60.4%).

Synthesis of Phytanyl-MC4

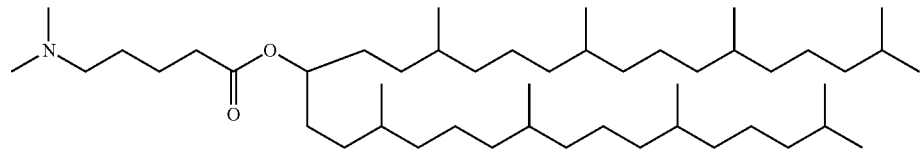 [SMILES: CC(C)CCCC(C)CCCC(C)CCCC(C)CCC(CCC(C)CCCC(C)CCCC(C)CCCC(C)C)OC(=O)CCCCN(C)C]

A solution of diphytanyl methanol (0.8 g, 1.3 mmol) and 4-(dimethylamino) pentanoic acid (0.24 g, 1.7 mmol) in anhydrous dichloromethane (10 mL) under nitrogen at room temperature was added EDC (0.347 g, 1.8 mmol), diisopropylethylamine (0.67 mL, 3.9 mmol), and 4-dimethylaminopyridine (45 mg, 0.37 mmol). After 20 hours additional 5-(dimethylamino)pentanoic acid (0.05 g, 0.34 mmol) was added to encourage the reaction. The reaction was stirred for an additional 52 hours and then diluted to 50 mL using dichloromethane. The organic phase was washed with saturated NaHCO$_3$, water, and brine, and the combined aqueous layers backextracted with dichloromethane. The combined organic layers were dried on MgSO$_4$, filtered, and concentrated. The resulting yellow oil was purified by column chromatography (column 10"L×1¼" W; eluted with a gradient of 100% hexanes→10%→50% ethyl acetate in hexanes) to afford the product as a pale yellow oil (474 mg, 51%) with recovery of some diphytanyl methanol (348 mg, 43.5%).

Example 12

Synthesis of Pan-MC5

Phytanyl-MC5 ("Pan-MC5") (Compound 19) having the structure shown below was synthesized as described in Scheme 14 below.

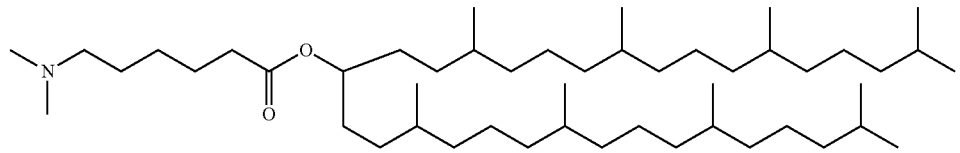

Pan-MC5

Scheme 14

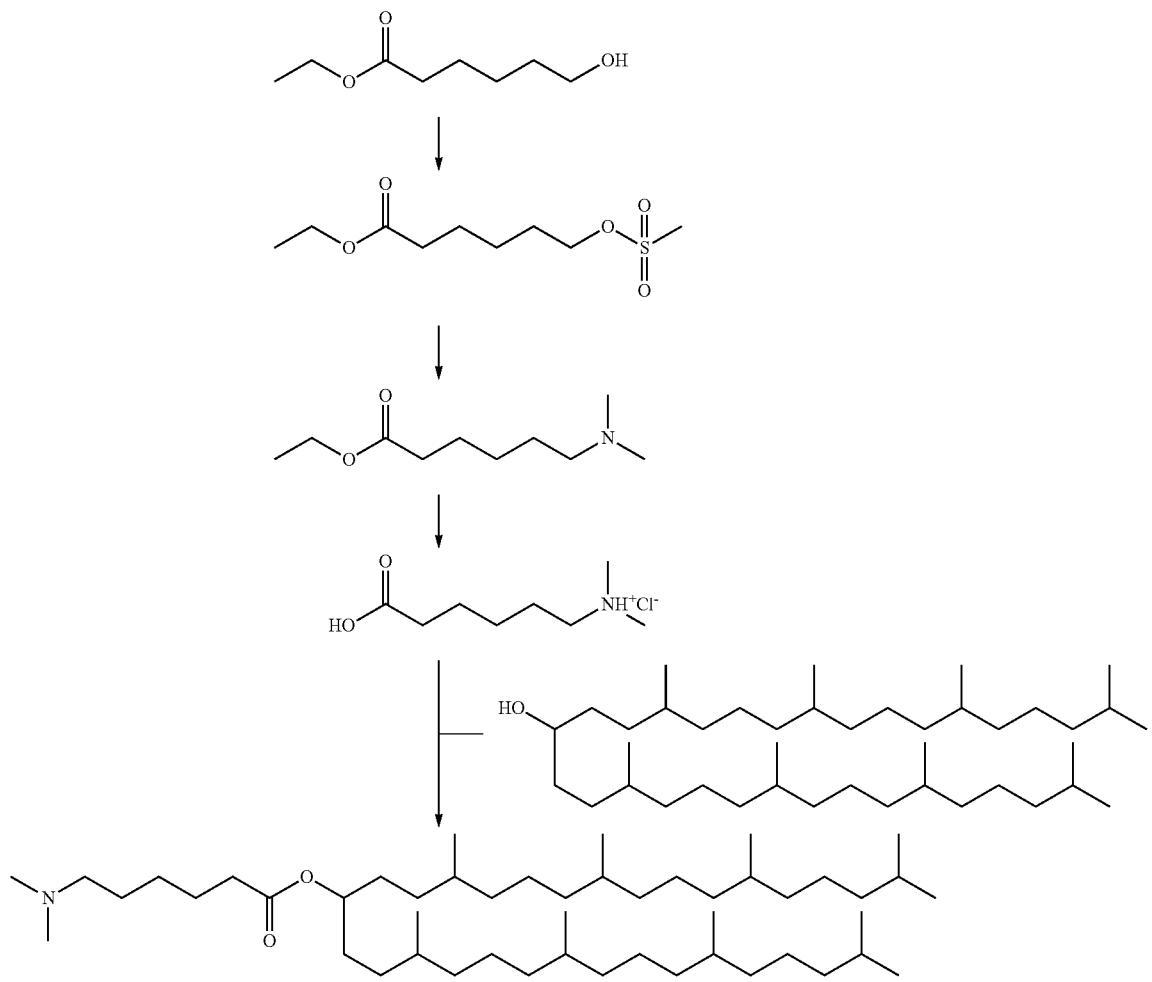

Synthesis of Ethyl 6-(Methanesulfonyl)Hexanoate

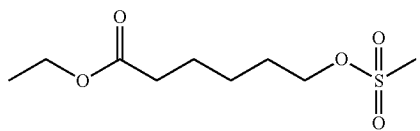

To a solution of ethyl 6-hydroxyhexanoate (5 g, 31.2 mmol) in anhydrous dichloromethane (115 mL) under nitrogen at −10° C. was added triethylamine (8.7 mL, 62.5 mmol) followed by methanesulfonyl chloride (4.8 mL, 62.5 mmol) dropwise over 1 hour. The resulting solution was stirred at room temperature for 6 hours and then diluted to 300 mL using dichloromethane. The solution was washed with twice saturated NaHCO$_3$, and the aqueous layers backextracted with dichloromethane. The combined organics were dried over MgSO$_4$, filtered, and concentrated. The resulting dark orange oil was purified by column chromatography (column 5"L×2"W; eluted with a gradient of 100% hexanes→10%→20% ethyl acetate in hexanes) to afford the product as a pale yellow oil.

Synthesis of Ethyl 6-(Dimethylamino)Hexanoate

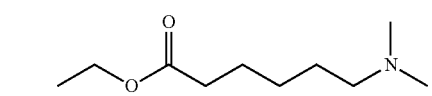

Ethyl 6-(methanesulfonyl)hexanoate was allowed to react in a 5.6M solution of dimethylamine in ethanol (100 mL) for 17 hours. The solution was then concentrated in vacuo to dryness. The resulting bright orange paste was purified by column chromatography (column 5"L×2"W; eluted with a gradient of 100% dichloromethane→1%/0.25%→2%/0.5% MeOH/NH$_4$OH in dichloromethane) to afford the product as a yellow oil.

Synthesis of 6-(Dimethylamino)Hexanoic Acid Hydrochloride

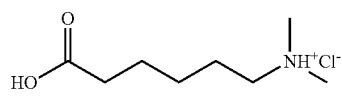

To a solution of Ethyl 6-(dimethylamino)hexanoate (5.85 g, 31.2 mmol) in dioxane (200 mL) was added 1M NaOH (200 mL). The solution was stirred vigorously at room temperature for 2 hours and then dioxane was removed in vacuo. The resulting aqueous solution was made slightly acidic using concentrated HCl (15 mL). At this point, dichloromethane and ether were used in an attempt to extract the product from solution. However, all attempts failed. Instead, water was removed under high vacuum to afford the product as an off-white solid, a mixture of approximately 35% 6-(dimethylamino)hexanoic acid hydrochloride in NaCl by weight.

Synthesis of Phytanyl-MC5

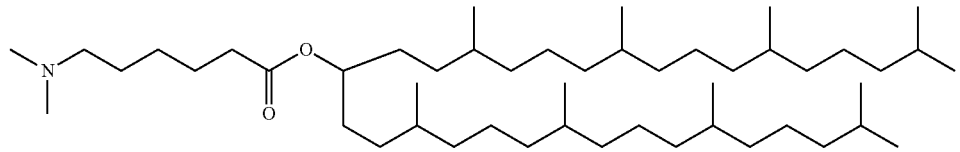 [SMILES: CC(C)CCCC(C)CCCC(C)CCCC(C)CCC(CCC(C)CCCC(C)CCCC(C)CCCC(C)C)OC(=O)CCCCCN(C)C]

To a solution of diphytanyl methanol (1.5 g, 2.4 mmol) and 35% 6-(dimethylamino) hexanoic acid hydrochloride (1.79 g, 3.2 mmol) in anhydrous dichloromethane (15 mL) under nitrogen at room temperature was added EDC (0.65 g, 3.4 mmol), diisopropylethylamine (1.26 mL, 7.2 mmol) and 4-dimethylaminopyridine (10 mg). After 48 hours additional 35% 6-(dimethylamino)hexanoic acid (1 g, 1.8 mmol), EDC (0.32 g, 1.7 mmol) and 4-dimethylaminopyridine (15 mg) were added. After an additional 72 hours the reaction mixture was diluted to 75 mL using dichloromethane and then washed with water, saturated NaHCO$_3$, and brine. The combined aqueous layers were backextracted twice with dichloromethane and the combined organic layers dried over MgSO$_4$, filtered, and concentrated. The resulting yellow oil was purified by column chromatography (column 1¼"W× 10"L; eluted with a gradient of 100% hexanes→10%→50% ethyl acetate in hexanes) to afford the product as a yellow oil (175 mg, 10%) with some recovery of diphytanyl methanol.

Example 13

Synthesis of MC3 Thioester

MC3 Thioester (Compound 20) having the structure shown below was synthesized as described in Scheme 15 below.

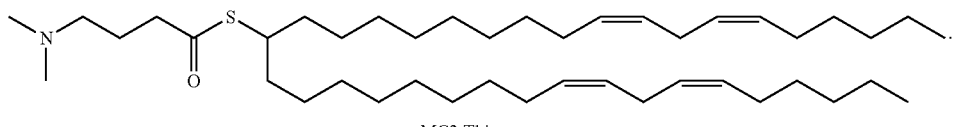

MC3 Thioester

Scheme 15

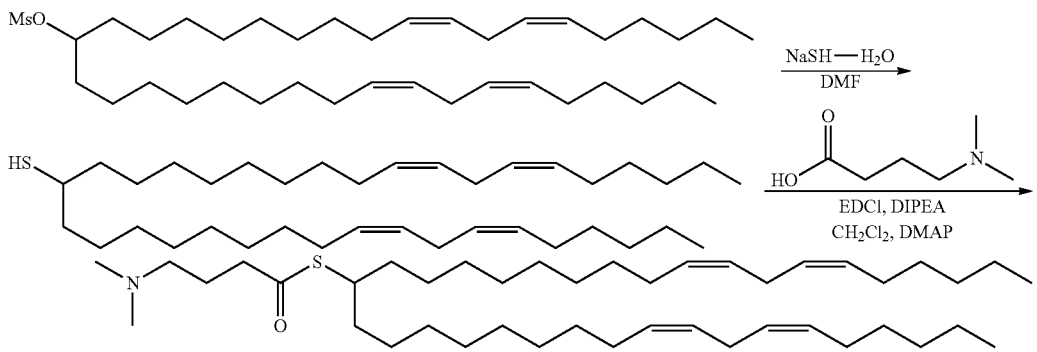

Synthesis of (6Z,9Z,28Z,31Z)-heptatriaconta-6,9,28, 31-tetraene-19-thiol

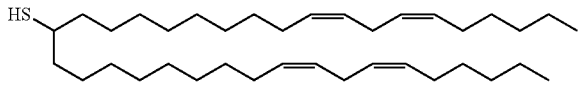 [SMILES: CCCCC/C=C\C/C=C\CCCCCCCCC(S)CCCCCCCC/C=C\C/C=C\CCCCC]

A solution of (6Z,9Z,28Z,31Z)-heptatriaconta-6,9,28,31-tetraen-19-yl methanesulfonate (2.0 g, 3.3 mmol) in anhydrous DMF (15 mL) was treated with NaSH.H$_2$O (925 mg, 16.5 mmol) and heated (70° C., 2 h). The mixture was cooled (rt), diluted with H$_2$O and extracted with Et$_2$O (3×). The organic extract was washed with brine, then dried (Na$_2$SO$_4$), filtered and concentrated. The crude material was subjected to chromatography (hexanes→2% EtOAc-hexanes) to yield (6Z,9Z,28Z,31Z)-heptatriaconta-6,9,28,31-tetraene-19-thiol (1.31 g, 73%) as a pale yellow oil. Rf 0.9 (10% EtOAc-hexanes), FW 544.50, C$_{37}$H$_{68}$S.

Synthesis of S-(6Z,9Z,28Z,31Z)-heptatriaconta-6,9, 28,31-tetraene-19-yl 4 (dimethylamino) butanethioate (MC3 Thioester)

A solution of (6Z,9Z,28Z,31Z)-heptatriaconta-6,9,28,31-tetraene-19-thiol (500 mg, 0.92 mmol) and N,N-dimethylamino-butyric acid hydrochloride (200 mg, 1.2 mmol) in anhydrous CH$_2$Cl$_2$ (3 mL) was treated with EDC (229 mg, 1.2 mmol), Hünig's base (481 µL, 2.8 mmol) and DMAP (18 mg). After stirring (2 h) the solution was diluted with CH$_2$Cl$_2$, washed with NaHCO$_3$ (sat. aq.) and brine then dried (Na$_2$SO$_4$), filtered and concentrated. The crude material was subjected to chromatography (CH$_2$Cl$_2$→3% CH$_3$OH—CH$_2$Cl$_2$) to yield S-(6Z,9Z,28Z,31Z)-heptatriaconta-6,9,28,31-tetraen-19-yl 4 (dimethylamino) butanethioate (197 mg, 33%) as a colorless oil. Rf 0.4 (8% CH$_3$OH—CHCl$_3$), $^1$H NMR (400 MHz, CDCl$_3$, δ$_H$) 5.41-5.28 (m, 8H, HC═CH×8), 3.53-3.45 (m, 1H, CHSCO), 2.77 (app. t, 4H, C═CHCH$_2$HC═C×2), 2.56 (t, 2H, CH$_2$COS), 2.27 (t, 2H, CH$_2$N(CH$_3$)$_2$), 2.21 (s, 6H, N(CH$_3$)$_2$), 2.10-1.97 (m, 8H, CH$_2$C═C×4), 1.85-1.76 (m, 2H, CH$_2$), 1.63-1.43 (m, 4H, CH$_2$×2), 1.42-1.20 (m, 36H, CH$_2$×18), 0.89 (t, 6H, CH$_3$×2). FW 659.14, C$_{43}$H$_{79}$NOS.

Example 14

Synthesis of Compounds 21-24

(6Z,9Z,27Z,30Z)-19-oxohexatriaconta-6,9,27,30-tetraen-18-yl 3-(dimethylamino)propanoate (Compound 21), (6Z, 9Z,27Z,30Z)-19-hydroxyhexatriaconta-6,9,27,30-tetraen-18-yl 3-(dimethylamino)propanoate (Compound 22), (6Z, 9Z,27Z,30Z)-19-oxohexatriaconta-6,9,27,30-tetraen-18-yl 4-(dimethylamino)butanoate (Compound 23), and (6Z,9Z, 27Z,30Z)-19-hydroxyhexatriaconta-6,9,27,30-tetraen-18-yl 4-(dimethylamino)butanoate (Compound 24) having the structures shown below were synthesized as described in Scheme 16 below.

Compound 21

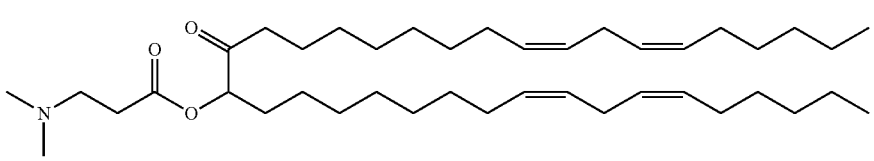

-continued
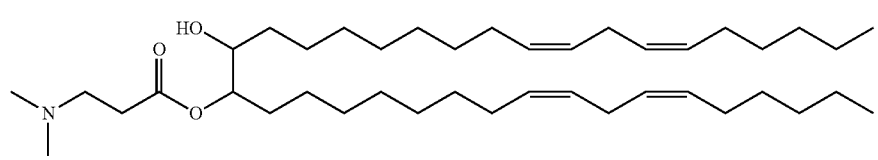
Compound 22
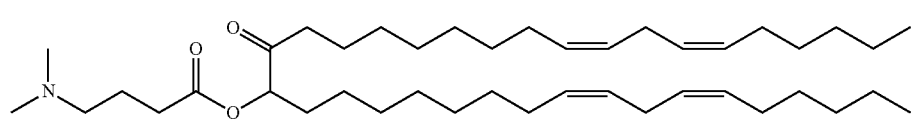
Compound 23
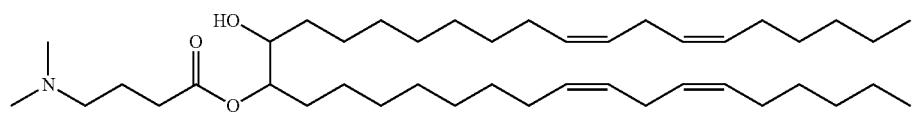
Compound 24

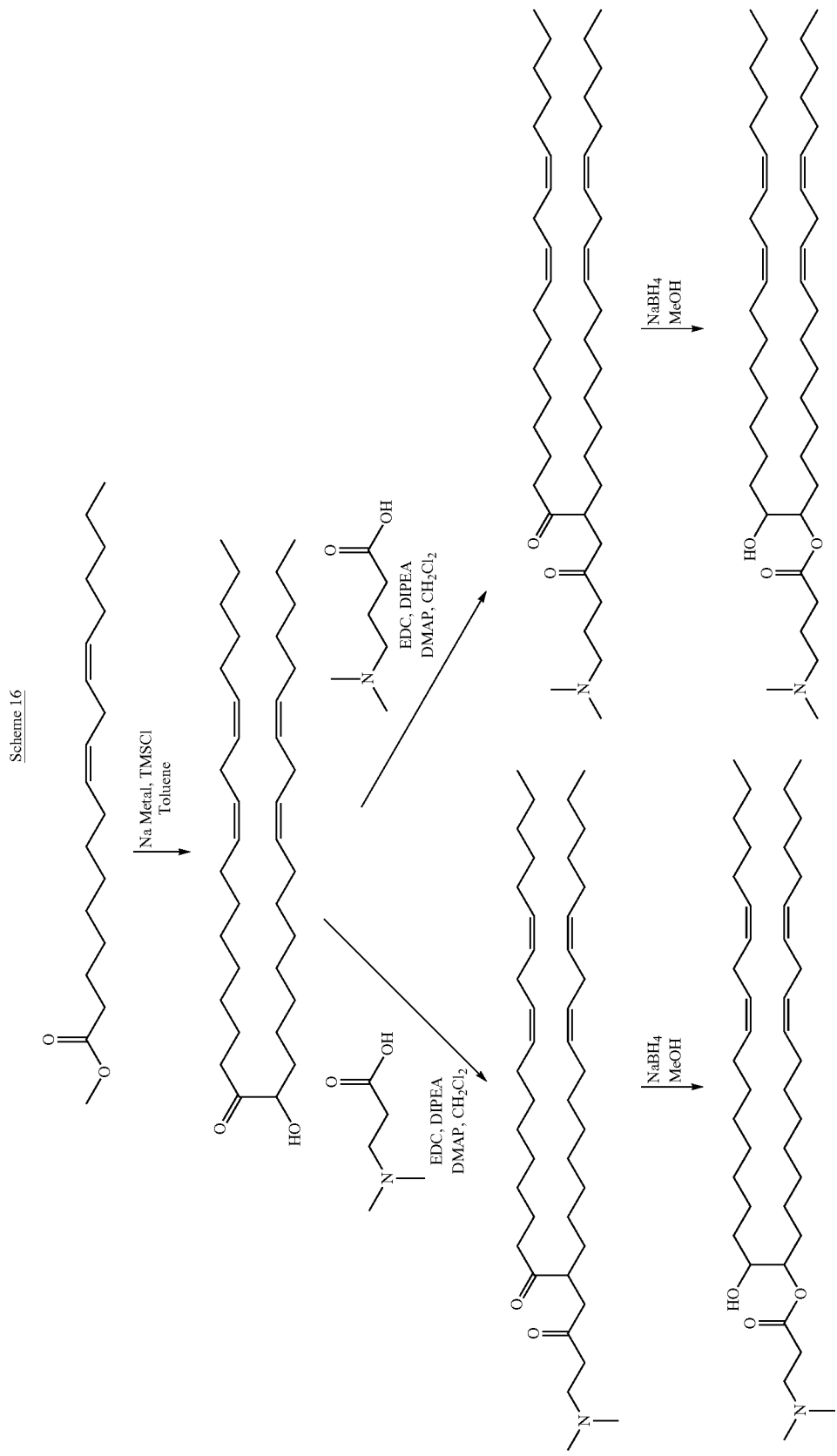

Synthesis of (6Z,9Z,27Z,30Z)-19-hydroxyhexatriaconta-6,9,27,30-tetraen-18-one

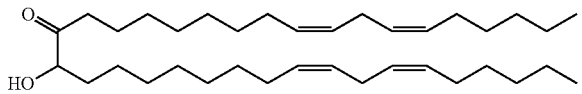 [SMILES: CCCCC/C=C\C/C=C\CCCCCCCC(=O)C(O)CCCCCCC/C=C\C/C=C\CCCCC]

To a 500 mL round bottom flask, purged with nitrogen, was added anhydrous toluene (70 mL) followed by finely sliced pieces of sodium metal (425 g, 185 mmol). chlorotrimethylsilane (17 mL, 136.1 mmol) was added slowly and the reaction was heated to 40° C. To this solution was added methyl linoleate (10 g, 32.4 mmol) drop wise over 45 minutes. The solution was brought to reflux for 2 hours where upon the sodium changed from a large mass to small 1-2 mm beads (reaction turned purple after ~1.5 hours). The reaction was cooled to room temperature and slowly quenched with methanol (25 mL) at 0° C. over 30 minutes. Once the unreacted sodium metal had dissolved, the reaction mixture was filtered through celite with ether rinses (400 mL). The filtrate (~400-500 mL) was stirred vigorously with saturated ammonium chloride (300 mL) for 16 hours. Upon completion, the ether/toluene layer was separated and washed with brine (1×100 mL). The organic layer was dried on magnesium sulfate, filtered and concentrated in vacuo to dryness. The yellow oil was purified by column chromatography (gradient: 100% Hexanes to 5% EtOAc in hexanes) to afford the title compound as a pale yellow oil (4.8 g, 56%).

Synthesis of (6Z,9Z,27Z,30Z)-19-oxohexatriaconta-6,9,27,30-tetraen-18-yl 3-(dimethylamino)propanoate (Compound 21)

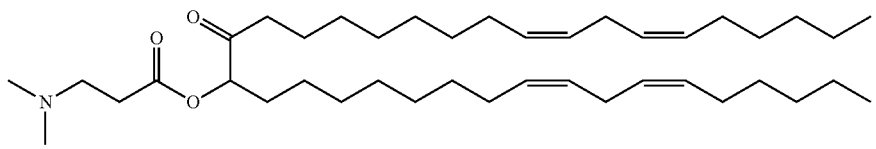 [SMILES: CCCCC/C=C\C/C=C\CCCCCCCC(=O)C(CCCCCCC/C=C\C/C=C\CCCCC)OC(=O)CCN(C)C]

To a solution of (6Z,9Z,27Z,30Z)-19-hydroxyhexatriaconta-6,9,27,30-tetraen-18-one (1.0 g, 1.9 mmol), 3-(dimethylamino)propanoic acid hydrogen chloride (876 mg, 5.7 mmol) and EDCI (1.2 g, 6.3 mmol), in dichloromethane (20 mL) was added DIPEA (1.0 mL, 5.7 mmol) and DMAP (20 mg). The solution was stirred at room temperature for 16 hours under nitrogen. Upon completion, the reaction was diluted with dichloromethane (50 mL) and washed with sodium bicarbonate solution (50 mL). The dichloromethane layer was dried on magnesium sulfate, filtered and concentrated in vacuo to dryness. The residue was purified by column chromatography (100% ethyl acetate) to afford the title compound as a colorless oil (675 mg, 57%). $^1$H NMR (400 MHz, CDCl$_3$): δ 5.43-5.28 (m, 8H), 5.03-4.98 (m, 1H), 2.80-2.75 (m, 4H), 2.74-2.56 (m, 4H), 2.54-2.36 (m, 2H), 2.28 (s, 6H), 2.09-2.01 (m, 8H), 1.82-1.64 (m, 2H), 1.63-1.52 (m, 2H), 1.42-1.23 (m, 30H), 0.93-0.86 (m, 6H).

Synthesis of (6Z,9Z,27Z,30Z)-19-hydroxyhexatriaconta-6,9,27,30-tetraen-18-yl 3-(dimethylamino)propanoate (Compound 22)

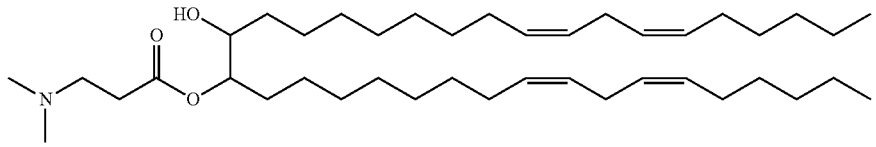 [SMILES: CCCCC/C=C\C/C=C\CCCCCCCC(O)C(CCCCCCC/C=C\C/C=C\CCCCC)OC(=O)CCN(C)C]

To a solution of (6Z,9Z,27Z,30Z)-19-oxohexatriaconta-6,9,27,30-tetraen-18-yl 3-(dimethylamino)propanoate (450 mg, 0.72 mmol) in anhydrous methanol (20 mL) was slowly added sodium borohydride (222 mg, 5.9 mmol). The solution was stirred for 16 hours at room temperature then quenched with water (20 mL). The solution was washed with dichloromethane (3×50 mL) and the combined extracts were dried on magnesium sulfate, filtered and concentrated in vacuo to dryness. The residue was purified by column chromatography (100% ethyl acetate) to afford the title compound as a colorless oil (416 mg, 91%). $^1$H NMR (400 MHz, CDCl$_3$): δ 5.45-5.28 (m, 8H), 5.02-4.82 (m, 1H), 3.69-3.43 (m, 1H), 2.84-2.45 (m, 8H), 2.30 (s, 6H), 2.09-2.02 (m, 8H), 1.67-1.20 (m, 36H), 0.93-0.86 (m, 6H).

Synthesis of (6Z,9Z,27Z,30Z)-19-oxohexatriaconta-6,9,27,30-tetraen-18-yl 4-(dimethylamino)butanoate (Compound 23)

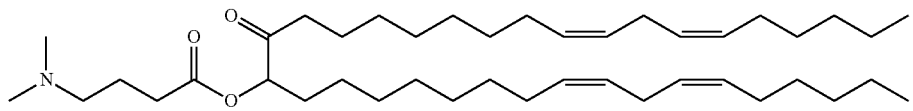 [SMILES: CCCCC/C=C\C/C=C\CCCCCCCC(=O)C(CCCCCCC/C=C\C/C=C\CCCCC)OC(=O)CCCN(C)C]

Using an analogous procedure to that described for the synthesis of (6Z,9Z,27Z,30Z)-19-oxohexatriaconta-6,9,27,30-tetraen-18-yl 3-(dimethylamino)propanoate, (6Z,9Z,27Z,30Z)-19-oxohexatriaconta-6,9,27,30-tetraen-18-yl 4-(dimethylamino)butanoate was obtained as a colorless oil (980 mg, 80%). $^1$H NMR (400 MHz, CDCl$_3$): δ 5.43-5.29 (m, 8H), 5.02-4.97 (m, 1H), 2.81-2.75 (m, 4H), 2.54-2.33 (m, 6H), 2.39 (s, 6H), 2.09-2.01 (m, 8H), 1.92-1.82 (m, 2H), 1.80-1.64 (m, 2H), 1.62-1.53 (m, 2H), 1.42-1.24 (m, 30H), 0.93-0.86 (m, 6H).

Synthesis of (6Z,9Z,27Z,30Z)-19-hydroxyhexatriaconta-6,9,27,30-tetraen-18-yl 4-(dimethylamino)butanoate (Compound 24)

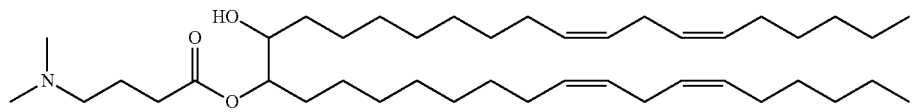 [SMILES: CCCCC/C=C\C/C=C\CCCCCCCC(O)C(CCCCCCC/C=C\C/C=C\CCCCC)OC(=O)CCCN(C)C]

Using an analogous procedure to that described for the synthesis of (6Z,9Z,27Z,30Z)-19-hydroxyhexatriaconta-6,9,27,30-tetraen-18-yl 3-(dimethylamino)propanoate, 6Z,9Z,27Z,30Z)-19-hydroxyhexatriaconta-6,9,27,30-tetraen-18-yl 4-(dimethylamino)butanoate was obtained as a colorless oil (218 mg, 31%). $^1$H NMR (400 MHz, CDCl$_3$): δ 5.44-5.29 (m, 8H), 4.92-4.81 (m, 1H), 3.71-3.54 (m, 1H), 2.81-2.75 (m, 4H), 2.46-2.34 (m, 1H), 2.28 (s, 3H), 2.27 (s, 3H), 2.09-2.02 (m, 8H), 1.94-1.78 (m, 2H), 1.69-1.20 (m, 36H), 0.93-0.86 (m, 6H).

Example 15

Synthesis of Compound 25

(6Z,9Z,28E,31E)-heptatriaconta-6,9,28,31-tetraen-19-yl 4-(dimethylamino)butanoate (Compound 25) having the structure shown below was synthesized as described in Scheme 17 below.

Compound 25

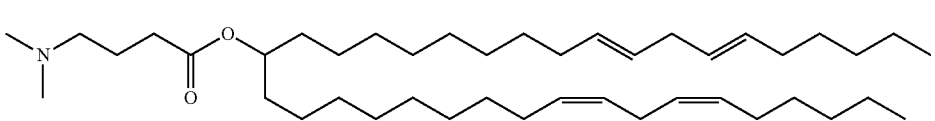

Scheme 17

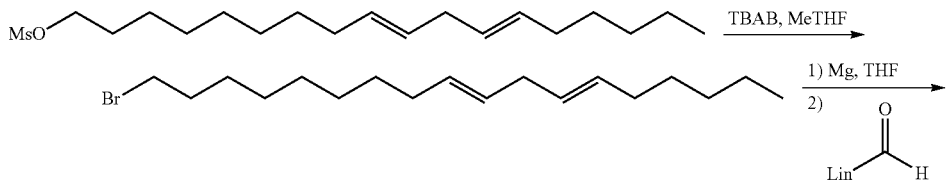

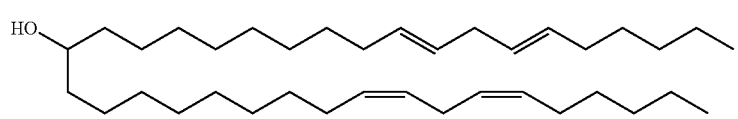

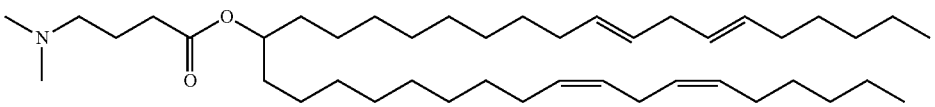

Synthesis of (6E,9E)-18-bromooctadeca-6,9-diene

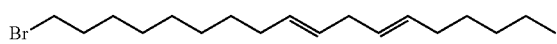 [SMILES: CCCCC/C=C/C/C=C/CCCCCCCCBr]

Using an analogous procedure to that described for the synthesis of linoleyl bromide, (6E,9E)-18-bromooctadeca-6,9-diene was obtained as a colorless oil (9.1 g, 87%).

Synthesis of (10Z,13Z)-nonadeca-10,13-dienal

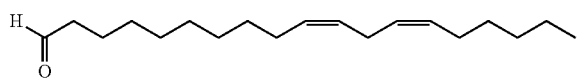 [SMILES: CCCCC/C=C\C/C=C\CCCCCCCCC=O]

A 100 mL round bottom flask charged with magnesium turnings (462 mg, 19.0 mmol) and a stir bar was dried with a high temperature heat gun for 5 minutes. The flask was cooled to room temperature under nitrogen then charged with THF (25 mL). Linoleyl bromide (1.9 g, 5.76 mmol) was added drop wise and the solution was heated to 45° C. for 3 hours under nitrogen. Upon completion, DMF (1.3 mL, 16.7 mmol) was added slowly and the solution was stirred for 1 hour at room temperature. The solution was diluted with ether (75 mL) and washed with 5% HCl (3×50 mL). The ether solution was dried on magnesium sulfate, filtered and concentrated in vacuo to dryness. The residue was purified by column chromatography (column: 2"×10"; eluted with 2% ether/hexanes) to afford the title compound as a colorless oil (3.5 g, 83%).

Synthesis of (6Z,9Z,28E,31E)-heptatriaconta-6,9,28,31-tetraen-19-ol

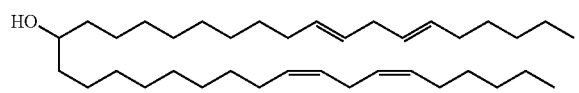 [SMILES: CCCCC/C=C\C/C=C\CCCCCCCCC(O)CCCCCCCC/C=C/C/C=C/CCCCC]

A 100 mL round bottom flask, charged with magnesium turnings (355 mg, 14.6 mmol) and a stir bar, was dried with a high temperature heat gun for 5 minutes. Upon cooling under nitrogen, THF (6 mL) was added followed by linolaidyl bromide (6.02 g, 18.3 mmol). The mixture was heated to 45° C. and a single grain of iodine was added. The reaction was refluxed for 2.5 hours then cooled to room temperature whereupon a solution of (10Z,13Z)-nonadeca-10,13-dienal (3.4 g, 12.4 mmol) in THF (10 mL) was added. The solution was stirred for 1.5 hours at room temperature then poured into water (150 mL) and 5% HCl (50 mL) was added. Upon dissolution of the magnesium, the solution was extracted with ether (2×150 mL). The combined ether extracts were dried on magnesium sulfate, filtered and concentrated in vacuo to dryness. The residue was purified by column chromatography (100% hexanes) to afford the title compound as a colorless oil (4.57 g, 71%).

Synthesis of (6Z,9Z,28E,31E)-heptatriaconta-6,9,28,31-tetraen-19-yl 4-(dimethylamino)butanoate (Compound 25)

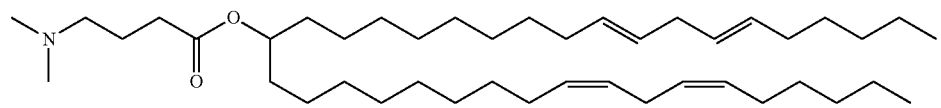 [SMILES: CCCCC/C=C\C/C=C\CCCCCCCCC(CCCCCCCC/C=C/C/C=C/CCCCC)OC(=O)CCCN(C)C]

Using an analogous procedure to that described for the synthesis of (6Z,9Z,28Z,31Z)-heptatriaconta-6,9,28,31-tetraen-19-yl-4-(dimethylamino)butanoate, (6Z,9Z,28E,31E)-heptatriaconta-6,9,28,31-tetraen-19-yl 4-(dimethylamino)butanoate was obtained as a pale yellow oil (1.12 g, 93%). $^1$H NMR (400 MHz, CDCl$_3$): δ 5.47-5.29 (m, 8H), 4.91-4.83 (m, 1H), 2.81-2.75 (m, 2H), 2.70-2.65 (m, 2H), 2.58-2.30 (m, 10H), 2.10-1.85 (m, 10H), 1.57-1.45 (m, 4H), 1.41-1.20 (m, 36H), 0.93-0.86 (m, 6H).

Example 16

Synthesis of Compound 26

(6R,8Z,27Z,30Z)-6-hydroxyhexatriaconta-8,27,30-trien-18-yl-4-(dimethylamino)butanoate (Compound 26) having the structure shown below was synthesized as described in Scheme 18 below.

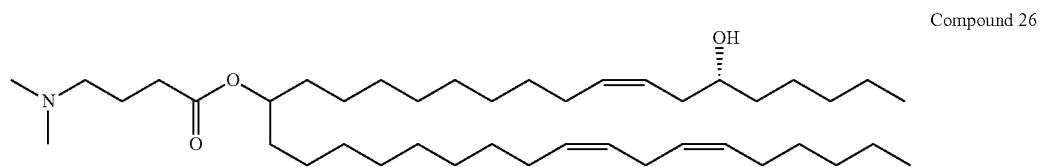 [SMILES: CCCCC/C=C\C/C=C\CCCCCCCCC(CCCCCCCC/C=C\C[C@H](O)CCCCC)OC(=O)CCCN(C)C]
Compound 26
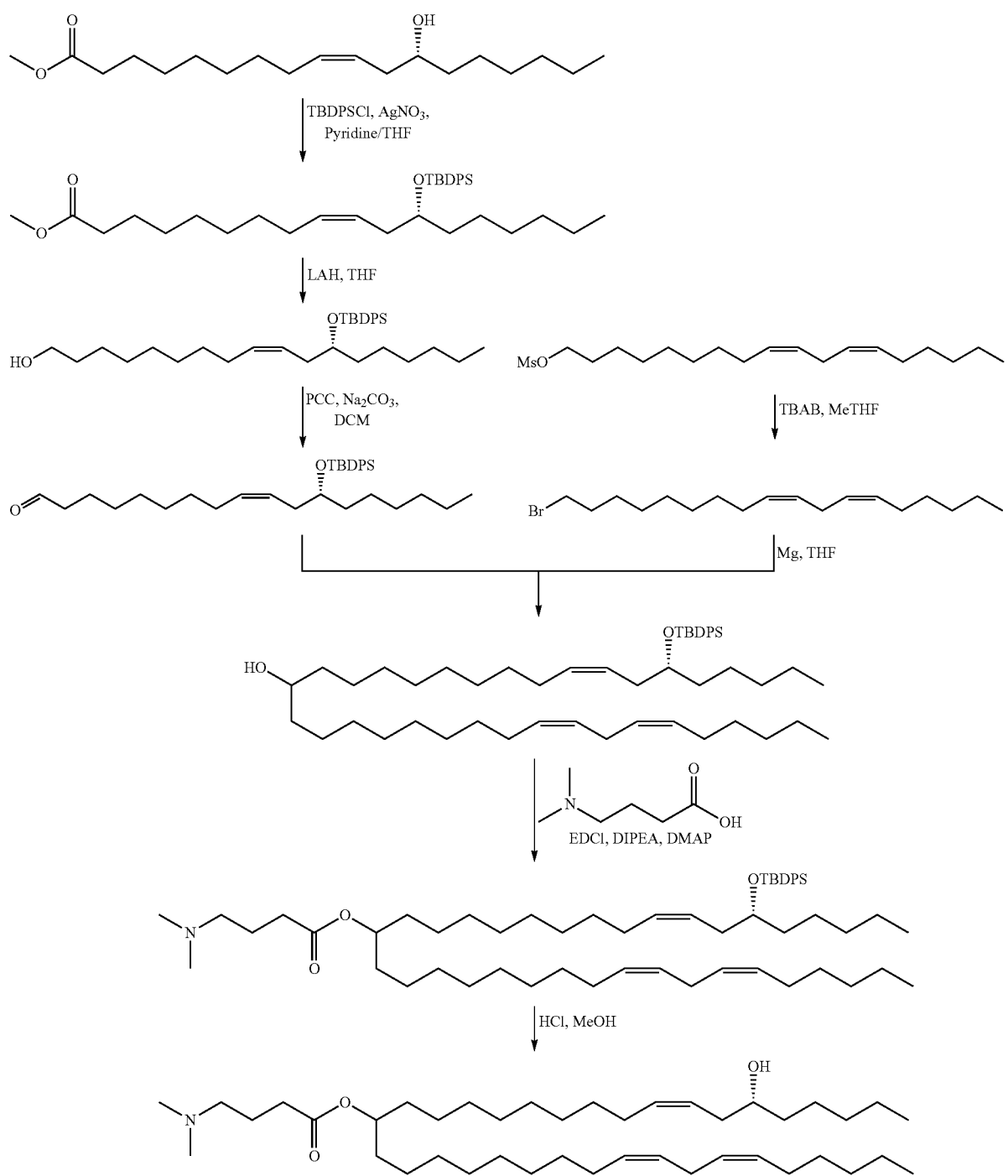
Scheme 18

Synthesis of (R,Z)-Methyl 12-(tert-butyldiphenylsilyloxy)octadec-9-enoate

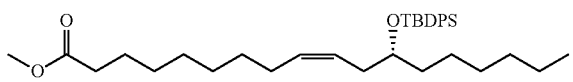

To a solution of methyl ricinoleate (8.0 g, 32 mmol) in anhydrous pyridine (90 mL) and anhydrous THF (45 mL) was added t-butylchlorodimethyl silane (8.5 mL, 33.3 mmol) and silver nitrate (5.65 g, 33.3 mmol). The solution was stirred at room temperature for 90 minutes under nitrogen. The solution was filtered through celite and the filter cake was rinsed with THF (400 mL). The filtrate was concentrated in vacuo and the residue was dissolved in dichloromethane (300 mL) and washed with 5% HCl (150 mL). The aqueous layer was separated and washed with dichloromethane (2×200 mL). The combined dichloromethane extracts were washed with brine (350 mL), dried on magnesium sulphate, filtered and concentrated in vacuo to dryness. The residue was purified by column chromatography (gradient: 100% hexanes to 10% ethyl acetate in hexanes) to afford the title compound as a colourless oil (13.1 g, 93%).

Synthesis of (R,Z)-12-(tert-buldiphenylsilyloxy)octadec-9-en-1-ol

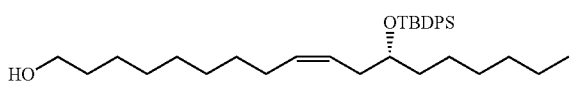

To a suspension of lithium aluminium hydride (1.8 g, 47.5 mmol) in anhydrous THF (30 mL) was added drop wise a solution of (R,Z)-methyl 12-(tert-butyldiphenylsilyloxy)octadec-9-enoate (13.1 g, 23.7 mmol) in THF (30 mL) over 30 minutes. The reaction was stirred for 1 hour at room temperature under nitrogen. Upon completion, 5M NaOH (4 mL) was added drop wise at 0° C. The mixture was dried on magnesium sulfate, filtered and concentrated in vacuo to dryness to afford the title compound as a light yellow oil. The product was used in the next step without further purification (11.1 g, 89%).

Synthesis of (R,Z)-12-(tert-butyldiphenylsilyloxy)octadec-9-enal

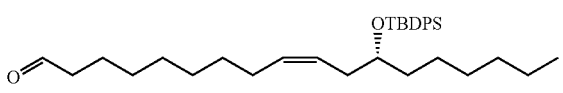

To a solution of (R,Z)-12-(tert-butyldiphenylsilyloxy)octadec-9-en-1-ol (11.1 g, 21.2 mmol) in anhydrous dichloromethane (160 mL) was added pyridinium chlorochromate (215.6 g, 110.3 mmol) and sodium carbonate (1.1 g, 18.4 mmol). The mixture was stirred at room temperature for 3 hours then filtered through a pad of silica (eluted with 100% ethyl acetate). The filtrate was concentrated in vacuo to dryness and the residue was purified by column chromatography (gradient: 100% hexanes to 10% ethyl acetate in hexanes) to afford the title compound as a yellow oil (8.9 g, 81%).

Synthesis of (6R,8Z,27Z,30Z)-6-(tert-butyldiphenylsilyloxy)hexatriaconta-8,27,30-trien-18-ol

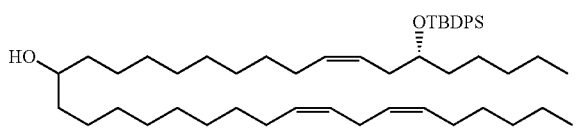

A 100 mL round bottom flask charged with magnesium turnings (0.16 g, 6.53 mmol) and a stir bar was dried with a high temperature heat gun for 5 minutes. The flask was cooled to room temperature under nitrogen then charged with THF (1.1 mL). A solution of linoleyl bromide (1.9 g, 5.76 mmol) in THF (1.9 mL) was added drop wise and the solution was heated to 55° C. for 2 hours under nitrogen. Upon completion, the reaction mixture was cooled to room temperature and a solution of (R,Z)-12-(tert-butyldiphenylsilyloxy)octadec-9-enal (2.0 g, 3.84 mmol) in THF (20 mL) was added slowly over 10 minutes. The solution was stirred for 1 hour at room temperature and then quenched with 5M HCl (20 mL) and water (100 mL). The remaining solution was extracted with diethyl ether (3×150 mL) and the combined diethyl ether extracts were dried on magnesium sulfate, filtered and concentrated in vacuo to dryness. The residue was purified by column chromatography (gradient: 100% Hexanes to 5% ethyl acetate hexanes) to afford the title compound as a yellow oil (1.8 g, 60%).

Synthesis of (6R,8Z,27Z,30Z)-6-(tert-butyldiphenylsilyloxy)hexatriaconta-8,27,30-trien-18-yl 4-(dimethylamino)butanoate

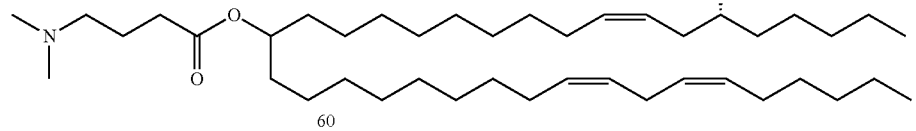

Using an analogous procedure to that described for the synthesis of (6Z,9Z,28Z,31Z)-heptatriaconta-6,9,28,31-tetraen-19-yl 4-(dimethylamino)butanoate, (6R,8Z,27Z,30Z)-6-(tert-butyldiphenylsilyloxy)hexatriaconta-8,27,30-trien-18-yl 4-(dimethylamino)butanoate was obtained as a colorless oil (800 mg, 78%).

Synthesis of (6R,8Z,27Z,30Z)-6-hydroxyhexatriaconta-8,27,30-trien-18-yl 4-(dimethylamino)butanoate (Compound 26)

A solution of (6R,8Z,27Z,30Z)-6-(tert-butyldiphenylsilyloxy)hexatriaconta-8,27,30-trien-18-yl 4-(dimethylamino)butanoate (800 mg, 0.95 mmol) in the saturated $HCl_{(g)}$/MeOH (50 mL) was stirred for 10 minutes. The starting material did not dissolve so anhydrous DCM (12 mL) was added, and the mixture was stirred for 30 minutes. Upon completion, the solution was concentrated in vacuo, saturated sodium bicarbonate (75 mL) was added, and the solution was extracted with ethyl acetate (3×100 mL). The combined ethyl acetate extracts were washed with brine (100 mL), dried on magnesium sulfate, filtered and concentrated in vacuo to dryness. The residue was purified by column chromatography (100% ethyl acetate) to afford the title compound as a colorless oil (0.228 g, 39%). $^1H$ NMR (400 MHz, $CDCl_3$): δ5.61-5.52 (m, 1H), 5.45-5.29 (m, 4H), 4.91-4.83 (m, 1H), 3.66-3.58 (m, 1H), 2.81-235 (m, 2H), 2.75-2.44 (m, 7H), 2.42-2.36 (m, 2H), 2.24-2.18 (m, 2H), 2.10-1.93 (m, 7H), 1.56-1.41 (m, 6H), 1.40-1.20 (m, 36H), 0.93-0.85 (m, 6H).

Example 17

Synthesis of Compounds 27 and 28

(6Z,9Z,28Z,31Z)-heptatriaconta-6,9,28,31-tetraen-18-yl 3-(dimethylamino)propyl(hexyl)carbamate (Compound 27) and (6Z,9Z,28Z,31Z)-heptatriaconta-6,9,28,31-tetraen-18-yl 3-(dimethylamino)propyl((Z)-hept-4-enyl)carbamate (Compound 28) having the structures shown below were synthesized as described in Scheme 19 below.

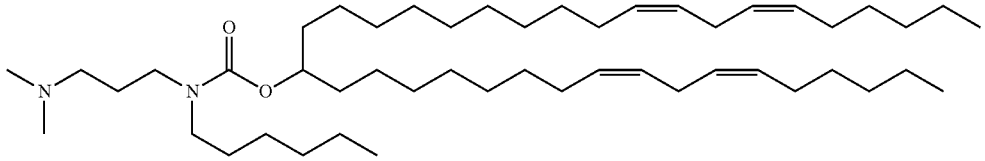 [SMILES: CCCCC/C=C\C/C=C\CCCCCCCCCC(CCCCCCC/C=C\C/C=C\CCCCC)OC(=O)N(CCCCCC)CCCN(C)C]

Compound 27

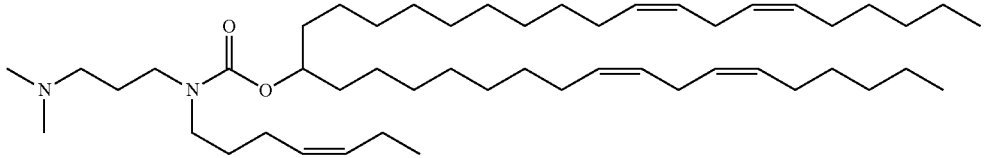 [SMILES: CC/C=C\CCCN(CCCN(C)C)C(=O)OC(CCCCCCC/C=C\C/C=C\CCCCC)CCCCCCCCC/C=C\C/C=C\CCCCC]

Compound 28

Scheme 19

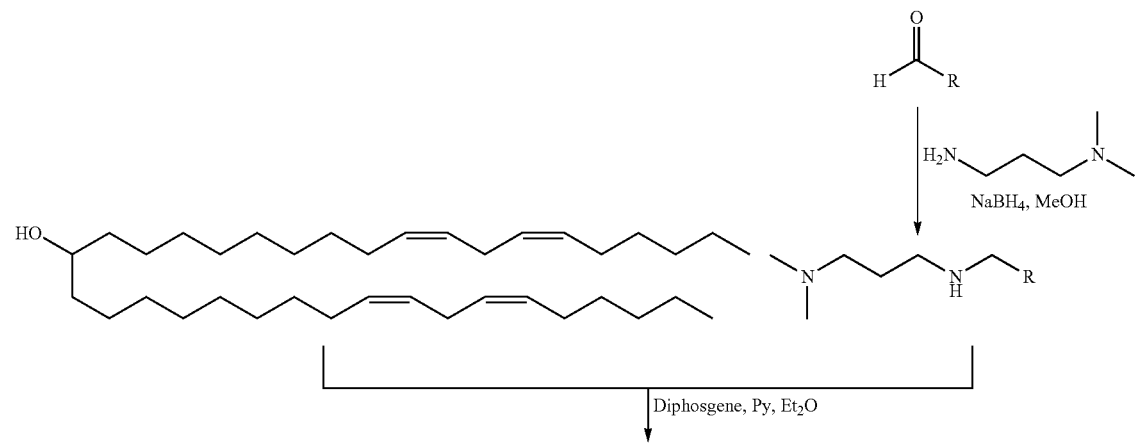

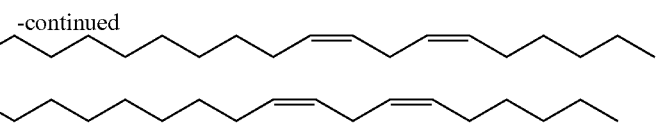

R = 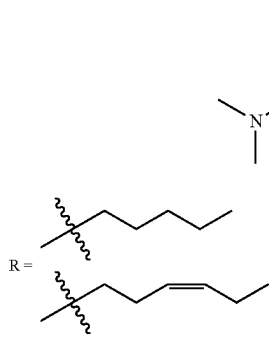

Synthesis of N-hexyl-N',N'-dimethylpropane-1,3-diamine

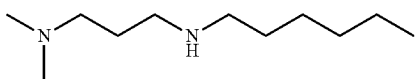

A solution of n-capronaldehyde (3.79 g, 37.8 mmol) and N,N-dimethylpropane-1,3-diamine (5 mL, 39.7 mmol) in anhydrous methanol (140 mL) was stirred at room temperature for 3 hours. To this solution was added slowly sodium borohydride (2.15 g, 56.8 mmol) over 5 minutes. The solution was stirred for 30 minutes then quenched with 1M NaOH (75 mL), diluted with water (125 mL) and extracted with ethyl acetate (3×150 mL). The combined ethyl acetate extracts were dried on magnesium sulfate, filtered and concentrated in vacuo to dryness. The residue was purified by column chromatography (gradient: 100% DCM to 10% MeOH in DCM with 1% NH$_4$OH) to afford the title compound as a pale yellow oil (3.79 g, 54%).

Synthesis of (6Z,9Z,28Z,31Z)-heptatriaconta-6,9,28,31-tetraen-18-yl 3-(dimethylamino)propyl(hexyl)carbamate (Compound 27)

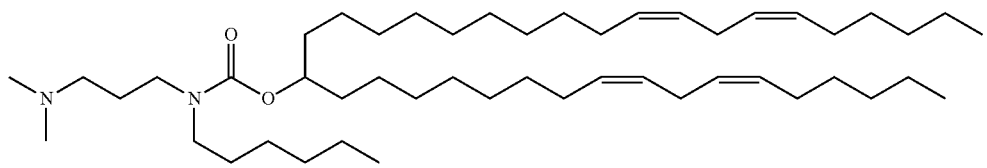

To a solution of dilinoleyl methanol (1.0 g, 1.9 mmol) and pyridine (230 μL, 4.7 mmol) in anhydrous ether (10 mL) cooled to −15° C. under nitrogen was slowly added diphosgene (380 μL, 3.1 mmol). The reaction was stirred for 20 minutes at −15° C., then N-hexyl-N',N'-dimethylpropane-1,3-diamine (3.8 g, 20.3 mmol) was added as a solution in 4:1 ether/dichloromethane (10 mL). The solution was warmed to room temperature and stirring was continued for 20 minutes. Upon completion, the solution was diluted with diethyl ether (100 mL) and washed with saturated sodium bicarbonate (2×50 mL). The ether extract was dried on magnesium sulphate, filtered, concentrated in vacuo to dryness. The residue was purified by column chromatography (100% ethyl acetate) to afford the title compound as a colorless oil (1.1 g, 76%). $^1$H NMR (400 MHz, CDCl$_3$): δ 5.43-5.26 (m, 8H), 4.80-4.68 (m, 1H), 3.35-3.15 (m, 4H), 2.81-2.75 (m, 4H), 2.66-2.25 (m, 8H), 2.10-1.70 (m, 14H), 1.64-1.46 (m, 6H), 1.40-1.20 (m, 38H), 1.00-0.93 (m, 3H), 0.92-0.86 (m, 6H).

Synthesis of (Z)—N-(hept-4-enyl)-N',N'-dimethylpropane-1,3-diamine

Using an analogous procedure to that described for the synthesis of N-hexyl-N',N'-dimethylpropane-1,3-diamine, (Z)—N-(hept-4-enyl)-N',N'-dimethylpropane-1,3-diamine was obtained as a pale yellow oil (5.11 g, 68%).

Synthesis of (6Z,9Z,28Z,31Z)-heptatriaconta-6,9,28,31-tetraen-18-yl 3-(dimethylamino)propyl((Z)-hept-4-enyl)carbamate (Compound 28)

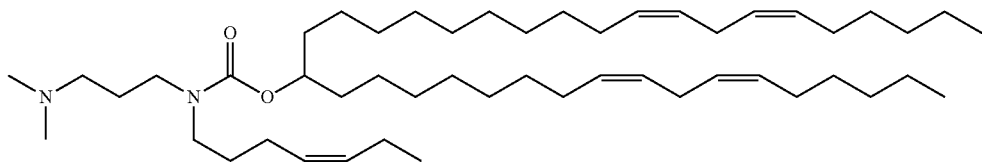

Using an analogous procedure to that described for the synthesis of (6Z,9Z,28Z,31Z)-heptatriaconta-6,9,28,31-tetraen-18-yl 3-(dimethylamino)propyl(hexyl)carbamate, (6Z,9Z,28Z,31Z)-heptatriaconta-6,9,28,31-tetraen-18-yl 3-(dimethylamino)propyl((Z)-hept-4-enyl)carbamate was obtained as a colorless oil (1.31 g, 92%). ¹H NMR (400 MHz, CDCl₃): δ 5.44-5.27 (m, 10H), 4.80-4.67 (m, 1H), 3.35-3.15 (m, 4H), 2.81-2.74 (m, 4H), 2.69-2.26 (m, 8H), 2.10-1.98 (m, 12H), 1.98-1.72 (m, 2H), 1.64-1.46 (m, 6H), 1.41-1.22 (m, 36H), 0.96 (t, J=7.5 Hz, 3H), 0.92-0.86 (m, 6H).

Example 18

Synthesis of Compound 29

(6Z,9Z,28Z,31Z)-heptatriaconta-6,9,28,31-tetraen-18-yl 2-(dimethylamino)ethyl(ethyl)carbamate (Compound 29) having the structure shown below was synthesized as described in Scheme 20 below.

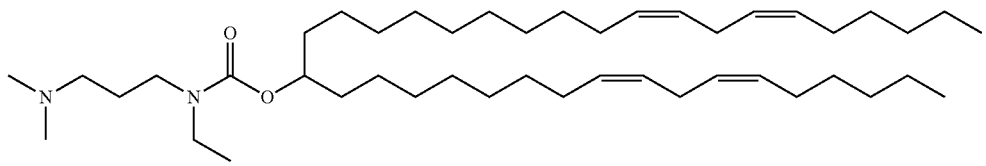 [SMILES: CCCCC/C=C\C/C=C\CCCCCCCCCC(CCCCCCC/C=C\C/C=C\CCCCC)OC(=O)N(CC)CCCN(C)C]

Scheme 20

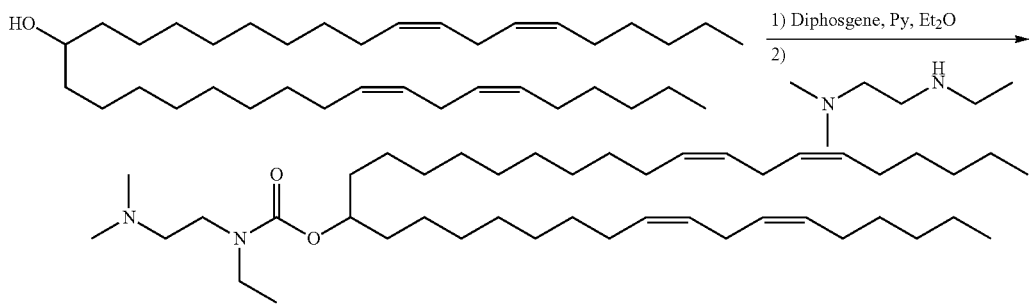

Synthesis of (6Z,9Z,28Z,31Z)-heptatriaconta-6,9,28,31-tetraen-18-yl 2-(dimethylamino)ethyl(ethyl)carbamate (Compound 29)

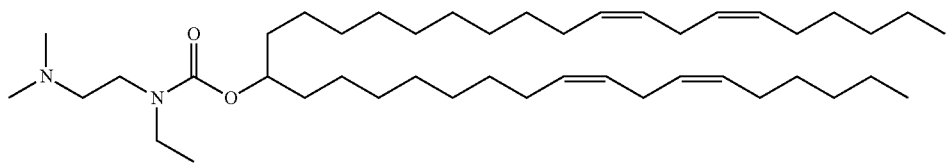 [SMILES: CCCCC/C=C\C/C=C\CCCCCCCCCC(CCCCCCC/C=C\C/C=C\CCCCC)OC(=O)N(CC)CCN(C)C]

To a solution of dilinoleyl methanol (1.0 g, 1.9 mmol) and pyridine (230 μL, 4.7 mmol) in anhydrous ether (10 mL) cooled to −15° C. under nitrogen was slowly added diphosgene (0.38 mL, 3.14 mmol). The reaction was stirred for 1 hour at −15° C., then N,N-dimethyl-N'-ethyl-ethylenediamine (2.2 mL, 14.2 mmol) was added. The solution was warmed to room temperature and stirred for 30 minutes. The solution was diluted with diethyl ether (50 mL) and filtered to remove the urea and ammonium salts. The ether filtrate was concentrated in vacuo to dryness and the residue was purified by column chromatography (100% ethyl acetate) to afford the title compound as a colorless oil (990 mg, 78%). ¹H NMR (400 MHz, CDCl₃): δ 5.41-5.27 (m, 8H), 4.77-4.69 (m, 1H), 3.55-3.20 (m, 4H), 2.79-2.72 (m, 4H), 2.72-2.56 (m, 1H), 2.55-2.21 (m, 7H), 2.08-1.96 (m, 8H), 1.58-1.44 (m, 4H), 1.39-1.15 (m, 36H), 1.10 (t, J=7.0 Hz, 3H), 0.90-0.82 (m, 6H).

Example 19

Synthesis of Compounds 30 and 31

(6Z,9Z,28Z,31Z)-heptatriaconta-6,9,28,31-tetraen-19-yl (3-(ethyl(methyl)amino)propyl)(methyl)carbamate (Compound 30) and (6Z,9Z,28Z,31Z)-heptatriaconta-6,9,28,31-tetraen-19-yl (3-(diethylamino)propyl)(methyl)carbamate (Compound 31) having the structures shown below were synthesized as described in Scheme 21 below.

A solution of trichloromethyl chloroformate (340 µL, 2.8 mmol) in anhydrous Et$_2$O (5 mL) was cooled (−15° C.) and treated with a solution of dilinoleyl methanol (1.0 g, 1.9 mmol) and pyridine (230 µL, 2.8 mmol) in Et$_2$O (5 mL). After stirring (1 h) the reaction mixture was filtered through a frit and the filtrate was added, dropwise, to a cool (0° C.) solution of 3-methylamino-propan-1-ol (1.1 mL, 11.3 mmol) in Et$_2$O (5 mL). After stirring (5 min) the reaction mixture was filtered and concentrated. The crude material was subjected to chromatography (12%→20% EtOAc-hexanes) to yield (6Z,9Z,

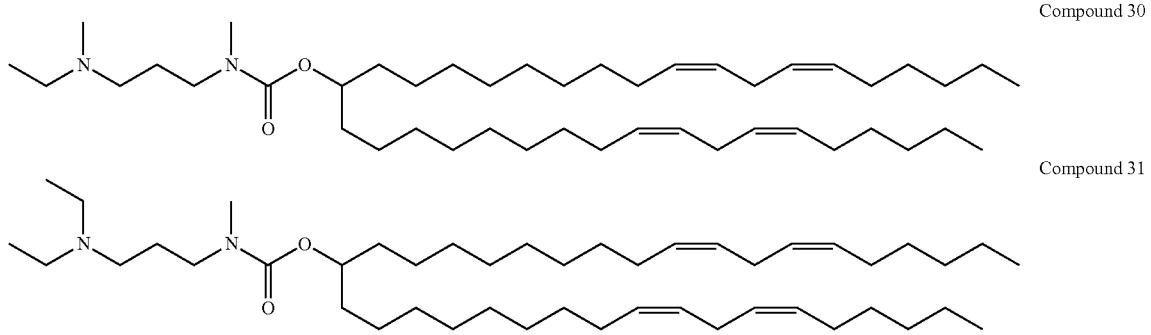

Compound 30

Compound 31

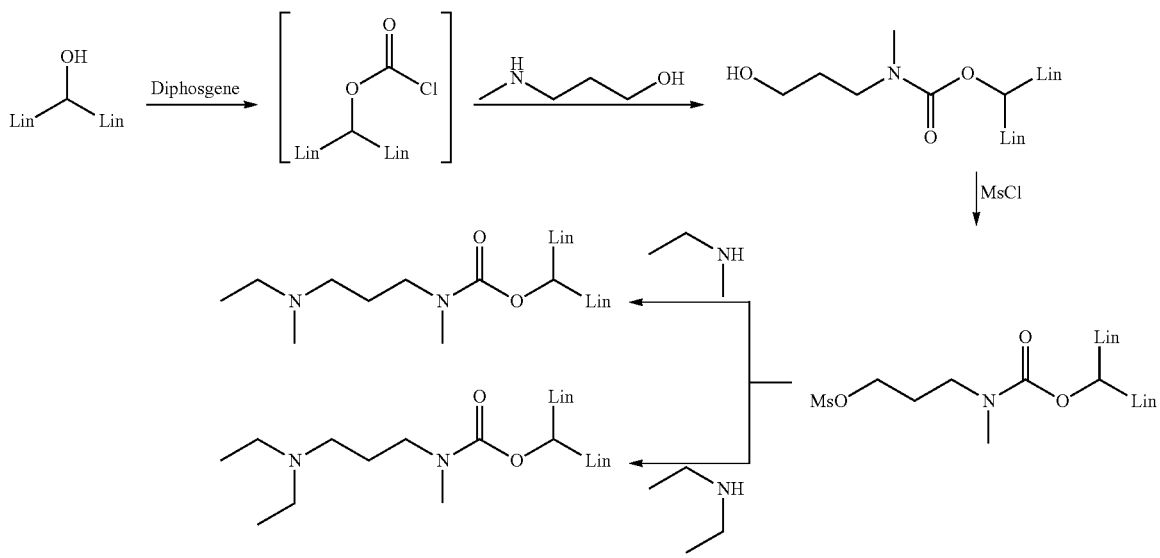

Scheme 21

Synthesis of (6Z,9Z,28Z,31Z)-heptatriaconta-6,9,28,31-tetraen-19-yl (3-hydroxypropyl)(methyl)carbamate 28Z,31Z)-heptatriaconta-6,9,28,31-tetraen-19-yl (3-hydroxypropyl)(methyl)carbamate (960 mg, 79%) as a colorless oil. Rf 0.17 (10% EtOAc-hexanes), FW 644.07, C$_{42}$H$_{77}$NO$_3$.

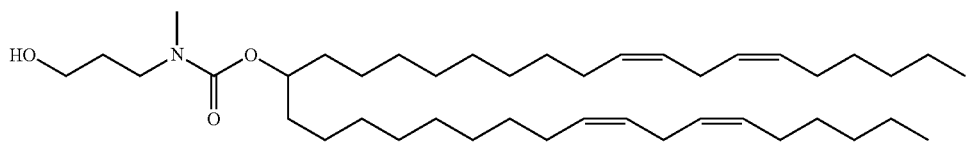 [SMILES: CCCCC/C=C\C/C=C\CCCCCCCCC(CCCCCCCC/C=C\C/C=C\CCCCC)OC(=O)N(C)CCCO]

Synthesis of 3-(((((6Z,9Z,28Z,31Z)-heptatriaconta-6,9,28,31-tetraen-19-yloxy)carbonyl)(methyl)amino)propyl methanesulfonate

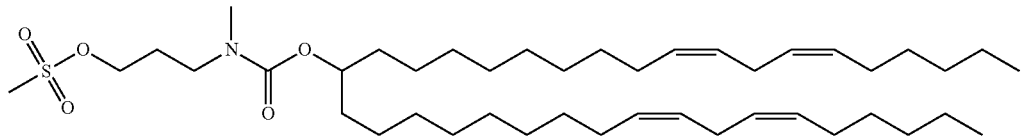 [SMILES: CCCCC/C=C\C/C=C\CCCCCCCCC(CCCCCCCC/C=C\C/C=C\CCCCC)OC(=O)N(C)CCCOS(C)(=O)=O]

A solution of the alcohol (6Z,9Z,28Z,31Z)-heptatriaconta-6,9,28,31-tetraen-19-yl (3-hydroxypropyl)(methyl)carbamate (960 mg, 1.5 mmol) and triethylamine (0.7 mL) in anhydrous $CH_2Cl_2$ (7 mL) was cooled (−15° C.) and treated with a solution of methanesulphonyl chloride (230 μL) in $CH_2Cl_2$ (5 mL) over 5 min. After stirring (45 min) the solution was diluted with $CH_2Cl_2$ and washed with $NaHCO_3$ (Sat. aq.) and brine, dried ($Na_2SO_4$), filtered and concentrated. The crude material was subjected to chromatography (20% EtOAc-hexanes) to yield 3-(((((6Z,9Z,28Z,31Z)-heptatriaconta-6,9,28,31-tetraen-19-yloxy)carbonyl)(methyl)amino)propyl methanesulfonate (1.0 g, 95%) as a colorless oil. Rf 0.5 ($CH_2Cl_2$), FW 722.16, $C_{43}H_{79}NO_5S$.

Synthesis of (6Z,9Z,28Z,31Z)-heptatriaconta-6,9,28,31-tetraen-19-yl (3-(ethyl(methyl)amino)propyl)(methyl)carbamate (Compound 30)

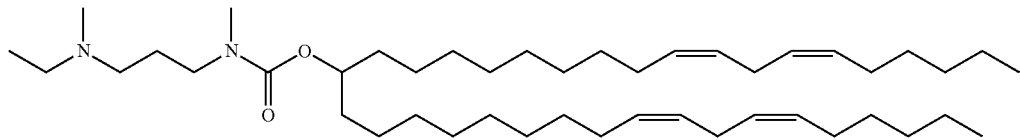 [SMILES: CCCCC/C=C\C/C=C\CCCCCCCCC(CCCCCCCC/C=C\C/C=C\CCCCC)OC(=O)N(C)CCCN(C)CC]

A solution of ethylmethylamine (2 mL) in EtOH (10 mL) was treated with 3-(((((6Z,9Z,28Z,31Z)-heptatriaconta-6,9,28,31-tetraen-19-yloxy)carbonyl)(methyl)amino)propyl methanesulfonate (500 mg, 0.7 mmol) in $CH_2Cl_2$ (2.5 mL). The solution was stirred (50 h), concentrated and subjected to chromatography (EtOAc) to yield (6Z,9Z,28Z,31Z)-heptatriaconta-6,9,28,31-tetraen-19-yl (3-(ethyl(methyl)amino)propyl)(methyl)carbamate (305 mg, 64%) as a pale yellow oil. Rf 0.41 (10% $CH_3OH$—$CH_2Cl_2$), $^1H$ NMR (400 MHz, $CDCl_3$, $\delta_H$) 5.47-5.34 (m, 8H, C=C$\underline{H}$×8), 4.81-4.75 (m, 1H, C$\underline{H}O_2CNR_2$), 3.33 (br. s, 2H, C$\underline{H}_2NCH_3$), 2.94 (br. s, 3H, $CO_2NC\underline{H}_3$), 2.83 (app. t, 4H), 2.45 (q, 2H, $N(CH_3)C\underline{H}_2CH_3$), 2.37 (t, 2H, C$\underline{H}_2N(CH_3)CH_2CH_3$), 2.25 (s, 3H, N(C$\underline{H}_3$)$CH_2CH_3$), 2.14-2.07 (m, 8H, C$\underline{H}_2$HC=C×4), 1.81-1.70 (m, 4H, C$\underline{H}_2$×2), 1.62-1.50 (m, 4H, C$\underline{H}_2$×2), 1.46-1.25 (m, 34H, C$\underline{H}_2$×17), 1.09 (t, 3H, $CH_3NCH_2C\underline{H}_3$), 0.93 (t, 6H, $\underline{H}_3$×2), FW 685.16, $C_{45}H_{84}N_2O_2$.

Synthesis of (6Z,9Z,28Z,31Z)-heptatriaconta-6,9,28,31-tetraen-19-yl (3-(diethylamino)propyl)(methyl)carbamate (Compound 31)

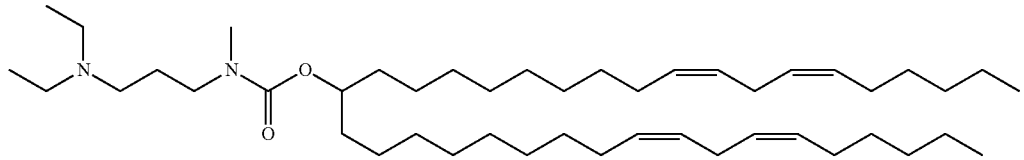 [SMILES: CCCCC/C=C\C/C=C\CCCCCCCCC(CCCCCCCC/C=C\C/C=C\CCCCC)OC(=O)N(C)CCCN(CC)CC]

A solution of diethylamine (2 mL) in EtOH (10 mL) was treated with 3-((((6Z,9Z,28Z,31Z)-heptatriaconta-6,9,28,31-tetraen-19-yloxy)carbonyl)(methyl)amino)propyl methanesulfonate (500 mg, 0.7 mmol) in CH$_2$Cl$_2$ (2.5 mL). The solution was stirred (50 h), concentrated and subjected to chromatography (EtOAc) to yield (6Z,9Z,28Z,31Z)-heptatriaconta-6,9,28,31-tetraen-19-yl (3-(diethylamino)propyl)(methyl)carbamate (207 mg, 42%) as a pale yellow oil. Rf 0.43 (10% CH$_3$OH—CH$_2$Cl$_2$), $^1$H NMR (400 MHz, CDCl$_3$, $\delta_H$) 5.41-5.28 (m, 8H, C=CHx8), 4.79-4.70 (m, 1H, CHO$_2$CNR$_2$), 3.28 (br. s, 2H, CH$_2$NCH$_3$), 2.94-2.83 (br. s, 3H, CO$_2$NCH$_3$), 2.79 (app. t, 4H, bis-allylic CH$_2$×2), 2.52 (q, 4H, N(CH$_2$CH$_3$)$_2$), 2.09-2.01 (m, 8H, CH$_2$HC=C×4), 1.75-1.65 (m 4H, CH$_2$×2), 1.59-1.45 (m, 4H, CH$_2$×2), 1.42-1.22 (m, 36H, CH$_2$×18), 1.15 (t, 6H, N(CH$_2$CH$_3$)$_2$), 0.90 (t, 6H, CH$_3$×2). FW 699.19, C$_{46}$H$_{86}$N$_2$O$_2$.

Example 20

Synthesis of Compound 32

(6Z,9Z,28Z,31Z)-heptatriaconta-6,9,28,31-tetraen-19-yl 2-(1H-imidazol-1-yl)acetate (Compound 32) having the structure shown below was synthesized as described in Scheme 22 below.

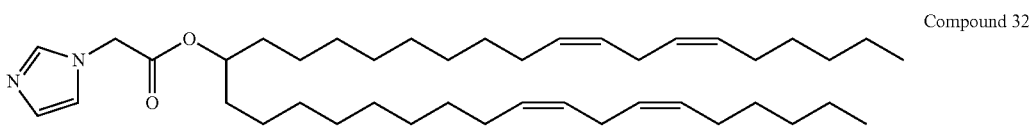 [SMILES: CCCCC/C=C\C/C=C\CCCCCCCCC(CCCCCCCC/C=C\C/C=C\CCCCC)OC(=O)Cn1ccnc1]

Compound 32

Scheme 22

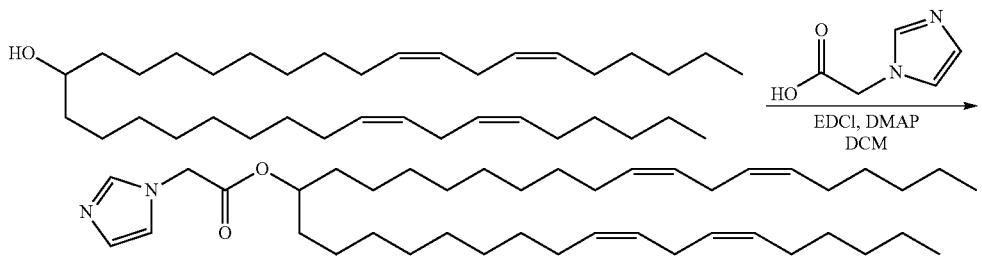

A solution of dilinoleyl methanol (1.5 g, 2.8 mmol), 2-(1H-imidazol-1-yl)acetic acid (1.07 g, 8.5 mmol), EDCI hydrochloride (1.8 g, 9.4 mmol) in anhydrous dichloromethane (25 mL) was added DMAP (10 mg). The solution was refluxed for 16 hours under nitrogen. Upon completion, the solution was diluted with dichloromethane (100 mL) and washed with saturated sodium bicarbonate (100 mL). The sodium bicarbonate solution was back extracted with dichloromethane (2×100 mL). The combined dichloromethane extracts were dried on magnesium sulfate, filtered and concentrated in vacuo to dryness. The residue was purified by column chromatography on silica gel 60 (column: 2"×6" L; eluted with 1:1 hexanes/ethyl acetate) to afford the title compound as a colorless oil (700 mg, 39%). $^1$H NMR (400 MHz, CDCl$_3$): δ 7.91 (s, 1H), 7.16 (s, 1H), 7.00 (s, 1H), 5.44-5.28 (m, 8H), 4.99-4.90 (m, 1H), 4.77 (s, 2H), 2.81-2.75 (m, 4H), 2.09-2.02 (m, 8H), 1.58-1.49 (m, 4H), 1.41-1.20 (m, 36H), −0.93-0.86 (m, 6H).

Example 21

Synthesis of Compound 33

1-(2-((6Z,9Z,28Z,31Z)-heptatriaconta-6,9,28,31-tetraen-19-yloxy)ethyl)-1H-imidazole (Compound 33) having the structure shown below was synthesized as described in Scheme 23 below.

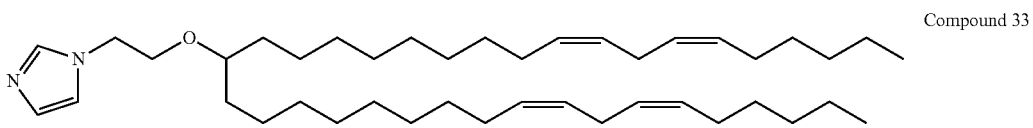 [SMILES: CCCCC/C=C\C/C=C\CCCCCCCCC(CCCCCCCC/C=C\C/C=C\CCCCC)OCCn1ccnc1]

Compound 33

Scheme 23

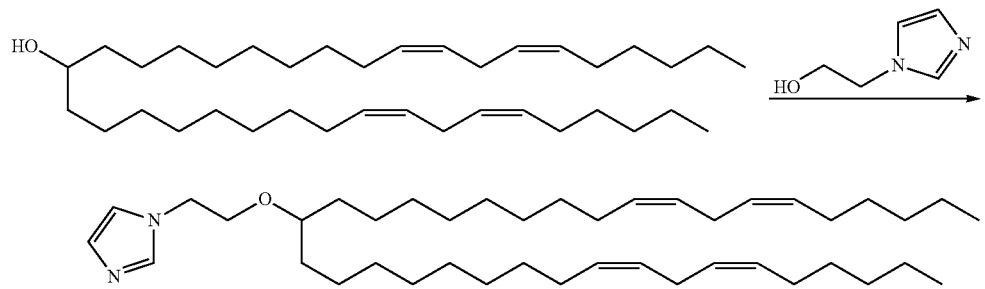

Using an analogous procedure to that described for the synthesis of 3-((6Z,9Z,28Z,31Z)-heptatriaconta-6,9,28,31-tetraen-19-yloxy)-N,N-dimethylpropan-1-amine (MC3 Ether), 1-(2-((6Z,9Z,28Z,31Z)-heptatriaconta-6,9,28,31-tetraen-19-yloxy)ethyl)-1H-imidazole was obtained as a pale yellow oil (600 mg, 24%). $^1$H NMR (400 MHz, CDCl$_3$): δ 8.12 (s, 1H), 7.15 (s, 1H), 7.09 (s, 1H), 5.43-5.30 (m, 8H), 4.20 (t, J=4.9 Hz, 2H), 3.70 (t, J=5 Hz, 2H), 3.26-3.18 (m, 1H), 2.82-2.75 (m, 4H), 2.10-2.04 (m, 8H), 1.46-1.12 (m, 40H), 0.93-0.86 (m, 6H).

Example 22

Synthesis of Compounds 34-37

3-((3Z,6Z,9Z,28Z,31Z,34Z)-heptatriaconta-3,6,9,28,31,34-hexaen-19-yloxy)-N,N-dimethylpropan-1-amine (Compound 34), 4-(3Z,6Z,9Z,28Z,31Z,34Z)-heptatriaconta-3,6,9,28,31,34-hexaen-19-yloxy)-N,N-dimethylbutan-1-amine (Compound 35), 2-((6Z,9Z,28Z,31Z)-heptatriaconta-6,9,28,31-tetraen-19-yloxy)-N,N-dimethylethanamine (Compound 36), and 3-((6E,9E,28E,31E)-heptatriaconta-6,9,28,31-tetraen-19-yloxy)-N,N-dimethylpropan-1-amine (Compound 37) having the structures shown below were synthesized as described in Scheme 24 below.

Compound 34

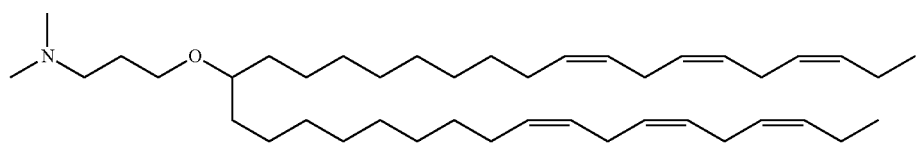 [SMILES: CC/C=C\C/C=C\C/C=C\CCCCCCCCC(CCCCCCCC/C=C\C/C=C\C/C=C\CC)OCCCN(C)C]

Compound 35

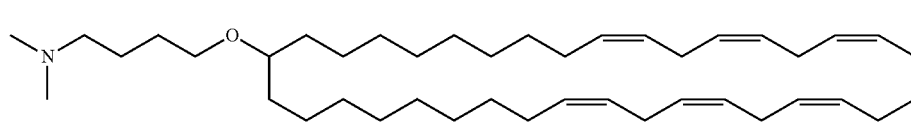

Compound 36

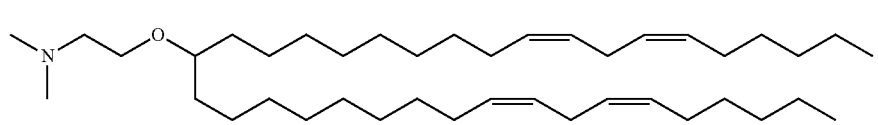 [SMILES: CCCCC/C=C\C/C=C\CCCCCCCCC(CCCCCCCC/C=C\C/C=C\CCCCC)OCCN(C)C]

Compound 37

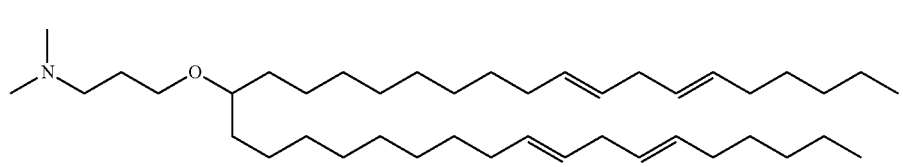 [SMILES: CCCCC/C=C/C/C=C/CCCCCCCCC(CCCCCCCC/C=C/C/C=C/CCCCC)OCCCN(C)C]

Scheme 24

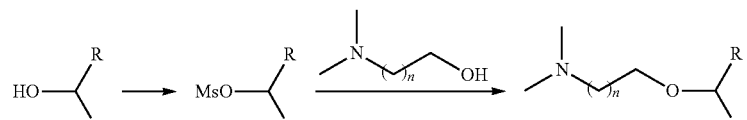

n = 1, 2, 3

R =

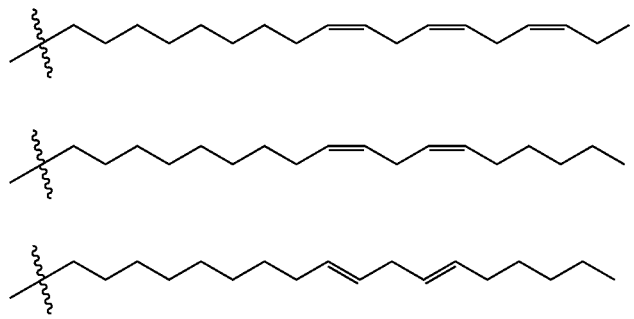

Synthesis of 3-((3Z,6Z,9Z,28Z,31Z,34Z)-heptatriaconta-3,6,9,28,31,34-hexaen-19-yloxy)-N,N-dimethylpropan-1-amine (Compound 34)

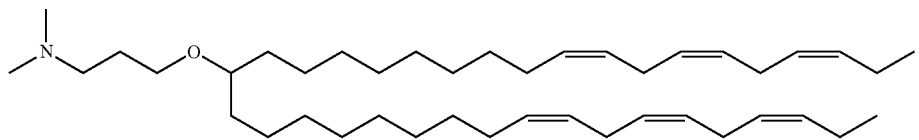

In the same fashion as 3-((6Z,9Z,28Z,31Z)-heptatriaconta-6,9,28,31-tetraen-19-yloxy)-N,N-dimethylpropan-1-amine (MC3 Ether), 3-((3Z,6Z,9Z,28Z,31Z,34Z)-heptatriaconta-3,6,9,28,31,34-hexaen-19-yloxy)-N,N-dimethylpropan-1-amine (2.26 g, 54%) was prepared as a pale yellow oil. $^1$H NMR (400 MHz, CDCl$_3$, $\delta_H$) 5.43-5.27 (m, 12H), 3.46 (t, 2H), 3.18 (app. p, 1H), 3.07-2.91 (m, 3H), 2.84-2.77 (m, 8H), 2.61-2.45 (m, 2H), 2.44-2.30 (br. s, 6H), 2.11-2.04 (m, 8H), 1.89-1.78 (br. s, 2H), 1.45-1.20 (m, 28H), 0.95 (t, 6H). UPLC 95.6%. FW 610.05, C$_{42}$H$_{75}$NO.

Synthesis of 4-((3Z,6Z,9Z,28Z,31Z,34Z)-heptatriaconta-3,6,9,28,31,34-hexaen-19-yloxy)-N,N-dimethylbutan-1-amine (Compound 35)

In the same fashion as 3-((6Z,9Z,28Z,31Z)-heptatriaconta-6,9,28,31-tetraen-19-yloxy)-N,N-dimethylpropan-1-amine (MC3 Ether), 4-((3Z,6Z,9Z,28Z,31Z,34Z)-heptatriaconta-3,6,9,28,31,34-hexaen-19-yloxy)-N,N-dimethylbutan-1-amine (1.33 g, 74%) was prepared as a pale yellow oil. $^1$H NMR (400 MHz, CDCl$_3$, $\delta_H$) 5.48-5.27 (m, 12H), 3.41 (t, 2H), 3.21-3.17 (m, 1H), 2.86-2.79 (m, 8H), 2.50-2.40 (m, 2H), 2.35 (s, 6H), 2.12-2.02 (m, 8H), 1.70-1.56 (m, 4H), 1.50-1.20 (m, 28H), 0.98 (t, 6H). FW 624.08, C$_{43}$H$_{77}$NO.

Synthesis of 2-((6Z,9Z,28Z,31Z)-heptatriaconta-6,9,28,31-tetraen-19-yloxy)-N,N-dimethylethanamine (Compound 36)

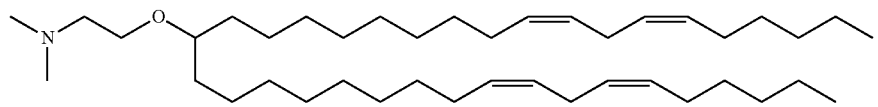

In the same fashion as 3-((6Z,9Z,28Z,31Z)-heptatriaconta-6,9,28,31-tetraen-19-yloxy)-N,N-dimethylpropan-1-amine (MC3 Ether), 2-((6Z,9Z,28Z,31Z)-heptatriaconta-6,9,28,31-tetraen-19-yloxy)-N,N-dimethylethanamine (1.30 g, 52%) was prepared as a pale yellow oil. $^1$H NMR (400 MHz, CDCl$_3$, $\delta_H$) 5.42-5.26 (m, 8H), 3.58 (t, 2H), 3.23-3.18 (m, 1H), 2.77 (app. t, 4H), 2.63-2.58 (m, 2H), 2.37 (s, 6H), 2.10-2.00 (m, 8H), 1.56-1.21 (m, 40H), 0.90 (t, 6H). FW 600.06, C$_{41}$H$_{77}$NO.

Synthesis of 3-((6E,9E,28E,31E)-heptatriaconta-6,9,28,31-tetraen-19-yloxy)-N,N-dimethylpropan-1-amine (Compound 37)

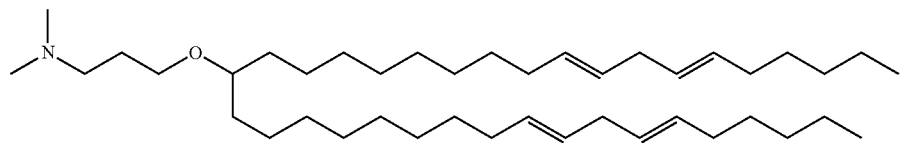

In the same fashion as 3-((6Z,9Z,28Z,31Z)-heptatriaconta-6,9,28,31-tetraen-19-yloxy)-N,N-dimethylpropan-1-amine (MC3 Ether), 3-((6E,9E,28E,31E)-heptatriaconta-6,9,28,31-tetraen-19-yloxy)-N,N-dimethylpropan-1-amine (0.22 g, 56%) was prepared as a colorless oil. $^1$H NMR (400 MHz, CDCl$_3$, $\delta_H$) 5.50-5.35 (m, 8H), 3.43 (t, 2H), 3.21-3.18 (m, 1H), 2.74-2.60 (m, 4H), 2.48-2.40 (m, 2H), 2.30 (s, 6H), 2.16-1.91 (m, 8H), 1.82-1.73 (m, 2H), 1.51-1.20 (m, 40H), 0.92 (t, 6H). FW 614.08, C$_{42}$H$_{79}$NO.

Example 23

Synthesis of Compound 38

3-((6Z,9Z,28E,31E)-heptatriaconta-6,9,28,31-tetraen-19-yloxy)-N,N-dimethylpropan-1-amine (Compound 38) having the structure shown below was synthesized as described in Scheme 25 below.

Compound 38

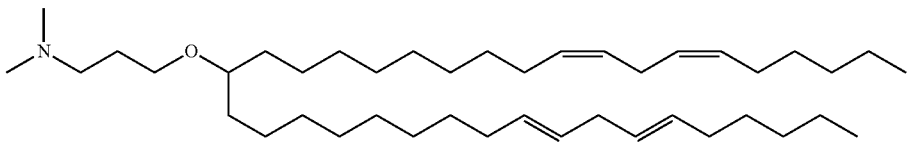

Scheme 25

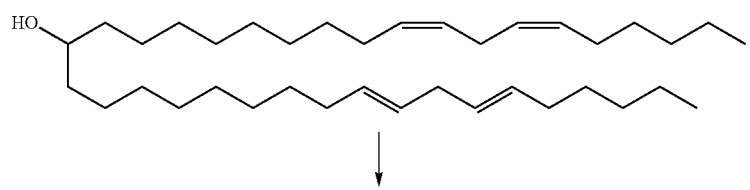

↓

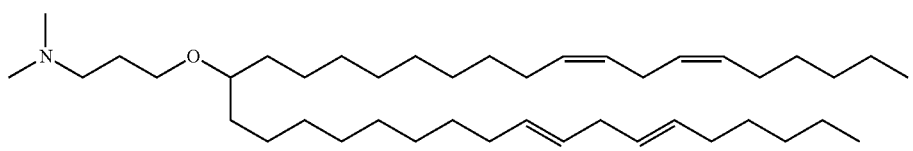

In the same fashion as 3-((6Z,9Z,28Z,31Z)-heptatriaconta-6,9,28,31-tetraen-19-yloxy)-N,N-dimethylpropan-1-amine (MC3 Ether), 3-((6Z,9Z,28E,31E)-heptatriaconta-6,9,28,31-tetraen-19-yloxy)-N,N-dimethylpropan-1-amine (1.23 g, 50%) was prepared as a colorless oil from (6Z,9Z,28E,31E)-heptatriaconta-6,9,28,31-tetraen-19-ol. $^1$H NMR (400 MHz, CDCl$_3$, $\delta_H$) 5.50-5.32 (m, 8H), 3.49 (t, 2H), 3.22-3.18 (m, 1H), 2.79 (app, t, 2H), 2.76-2.62 (m, 4H), 2.45 (br. s, 6H), 2.30-2.15 (m, 4H), 2.15-1.96 (m, 4H), 1.94-1.83 (m, 2H), 1.51-1.20 (m, 40H), 0.95-0.88 (m, 6H). FW 614.08, C$_{42}$H$_{79}$NO.

Example 24

Synthesis of Compound 39

N,N-diethyl-4-((6Z,9Z,28Z,31Z)-heptatriaconta-6,9,28,31-tetraen-19-yloxy)but-2-yn-1-amine (Compound 39) having the structure shown below was synthesized as described in Scheme 26 below.

Compound 39

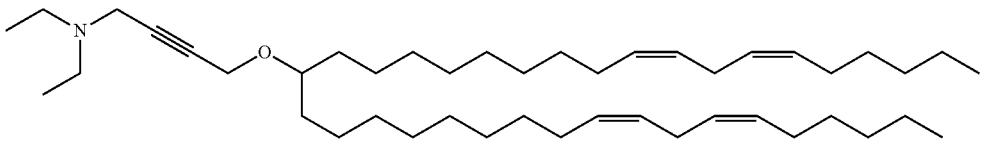

Scheme 26

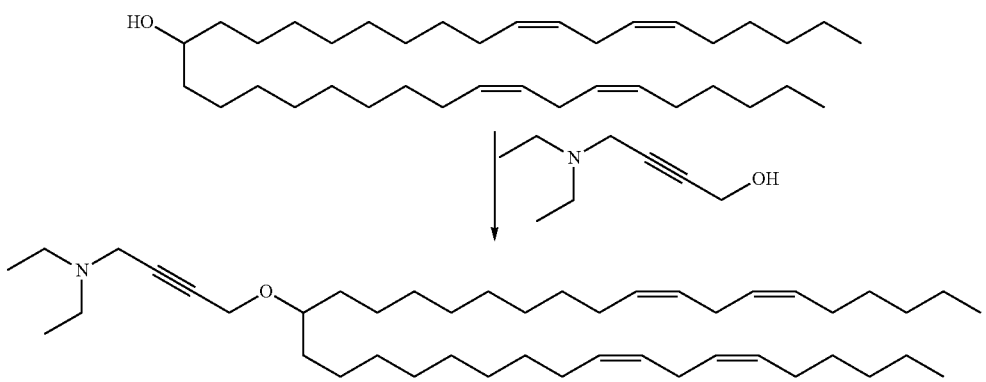

In the same fashion as 3-((6Z,9Z,28Z,31Z)-heptatriaconta-6,9,28,31-tetraen-19-yloxy)-N,N-dimethylpropan-1-amine (MC3 Ether), N,N-diethyl-4-((6Z,9Z,28Z,31Z)-heptatriaconta-6,9,28,31-tetraen-19-yloxy)but-2-yn-1-amine (511 mg, 48%) was prepared from di-linoleyl mesylate (1.0 g, 1.6 mmol) and 4-diethylaminobutyn-1-ol (1.2 mL, 8.2 mmol). $^1$H NMR (400 MHz, CDCl$_3$, $\delta_H$) 5.46-5.35 (m, 8H), 4.20 (s, 2H), 3.50-3.39 (m, 3H), 2.80 (app. t, 4H), 2.59 (q, 4H), 2.15-2.00 (m, 8H), 1.65-1.58 (br. s, 2H), 1.52-1.25 (m, 42H), 1.10 (t, 6H), 0.88 (t, 6H), FW 652.13, C$_{45}$H$_{81}$NO.

Example 25

Synthesis of Compound 40

(6E,9E,28E,31E)-heptatriaconta-6,9,28,31-tetraen-19-yl 4-(dimethylamino)butanoate (Compound 40) having the structure shown below was synthesized as described in Scheme 27 below.

Compound 40

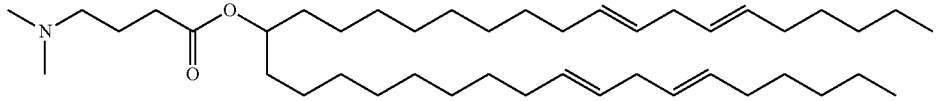

Scheme 27

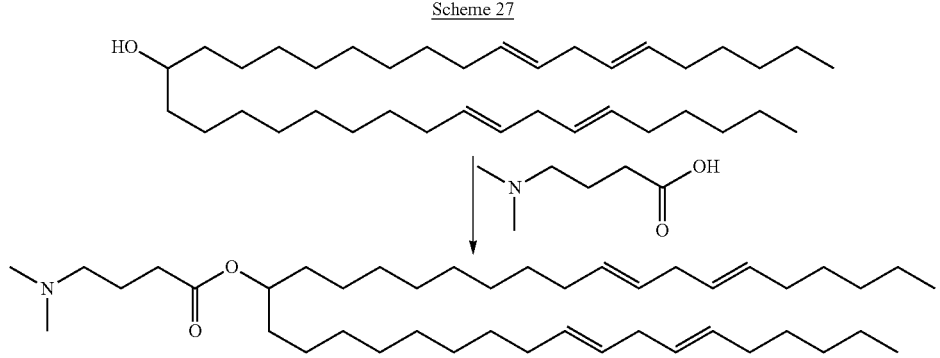

In the same fashion as (6Z,9Z,28Z,31Z)-heptatriaconta-6,9,28,31-tetraen-19-yl 4-(dimethylamino)butanoate (MC3), (6E,9E,28E,31E)-heptatriaconta-6,9,28,31-tetraen-19-yl 4-(dimethylamino)butanoate (2.9 g, 59%) was prepared as a colorless oil. $^1$H NMR (400 MHz, CDCl$_3$, δ$_H$) 5.49-5.35 (m, 8H), 4.87 (app. p, 1H), 2.75-2.61 (m, 4H), 2.36-2.24 (m, 4H), 2.22 (s, 6H), 2.04-1.91 (m, 8H), 1.83-1.72 (m, 3H), 1.56-1.44 (m, 4H), 1.40-1.19 (m, 38H), 0.89 (t, 6H). FW 642.09, C$_{43}$H$_{79}$NO$_2$.

Example 26

Synthesis of Compound 41

3-((7E,9Z,28Z,30E)-heptatriaconta-7,9,28,30-tetraen-19-yloxy)-N,N-dimethylpropan-1-amine (Compound 41) having the structure shown below was synthesized as described in Scheme 28 below.

Compound 41

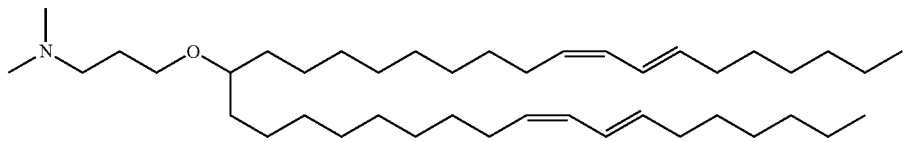

Scheme 28

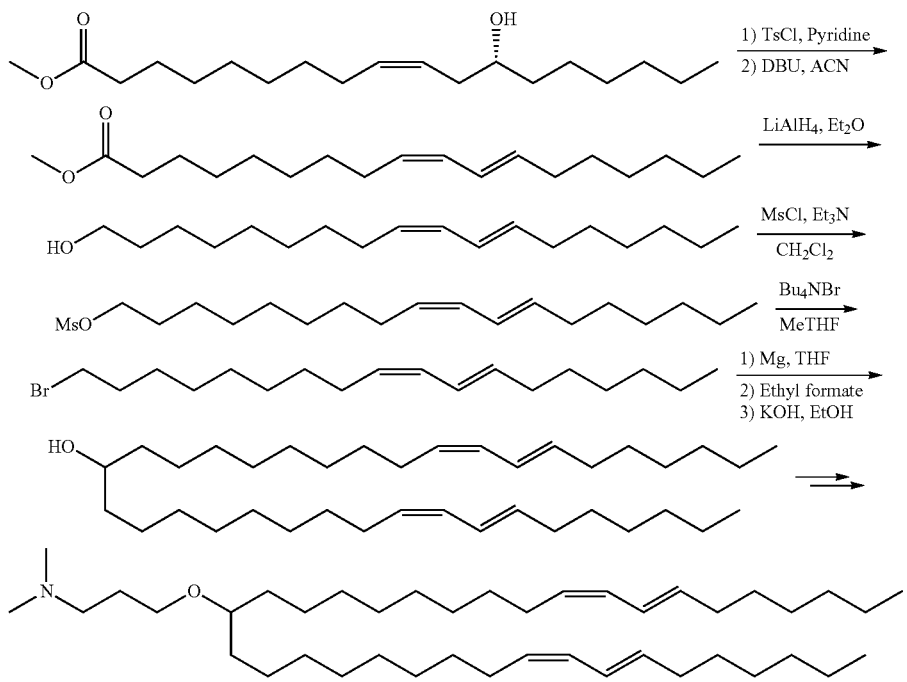

Synthesis of (9Z,11E)-methyl octadeca-9,11-dienoate

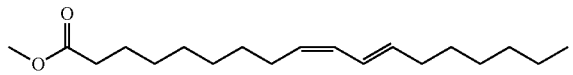

(9Z,11E)-methyl octadeca-9,11-dienoate was synthesized according to the procedure described in U.S. Pat. No. 5,892,074, the disclosure of which is herein incorporated by reference in its entirety for all purposes.

Synthesis of (9Z,11E)-octadeca-9,11-dien-1-ol

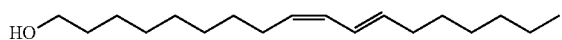

To a suspension of lithium aluminum hydride (1.5 g, 38.7 mmol) in anhydrous ether (50 mL) cooled to 0° C. under nitrogen was slowly added a solution of (9Z,11E)-methyl octadeca-9,11-dienoate (11.6 g, 38.7 mmol) in anhydrous diethyl ether (50 mL+25 mL rinse) via cannula transfer. The solution was stirred for 2 hours at 0° C. then quenched slowly with 1M NaOH (3.5 mL). The solution was dried on magnesium sulfate, filtered and concentrated in vacuo to dryness to afford the product as a colorless oil (9.5 g, 92%).

Synthesis of (9Z,11E)-octadeca-9,11-dienyl methanesulfonate

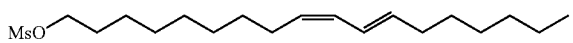

Using an analogous procedure to that described for the synthesis of dilinoleyl mesylate, (9Z,11E)-octadeca-9,11-dienyl methanesulfonate was obtained as a pale yellow oil (11.8 g, 96%).

Synthesis of (7E,9Z)-18-bromooctadeca-7,9-diene

Using an analogous procedure to that described for the synthesis of linoleyl bromide, (7E,9Z)-18-bromooctadeca-7,9-diene was obtained as a pale yellow oil (11.0 g, 97%).

Synthesis of (7E,9Z,28Z,30E)-heptatriaconta-7,9,28,30-tetraen-19-ol

Using an analogous procedure to that described for the synthesis of dilinoleyl methanol, (7E,9Z,28Z,30E)-heptatriaconta-7,9,28,30-tetraen-19-ol was obtained as a pale yellow oil (4.7 g, 53%).

Synthesis of 3-((7E,9Z,28Z,30E)-heptatriaconta-7,9,28,30-tetraen-19-yloxy)-N,N-dimethylpropan-1-amine (Compound 41)

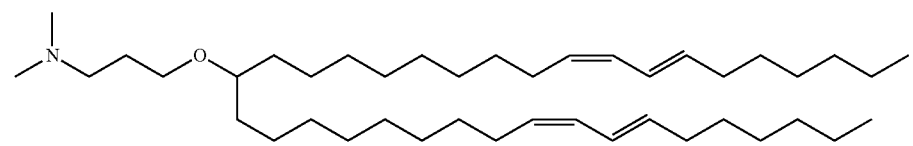 [SMILES: CCCCCC/C=C/C=C\CCCCCCCCC(CCCCCCCC/C=C\C=C\CCCCCC)OCCCN(C)C]

Using an analogous procedure to that described for the synthesis of 3-((6Z,9Z,28Z,31Z)-heptatriaconta-6,9,28,31-tetraen-19-yloxy)-N,N-dimethylpropan-1-amine, 3-((7E,9Z,28Z,30E)-heptatriaconta-7,9,28,30-tetraen-19-yloxy)-N,N-dimethylpropan-1-amine was obtained as a pale yellow oil (1.3 g). $^1$H NMR (400 MHz, CDCl$_3$): δ 6.35-5.26 (m, 8H), 3.49-3.44 (m, 2H), 3.23-3.15 (m, 1H), 2.60-2.50 (m, 2H), 2.38 (s, 6H), 2.21-1.95 (m, 8H), 1.88-1.77 (m, 2H), 1.50-1.21 (m, 44H), 0.92-0.86 (m, 6H).

Example 27

Synthesis of Compound 42

3-((9Z,28Z)-heptatriaconta-9,28-dien-19-yloxy)-N,N-dimethylpropan-1-amine (Compound 42) having the structure shown below was synthesized as described in Scheme 29 below.

Compound 42

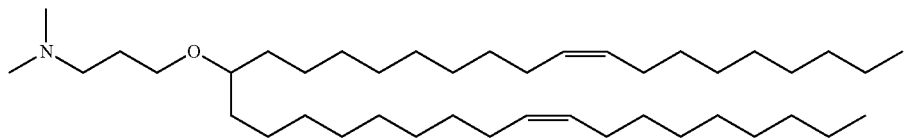

Scheme 29

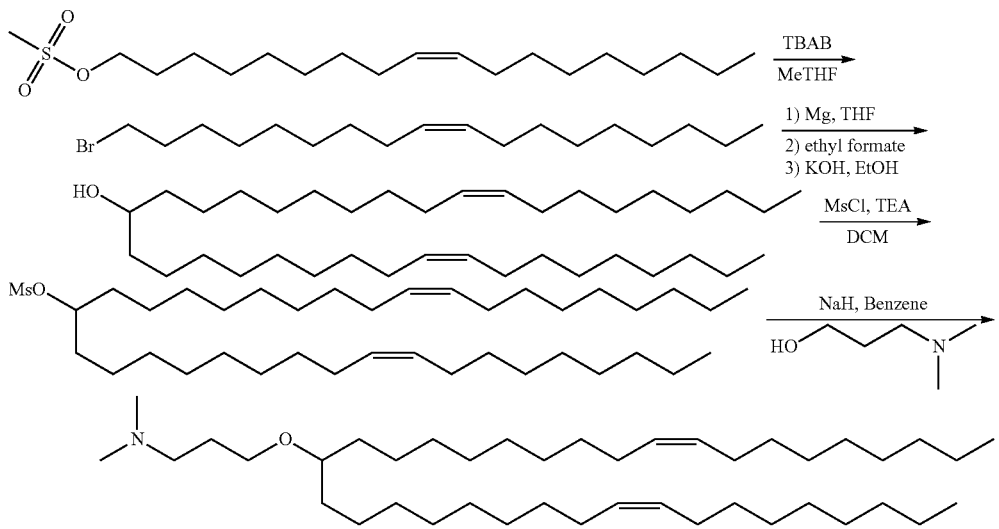

Synthesis of Oleyl Bromide

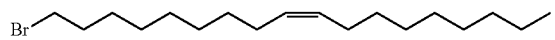 [SMILES: CCCCCCCC/C=C\CCCCCCCCBr]

Using an analogous procedure to that described for the synthesis of linoleyl bromide, oleyl bromide was obtained as a colorless oil (70.2 g, quantitative).

Synthesis of Dioleyl Methanol

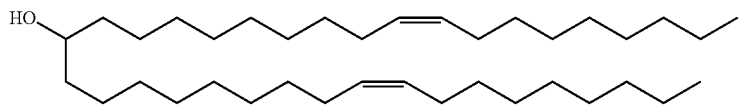 [SMILES: CCCCCCCC/C=C\CCCCCCCCC(O)CCCCCCCC/C=C\CCCCCCCC]

Using an analogous procedure to that described for the synthesis of dilinoleyl methanol, dioleyl methanol was obtained as a colorless oil (46.6 g, 82%).

Synthesis of Dioleyl Mesylate

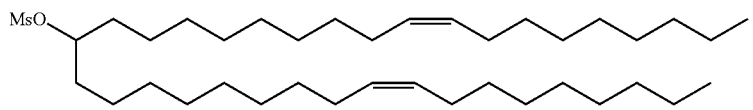 [SMILES: CCCCCCCC/C=C\CCCCCCCCC(CCCCCCCC/C=C\CCCCCCCC)OS(C)(=O)=O]

Using an analogous procedure to that described for the synthesis of dilinoleyl mesylate, dioleyl mesylate was obtained as a pale yellow oil (51.7 g, 97%).

Synthesis of 3-((9Z,28Z)-heptatriaconta-9,28-dien-19-yloxy)-N,N-dimethylpropan-1-amine (Compound 42)

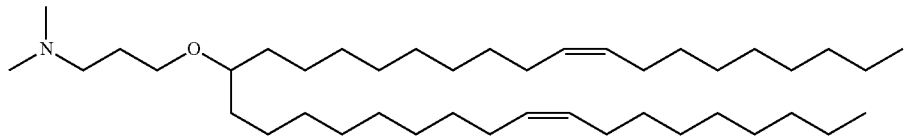 [SMILES: CCCCCCCC/C=C\CCCCCCCCC(CCCCCCCC/C=C\CCCCCCCC)OCCCN(C)C]

Using an analogous procedure to that described for the synthesis of 3-((6Z,9Z,28Z,31Z)-heptatriaconta-6,9,28,31-tetraen-19-yloxy)-N,N-dimethylpropan-1-amine, 3-((9Z,28Z)-heptatriaconta-9,28-dien-19-yloxy)-N,N-dimethylpropan-1-amine was obtained as a colorless oil (14.7 g, 28%). $^1$H NMR (400 MHz, CDCl$_3$): δ 5.41-5.30 (m, 4H), 3.46 (t, J=6.4 Hz, 2H), 3.23-3.16 (m, 1H), 2.46-2.38 (m, 2H), 2.29 (s, 6H), 2.08-1.96 (m, 8H), 1.81-1.72 (m, 2H), 1.52-1.20 (m, 52H), 0.93-0.86 (m, 6H).

Example 28

Synthesis of Compound 43

1-(1-((6Z,9Z,28Z,31Z)-heptatriaconta-6,9,28,31-tetraen-19-yl)-1H-1,2,3-triazol-4-yl)-N,N-dimethylmethanamine (Compound 43) having the structure shown below was synthesized as described in Scheme 30 below.

Compound 43

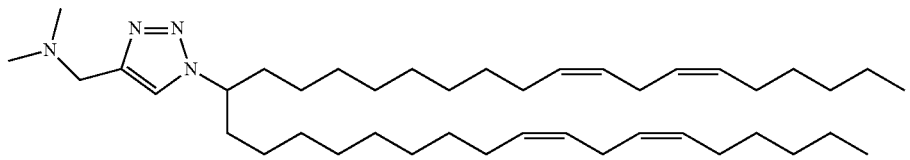 [SMILES: CCCCC/C=C\C/C=C\CCCCCCCCC(CCCCCCCC/C=C\C/C=C\CCCCC)n1cc(CN(C)C)nn1]

Scheme 30

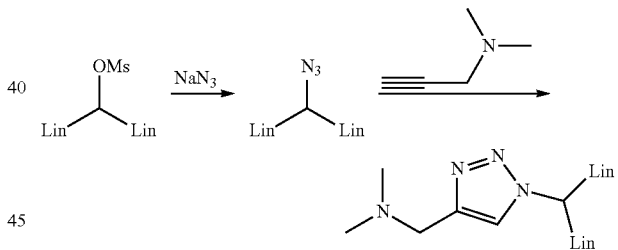

Synthesis of Dilinoleyl Methyl Azide

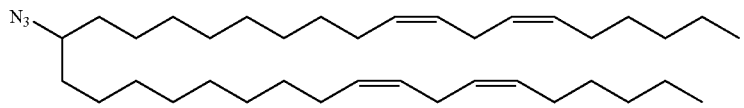

A solution of dilinoleyl mesylate (6.27 g, 10.3 mmol) in anhydrous DMF (110 mL) was treated with NaN$_3$ (3.35 g, 51.6 mmol) and subsequently heated (80° C., 18 h). The DMF was then removed under reduced pressure. The residue was taken up in CH$_2$Cl$_2$ and washed with sat. aq. NaHCO$_3$ (2×) and brine, dried (Na$_2$SO$_4$), filtered, concentrated, and purified via column chromatography (0.5%→1% ethyl acetate/hexanes) to yield dilinoleyl methyl azide (4.89 g, 86%) as a colorless oil. FW 553.95, C$_{37}$H$_{67}$N$_3$.

Synthesis of 1-(1-((6Z,9Z,28Z,31Z)-heptatriaconta-6,9,28,31-tetraen-19-yl)-1H-1,2,3-triazol-4-yl)-N,N-dimethylmethanamine (Compound 43)

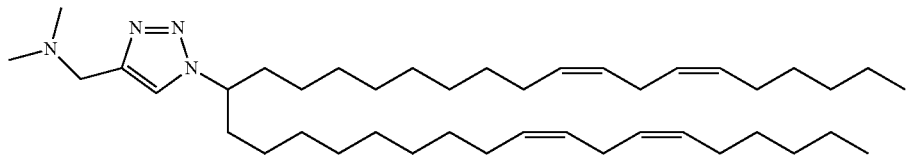

A solution of dilinoleyl methyl azide (500 mg, 0.90 mmol) and 3-dimethylamino-1-propyne (75 mg, 0.90 mmol) in H$_2$O and tert-butyl alcohol (1:1, 12 mL) was treated with sodium ascorbate (0.090 mmol, 17.94 taken from a 1M solution in water), followed by CuSO$_4$.5H$_2$O (2.3 mg, dissolved in 30 µL of water) and stirred (96 h). The solution was then diluted with H$_2$O (50 mL) and extracted with CH$_2$Cl$_2$ (3×), dried (Na$_2$SO$_4$), filtered, concentrated and purified via column chromatography (2%→4% MeOH/CH$_2$Cl$_2$) to yield the title compound as a colorless oil (524 mg, 91%). $^1$H NMR (400 MHz, CDCl$_3$, δ$_H$) 7.76 (br. s, 1H), 5.47-5.25 (m, 8H), 4.48 (p, 1H), 3.80 (br. s, 2H), 2.75 (app. t, 4H), 2.49 (s, 6H), 2.15-2.00 (m, 8H), 1.91-1.75 (m, 4H), 1.40-1.12 (m, 34H), 1.11-0.98 (m, 2H), 0.85 (t, 6H). FW 637.08, C$_{42}$H$_{76}$N$_4$.

Example 29

Synthesis of Compound 44

3-((6Z,9Z,28Z,31Z)-heptatriaconta-6,9,28,31-tetraen-19-yloxy)-N,N,N-trimethylpropan-1-aminium chloride (Compound 44) having the structure shown below was synthesized as described in Scheme 31 below.

To a solution of Compound 13 (3.0 g, 4.9 mmol) in dichloromethane (10 mL) was added iodomethane (4.5 mL, 73.5 mmol). The solution was stirred at room temperature for 16 hours at room temperature under nitrogen. Upon completion, the solution was concentrated in vacuo to dryness and dissolved in dichloromethane (150 mL). The solution was transferred to a separatory funnel and washed with 1M HCl in methanol solution (40 mL). To this solution was added brine (50 mL) and the mixture was shaken well. The aqueous phase was removed and previous wash procedure was repeated four more times to complete the ion exchange process. The dichloromethane solution was dried on magnesium sulfate, filtered and concentrated in vacuo to dryness. The yellow residue was purified by column chromatography on silica gel (100% ethyl acetate to 15% MeOH in ethyl acetate) to afford the title compound as a colorless oil (2.3 g, 71%). $^1$Hl NMR (400 MHz, CDCl$_3$): δ 5.43-5.28 9m, 8H), 3.63-3.56 (m, 2H), 3.54-3.45 (m, 11H), 3.23-3.16 (m, 1H), 2.81-2.76 (m, 4H), 2.09-2.01 (m, 10H), 1.45-1.20 (m, 40H), 0.92-0.86 (m, 6H).

Compound 44

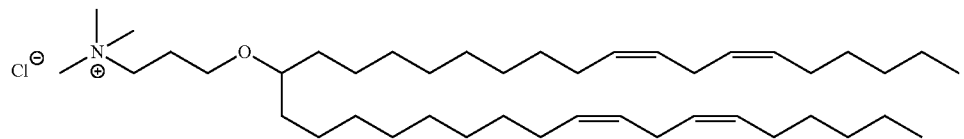

Scheme 31

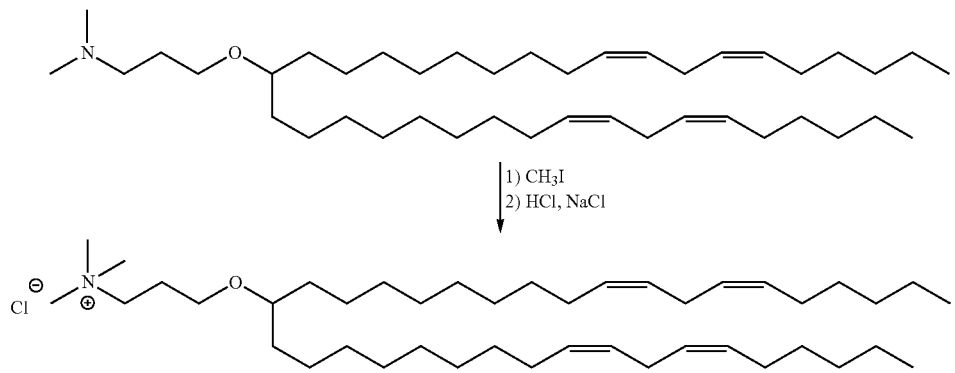

Example 30

Synthesis of CP-MC3

CP-MC3 (Compound 45) having the structure shown below was synthesized as described in Scheme 32 below.

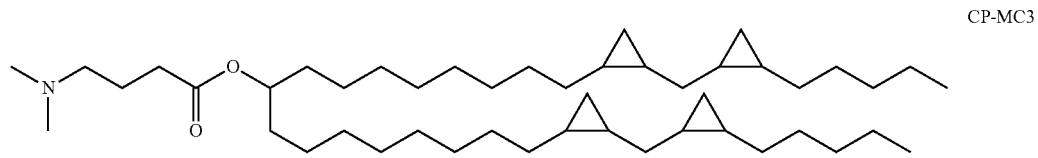 [SMILES: CCCCCC1CC1CC1CC1CCCCCCCCC(CCCCCCCCC1CC1CC1CC1CCCCC)OC(=O)CCCN(C)C]

CP-MC3

Scheme 32

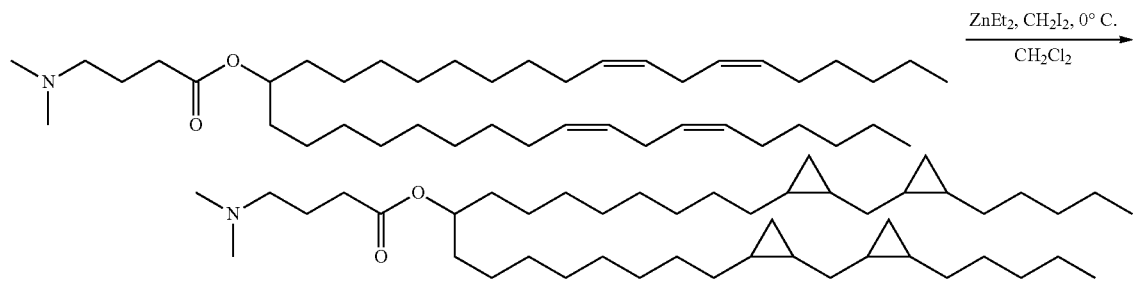

To a solution of MC3 (2.1 g, 3.27 mmol) in anhydrous $CH_2Cl_2$ (60 mL) at 0° C. under nitrogen was added 2.5 equivalents diethyl zinc (1M solution in hexanes) (31 mL, 31 mmol). The solution was stirred for 1 hour and then 2.5 equivalents diiodomethane (2.5 mL, 31 mmol) added. The reaction was stirred overnight at room temp. The white suspension was poured into ice (50 mL) and diluted to 200 mL using ethyl acetate (white solid dissolved). 5% HCl (100 mL) was added to wash. The aqueous (acidic) layer was removed and extracted with ethyl acetate (2×125 mL). The organic (top) layer was washed again with 5% HCl, then saturated $NaHCO_3$, water, and brine (150 mL each), dried on $MgSO_4$, filtered, and concentrated to yield a cloudy pale yellow oil. The procedure above was repeated once to ensure 100% cyclopropylation. Product was a pale yellow oil. The oil was purified by column chromatography eluting with $CHCl_3$ to afford a pale yellow oil. Final yield 1.11 g, 51%.

Example 31

Synthesis of CP-DLen-C2K-DMA

CP-DLen-C2K-DMA (Compound 46) having the structure shown below was synthesized as described in Scheme 33 below. CP-DLen-C2K-DMA is also known as CP-linolenyl-C2K, CP-Len-C2K, and CP-DLen-C2K.

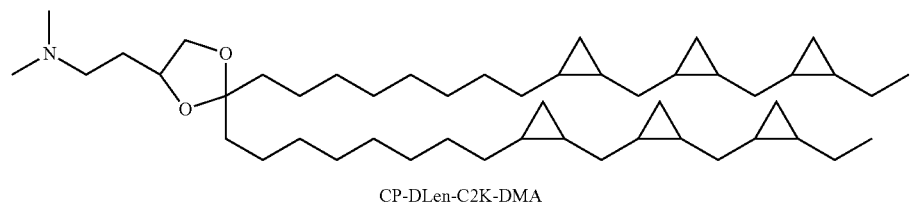 [SMILES: CCC1CC1CC1CC1CC1CC1CCCCCCCCC1(CCCCCCCCC2CC2CC2CC2CC2CC2CC)OCC(CCN(C)C)O1]

CP-DLen-C2K-DMA

Scheme 33

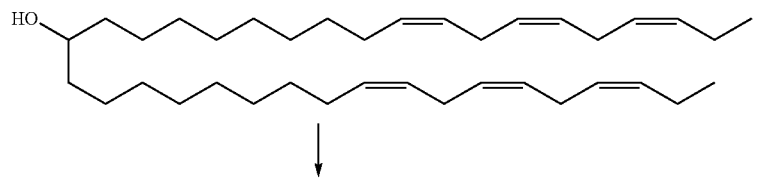

-continued

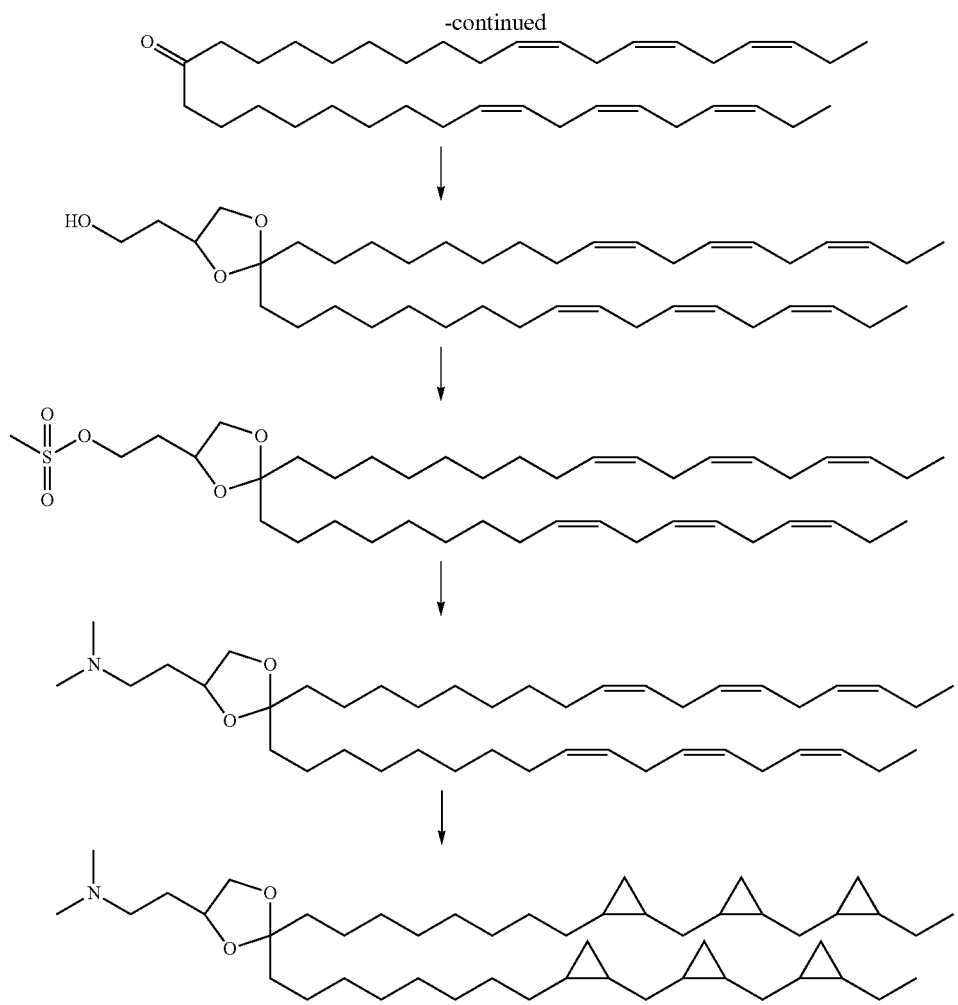

Synthesis of Dilinolenyl Ketone (Compound 47)

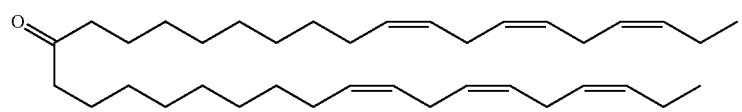 [SMILES: CC/C=C\C/C=C\C/C=C\CCCCCCCCC(=O)CCCCCCCC/C=C\C/C=C\C/C=C\CC]

To a 1000 mL RBF containing a solution of dilinolenyl methanol (6.0 g, 11.4 mmol) in anh. DCM (200 mL) was added pyridinium chlorochromate (7.39 g, 34.2 mmol), anh. sodium carbonate (1.0 g, 5.66 mmol) and a stirbar. The resulting suspension was stirred under nitrogen at RT for 3 h, after which time TLC indicated all SM to have been consumed. Ether (300 mL) was then added to the mixture and the resulting brown suspension filtered through a pad of silica (300 mL), washing the pad with ether (3×100 mL). The ether phases were combined, concentrated and purified to yield 4.2 g (8.0 mmol, 70%) of the ketone.

Synthesis of Linolenyl Ketal (Compound 48)

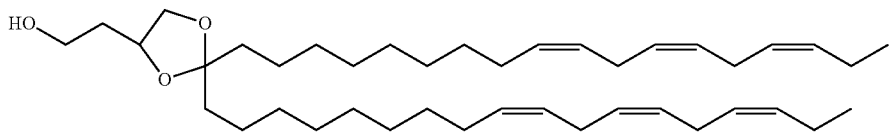 [SMILES: CC/C=C\C/C=C\C/C=C\CCCCCCCCC1(CCCCCCCC/C=C\C/C=C\C/C=C\CC)OCC(CCO)O1]

A 100 mL RBF was charged with dilinolenyl ketone (Compound 47) (4.2 g, 8.2 mmol), 1,2,4-butanetriol (3.4 g, 32 mmol), PPTS (200 mg, 0.8 mmol) and a stir bar. The flask was flushed with nitrogen and anhydrous toluene (60 mL) added. The reaction vessel was fitted with a Dean Stark tube and condenser and brought to reflux and the reaction was left overnight. After cooling to room temperature, the reaction mixture diluted with toluene (50 mL), and washed with 5% aq. Na$_2$CO$_3$ (2×50 mL), water (50 mL), dried (MgSO$_4$) and purified by chromatography to yield 3.0 g (4.9 mmol, 59%) of the ketal.

Mesylate Formation (Compound 49)

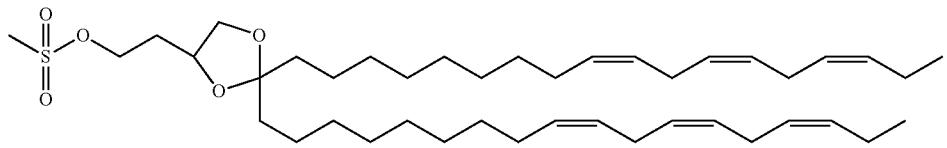 [SMILES: CC/C=C\C/C=C\C/C=C\CCCCCCCCC1(CCCCCCCC/C=C\C/C=C\C/C=C\CC)OCC(CCOS(C)(=O)=O)O1]

A 250 mL RBF was charged with the ketal (Compound 48) (3.0 g, 4.9 mmol), TEA (2.2 mL, 15.6 mmol) and a stir bar. The flask was flushed with nitrogen, anh. DCM (20 mL) added, and the solution cooled to −15° C. In a separate 50 mL flask, a solution of MsCl (9.7 mmol, 2 eqv.) in anhydrous DCM (30 mL) was prepared, then transferred to the reaction vessel by syringe over 20 minutes. The reaction was stirred for 90 minutes at −15° C., at which point starting material had been consumed. The reaction mixture was diluted with a further 50 mL of DCM, washed with NaHCO$_3$ (2×50 mL), dried (MgSO$_4$) and purified by chromatography. Final yield 3.1 g, 4.5 mmol, 92%.

Synthesis of D-Len-C2K-DMA (Compound 50)

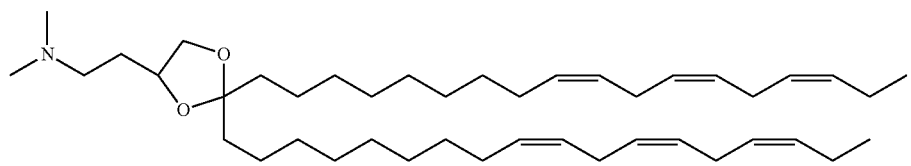 [SMILES: CC/C=C\C/C=C\C/C=C\CCCCCCCCC1(CCCCCCCC/C=C\C/C=C\C/C=C\CC)OCC(CCN(C)C)O1]

A 250 mL RBF was charged with the mesylate (Compound 49) (3.0 g, 4.35 mmol), isopropanol (25 mL) and a stir bar. The flask was flushed with nitrogen, sealed, and a 2.0 M solution of dimethylamine in methanol (120 mL) added via canulla. The reaction was stirred at room temperature for 3 days. The solution was concentrated and purified by chromatography. Final yield 2.49 g, 3.9 mmol, 90%.

Synthesis of CP-DLen-C2K-DMA (Compound 46)

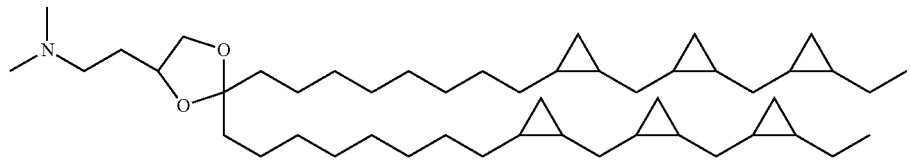 [SMILES: CCC1CC1CC1CC1CC1CC1CCCCCCCCC1(CCCCCCCCC2CC2CC2CC2CC2CC2CC)OCC(CCN(C)C)O1]

To a 250 mL RBF was added DLen-C2K-DMA (Compound 50) (1.28 g, 2 mmol), a stirbar and anh. DCM (40 mL). The flask was flushed with N$_2$ and cooled to 0° C., then a 1M solution of diethylzinc in hexanes added (60 mL, 60 mmol, 5 equivalents per olefin). The solution was stirred for 1 hour at 0° C., then diiodomethane (4.84 mL 60 mmol). The reaction mixture was concentrated and then redissolved in EtOAc (50 mL). The EtOAc was washed successively with 5% HCl (2×50 mL), water (50 mL), NaHCO$_3$ (50 mL), water (50 mL), and brine (50 mL). The aqueous washes were combined and extracted with DCM (2×50 mL). All organics were combined, dried and concentrated to yield crude CP-Len-C2K. $^1$H-NMR and HPLC indicated some olefins still to be present, so the compound was treated again, using the same procedures and amounts outlined above. This time $^1$H-NMR indicated total conversion of the olefins. Final yield after chromatography was 1.2 g, 1.66 mmol, 83%.

Example 32

Synthesis of CP-γDLen-C2K-DMA

CP-γDLen-C2K-DMA (Compound 51) having the structure shown below was synthesized as described in Scheme 34 below. CP-γDLen-C2K-DMA is also known as CP-γlinolenyl-C2K, CP-γLen-C2K, and CP-D-γ-Len-C2K.

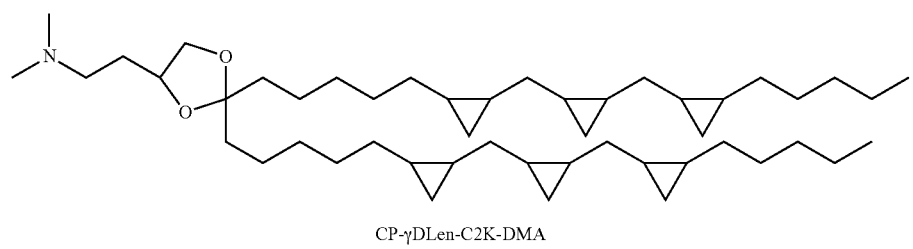 [SMILES: CCCCCC1CC1CC1CC1CC1CC1CCCCCC1(CCCCCC2CC2CC2CC2CC2CC2CCCCC)OCC(CCN(C)C)O1]

CP-γDLen-C2K-DMA

Scheme 34

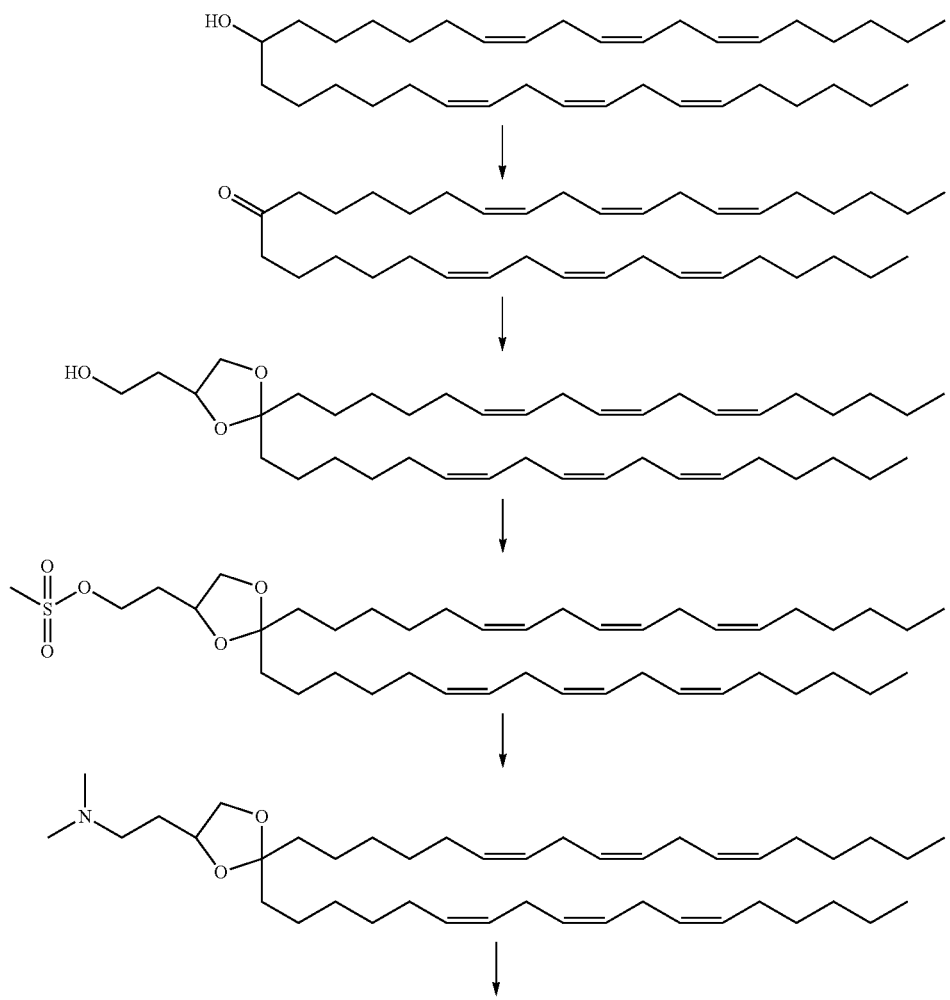

-continued

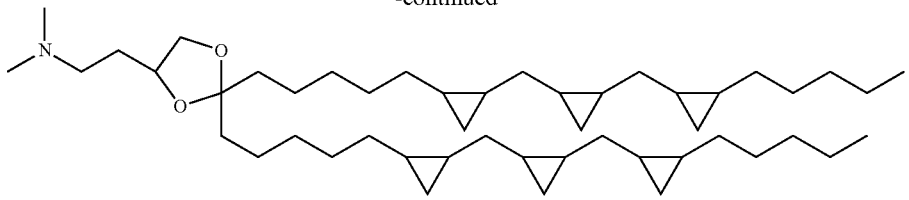

Synthesis of Di-γ-Linolenyl Ketone (Compound 52)

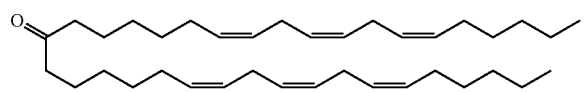

To a 1000 mL RBF containing a solution of di-γ-linolenyl methanol (6.0 g, 11.4 mmol) in anh. DCM (200 mL) was added pyridinium chlorochromate (7.39 g, 34.2 mmol), anh. sodium carbonate (1.0 g, 5.66 mmol) and a stirbar. The resulting suspension was stirred under nitrogen at RT for 3 h, after which time TLC indicated all SM to have been consumed. Ether (300 mL) was then added to the mixture and the resulting brown suspension filtered through a pad of silica (300 mL), washing the pad with ether (3×100 mL). The ether phases were combined, concentrated and purified to yield 5.5 g (10.5 mmol, 92%) of ketone.

Synthesis of γ-Linolenyl Ketal (Compound 53)

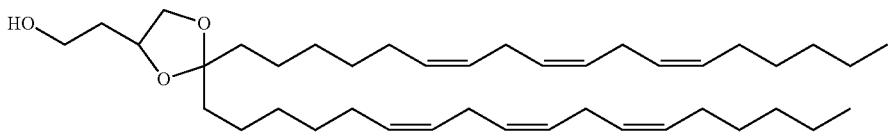 [SMILES: CCCCC/C=C\C/C=C\C/C=C\CCCCCC1(CCCCC/C=C\C/C=C\C/C=C\CCCCC)OCC(CCO)O1]

A 100 mL RBF was charged with di-γ-linolenyl ketone (Compound 52) (2.14 g, 4.1 mmol), 1,2,4-butanetriol (1.7 g, 16.0 mmol), PPTS (100 mg, 0.4 mmol) and a stir bar. The flask was flushed with nitrogen and anhydrous toluene (30 mL) added. The reaction vessel was fitted with a Dean Stark tube and condenser and brought to reflux and the reaction was left overnight. After cooling to room temperature, the reaction mixture was washed with 5% aq. $Na_2CO_3$ (2×50 mL), water (50 mL), dried ($MgSO_4$) and purified by chromatography to yield 1.34 g (2.2 mmol, 53%) of the ketal.

Mesylate Formation (Compound 54)

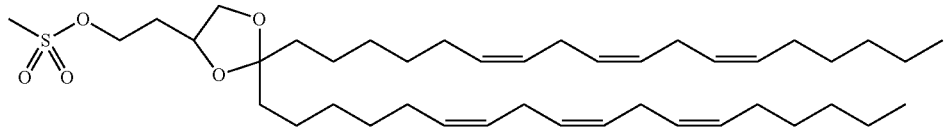 [SMILES: CCCCC/C=C\C/C=C\C/C=C\CCCCCC1(CCCCC/C=C\C/C=C\C/C=C\CCCCC)OCC(CCOS(C)(=O)=O)O1]

A 250 mL RBF was charged with the ketal (Compound 53) (1.34 g, 2.19 mmol), TEA (1 mL, 7.1 mmol) and a stir bar. The flask was flushed with nitrogen, anh. DCM (10 mL) added, and the solution cooled to −15° C. In a separate 50 mL flask, a solution of MsCl (342 μL, 4.4 mmol, 2 eqv.) in anhydrous DCM (15 mL) was prepared, then transferred to the reaction vessel by syringe over 20 minutes. The reaction was stirred for 90 minutes at −15° C., at which point starting material had been consumed. The reaction mixture was diluted with a further 50 mL of DCM, washed with $NaHCO_3$ (2×50 mL), dried ($MgSO_4$) and purified by chromatography. Final yield 1.31 g, 1.90 mmol, 87%.

Synthesis of D-γ-Len-C2K-DMA (Compound 55)

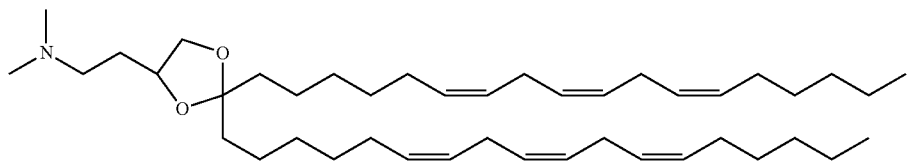 [SMILES: CCCCC/C=C\C/C=C\C/C=C\CCCCCC1(CCCCC/C=C\C/C=C\C/C=C\CCCCC)OCC(CCN(C)C)O1]

A 250 mL RBF was charged with the mesylate (Compound 54) (1.31 g, 1.9 mmol), isopropanol (10 mL) and a stir bar. The flask was flushed with nitrogen, sealed, and a 2.0 M solution of dimethylamine in methanol (60 mL) added via canulla. The reaction was stirred at room temperature for 3 days. The solution was concentrated and purified by chromatography. Final yield 1.1 g, 1.72 mmol, 91%.

Synthesis of CP-γDLen-C2K-DMA (Compound 51)

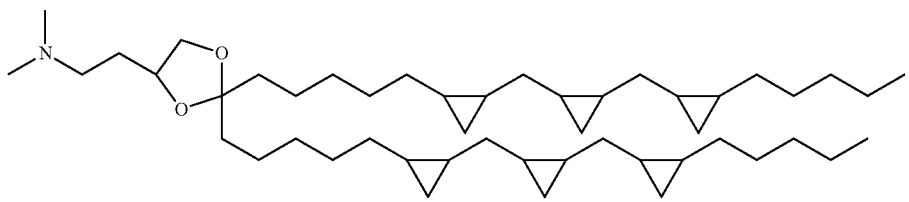 [SMILES: CCCCCC1CC1CC1CC1CC1CC1CCCCCC1(CCCCCC2CC2CC2CC2CC2CC2CCCCC)OCC(CCN(C)C)O1]

To a 250 mL RBF was added γ-Len-C2K (Compound 55) (638 mg, 1 mmol), a stirbar and anh. DCM (40 mL). The flask was flushed with $N_2$ and cooled to 0° C., then a 1M solution of diethylzinc in hexanes added (30 mL, 30 mmol, 5 equivalents per olefin). The solution was stirred for 1 hour at 0° C., then diiodomethane (2.42 mL 30 mmol). The reaction mixture was concentrated and then redissolved in EtOAc (50 mL). The EtOAc was washed successively with 5% HCl (2×50 mL), water (50 mL), $NaHCO_3$ (50 mL), water (50 mL), and brine (50 mL). The aqueous washes were combined and extracted with DCM (2×50 mL). All organics were combined, dried and concentrated to yield crude CP-γ-Len-C2K. As previously, $^1$H-NMR and HPLC indicated some olefins still to be present, so the compound was treated again, using the same procedures and amounts outlined above. This time $^1$H-NMR indicated total conversion of the olefins. Final yield after chromatography was 614 mg, 0.85 mmol, 85%.

Example 33

Synthesis of CP-C2K-DMA

CP-C2K-DMA (Compound 56) having the structure shown below was synthesized as described in Scheme 35 below. CP-C2K-DMA is also known as CP-C2K.

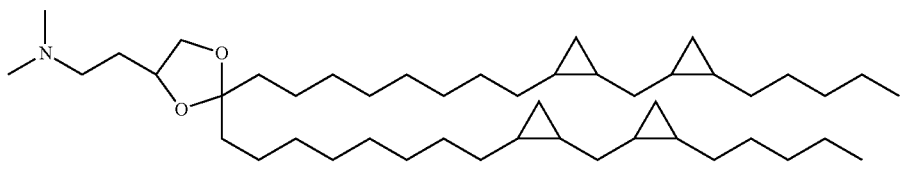

CP-C2K-DMA

Scheme 35

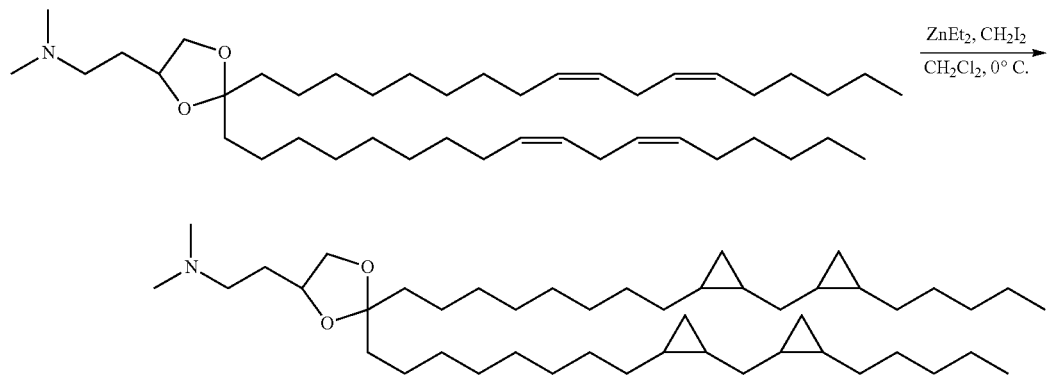

To a solution of DLin-C2K-DMA (1.2 g, 1.87 mmol) in anhydrous CH$_2$Cl$_2$ (36 mL) at 0° C. under nitrogen was added 2.5 equivalents diethyl zinc (1M solution in hexanes) (18.7 mL). The solution was stirred for 75 minutes and then 2.5 equivalents diiodomethane (1.5 mL, 18.7 mmol) was added. The reaction was stirred overnight at room temp. The white suspension was poured into ice (100 mL) and diluted to 150 mL using ethyl acetate (white solid dissolved upon the addition of ethyl acetate). 5% HCl (50 mL) was added and the aqueous layer backextracted with ethyl acetate (2×100 mL). The combined organics were washed with 5% HCl again, then saturated NaHCO$_3$, water, and brine (150 mL each), dried over MgSO$_4$, filtered, and concentrated to yield a brown yellow oil.

The above procedure was repeated once in order to ensure 100% cyclopropylation of the double bonds. The brown yellow oil was analyzed by HPLC and determined to be >99% pure. The oil was decolorized using a second column (column 2"L×2"W; eluted with 10% ethyl acetate in hexanes) to afford the product as a pale yellow oil. Final yield 740 mg.

Example 34

Synthesis of CP-DODMA

CP-DODMA (Compound 57) having the structure shown below was synthesized as described below.

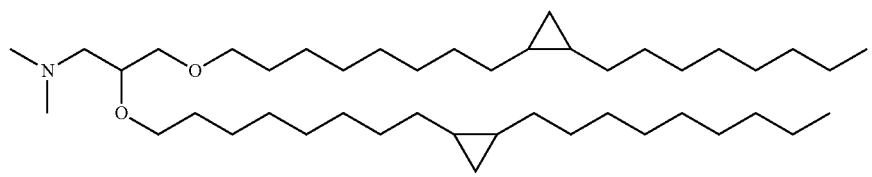

Chemical Formula: C$_{43}$H$_{85}$NO$_2$
Exact Mass: 647.66
Molecular Weight: 648.14
Elemental Analysis: C, 79.68; H, 13.22; N, 2.16; O, 4.94

A solution of DODMA (310 mg, 0.5 mmol) in anhydrous dichloromethane (10 mL) under nitrogen was cooled to 0° C. and a 1M solution of diethylzinc in hexanes (5 mL, 5 mmol, 5 eqv) added. The solution was stirred for 1 hour at 0° C. then diiodomethane (1.34 g, 404 µL, 5 mmol) was added and the solution was stirred for 16 hours at room temperature under nitrogen. TLC (8% MeOH in CHCl$_3$) showed that the starting material was consumed and a very slightly more polar product had formed. The reaction mixture was concentrated and purified by column chromatography. A polar (lower running) impurity coeluted with the product. After concentrating appropriate column fractions they were dissolved in EtOAc and washed with 5% HCl (2×10 mL), water (10 mL), sat. NaHCO$_3$ (10 mL), water (10 mL) and brine (10 mL). The solution was dried over MgSO$_4$ and concentrated to afford a clear pale yellow oil (200 mg, 62%). $^1$H NMR analysis showed complete conversion of the cis-alkenes to cyclopropyl groups.

Example 35

Synthesis of CP-DPetroDMA

CP-DPetroDMA (Compound 58) having the structure shown below was synthesized as described below.

Chemical Formula: $C_{43}H_{85}NO_2$
Exact Mass: 647.66
Molecular Weight: 648.14
Elemental Analysis: C, 79.68; H, 13.22; N, 2.16; O, 4.94

A solution of DPetroDMA (300 mg, 0.48 mmol) in anhydrous dichloromethane (10 mL) under nitrogen was cooled to 0° C. and a 1M solution of diethylzinc in hexanes (5 mL, 5 mmol, 5 eqv) added. The solution was stirred for 1 hour at 0° C. then diiodomethane (1.34 g, 404 μL, 5 mmol) was added and the solution was stirred overnight at room temperature under nitrogen. TLC (8% MeOH in CHCl$_3$) showed that the starting material was consumed and a very slightly more polar product had formed. The reaction mixture was concentrated and purified by column chromatography. A polar (lower running) impurity coeluted with the product. After concentrating appropriate column fractions they were dissolved in EtOAc and washed with 5% HCl (2×10 mL), water (10 mL), sat. NaHCO$_3$ (10 mL), water (10 mL) and brine (10 mL). The solution was dried over MgSO$_4$ and concentrated to afford a clear pale yellow oil (250 mg, 0.39 mmol, 80%). $^1$H NMR analysis showed complete conversion of the cis-alkenes to cyclopropyl groups.

Example 36

Synthesis of CP-DLinDMA

CP-DLinDMA (Compound 59) having the structure shown below was synthesized as described in Scheme 36 below.

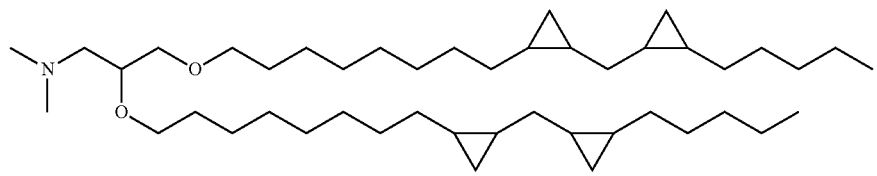

Chemical Formula: $C_{45}H_{85}NO_2$
Exact Mass: 671.66
Molecular Weight: 672.16
Elemental Analysis: C, 80.41; H, 12.75; N, 2.08; O, 4.76

Scheme 36

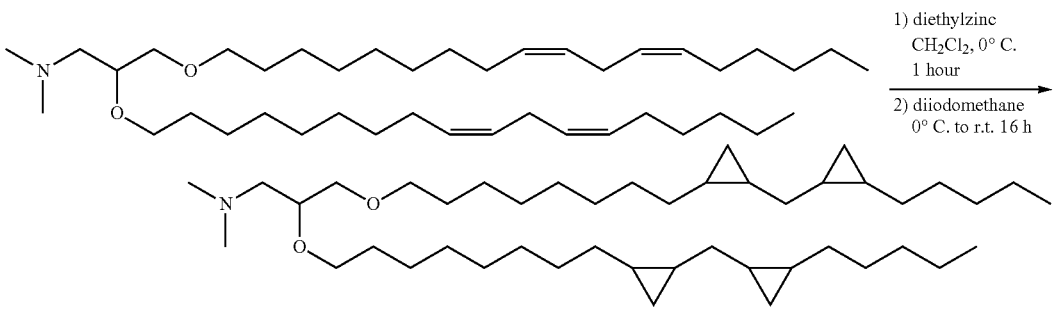

| | Reagent | MW | Amount | mmol | Equivalents |
|---|---|---|---|---|---|
| 1 | DLinDMA | 615.06 | 300 mg | 0.49 | 1 |
| 2 | Dichloromethane | — | 20 mL | — | — |
| 3 | Diethylzinc 1M in hexanes | — | 4.9 mL | 4.9 | 10 |
| 4 | Diiodomethane | 267.84 | 2.62 g (790 μL) | 9.8 | 20 |

To a solution of DLinDMA (300 mg, 0.49 mmol) in anhydrous dichloromethane (20 mL) cooled to 0° C. under nitrogen was added a 1M solution of diethylzinc in hexanes (4.9 mL). The solution was stirred for 1 hour at 0° C. then diiodomethane (2.62 g, 9.8 mmol) was added and the solution was stirred for 16 hours at room temperature under nitrogen. The solution was diluted with dichloromethane (20 mL), filtered and concentrated in vacuo to dryness. The residue was purified by column chromatography (10" L×0.5" D; eluted with 2.5% MeOH in CHCl₃) to afford the product as a light yellow oil (288 mg, 87%). See also, Tanaka et al., *Bioorg. Med. Chem. Lett.*, 13:1037-1040 (2003).

Example 37

Synthesis of CP-DLenDMA

CP-DLenDMA (Compound 60) having the structure shown below was synthesized as described in Scheme 37 below.

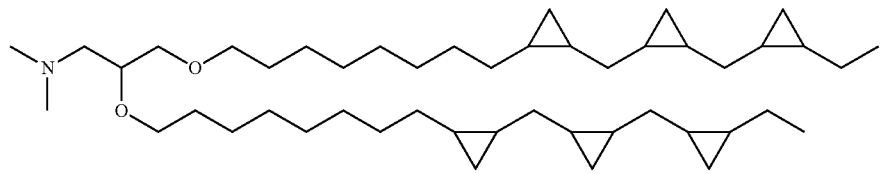

Chemical Formula: $C_{47}H_{85}NO_2$
Exact Mass: 695.66
Molecular Weight: 696.18
Elemental Analysis: C, 81.09; H, 12.31; N, 2.01; O, 4.60

Scheme 37

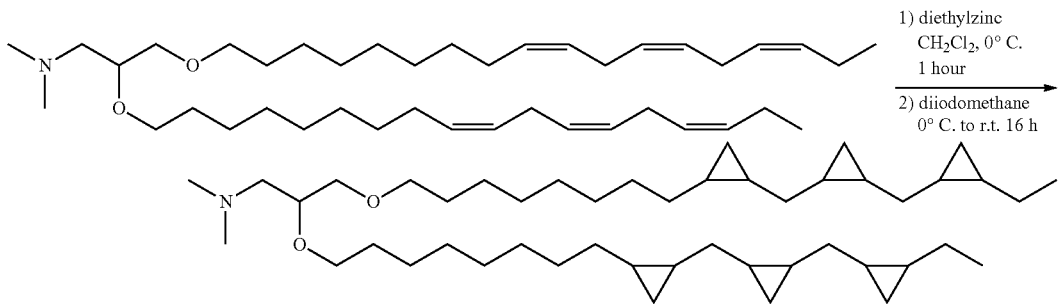

| | Reagent | MW | Amount | mmol | Equivalents |
|---|---|---|---|---|---|
| 1 | DLenDMA | 611.02 | 67 mg | 0.11 | 1 |
| 2 | Dichloromethane | — | 5 mL | — | — |
| 3 | Diethylzinc 1M in hexanes | — | 1.48 mL | 1.48 | 14 |
| 4 | Diiodomethane | 267.84 | 790 mg (237 µL) | 2.95 | 27 |

To a solution of DLenDMA (67 mg, 0.11 mmol) in anhydrous dichloromethane (5 mL) cooled to 0° C. under nitrogen was added a 1M solution of diethylzinc in hexanes (1.48 mL). The solution was stirred for 1 hour at 0° C. then diiodomethane (790 mg, 2.95 mmol) was added and the solution was stirred for 16 hours at room temperature under nitrogen. TLC (8% MeOH in CHCl₃) showed that the starting material was consumed and a very slightly more polar product had formed. The solution was purified by column chromatography without a workup (0.5" D×8" L; eluted with 4% MeOH in CHCl₃) to afford a clear pale yellow oil (73 mg, 96%). ¹H NMR analysis showed complete conversion of the cis-alkenes to cyclopropyl. See also, Tanaka et al., *Bioorg. Med. Chem. Lett.*, 13:1037-1040 (2003).

Example 38

Synthesis of γ-DLenDMA

γ-DLenDMA (Compound 61) having the structure shown below was synthesized as described below.

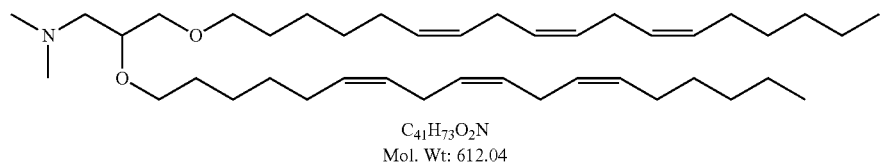 [SMILES: CCCCC/C=C\C/C=C\C/C=C\CCCCCOCC(CN(C)C)OCCCCC/C=C\C/C=C\C/C=C\CCCCC]

C$_{41}$H$_{73}$O$_2$N
Mol. Wt: 612.04

A 250 mL round bottom flask was charged with 3-(dimethylamino)-1,2-propanediol (0.8 g, 6.7 mmol), tetrabutylammonium hydrogen sulphate (1 g), gamma linolenyl mesylate (cis-6,9,12-octadecatriene sulphonic acid) (5 g, 14.6 mmol), and 30 mL toluene. After stirring for 15 minutes, the reaction was cooled to 0-5° C. A solution of 40% sodium hydroxide (15 mL) was added slowly. The reaction was left to stir for approximately 48 hours. An additional 15 mL of toluene was then added to the reaction vessel, along with 40% sodium hydroxide (15 mL). After the reaction was stirred for an additional 12 hours, water (50 mL) and isopropyl acetate (50 mL) were added and stirred for 15 minutes. The mixture was then transferred to a 500 mL separatory funnel and allowed to separate. The lower aqueous phase was nm off and the organic phase was washed with saturated sodium chloride (2×50 mL). Since the aqueous and organic phases resulting from the saturated sodium chloride washes could not be completely separated after 20 minutes, the lower aqueous phase (slightly yellow) was run off and back extracted with chloroform (~45 mL). The organic phase was dried with MgSO$_4$, filtered, and the solvent evaporated.

The crude product, an orange liquid, was purified on column chromatography using silica gel (60 g) with 0-3% methanol gradient in dichloromethane to yield 3.19 g. The product was further purified via column chromatography on silica gel (50 g) with 10-30% ethyl acetate gradient in hexanes to yield 1.26 g pure product.

Example 39

Synthesis of CP-γ-DLenDMA

CP-γ-DLenDMA (Compound 62) having the structure shown below was synthesized as described in Scheme 38 below.

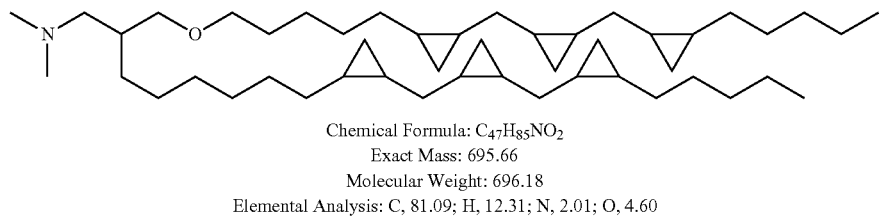 [SMILES: CCCCCC1CC1CC1CC1CC1CC1CCCCCCC(COCCCCCC1CC1CC1CC1CC1CC1CCCCC)CN(C)C]

Chemical Formula: C$_{47}$H$_{85}$NO$_2$
Exact Mass: 695.66
Molecular Weight: 696.18
Elemental Analysis: C, 81.09; H, 12.31; N, 2.01; O, 4.60

Scheme 38

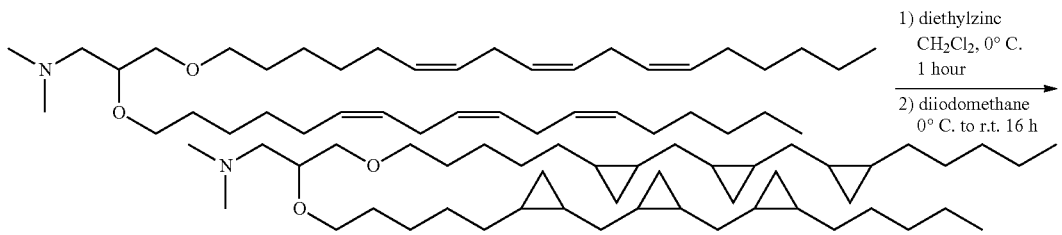

| Reagent | MW | Amount | mmol | Equivalents |
|---|---|---|---|---|
| 1 γ-DLenDMA | 612.02 | 100 mg | 0.16 | 1 |
| 2 Dichloromethane | — | 10 mL | — | — |
| 3 Diethylzinc 1M in hexanes | — | 2.5 mL | 2.45 | 15 |
| 4 Diiodomethane | 267.84 | 1.29 g (400 μL) | 4.8 | 30 |

To a solution of γ-DLenDMA (Compound 61) (100 mg, 0.16 mmol) in anhydrous dichloromethane (10 mL) cooled to 0° C. under nitrogen was added a 1M solution of diethylzinc in hexanes (2.5 mL, 2.45 mmol). The solution was stirred for 1 hour at 0° C. then diiodomethane (1.29 g, 4.8 mmol) was added and the solution was stirred for 16 hours at room temperature under nitrogen. Upon completion by TLC (8% MeOH in CHCl$_3$), the solution was concentrated in vacuo to dryness. The residue was purified by column chromatography (10" L×0.5" D; eluted with 100% CHCl$_3$) to afford the product as a yellow oil (111 mg, 98%). See also, Tanaka et al., Bioorg. Med. Chem. Lett., 13:1037-1040 (2003).

Example 40

Lipid Encapsulation of siRNA

All siRNA molecules used in these studies were chemically synthesized and annealed using standard procedures.

In some embodiments, siRNA molecules were encapsulated into serum-stable nucleic acid-lipid particles (SNALP) composed of the following lipids: (1) the lipid conjugate PEG2000-C-DMA (3-N-[(-methoxypoly(ethylene glycol) 2000)carbamoyl]-1,2-dimyristyloxypropylamine); (2) one or more cationic lipids or salts thereof (e.g., cationic lipids of Formulas I-III of the invention and/or other cationic lipids described herein); (3) the phospholipid DPPC (1,2-dipalmitoyl-sn-glycero-3-phosphocholine) (Avanti Polar Lipids; Alabaster, Ala.); and (4) synthetic cholesterol (Sigma-Aldrich Corp.; St. Louis, Mo.) in the molar ratio 1.4:57.1:7.1:34.3, respectively. In other words, siRNA molecules were encapsulated into SNALP of the following "1:57" formulation: 1.4% PEG2000-C-DMA; 57.1% cationic lipid; 7.1% DPPC; and 34.3% cholesterol. It should be understood that the 1:57 formulation is a target formulation, and that the amount of lipid (both cationic and non-cationic) present and the amount of lipid conjugate present in the formulation may vary. Typically, in the 1:57 formulation, the amount of cationic lipid will be 57.1 mol %±5 mol %, and the amount of lipid conjugate will be 1.4 mol %±0.5 mol %, with the balance of the 1:57 formulation being made up of non-cationic lipid (e.g., phospholipid, cholesterol, or a mixture of the two).

In other embodiments, siRNA were encapsulated into SNALP composed of the following lipids: (1) the lipid conjugate PEG750-C-DMA (3-N-[(-Methoxypoly(ethylene glycol)750)carbamoyl]-1,2-dimyristyloxypropylamine); (2) one or more cationic lipids or salts thereof (e.g., cationic lipids of Formulas I-III of the invention and/or other cationic lipids described herein); (3) the phospholipid DPPC; and (4) synthetic cholesterol in the molar ratio 6.76:54.06:6.75:32.43, respectively. In other words, siRNA were encapsulated into SNALP of the following "7:54" formulation: 6.76 mol % PEG750-C-DMA; 54.06 mol % cationic lipid; 6.75 mol % DPPC; and 32.43 mol % cholesterol. Typically, in the 7:54 formulation, the amount of cationic lipid will be 54.06 mol %±5 mol %, and the amount of lipid conjugate will be 6.76 mol %±1 mol %, with the balance of the 7:54 formulation being made up of non-cationic lipid (e.g., phospholipid, cholesterol, or a mixture of the two).

For vehicle controls, empty particles with identical lipid composition may be formed in the absence of siRNA.

Example 41

Characterization of SNALP Formulations Containing Novel Cationic Lipids

This example demonstrates the efficacy of 1:57 SNALP formulations containing various novel cationic lipids of Formula I described herein with an siRNA targeting ApoB in a mouse liver model. The ApoB siRNA sequence used in this study is provided in Table 1.

TABLE 1

| siRNA | ApoB siRNA Sequence | % 2'OMe-Modified | % Modified in DS Region |
|---|---|---|---|
| ApoB-10164 | 5'-AGUGCAUCACACUGAAUACC-3' (SEQ ID NO: 1)<br>3'-GUUCACAGUAGUGUGACUUAU-5' (SEQ ID NO: 2) | 7/42 = 16.7% | 7/38 = 18.4% |

Column 1: The number after "ApoB" refers to the nucleotide position of the 5' base of the sense strand relative to the human ApoB mRNA sequence NM_000384. Column 2: 2'OMe nucleotides are indicated in bold and underlined. The 3'-overhangs on one or both strands of the siRNA molecule may alternatively comprise 1-4 deoxythymidine (dT) nucleotides, 1-4 modified and/or unmodified uridine (U) ribonucleotides, or 1-2 additional ribonucleotides having complementarity to the target sequence or the complementary strand thereof. Column 3: The number and percentage of 2'OMe-modified nucleotides in the siRNA molecule are provided. Column 4: The number and percentage of modified nucleotides in the double-stranded (DS) region of the siRNA molecule are provided.

1:57 SNALP formulations containing encapsulated ApoB siRNA were prepared as described in Section V above with the following cationic lipids: (1) DLin-C2K-DMA ("C2K"); (2) DLin-M-C3-DMA ("MC3"); (3) γ-LenMC3 ("g-LenMC3"); (4) CP-γ-LenMC3 ("CP-g-Len-MC3"); (5) LenMC3; and (6) CP-LenMC3. Table 2 provides exemplary features of these SNALP formulations, including particle size, polydispersity, and percent encapsulation.

TABLE 2

| Formulation | Initial Size (nm) | Final Size (nm) | Poly | Encaps | Total siRNA (mg/ml) |
|---|---|---|---|---|---|
| 1:57 C2K | 80 | 88 | 0.030 | 98% | 5.2 |
| 1:57 MC3 | 80 | 84 | 0.034 | 99% | 4.6 |
| 1:57 g-Len-MC3 | 76 | 79 | 0.052 | 98% | 4.8 |
| 1:57 CP-g-Len-MC3 | 79 | 82 | 0.037 | 100% | 5.1 |
| 1:57 Len-MC3 | 79 | 84 | 0.049 | 98% | 5.8 |
| 1:57 CP-Len-MC3 | 76 | 83 | 0.029 | 100% | 5.6 |

For dose response studies, SNALP formulations were administered by IV injection at 0.01 mg/kg, 0.033 mg/kg, or 0.1 mg/kg into female Balb/c mice (n=3 per group). Liver ApoB mRNA levels were evaluated at 48 hours after SNALP administration by a branched DNA assay (QuantiGene assay) to assess ApoB mRNA relative to the housekeeping gene GAPDH.

Figure 2:
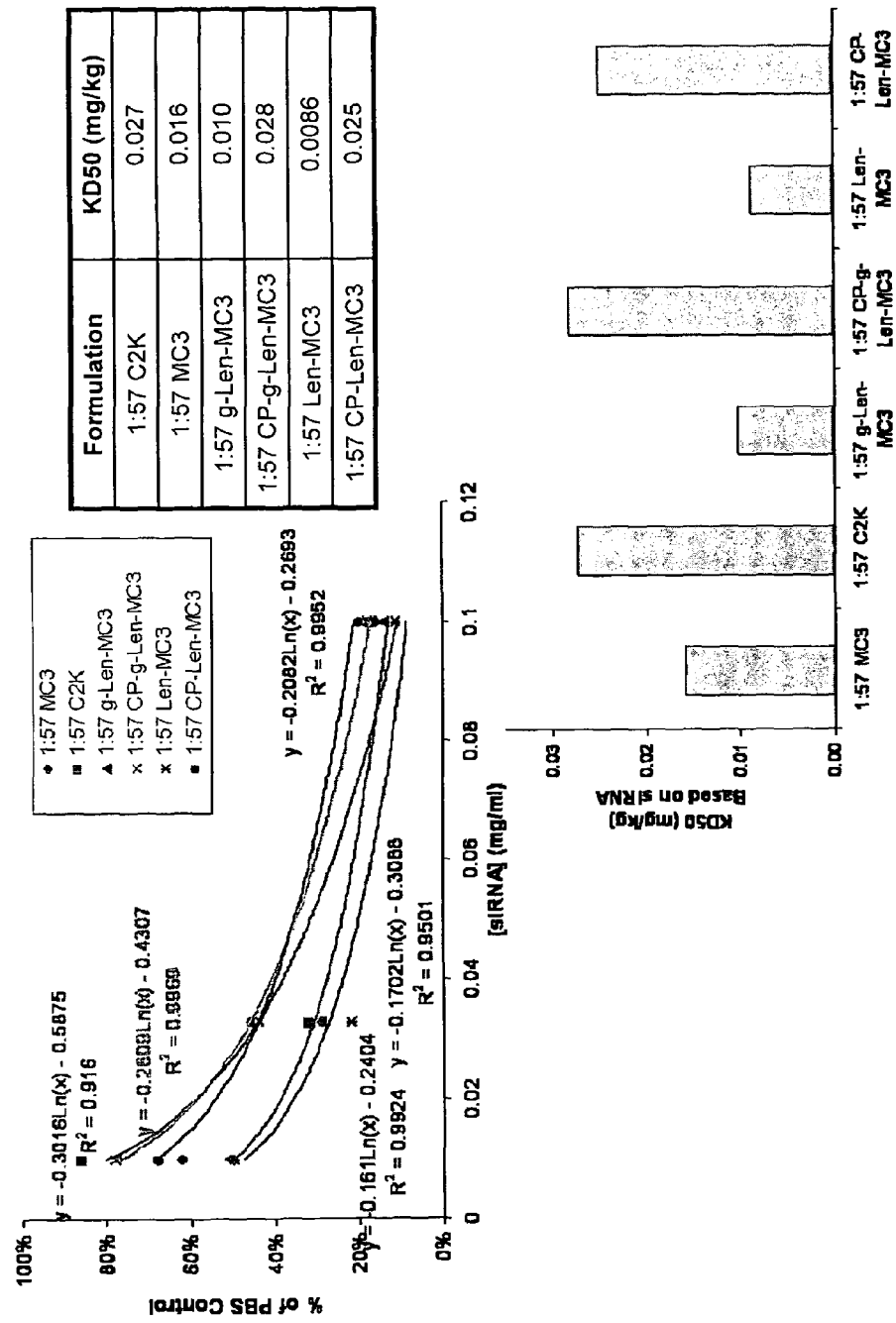
FIG. 2 shows the KD50 calculation and values obtained for each of the exemplary SNALP formulations containing cationic lipids of Formula I.

FIG. 1 shows a comparison of the liver ApoB mRNA knockdown activity of each of these SNALP formulations at three different doses (Error bars=SD). FIG. 2 shows the KD50 calculation and values obtained for each of these SNALP formulations. In particular, FIG. 1 shows that a SNALP formulation containing either MC3, γ-LenMC3, or LenMC3 displayed improved ApoB silencing activity compared to a SNALP formulation containing the C2K benchmark cationic lipid at all three doses. Notably, FIG. 2 illustrates that a SNALP formulation containing either MC3, γ-LenMC3, or LenMC3 displayed substantially lower KD50 values compared to a SNALP formulation containing the C2K benchmark cationic lipid. FIGS. 1 and 2 also show that a SNALP formulation containing either CP-γ-LenMC3 or CP-LenMC3 displayed similar ApoB silencing activity and similar KD50 values compared to a SNALP formulation containing the C2K benchmark cationic lipid.

Example 42

Characterization of Additional SNALP Formulations Containing Novel Cationic Lipids This example demonstrates the efficacy of 1:57 SNALP formulations containing various novel cyclic cationic lipids of Formula II described herein with an siRNA targeting ApoB in a mouse liver model. The ApoB siRNA sequence used in this study is provided in Table 1 above.

1:57 SNALP formulations containing encapsulated ApoB siRNA were prepared as described in Section V above with the following cationic lipids: (1) DLin-C2K-DMA ("C2K"); (2) DLin-M-C3-DMA ("MC3"); (3) LenMC3 ("DLen-MC3"); (4) CP-LenMC3 ("CP-DLen-MC3"); (5) D-γ-Len-C2K-DMA ("g-DLen-C2K-DMA"); (6) CP-D-γ-Len-C2K-DMA ("CP-g-DLen-C2K-DMA"); (7) DLen-C2K-DMA; and (8) CP-DLen-C2K-DMA.

For dose response studies, SNALP formulations were administered by IV injection at 0.01 mg/kg, 0.033 mg/kg, or 0.1 mg/kg into female Balb/c mice (n=3 per group). Liver ApoB mRNA levels were evaluated at 48 hours after SNALP administration by a branched DNA assay (QuantiGene assay) to assess ApoB mRNA relative to the housekeeping gene GAPDH.

Figure 3:
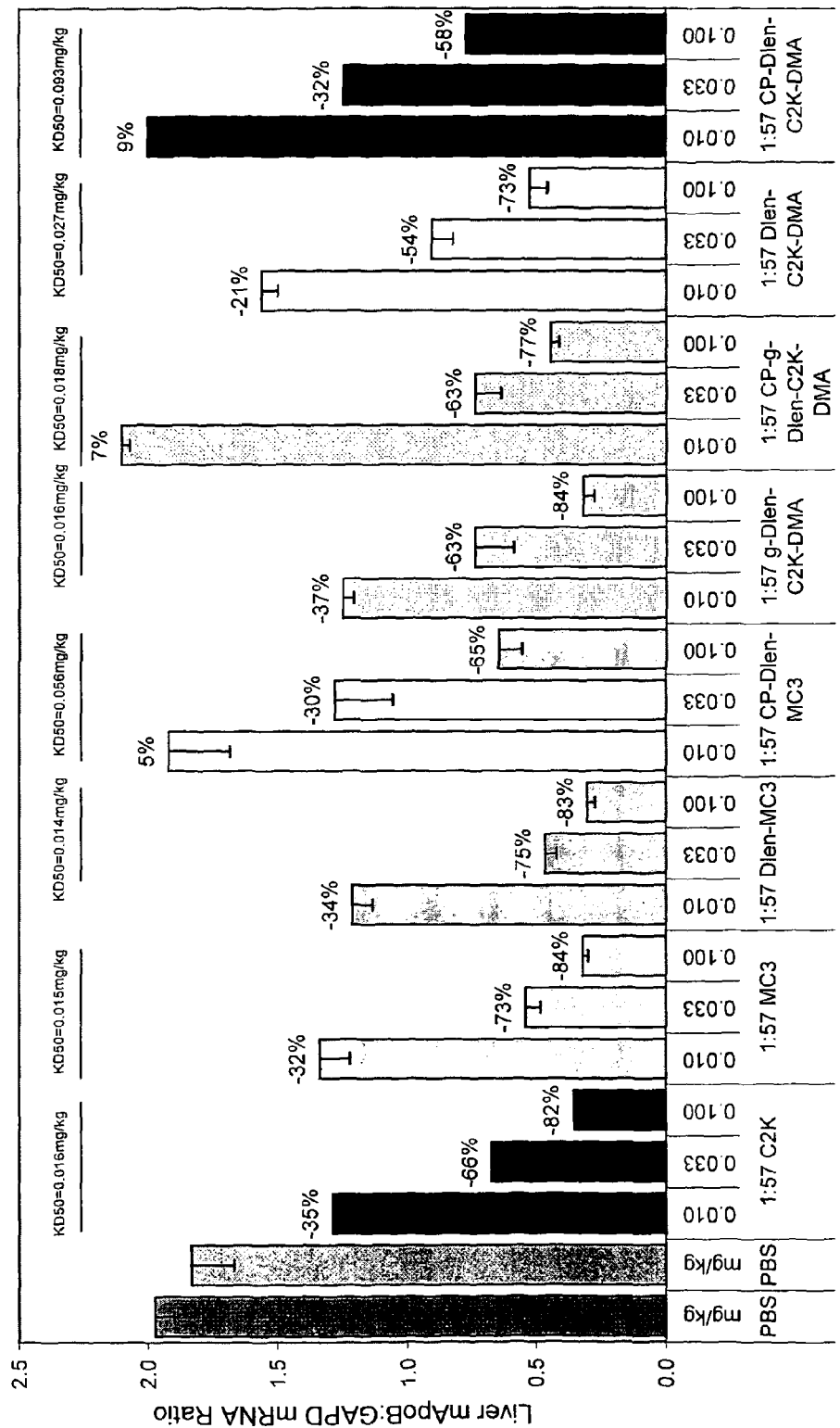
FIG. 3 shows a comparison of the liver ApoB mRNA knockdown activity of exemplary SNALP formulations containing cationic lipids of Formulas I-II.

FIG. 3 shows a comparison of the liver ApoB mRNA knockdown activity of each of these SNALP formulations at three different doses (Error bars=SD), as well as the KD50 values obtained for each of these formulations. In particular, FIG. 3 shows that a SNALP formulation containing CP-g-DLen-C2K-DMA displayed similar ApoB silencing activity at higher doses and similar KD50 value compared to a SNALP formulation containing the C2K benchmark cationic lipid. Furthermore, FIG. 3 shows that a SNALP formulation containing CP-DLen-C2K-DMA displayed considerable potency in silencing ApoB mRNA expression. The SNALP formulation containing CP-DLen-C2K-DMA also displayed a more favorable toxicity profile over a SNALP formulation containing the C2K benchmark cationic lipid when evaluated using various tolerability assessments such as, for example, liver enzyme levels (e.g., alanine aminotransferase (ALT) levels, aspartate aminotransferase (AST) levels, sorbital dehydrogenase (SDH) levels, etc.), body weight, globulin response, platelet count, number or ratio of neutrophils to lymphocytes, animal observations, alkaline phosphatase levels, bilirubin levels, and gamma glutamyl-transferase levels. In particular, mice that were administered SNALP containing CP-DLen-C2K-DMA displayed less body weight loss, a lower increase in liver enzyme levels, and a more favorable neutrophil to lymphocyte ratio compared to mice that were administered SNALP containing C2K. In addition, SNALP formulations containing the novel cyclic cationic lipids of Formula II displayed improved stability over SNALP formulations containing their polyunsaturated counterparts when evaluated under various different storage conditions using techniques such as, e.g., analysis of any change in particle size over time and/or determination of any degradation of the nucleic acid payload and/or cationic lipid.

Example 43

Characterization of Additional SNALP Formulations Containing Novel Cationic Lipids This example demonstrates the efficacy of 1:57 SNALP formulations containing various novel cyclic cationic lipids of Formula III described herein with an siRNA targeting ApoB in a mouse liver model. The ApoB siRNA sequence used in this study is provided in Table 1 above.

1:57 SNALP formulations containing encapsulated ApoB siRNA were prepared as described in Section V above with the following cationic lipids: (1) DLinDMA; (2) CP-DLinDMA; (3) CP-DLenDMA; (4) CP-γ-DLenDMA ("CP-g-DLenDMA"); (5) CP-DODMA; (6) CP-DPetroDMA; and (7) C2-TLinDMA. Table 3 provides exemplary features of these SNALP formulations, including particle size, polydispersity, and percent encapsulation.

TABLE 3

|  | Size (nm) | Poly | Encapsulation % |
| --- | --- | --- | --- |
| 1:57 DLinDMA | 76.11 | 0.045 | 81 |
| 1:57 CP-DODMA | 77.77 | 0.034 | 87 |
| 1:57 CP-DPetroDMA | 75.83 | 0.035 | 90 |
| 1:57 CP-DLinDMA | 72.39 | 0.028 | 90 |
| 1:57 CP-DLenDMA | 75.82 | 0.024 | 89 |
| 1:57 CP-g-DLenDMA | 68.15 | 0.062 | 83 |

Each SNALP formulation (6:1 L:D) was administered by intravenous (IV) injection at 0.1 mg/kg into female Balb/c mice (n=3 per group). Liver ApoB mRNA levels were evaluated at 48 hours after SNALP administration by a branched DNA assay (QuantiGene assay) to assess ApoB mRNA relative to the housekeeping gene GAPDH.

Figure 4:
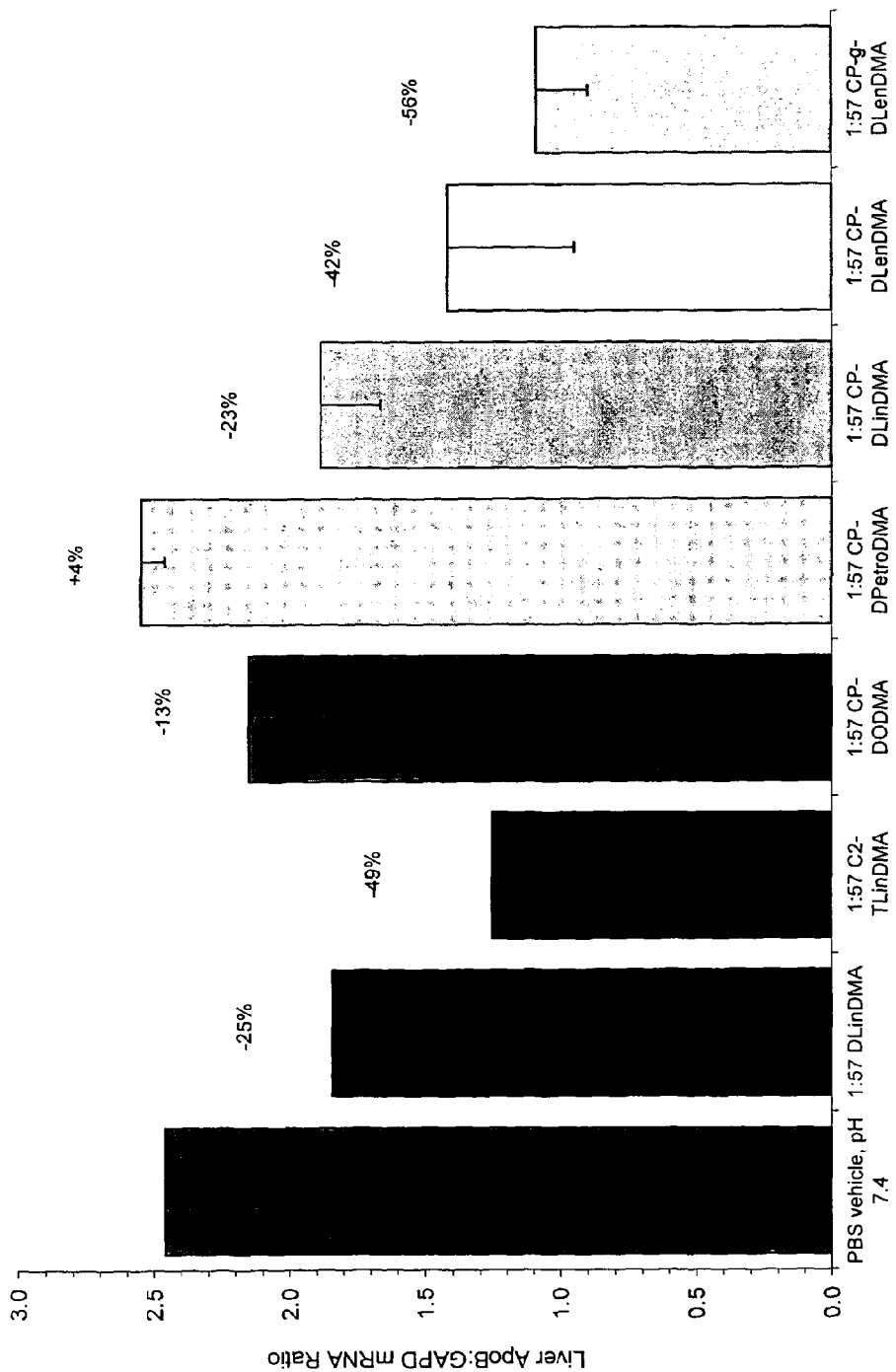
FIG. 4 shows a comparison of the liver ApoB mRNA knockdown activity of exemplary SNALP formulations containing cationic lipids of Formulas III.

FIG. 4 shows a comparison of the liver ApoB mRNA knockdown activity of each of these SNALP formulations (Error bars=SD). In particular, FIG. 4 shows that a SNALP formulation containing either CP-DLinDMA, CP-DLenDMA, or CP-γ-DLenDMA displayed similar or greater ApoB silencing activity compared to a SNALP formulation containing the DLinDMA benchmark cationic lipid. Notably, SNALP formulations containing the novel cyclic cationic lipids of Formula III displayed improved stability over SNALP formulations containing their polyunsaturated counterparts when evaluated under various different storage conditions using techniques such as, e.g., analysis of any change in particle size over time and/or determination of any degradation of the nucleic acid payload and/or cationic lipid.

Example 44

Characterization of Additional SNALP Formulations Containing Novel Cationic Lipids This example demonstrates the efficacy of 1:57 SNALP formulations containing various additional novel cationic lipids of Formulas I-II described herein with an siRNA targeting ApoB in a mouse liver model. The ApoB siRNA sequence used in this study is provided in Table 1 above.

1:57 SNALP formulations containing encapsulated ApoB siRNA were prepared as described in Section VI above with the following cationic lipids: (1) DLin-C2K-DMA ("C2K"); (2) MC2MC; (3) MC3 Ether; (4) Pan-MC3; (5) CP-MC3; and (6) CP-C2K.

SNALP formulations were administered by IV injection at 0.05 mg/kg into female Balb/c mice (n=3 per group). Liver ApoB mRNA levels were evaluated at 48 hours after SNALP administration by a branched DNA assay (QuantiGene assay) to assess ApoB mRNA relative to the housekeeping gene GAPDH.

Figure 5:
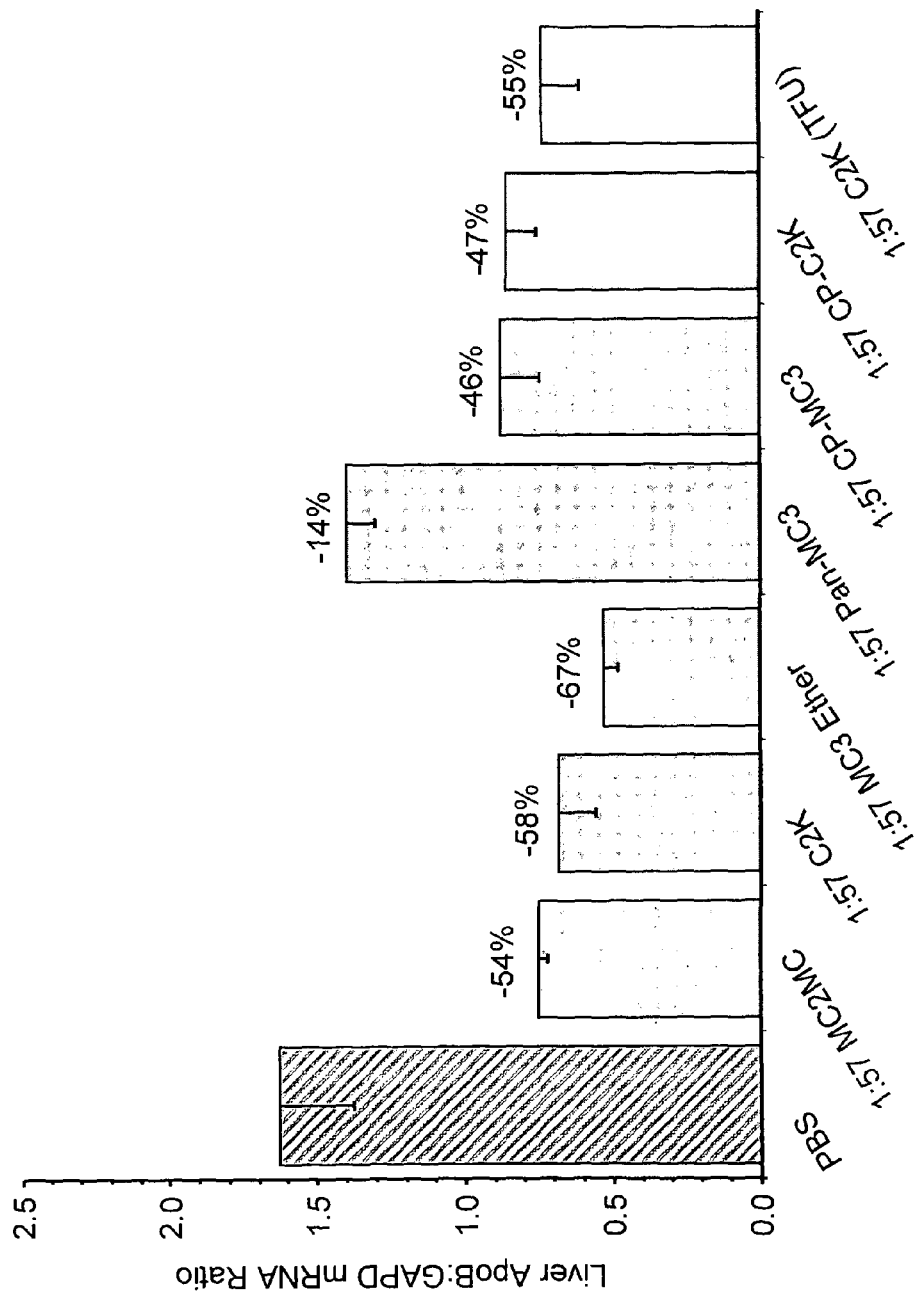
FIG. 5 shows a comparison of the liver ApoB mRNA knockdown activity of additional exemplary SNALP formulations containing cationic lipids of Formulas I-II.

FIG. 5 shows a comparison of the liver ApoB mRNA knockdown activity of each of these SNALP formulations (Error bars=SD). In particular, FIG. 5 shows that a SNALP formulation containing MC3 Ether displayed unexpectedly improved ApoB silencing activity compared to a SNALP formulation containing the C2K benchmark cationic lipid. FIG. 5 also shows that a SNALP formulation containing MC2MC displayed similar ApoB silencing activity compared to SNALP containing the C2K benchmark cationic lipid. In addition, FIG. 5 shows that a SNALP formulation containing either CP-MC3 or CP-C2K displayed similar ApoB silencing activity compared to a SNALP formulation containing the C2K benchmark cationic lipid. Notably, SNALP formulations containing these novel cyclic cationic lipids displayed improved stability over SNALP formulations containing their polyunsaturated counterparts when evaluated under various different storage conditions using techniques such as, e.g., analysis of any change in particle size over time and/or determination of any degradation of the nucleic acid payload and/or cationic lipid.

Example 45

In Vivo Activity of Modified APOB siRNAs in SNALP Formulations

This example demonstrates that APOB siRNAs having the same nucleotide sequence as ApoB-8 (the APOB siRNA shown in Table 1, and also called "ApoB-10164") but which have an increased number of modified nucleotides are at least as effective as ApoB-8 in knocking down ApoB mRNA expression.

Inflammatory response to SNALP formulations containing APOB siRNA can be evaluated by measuring cytokine induction in human whole blood samples obtained from subjects. In certain instances, the SNALPs can contain either no siRNA payload ("empty") or APOB siRNA payload (e.g., one or more of the APOB siRNAs shown in Table 4). Briefly, fresh blood can be isolated, immediately diluted 1:1 with 0.9% saline solution, and plated at 0.45 mL/well into 48 well tissue culture treated plates. SNALPs can be diluted in formulation PBS and added to the plated blood samples at a concentration of either 300 nM or 1200 nM. After 24 hours, the plates can be centrifuged at 1200 rpm for 20 minutes and the supernatant (plasma) collected. Cytokine induction (e.g., induction of TNF, IL-8, etc.) can be measured by ELISA and/or Cytometric Bead Array.

APOB siRNAs of the same nucleotide sequence as ApoB-8 (also referred to in this example as "1/1") were modified to incorporate an increasing number and alternate patterns of 2'OMe nucleotides. Six different sense strands (S-1 to S-6) and six different antisense strands (AS-1 to AS-6) were designed. Sense strand 1 (S-1) is the same pattern of modification as the ApoB-8 sense strand (SEQ ID NO:1), and antisense strand 1 (AS-1) is the same pattern of modification as the ApoB-8 antisense strand (SEQ ID NO:2), and were generated as synthesis controls. APOB double-stranded siRNAs were generated by mix and match annealing of sense strands 2-6 (S-2 to S-6) and antisense strands 2-6 (AS-2 to AS-6). Compared to siApoB-8, the number of modifications for double-stranded APOB siRNAs increased from 7 to about 9-12 in the double-stranded region. Additionally, some of the patterns of modification include 2'OMe-modified nucleotides in the 3' overhang of one or both strands of the siRNA, such that the number of modifications are further increased to about 10-14 in the entire siRNA molecule. Table 4 shows modified APOB sense strands 1-6 (S-1 to S-6), modified ApoB antisense strands 1-6 (AS-1 to AS-6), and the double-stranded APOB siRNAs that resulted from the mix and match annealing of S-2 to S-6 with AS-2 to AS-6.

TABLE 4

| siRNA | APOB siRNA Sequence | | % 2'OMe-Modified | % Modified in DS Region |
|---|---|---|---|---|
| S-1 | 5'-AGU<u>G</u>UCA<u>U</u>CACAC<u>U</u>GAAUACC-3' | (SEQ ID NO: 1) | 3/21 = 14.3% | 3/19 = 15.8% |
| S-2 | 5'-AGU<u>G</u>UCA<u>U</u>CACAC<u>U</u>GAA<u>U</u>ACC-3' | (SEQ ID NO: 3) | 5/21 = 23.8% | 5/19 = 26.3% |
| S-3 | 5'-AGU<u>G</u>UCA<u>U</u>CACAC<u>U</u>GA<u>AU</u>ACC-3' | (SEQ ID NO: 4) | 6/21 = 28.6% | 6/19 = 31.6% |
| S-4 | 5'-A<u>G</u>U<u>G</u>UCA<u>U</u>CACACU<u>G</u>AA<u>U</u>ACC-3' | (SEQ ID NO: 5) | 5/21 = 23.8% | 5/19 = 26.3% |
| S-5 | 5'-A<u>GUG</u>UCA<u>U</u>CACAC<u>U</u>GA<u>AU</u>ACC-3' | (SEQ ID NO: 6) | 7/21 = 33.3% | 7/19 = 36.8% |
| S-6 | 5'-A<u>G</u>U<u>G</u>UCA<u>U</u>CACAC<u>U</u>GAA<u>U</u>ACC-3' | (SEQ ID NO: 7) | 7/21 = 33.3% | 7/19 = 36.8% |
| AS-1 | 5'-UAU<u>U</u>CA<u>G</u>U<u>G</u>UGAUGACAC<u>U</u>UG-3' | (SEQ ID NO: 2) | 4/21 = 19.0% | 4/19 = 21.1% |
| AS-2 | 5'-UAU<u>U</u>CAGU<u>G</u>U<u>G</u>AUGACAC<u>U</u>UG-3' | (SEQ ID NO: 8) | 5/21 = 23.8% | 5/19 = 26.3% |
| AS-3 | 5'-UAU<u>U</u>CA<u>G</u>U<u>G</u>UGAUGACAC<u>U</u>UG-3' | (SEQ ID NO: 9) | 5/21 = 23.8% | 5/19 = 26.3% |
| AS-4 | 5'-UAU<u>U</u>CA<u>G</u>U<u>G</u>UGAUGACAC<u>UUG</u>-3' | (SEQ ID NO: 10) | 6/21 = 28.6% | 4/19 = 21.1% |
| AS-5 | 5'-UAU<u>U</u>CA<u>GUG</u>U<u>G</u>AUGACAC<u>UUG</u>-3' | (SEQ ID NO: 11) | 7/21 = 33.3% | 5/19 = 26.3% |
| AS-6 | 5'-UAU<u>U</u>CA<u>GUG</u>U<u>G</u>AUGACAC<u>UUG</u>-3' | (SEQ ID NO: 12) | 7/21 = 33.3% | 5/19 = 26.3% |
| 1/1 | 5'-AGU<u>G</u>UCA<u>U</u>CACAC<u>U</u>GAAUACC-3'<br>3'-GU<u>U</u>CACAGUAGU<u>G</u>U<u>G</u>ACUUAU-5' | (SEQ ID NO: 1)<br>(SEQ ID NO: 2) | 7/42 = 16.7% | 7/38 = 18.4% |
| 2/2 | 5'-AGU<u>G</u>UCA<u>U</u>CACAC<u>U</u>GAA<u>U</u>ACC-3'<br>3'-GU<u>U</u>CACA<u>G</u>UA<u>G</u>U<u>G</u>UGACU<u>U</u>AU-5' | (SEQ ID NO: 3)<br>(SEQ ID NO: 8) | 10/42 = 23.8% | 10/38 = 26.3% |

TABLE 4-continued

| siRNAAPOB | siRNA Sequence | % 2'OMe-Modified | % Modified in DS Region |
|---|---|---|---|
| 2/3 | 5'-AGUGUCAUCACACUGAAUACC-3' (SEQ ID NO:3)<br>3'-GUUCACAGUAGUGUGACUUAU-5' (SEQ ID NO: 9) | 10/42 = 23.8% | 10/38 = 26.3% |
| 3/2 | 5'-AGUGUCAUCACACUGAAUACC-3' (SEQ ID NO: 4)<br>3'-GUUCACAGUAGUGUGACUUAU-5' (SEQ ID NO: 8) | 11/42 = 26.2% | 11/38 = 28.9% |
| 3/3 | 5'-AGUGUCAUCACACUGAAUACC-3' (SEQ ID NO: 4)<br>3'-GUUCACAGUAGUGUGACUUAU-5' (SEQ ID NO: 9) | 11/42 = 26.2% | 11/38 = 28.9% |
| 4/2 | 5'-AGUGUCAUCACACUGAAUACC-3' (SEQ ID NO: 5)<br>3'-GUUCACAGUAGUGUGACUUAU-5' (SEQ ID NO: 8) | 10/42 = 23.8% | 10/38 = 26.3% |
| 4/3 | 5'-AGUGUCAUCACACUGAAUACC-3' (SEQ ID NO: 5)<br>3'-GUUCACAGUAGUGUGACUUAU-5' (SEQ ID NO: 9) | 10/42 = 23.8% | 10/38 = 26.3% |
| 5/2 | 5'-AGUGUCAUCACACUGAAUACC-3' (SEQ ID NO: 6)<br>3'-GUUCACAGUAGUGUGACUUAU-5' (SEQ ID NO: 8) | 12/42 = 28.6 | 12/38 = 31.6% |
| 5/3 | 5'-AGUGUCAUCACACUGAAUACC-3' (SEQ ID NO: 6)<br>3'-GUUCACAGUAGUGUGACUUAU-5' (SEQ ID NO: 9) | 12/42 = 28.6 | 12/38 = 31.6% |
| 6/2 | 5'-AGUGUCAUCACACUGAAUACC-3' (SEQ ID NO: 7)<br>3'-GUUCACAGUAGUGUGACUUAU-5' (SEQ ID NO: 8) | 12/42 = 28.6 | 12/38 = 31.6% |
| 6/3 | 5'-AGUGUCAUCACACUGAAUACC-3' (SEQ ID NO: 7)<br>3'-GUUCACAGUAGUGUGACUUAU-5' (SEQ ID NO: 9) | 12/42 = 28.6 | 12/38 = 31.6% |
| 2/4 | 5'-AGUGUCAUCACACUGAAUACC-3' (SEQ ID NO: 3)<br>3'-GUUCACAGUAGUGUGACUUAU-5' (SEQ ID NO: 10) | 11/42 = 26.2% | 9/38 = 23.7% |
| 2/5 | 5'-AGUGUCAUCACACUGAAUACC-3' (SEQ ID NO: 3)<br>3'-GUUCACAGUAGUGUGACUUAU-5' (SEQ ID NO: 11) | 12/42 = 28.6% | 10/38 = 26.3% |
| 2/6 | 5'-AGUGUCAUCACACUGAAUACC-3' (SEQ ID NO: 3)<br>3'-GUUCACAGUAGUGUGACUUAU-5' (SEQ ID NO: 12) | 12/42 = 28.6% | 10/38 = 26.3% |
| 3/4 | 5'-AGUGUCAUCACACUGAAUACC-3' (SEQ ID NO: 4)<br>3'-GUUCACAGUAGUGUGACUUAU-5' (SEQ ID NO: 10) | 12/42 = 28.6% | 10/38 = 26.3% |
| 3/5 | 5'-AGUGUCAUCACACUGAAUACC-3' (SEQ ID NO: 4)<br>3'-GUUCACAGUAGUGUGACUUAU-5' (SEQ ID NO: 11) | 13/42 = 31.0% | 11/38 = 28.9% |
| 3/6 | 5'-AGUGUCAUCACACUGAAUACC-3' (SEQ ID NO: 4)<br>3'-GUUCACAGUAGUGUGACUUAU-5' (SEQ ID NO: 12) | 13/42 = 31.0% | 11/38 = 28.9% |
| 4/4 | 5'-AGUGUCAUCACACUGAAUACC-3' (SEQ ID NO: 5)<br>3'-GUUCACAGUAGUGUGACUUAU-5' (SEQ ID NO: 10) | 11/42 = 26.2% | 9/38 = 23.7% |
| 4/5 | 5'-AGUGUCAUCACACUGAAUACC-3' (SEQ ID NO: 5)<br>3'-GUUCACAGUAGUGUGACUUAU-5' (SEQ ID NO: 11) | 12/42 = 28.6% | 10/38 = 26.3% |
| 4/6 | 5'-AGUGUCAUCACACUGAAUACC-3' (SEQ ID NO: 5)<br>3'-GUUCACAGUAGUGUGACUUAU-5' (SEQ ID NO: 12) | 12/42 = 28.6% | 10/38 = 26.3% |
| 5/4 | 5'-AGUGUCAUCACACUGAAUACC-3' (SEQ ID NO: 6)<br>3'-GUUCACAGUAGUGUGACUUAU-5' (SEQ ID NO: 10) | 13/42 = 31.0% | 11/38 = 28.9% |
| 5/5 | 5'-AGUGUCAUCACACUGAAUACC-3' (SEQ ID NO: 6)<br>3'-GUUCACAGUAGUGUGACUUAU-5' (SEQ ID NO: 11) | 14/42 = 33.3% | 12/38 = 31.6% |
| 5/6 | 5'-AGUGUCAUCACACUGAAUACC-3' (SEQ ID NO: 6)<br>3'-GUUCACAGUAGUGUGACUUAU-5' (SEQ ID NO: 12) | 14/42 = 33.3% | 12/38 = 31.6% |
| 6/4 | 5'-AGUGUCAUCACACUGAAUACC-3' (SEQ ID NO: 7)<br>3'-GUUCACAGUAGUGUGACUUAU-5' (SEQ ID NO: 10) | 13/42 = 31.0% | 11/38 = 28.9% |

TABLE 4-continued

| siRNA APOB | siRNA Sequence | | % 2'OMe-Modified | % Modified in DS Region |
|---|---|---|---|---|
| 6/5 | 5'-AGUGUCAUCACACUGAAUACC-3'<br>3'-GUUCACAGUAGUGUGACUUAU-5' | (SEQ ID NO: 7)<br>(SEQ ID NO: 11) | 14/42 = 33.3% | 12/38 = 31.6% |
| 6/6 | 5'-AGUGUCAUCACACUGAAUACC-3'<br>3'-GUUCACAGUAGUGUGACUUAU-5' | (SEQ ID NO: 7)<br>(SEQ ID NO: 12) | 14/42 = 33.3% | 12/38 = 31.6% |

Column 1: Sense strand, antisense strand, or sense strand/antisense strand. APOB sense strands 1-6 and antisense strands 1-6 were designed with alternate patterns of modification. APOB sense strands 2-6 were mix and match annealed to APOB antisense strands 2-6 (e.g., sense strand 2 annealed to antisense strand 5 = 2/5). 1/1, which is the same as ApoB-10164 in Example 5, was a synthesis control. Column 2: 2'OMe nucleotides are indicated in bold and underlined. The 3'-overhangs on one or both strands of the siRNA molecule may alternatively comprise 1-4 deoxythymidine (dT) nucleotides, 1-4 modified and/or unmodified uridine (U) ribonucleotides, or 1-2 additional ribonucleotides having complementarity to the target sequence or the complementary strand thereof. Column 3: The number and percentage of 2'OMe-modified nucleotides in the siRNA molecule are provided. Column 4: The number and percentage of modified nucleotides in the double-stranded (DS) region of the siRNA molecule are provided.

1:57 SNALP formulations containing encapsulated APOB duplexes as described in Table 4 can be prepared at 3 mg scale with the cationic lipid DLin-M-C3-DMA ("MC3"), MC3 Ether, MC2MC, and/or CP-DLen-C2K-DMA. For the in vitro assays, transfections of human primary hepatocytes can be performed on Primaria plates according to standard protocols using a SNALP dose range of about 0.125-0.00781 µg/mL. Cells can be plated at 50,000 cells/well and incubated overnight at 37° C. At transfection, SNALP can be diluted to the desired dose and pre-incubated with serum at 37° C. for 1 hour, then the cell media can be replaced with 80 µL fresh media and 20 µL pre-incubated SNALP. The cells can be incubated with SNALP for 24 hours, then the media can be removed and the cells lysed for QuantiGene Analysis. Quantitation of mRNA levels can be accomplished using individual standard curves.

Figure 6:
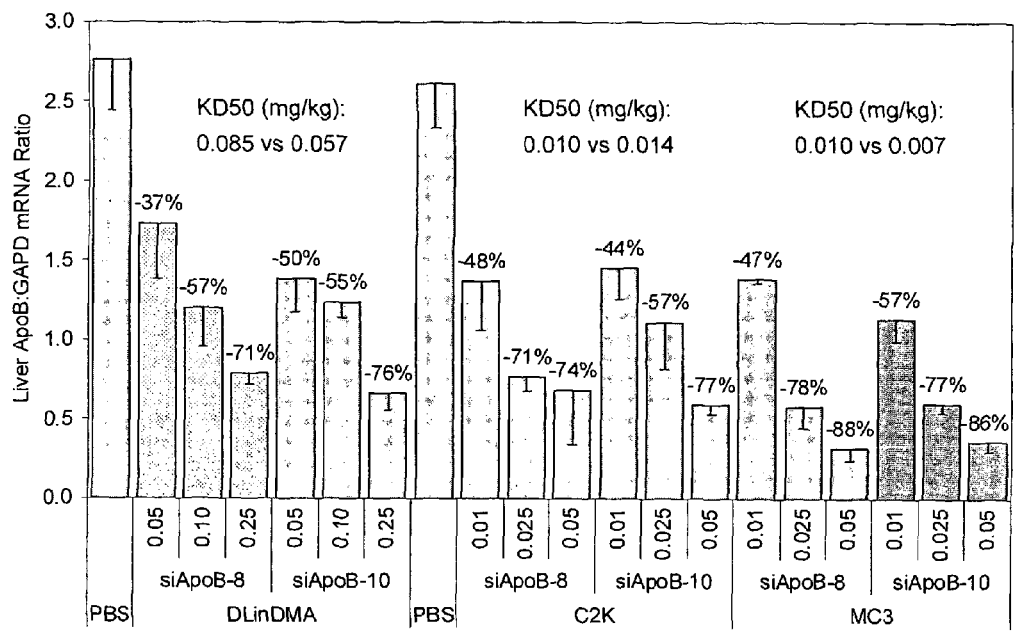
FIG. 6 shows a dose response evaluation of three different doses of exemplary APOB SNALP formulations containing either DLinDMA, C2K, or MC3 and either APOB siRNA 1/1 ("siApoB-8") or APOB siRNA 3/5 ("siApoB-10") on liver ApoB mRNA knockdown activity.

FIG. 6 shows the silencing activity of APOB siRNA 1/1 ("siApoB-8") or APOB siRNA ⅗ ("siApoB-10") formulated in 1:57 SNALP containing DLinDMA, DLin-C2K-DMA ("C2K"), or DLin-M-C3-DMA ("MC3"). For these dose response studies, SNALP formulations were administered by IV injection at 0.05, 0.10, or 0.25 mg/kg for DLinDMA and at 0.01, 0.025, or 0.05 mg/kg for C2K or MC3 into female Balb/c mice (n=4 per group). Liver ApoB mRNA levels were evaluated at 48 hours after SNALP administration (Error bars=SD). In particular, FIG. 6 shows that DLinDMA SNALP formulations containing either siApoB-8 or siApoB-10 displayed similar silencing activities based on the KD$_{50}$ for liver ApoB mRNA silencing in mice. Similarly, FIG. 6 shows that C2K SNALP formulations containing either siApoB-8 or siApoB-10 displayed similar silencing activities based on the KD$_{50}$ for liver ApoB mRNA silencing in mice. Likewise, FIG. 6 shows that MC3 SNALP formulations containing either siApoB-8 or siApoB-10 displayed similar silencing activities based on the KD$_{50}$ for liver ApoB mRNA silencing in mice. Notably, MC3 SNALP formulations containing either siApoB-8 or siApoB-10 were more potent than the corresponding DLinDMA or C2K SNALP formulations based on a comparison of their KD$_{50}$ values. Furthermore, FIG. 6 shows that increasing the number of modifications, from 7 in siApoB-8 to 13 in siApoB-10, does not decrease activity, and in some cases increases silencing activity (see, e.g., MC3 SNALP KD$_{50}$ values shown in FIG. 6).

Example 46

Characterization of SNALP Formulations Containing Novel Cationic Lipids

This example demonstrates the efficacy of 1:57 SNALP formulations containing various novel cationic lipids of Formula I described herein with an siRNA targeting ApoB in a mouse liver model. The ApoB siRNA sequence used in this study is provided in Table 5.

TABLE 5

| siRNA | ApoB siRNA Sequence | | % 2'OMe-Modified | % Modified in DS Region |
|---|---|---|---|---|
| ApoB-10164 | 5'-AGUGUCAUCACACUGAAUACC-3'<br>3'-GUUCACAGUAGUGUGACUUAU-5' | (SEQ ID NO: 1)<br>(SEQ ID NO: 2) | 7/42 = 16.7% | 7/38 = 18.4% |

Column 1: The number after "ApoB" refers to the nucleotide position of the 5' base of the sense strand relative to the human ApoB mRNA sequence NM_000384. Column 2: 2'OMe nucleotides are indicated in bold and underlined. The 3'-overhangs on one or both strands of the siRNA molecule may alternatively comprise 1-4 deoxythymidine (dT) nucleotides, 1-4 modified and/or unmodified uridine (U) ribonucleotides, or 1-2 additional ribonucleotides having complementarity to the target sequence or the complementary strand thereof. Column 3: The number and percentage of 2'OMe-modified nucleotides in the siRNA molecule are provided. Column 4: The number and percentage of modified nucleotides in the double-stranded (DS) region of the siRNA molecule are provided.

1:57 SNALP formulations containing encapsulated ApoB siRNA were prepared as described in Section VI above with DLin-C2K-DMA ("C2K") or Compound 1 (DLin-M-C3-DMA ("MC3")), 4, 5, 8, 9, 10, 11, 13, 15, 17, 18, 20, 22, 23, 25, 27, 28, 29, 30, 31, 34, 35, 40, or 41.

SNALP formulations were administered by IV injection at 0.033 mg/kg or at 0.05 mg/kg into Balb/c mice (n=3 per group). Liver ApoB mRNA levels were evaluated at 48 hours after SNALP administration by a branched DNA assay (QuantiGene assay) to assess ApoB mRNA relative to the housekeeping gene GAPDH.

Table 6 shows a comparison of the liver ApoB mRNA knockdown activity of each of these SNALP formulations. As non-limiting examples, Table 6 illustrates that a SNALP formulation containing Compound 1, 4, 8, 13, 15, 27, 28, or 35 displayed unexpectedly improved ApoB silencing activity compared to a SNALP formulation containing the C2K benchmark cationic lipid when administered at the same dose.

TABLE 6

Effect on ApoB:GAPD of 1:57 SNALP Containing Novel Cationic Lipids Administered at 0.05 or 0.033 mg/kg to Balb/c Mice (48 h, n = 3)

| Compound | Dose (mg/kg) | ApoB knockdown relative to PBS control (%) |
|---|---|---|
| C2K | 0.033 | −51 |
|  | 0.05 | −66 |
| 1 (MC3) | 0.033 | −71 |
|  | 0.05 | −81 |
| 4 | 0.033 | −78 |
| 5 | 0.033 | −56 |
| 8 | 0.033 | −71 |
| 9 | 0.033 | −54 |
| 10 | 0.033 | −50 |
| 11 | 0.05 | −54 |
| 13 | 0.033 | −69 |
| 15 | 0.05 | −77 |
| 17 | 0.05 | −14 |
| 18 | 0.05 | −46 |
| 20 | 0.05 | −50 |
| 22 | 0.033 | −30 |
| 23 | 0.033 | −33 |
| 25 | 0.05 | −66 |
| 27 | 0.033 | −66 |
| 28 | 0.033 | −68 |
| 29 | 0.05 | −59 |
| 30 | 0.05 | −65 |
| 31 | 0.05 | −62 |
| 34 | 0.033 | −41 |
| 35 | 0.033 | −78 |
| 40 | 0.05 | −58 |
| 41 | 0.033 | −52 |

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications, patents, PCT publications, and Genbank Accession Nos., are incorporated herein by reference for all purposes.

---

What is claimed is:

1. A nucleic acid-lipid particle comprising:
   (a) an siRNA that silences Apolipoprotein B (APOB) expression,
       wherein the siRNA consists of the following sense and antisense strand sequences:

5'-AGUGUCAUCACACUGAAUACC-3'   (SEQ ID NO: 4)

3'-GUUCACAGUAGUGUGACUUAU-5',   (SEQ ID NO: 11)

wherein the bolded and underlined nucleotides are 2'OMe nucleotides;
   (b) a cationic lipid of Formula I having the following structure:

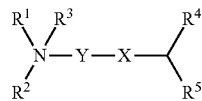

(I)

or salts thereof, wherein:
   $R^1$ and $R^2$ are either the same or different and are independently hydrogen (H) or an optionally substituted $C_1$-$C_6$ alkyl, $C_2$-$C_6$ alkenyl, or $C_2$-$C_6$ alkynyl, or $R^1$ and $R^2$ may join to form an optionally substituted heterocyclic ring;
   $R^3$ is either absent or is hydrogen (H) or a $C_1$-$C_6$ alkyl to provide a quaternary amine;
   $R^4$ and $R^5$ are either the same or different and are independently an optionally substituted $C_{10}$-$C_{24}$ alkyl, $C_{10}$-$C_{24}$ alkenyl, $C_{10}$-$C_{24}$ alkynyl, or $C_{10}$-$C_{24}$ acyl;
   X is O, S, N($R^6$), C(O), C(O)O, OC(O), C(O)N($R^6$), N($R^6$)C(O), OC(O)N($R^6$), N($R^6$)C(O)O, C(O)S, C(S)O, S(O), S(O)(O), C(S), or an optionally substituted heterocyclic ring, wherein $R^6$ is hydrogen (H) or an optionally substituted $C_1$-$C_{10}$ alkyl, $C_2$-$C_{10}$ alkenyl, or $C_2$-$C_{10}$ alkynyl; and
   Y is either absent or is an optionally substituted $C_1$-$C_6$ alkyl, $C_2$-$C_6$ alkenyl, or $C_2$-$C_6$ alkynyl; and
   (c) a non-cationic lipid.

2. The nucleic acid-lipid particle of claim 1, wherein $R^1$ and $R^2$ are independently selected from the group consisting of a methyl group and an ethyl group.

3. The nucleic acid-lipid particle of claim 1, wherein $R^1$ and $R^2$ are both methyl groups.

4. The nucleic acid-lipid particle of claim 1, wherein $R^1$ and $R^2$ are joined to form an optionally substituted heterocyclic ring having from 2 to 5 carbon atoms and from 1 to 3 heteroatoms selected from the group consisting of nitrogen (N), oxygen (O), sulfur (S), and combinations thereof.

5. The nucleic acid-lipid particle of claim 1, wherein X is O, C(O)O, C(O)N($R^6$), N($R^6$)C(O)O, or C(O)S.

6. The nucleic acid-lipid particle of claim 1, wherein $R^6$ is selected from the group consisting of hydrogen (H) and an optionally substituted methyl group, ethyl group, or $C_3$-$C_{10}$ alkyl, alkenyl, or alkynyl group.

7. The nucleic acid-lipid particle of claim 1, wherein X is an optionally substituted heterocyclic ring having from 2 to 5 carbon atoms and from 1 to 3 heteroatoms selected from the group consisting of nitrogen (N), oxygen (O), sulfur (S), and combinations thereof.

8. The nucleic acid-lipid particle of claim 1, wherein Y is $(CH_2)_n$ and n is 0, 1, 2, 3, 4, 5, or 6.

9. The nucleic acid-lipid particle of claim 8, wherein n is 2, 3, or 4.

10. The nucleic acid-lipid particle of claim 1, wherein at least one of $R^4$ and $R^5$ comprises at least one site of unsaturation.

11. The nucleic acid-lipid particle of claim 10, wherein $R^4$ and $R^5$ are independently selected from the group consisting of a dodecenyl moiety, a tetradecenyl moiety, a hexadecenyl moiety, an octadecenyl moiety, and an icosenyl moiety.

12. The nucleic acid-lipid particle of claim 11, wherein the octadecenyl moiety is an oleyl moiety.

13. The nucleic acid-lipid particle of claim 12, wherein $R^4$ and $R^5$ are both oleyl moieties.

14. The nucleic acid-lipid particle of claim 1, wherein at least one of $R^4$ and $R^5$ comprises at least two sites of unsaturation.

15. The nucleic acid-lipid particle of claim 14, wherein $R^4$ and $R^5$ are independently selected from the group consisting of a dodecadienyl moiety, a tetradecadienyl moiety, a hexadecadienyl moiety, an octadecadienyl moiety, and an icosadienyl moiety.

16. The nucleic acid-lipid particle of claim 15, wherein the octadecadienyl moiety is a linoleyl moiety.

17. The nucleic acid-lipid particle of claim 16, wherein $R^4$ and $R^5$ are both linoleyl moieties.

18. The nucleic acid-lipid particle of claim 1, wherein at least one of $R^4$ and $R^5$ comprises at least three sites of unsaturation.

19. The nucleic acid-lipid particle of claim 18, wherein $R^4$ and $R^5$ are independently selected from the group consisting of a dodecatrienyl moiety, a tetradectrienyl moiety, a hexadecatrienyl moiety, an octadecatrienyl moiety, and an icosatrienyl moiety.

20. The nucleic acid-lipid particle of claim 19, wherein the octadecatrienyl moiety is a linolenyl moiety or a γ-linolenyl moiety.

21. The nucleic acid-lipid particle of claim 20, wherein $R^4$ and $R^5$ are both linolenyl moieties or γ-linolenyl moieties.

22. The nucleic acid-lipid particle of claim 10, wherein each of the at least one, two, or three sites of unsaturation correspond to a cis double bond, a trans double bond, or combinations thereof at specific positions in at least one of $R^4$ and $R^5$.

23. The nucleic acid-lipid particle of claim 1, wherein at least one of $R^4$ and $R^5$ comprises a substituted $C_{12}$-$C_{24}$ alkyl.

24. The nucleic acid-lipid particle of claim 23, wherein the substituted $C_{12}$-$C_{24}$ alkyl comprises a $C_{12}$-$C_{24}$ alkyl having at least 1-6 $C_1$-$C_6$ alkyl substituents.

25. The nucleic acid-lipid particle of claim 24, wherein $R^4$ and $R^5$ are both phytanyl moieties.

26. The nucleic acid-lipid particle of claim 1, wherein the cationic lipid of Formula I is selected from the group consisting of Compounds 1, 4, 5, 8, 9, 10, 11, 12, 13, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 63, 64, 65, and combinations thereof.

27. The nucleic acid-lipid particle of claim 1, wherein the non-cationic lipid is a phospholipid.

28. The nucleic acid-lipid particle of claim 1, wherein the non-cationic lipid is cholesterol or a cholesterol derivative.

29. The nucleic acid-lipid particle of claim 1, wherein the non-cationic lipid is a mixture of a phospholipid and cholesterol or a cholesterol derivative.

30. The nucleic acid-lipid particle of claim 1, wherein the non-cationic lipid is a mixture of DPPC and cholesterol.

31. The nucleic acid-lipid particle of claim 1, further comprising a conjugated lipid that inhibits aggregation of particles.

32. The nucleic acid-lipid particle of claim 31, wherein the conjugated lipid that inhibits aggregation of particles is a polyethyleneglycol (PEG)-lipid conjugate.

33. The nucleic acid-lipid particle of claim 32, wherein the PEG-lipid conjugate is a member selected from the group consisting of a PEG-diacylglycerol (PEG-DAG) conjugate, a PEG dialkyloxypropyl (PEG-DAA) conjugate, a PEG-phospholipid conjugate, a PEG-ceramide (PEG-Cer) conjugate, and a mixture thereof.

34. The nucleic acid-lipid particle of claim 33, wherein the PEG-lipid conjugate is a PEG-DAA conjugate.

35. The nucleic acid-lipid particle of claim 34, wherein the PEG-DAA conjugate is a member selected from the group consisting of a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, a PEG-distearyloxypropyl ($C_{18}$) conjugate, and a mixture thereof.

36. The nucleic acid-lipid particle of claim 1, wherein the cationic lipid comprises from about 50 mol % to about 80 mol % of the total lipid present in the particle.

37. The nucleic acid-lipid particle of claim 1, wherein the cationic lipid comprises from about 50 mol % to about 65 mol % of the total lipid present in the particle.

38. The nucleic acid-lipid particle of claim 37, wherein the non-cationic lipid comprises a mixture of a phospholipid and cholesterol or a derivative thereof comprising from about 25 mol % to about 50 mol % of the total lipid present in the particle.

39. The nucleic acid-lipid particle of claim 31, wherein the conjugated lipid that inhibits aggregation of particles comprises from about 0.5 mol % to about 2 mol % of the total lipid present in the particle.

40. The nucleic acid-lipid particle of claim 32, wherein the nucleic acid-lipid particle comprises about 57.1 mol % cationic lipid, a non-cationic lipid mixture of about 7.1 mol % phospholipid and about 34.3 mol % cholesterol or a derivative thereof, and about 1.4 mol % PEG-lipid conjugate.

41. A pharmaceutical composition comprising a nucleic acid-lipid particle of claim 1 and a pharmaceutically acceptable carrier.

42. A method for introducing an siRNA that silences APOB expression into a cell in a mammal, the method comprising:
    contacting the cell with a nucleic acid-lipid particle of claim 1.

43. The method of claim 42, wherein the mammal is a human having a disease or disorder associated with APOB expression or overexpression and wherein APOB expression is silenced by the siRNA.

44. The nucleic acid-lipid particle of claim 26, wherein the cationic lipid of Formula I is Compound 1.

45. The composition of claim 41, wherein the cationic lipid of Formula I is Compound 1.

46. The method of claim 42, wherein the cationic lipid of Formula I is Compound 1.

* * * * *

SEQUENCE LISTING

<160> NUMBER OF SEQ ID NOS: 18

<210> SEQ ID NO 1
<211> LENGTH: 21
<212> TYPE: RNA
<213> ORGANISM: Artificial Sequence
<220> FEATURE:
<223> OTHER INFORMATION: synthetic Apolipoprotien B (ApoB, APOB) siRNA
      sense strand S-1
<220> FEATURE:
<221> NAME/KEY: modified_base
<222> LOCATION: (4)...(4)
<223> OTHER INFORMATION: n = gm
<220> FEATURE:
<221> NAME/KEY: modified_base
<222> LOCATION: (8)...(14)
<223> OTHER INFORMATION: n = um

<400> SEQUENCE: 1
agunucanca cacngaauac c                                            21

<210> SEQ ID NO 2
<211> LENGTH: 21
<212> TYPE: RNA
<213> ORGANISM: Artificial Sequence
<220> FEATURE:
<223> OTHER INFORMATION: synthetic Apolipoprotien B (ApoB, APOB) siRNA
      antisense strand AS-1
<220> FEATURE:
<221> NAME/KEY: modified_base
<222> LOCATION: (4)...(4)
<223> OTHER INFORMATION: n = um
<220> FEATURE:
<221> NAME/KEY: modified_base
<222> LOCATION: (7)...(9)
<223> OTHER INFORMATION: n = gm
<220> FEATURE:
<221> NAME/KEY: modified_base
<222> LOCATION: (19)...(19)
<223> OTHER INFORMATION: n = um

<400> SEQUENCE: 2
uauncanunu gaugacacnu g                                            21

<210> SEQ ID NO 3
<211> LENGTH: 21
<212> TYPE: RNA
<213> ORGANISM: Artificial Sequence
<220> FEATURE:
<223> OTHER INFORMATION: synthetic Apolipoprotien B (ApoB, APOB) siRNA sense strand S-2
<220> FEATURE:
<221> NAME/KEY: modified_base
<222> LOCATION: (3)...(18)
<223> OTHER INFORMATION: n = um

<400> SEQUENCE: 3
agngncanca cacngaanac c                                                   21

<210> SEQ ID NO 4
<211> LENGTH: 21
<212> TYPE: RNA
<213> ORGANISM: Artificial Sequence
<220> FEATURE:
<223> OTHER INFORMATION: synthetic Apolipoprotien B (ApoB, APOB) siRNA sense strand S-3
<220> FEATURE:
<221> NAME/KEY: modified_base
<222> LOCATION: (3)...(14)
<223> OTHER INFORMATION: n = um
<220> FEATURE:
<221> NAME/KEY: modified_base
<222> LOCATION: (15)...(15)
<223> OTHER INFORMATION: n = gm
<220> FEATURE:
<221> NAME/KEY: modified_base
<222> LOCATION: (18)...(18)
<223> OTHER INFORMATION: n = um

<400> SEQUENCE: 4
agngncanca cacnnaanac c                                                   21

<210> SEQ ID NO 5
<211> LENGTH: 21
<212> TYPE: RNA
<213> ORGANISM: Artificial Sequence
<220> FEATURE:
<223> OTHER INFORMATION: synthetic Apolipoprotien B (ApoB, APOB) siRNA sense strand S-4
<220> FEATURE:
<221> NAME/KEY: modified_base
<222> LOCATION: (2)...(4)
<223> OTHER INFORMATION: n = gm
<220> FEATURE:
<221> NAME/KEY: modified_base
<222> LOCATION: (8)...(8)
<223> OTHER INFORMATION: n = um
<220> FEATURE:
<221> NAME/KEY: modified_base
<222> LOCATION: (15)...(15)
<223> OTHER INFORMATION: n = gm
<220> FEATURE:
<221> NAME/KEY: modified_base
<222> LOCATION: (18)...(18)
<223> OTHER INFORMATION: n = um

<400> SEQUENCE: 5
anunucanca cacunaanac c                                                   21

<210> SEQ ID NO 6
<211> LENGTH: 21
<212> TYPE: RNA
<213> ORGANISM: Artificial Sequence
<220> FEATURE:
<223> OTHER INFORMATION: synthetic Apolipoprotien B (ApoB, APOB) siRNA

```
      sense strand S-5
<220> FEATURE:
<221> NAME/KEY: modified_base
<222> LOCATION: (2)...(2)
<223> OTHER INFORMATION: n = gm
<220> FEATURE:
<221> NAME/KEY: modified_base
<222> LOCATION: (3)...(3)
<223> OTHER INFORMATION: n = um
<220> FEATURE:
<221> NAME/KEY: modified_base
<222> LOCATION: (4)...(4)
<223> OTHER INFORMATION: n = gm
<220> FEATURE:
<221> NAME/KEY: modified_base
<222> LOCATION: (5)...(18)
<223> OTHER INFORMATION: n = um

<400> SEQUENCE: 6
annnncanca cacngaanac c                                              21

<210> SEQ ID NO 7
<211> LENGTH: 21
<212> TYPE: RNA
<213> ORGANISM: Artificial Sequence
<220> FEATURE:
<223> OTHER INFORMATION: synthetic Apolipoprotien B (ApoB, APOB) siRNA
      sense strand S-6
<220> FEATURE:
<221> NAME/KEY: modified_base
<222> LOCATION: (2)...(2)
<223> OTHER INFORMATION: n = gm
<220> FEATURE:
<221> NAME/KEY: modified_base
<222> LOCATION: (3)...(14)
<223> OTHER INFORMATION: n = um
<220> FEATURE:
<221> NAME/KEY: modified_base
<222> LOCATION: (15)...(15)
<223> OTHER INFORMATION: n = gm
<220> FEATURE:
<221> NAME/KEY: modified_base
<222> LOCATION: (18)...(18)
<223> OTHER INFORMATION: n = um

<400> SEQUENCE: 7
anngncauca cacnnaanac c                                              21

<210> SEQ ID NO 8
<211> LENGTH: 21
<212> TYPE: RNA
<213> ORGANISM: Artificial Sequence
<220> FEATURE:
<223> OTHER INFORMATION: synthetic Apolipoprotien B (ApoB, APOB) siRNA
      antisense strand AS-2
<220> FEATURE:
<221> NAME/KEY: modified_base
<222> LOCATION: (4)...(19)
<223> OTHER INFORMATION: n = um

<400> SEQUENCE: 8
uauucagugu gaugacacuu g                                              21

<210> SEQ ID NO 9
<211> LENGTH: 21
<212> TYPE: RNA
<213> ORGANISM: Artificial Sequence
<220> FEATURE:
<223> OTHER INFORMATION: synthetic Apolipoprotien B (ApoB, APOB) siRNA
      antisense strand AS-3
<220> FEATURE:
<221> NAME/KEY: modified_base
<222> LOCATION: (4)...(4)
```

```
<223> OTHER INFORMATION: n = um
<220> FEATURE:
<221> NAME/KEY: modified_base
<222> LOCATION: (7)...(11)
<223> OTHER INFORMATION: n = gm
<220> FEATURE:
<221> NAME/KEY: modified_base
<222> LOCATION: (19)...(19)
<223> OTHER INFORMATION: n = um

<400> SEQUENCE: 9
uauucagugu gaugacacuu g                                              21

<210> SEQ ID NO 10
<211> LENGTH: 21
<212> TYPE: RNA
<213> ORGANISM: Artificial Sequence
<220> FEATURE:
<223> OTHER INFORMATION: synthetic Apolipoprotien B (ApoB, APOB) siRNA
      antisense strand AS-4
<220> FEATURE:
<221> NAME/KEY: modified_base
<222> LOCATION: (4)...(4)
<223> OTHER INFORMATION: n = um
<220> FEATURE:
<221> NAME/KEY: modified_base
<222> LOCATION: (7)...(9)
<223> OTHER INFORMATION: n = gm
<220> FEATURE:
<221> NAME/KEY: modified_base
<222> LOCATION: (19)...(20)
<223> OTHER INFORMATION: n = um
<220> FEATURE:
<221> NAME/KEY: modified_base
<222> LOCATION: (21)...(21)
<223> OTHER INFORMATION: n = gm

<400> SEQUENCE: 10
uauucagugu gaugacacuu g                                              21

<210> SEQ ID NO 11
<211> LENGTH: 21
<212> TYPE: RNA
<213> ORGANISM: Artificial Sequence
<220> FEATURE:
<223> OTHER INFORMATION: synthetic Apolipoprotien B (ApoB, APOB) siRNA
      antisense strand AS-5
<220> FEATURE:
<221> NAME/KEY: modified_base
<222> LOCATION: (4)...(20)
<223> OTHER INFORMATION: n = um
<220> FEATURE:
<221> NAME/KEY: modified_base
<222> LOCATION: (21)...(21)
<223> OTHER INFORMATION: n = gm

<400> SEQUENCE: 11
uauucagugu gaugacacuu g                                              21

<210> SEQ ID NO 12
<211> LENGTH: 21
<212> TYPE: RNA
<213> ORGANISM: Artificial Sequence
<220> FEATURE:
<223> OTHER INFORMATION: synthetic Apolipoprotien B (ApoB, APOB) siRNA
      antisense strand AS-6
<220> FEATURE:
<221> NAME/KEY: modified_base
<222> LOCATION: (4)...(4)
<223> OTHER INFORMATION: n = um
<220> FEATURE:
<221> NAME/KEY: modified_base
<222> LOCATION: (7)...(11)
```

```
<223> OTHER INFORMATION: n = gm
<220> FEATURE:
<221> NAME/KEY: modified_base
<222> LOCATION: (19)...(20)
<223> OTHER INFORMATION: n = um
<220> FEATURE:
<221> NAME/KEY: modified_base
<222> LOCATION: (21)...(21)
<223> OTHER INFORMATION: n = gm

<400> SEQUENCE: 12
uauucagugu gaugacacuu g                                              21

<210> SEQ ID NO 13
<211> LENGTH: 19
<212> TYPE: RNA
<213> ORGANISM: Artificial Sequence
<220> FEATURE:
<223> OTHER INFORMATION: synthetic Apolipoprotien B (ApoB, APOB) siRNA
      antisense strand

<400> SEQUENCE: 13
uauucagugu gaugacacu                                                 19

<210> SEQ ID NO 14
<211> LENGTH: 19
<212> TYPE: RNA
<213> ORGANISM: Artificial Sequence
<220> FEATURE:
<223> OTHER INFORMATION: synthetic Apolipoprotien B (ApoB, APOB) siRNA
      antisense strand

<400> SEQUENCE: 14 agugcauca cacugaaua                                                  19

<210> SEQ ID NO 15
<211> LENGTH: 19
<212> TYPE: RNA
<213> ORGANISM: Artificial Sequence
<220> FEATURE:
<223> OTHER INFORMATION: synthetic Apolipoprotien B (ApoB, APOB) siRNA
      antisense strand
<220> FEATURE:
<221> NAME/KEY: modified_base
<222> LOCATION: (4)...(19)
<223> OTHER INFORMATION: n = um

<400> SEQUENCE: 15
uauncagngn gangacacn                                                 19

<210> SEQ ID NO 16
<211> LENGTH: 19
<212> TYPE: RNA
<213> ORGANISM: Artificial Sequence
<220> FEATURE:
<223> OTHER INFORMATION: synthetic Apolipoprotien B (ApoB, APOB) siRNA
      sense strand
<220> FEATURE:
<221> NAME/KEY: modified_base
<222> LOCATION: (3)...(14)
<223> OTHER INFORMATION: n = um
<220> FEATURE:
<221> NAME/KEY: modified_base
<222> LOCATION: (15)...(15)
<223> OTHER INFORMATION: n = gm
<220> FEATURE:
<221> NAME/KEY: modified_base
<222> LOCATION: (18)...(18)
<223> OTHER INFORMATION: n = um

<400> SEQUENCE: 16
```

```
agngncanca cacnnaana                                                  19

<210> SEQ ID NO 17
<211> LENGTH: 21
<212> TYPE: RNA
<213> ORGANISM: Artificial Sequence
<220> FEATURE:
<223> OTHER INFORMATION: synthetic Apolipoprotien B (ApoB, APOB) siRNA
      sense strand

<400> SEQUENCE: 17
gucaucacac ugaauaccaa u                                               21

<210> SEQ ID NO 18
<211> LENGTH: 23
<212> TYPE: RNA
<213> ORGANISM: Artificial Sequence
<220> FEATURE:
<223> OTHER INFORMATION: synthetic Apolipoprotien B (ApoB, APOB) siRNA
      antisense strand

<400> SEQUENCE: 18
auugguauuc agugugauga cac                                             23
```